(12) United States Patent
Barbas, III et al.

(10) Patent No.: US 8,685,687 B2
(45) Date of Patent: Apr. 1, 2014

(54) CHIMERIC ZINC FINGER RECOMBINASES OPTIMIZED FOR CATALYSIS BY DIRECTED EVOLUTION

(75) Inventors: Carlos F. Barbas, III, Solana Beach, CA (US); Russell M. Gordley, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 561 days.

(21) Appl. No.: 12/309,096

(22) PCT Filed: Jul. 5, 2007

(86) PCT No.: PCT/US2007/072869
§ 371 (c)(1),
(2), (4) Date: Sep. 2, 2009

(87) PCT Pub. No.: WO2008/006028
PCT Pub. Date: Jan. 10, 2008

(65) Prior Publication Data
US 2010/0086532 A1 Apr. 8, 2010

Related U.S. Application Data

(60) Provisional application No. 60/818,908, filed on Jul. 5, 2006.

(51) Int. Cl.
*C12N 9/00* (2006.01)
(52) U.S. Cl.
USPC ......................................................... 435/183
(58) Field of Classification Search
USPC ......................................................... 435/183
See application file for complete search history.

(56) References Cited

U.S. PATENT DOCUMENTS

2006/0154240 A1* 7/2006 McCray et al. .................... 435/5
2006/0172373 A1* 8/2006 Stark et al. ..................... 435/69.1

FOREIGN PATENT DOCUMENTS

WO WO 2005/107790 A1 11/2005

OTHER PUBLICATIONS

International Search Report (ISR) WO 2008/006028 A3, Dec. 24, 2008, The Scripps Research Institute.
Supplementary European Search Report (ESR) EP 07 79 9328 A4, Oct. 21, 2009, The Scripps Research Institute.
Akopian & Marshall, "Site-specific DNA recombinases as instruments for genomic surgery", *Adv. Genet.*, 55:1-23 (2005).
Akopian et al., "Chimeric recombinases with designed DNA sequence recognition", *Proc. Natl. Acad. Sci. USA.*, 100(15):8688-8691 (2003).
Buchholz & Stewart, "Alteration of Cre recombinase site specificity by substrate-linked protein evolution", *Nat. Biotechnol.*, 19(11):1047-1052 (2001).
Gordley et al., "Evolution of programmable zinc finger-recombinases with activity in human cells", *J. Mol. Biol.*, 367(3):802-13 (2007).
Gordley et al., "Synthesis of programmable integrases", *Proc. Natl. Acad. Sci. USA.*, 106(13):5053-5058 (2009).
Segal et al., "Evaluation of a modular strategy for the construction of novel polydactyl zinc finger DNA-binding proteins", *Biochemistry*, 42(7):2137-48 (2003).
Smith & Thorpe, "Diversity in the serine recombinases", *Mol. Microbiol.*, 44(2):299-307 (2002).
Arnold et al., "Mutants of Tn3 resolvase which do not require accessory binding sites for recombination activity", *EMBO J.*, 18(5):1407-14 (1999).
Communication from European Patent Office from application No. EP 07 799 328.5, (2013).

\* cited by examiner

*Primary Examiner* — Tekchand Saidha
(74) *Attorney, Agent, or Firm* — DLA Piper LLP (US)

(57) ABSTRACT

The present invention is directed to chimeric recombinases comprising a serine recombinase operatively linked to a zinc finger nucleotide binding domain such that the chimeric recombinase protein catalyzes site-specific recombination at a DNA site specifically bound by the zinc finger nucleotide binding domain. The serine recombinase can be one of several naturally occurring serine recombinases. The invention also includes nucleic acids encoding the chimeric recombinases, vectors including the nucleic acids, host cells transformed or transfected with the vectors, methods of using the chimeric recombinases to carry out recombination, methods of using substrate-linked protein evolution to generate additional chimeric recombinases, methods of using the chimeric recombinases for gene therapy, and pharmaceutical compositions.

9 Claims, 15 Drawing Sheets

A.

B.

A.

B.

A.

B.
1) GAGGAG-22T-CTCCTC—GFP—GAGGAG-22T-CTCCTC
2) CGGGAG-22T-CTCCTC—GFP—GAGGAG-22T-CTCCCG
3) GTGGAG-22T-CTCCTC—GFP—GAGGAG-22T-CTCCAC
4) GCAGAG-22T-CTCCTC—GFP—GAGGAG-22T-CTCCGC
5) GAGGAG-22T-CTCCTC
6) GGGGAG-22T-CTCCCC
7) GTGGAG-22T-CTCCAC
8) GCGGAG-22T-CTCCGC

C.

A.

B.

C.

A.

B.

CHIMERIC ZINC FINGER RECOMBINASES OPTIMIZED FOR CATALYSIS BY DIRECTED EVOLUTION

CROSS-REFERENCES

This application claims priority from U.S. Provisional Application Ser. No. 60/818,908 by Barbas, III et al., entitled "Chimeric Zinc Finger Recombinases Optimized for Catalysis by Directed Evolution," filed Jul. 5, 2006, which is incorporated herein in its entirety by this reference.

BACKGROUND OF THE INVENTION

This invention is directed to chimeric recombinases incorporating a novel DNA binding domain preferably but not limited to at least one zinc finger domain and at least one domain that has catalytic activity that promotes recombination and methods for optimizing the activity of these recombinases by directed evolution, as well as to applications of the chimeric recombinases and the methods in gene therapy and the modification of DNA in other organisms, for example for endowing crop plants, animals and industrial organisms with favorable phenotypes.

At present, no strategy for gene therapy enables targeted and site-specific recombination of the endogenous human genome. Such a strategy would allow the rapid excision of harmful genes and the safe integration of beneficial ones.

The Cre-loxP recombination system enables researchers to efficiently alter the genome of discrete cells in vivo. Once genomic lox sites have been introduced by homologous recombination, the Cre recombinase may catalyze excision, inversion, or integration, at those loci. This revolutionary tool continues to find novel applications including circumvention of embryonic lethality with induced gene inactivation and delineation of cellular lineages during embryogenesis (16). With the development of Cre, the Flp recombinase and the φC31 integrase, site-specific recombinases (SSRs) now comprise a toolbox for genetic manipulation.

True to their name, SSRs are highly specific for the ~28 bp recombination sites present in their native substrates. While a few mutant recombination sites have been found to be functional, this fundamental requirement broadly prohibits the application of SSRs to endogenous genomes. Constrained by the prerequisite of homologous recombination, SSRs are barred from many potential applications, gene therapy being perhaps the most significant. This constraint has motivated several groups to modify SSR substrate specificity by directed protein evolution (18, 53, 54). Calos and coworkers characterized "pseudo" attP sites within the endogenous human and Mouse genomes at which φC31 mediates efficient integration (65). Their application of this enzyme to the treatment of junctional epidermolysis bullosa (48), Duchenne muscular dystrophy (50), and murine hereditary tyrosinemia type I (31) suggests the therapeutic potential of endogenous site-specific recombination.

The extent to which Cre and φC31 can be trained on new substrates is limited by the structural organization of their DNA binding interactions. Tyrosine recombinases, such as Cre, mediate DNA binding and catalysis with the same protein domain. This arrangement constrains the geometry of all potential DNA-protein interactions and precludes replacement with an exogenous DNA binding domain. Notably, the characterization of one mutant Cre-substrate interaction revealed recognition to be indirect —with contact to the altered base pair mediated by a bridging water molecule (7). In contrast to the well characterized tyrosine recombinases, the function of the φC31 integrase, and other large serine recombinases, remains largely obscure. In the absence of a three dimensional protein structure or known DNA binding domains, Calos and coworkers evolved φC31 by covering the entire protein sequence with random mutations (54). Modification of the large serine recombinases is further complicated by the potential multiplicity of significant DNA binding regions (2).

Accordingly, there is a need for a more generalized method of catalyzing targeted and site-specific recombination of the endogenous genome, particularly for gene therapy, as well as for enzymes that can catalyze such targeted and site-specific recombination. This is particularly useful for gene therapy, but would have many other applications in molecular biology, including in gene cloning and use in modification of industrial organisms and agricultural plants and animals.

SUMMARY OF THE INVENTION

Accordingly, one aspect of the present invention is a chimeric recombinase protein comprising a serine recombinase operatively linked to a zinc finger nucleotide binding domain such that the chimeric recombinase protein catalyzes site-specific recombination at a DNA site specifically bound by the zinc finger nucleotide binding domain and such that the serine recombinase is selected or evolved to catalyze recombination efficiently in the context of the chimeric protein. Typically, the serine recombinase domain is a recombinase domain with a catalytic serine nucleophile that catalyzes a general strand exchange mechanism. Particularly preferred chimeric recombinase proteins include $\text{In3}_{GAGGAG}$, $\text{Hin}_{GAGGAG}$, and $\text{Gin}_{GAGGAG}$, which have domains from Tn3, Hin, or Gin fused to a zinc finger nucleotide binding domain. Other chimeric recombinase proteins are included within the scope of the invention. Such chimeric recombinase proteins include, but are not limited to: a chimeric recombinase protein wherein the chimeric recombinase protein is $\text{Tn3Ch15}_G$ and has a mutated serine recombinase deriving from Tn3; a chimeric recombinase protein wherein the chimeric recombinase protein is $\text{GinL7C7}_{H1}$ and has a mutated serine recombinase deriving from Gin; a chimeric recombinase protein wherein the chimeric recombinase protein is $\text{GinL7C7}_{P2}$ and has a mutated serine recombinase deriving from Gin; a chimeric recombinase protein wherein one or more of the following mutations are introduced in the serine recombinase: (1) G70S, D102Y, or E124Q in a Tn3 serine recombinase catalytic domain; (2) H107Y in a Hin serine recombinase catalytic domain; (3) M70V, T96A, or H106Y in a Gin serine recombinase catalytic domain; or (4) I12V, D13G, K65R, M73V, I80M, V108A, K53E, and K151M in a Tn3 serine recombinase catalytic domain, together with mutations of corresponding homologous residues in Hin and Gin; a chimeric recombinase wherein the serine recombinase is a Gin domain that includes all of the following mutations: D12G, N14S, N20D, K50E, M70V, I94V, Y109H, M114V, and K148M; or a chimeric recombinase wherein the serine recombinase is a Gin domain that includes all of the following mutations: D12G, N14S N20D, K50E, M70V, I94V, and M114V.

Another aspect of the present invention is an isolated and purified nucleotide sequence encoding a chimeric recombinase protein as described above. The nucleotide sequence can be a DNA sequence.

Yet another aspect of the present invention is a vector including a DNA sequence as described above. The vector can be an expression vector.

Yet another aspect of the present invention is host cells transformed or transfected with a nucleotide sequence or vector as described above.

Yet another aspect of the present invention is a method of carrying out a site-specific recombination event comprising the steps of:

(1) providing a DNA sequence having therein at least two sites binding at least one chimeric recombinase protein according to the present invention, the sites being separated by a spacer; and (2) reacting the DNA sequence with the chimeric recombinase under conditions in which the at least one chimeric recombinase catalyzes a site-specific recombination event in which both strands of the DNA sequence are cleaved between the two sites specifically binding the chimeric recombinase so that a site-specific recombination event is carried out.

Yet another aspect of the present invention is a method of carrying out a site-specific recombination event comprising the steps of:

(1) providing two DNA sequences, a first sequence and a second sequence, each of the first sequence and the second sequence having a site therein binding at least one chimeric recombinase according to the present invention; and (2) reacting the first sequence and the second sequence with the at least one chimeric recombinase under conditions in which the chimeric recombinase catalyzes a site-specific recombination event in which both strands of the first sequence and the second sequence are cleaved so that a site-specific recombination event is carried out involving the first sequence and the second sequence.

Still another aspect of the present invention is a method of carrying out a site-specific recombination event comprising the steps of:

(1) providing two DNA sequences, a first sequence and a second sequence, one of the first sequence and the second sequence having a site therein binding at least one chimeric recombinase according to the present invention, and the other of the first sequence and the second sequence having a site therein binding at least one naturally-occurring serine recombinase; and (2) reacting the first sequence and the second sequence with the at least one chimeric recombinase and the naturally-occurring serine recombinase under conditions in which the chimeric recombinase and the naturally-occurring serine recombinase catalyze a site-specific recombination event in which both strands of the first sequence and the second sequence are cleaved so that a site-specific recombination event is carried out involving the first sequence and the second sequence.

Still another aspect of the present invention is a method of performing stable integration in a DNA molecule comprising the steps of:

(1) providing a DNA sequence having therein two sites for recombination, each site comprising:

(a) a mutated binding site for at least one chimeric recombinase according to the present invention binding the at least one chimeric recombinase at a substantially lowered affinity compared with an optimally binding site for a chimeric recombinase half-site; and (b) a binding site for at least one chimeric recombinase half site that is optimally binding, the sites specifically binding at least one chimeric recombinase according to the present invention, the sites being separated by a spacer; and (2) reacting the DNA sequence with at least one chimeric recombinase under conditions in which the at least one chimeric recombinase catalyzes a site-specific recombination event in which both strands of the DNA sequence are cleaved between the two sites specifically binding the chimeric recombinase so that a site-specific recombination event is carried out, the site-specific recombination event being integration; and such that a homodimer of mutated binding sites for chimeric recombinase half-sites is formed that is not functional for recombination so that the result of integration is stable.

Yet another aspect of the present invention is a method of performing recombination in a DNA molecule comprising the steps of:

(1) providing a first DNA sequence having therein a first site for recombination that is reactive with at least one first chimeric recombinase according to the present invention;

(2) providing a second DNA sequence having therein a second site for recombination that is reactive with at least one second chimeric recombinase according to the present invention, such that the first site and the second site are functionally orthogonal; and (3) reacting the first DNA sequence with the at least one first chimeric recombinase and reacting the second DNA sequence with the at least one second chimeric recombinase to effect recombination.

Another aspect of the present invention is a method of promoting cassette exchanges comprising the steps of:

(1) generating two plasmids:

(a) a first plasmid expressing a first chimeric recombinase according to the present invention comprising a first catalytic domain and a first zinc finger domain and expressing a first antibiotic resistance gene; and (b) a second plasmid expressing a second chimeric recombinase according to the present invention comprising a second catalytic domain and a second zinc finger domain and expressing a second antibiotic resistance gene, such that the first catalytic domain and the second catalytic domain are different and the first zinc finger domain and the second zinc finger domain are different, and such that the first and second antibiotic resistance genes confer resistance to two different antibiotics;

(2) assembling two cassettes by flanking an encoding region of a first gene and an encoding region of a second gene with non-repeating homodimer sites each binding one of the first chimeric recombinase according to the present invention and the second chimeric recombinase according to the present invention such that intra-plasmid excision by the two chimeric recombinases is precluded;

(3) inserting one cassette into each plasmid to generate two plasmids including cassettes therein; and (4) co-transfecting a bacterial host with the first plasmid including a cassette and the second plasmid including a cassette so that recombination occurs.

Another aspect of the present invention is a method of promoting cassette exchanges comprising the steps of:

(1) generating two plasmids:

(a) a first plasmid expressing a first chimeric recombinase according to the present invention comprising a first catalytic domain and a first zinc finger domain and expressing a first antibiotic resistance gene, wherein the first chimeric recombinase is mutated or selected to bind an endogenous flanking sequence of a first gene; and (b) a second plasmid expressing a second chimeric recombinase according to the present invention comprising a second catalytic domain and a second zinc finger domain and expressing a second antibiotic resistance gene, wherein the second chimeric recombinase is mutated or selected to bind an endogenous flanking sequence of a second gene, such that the first catalytic domain and the second catalytic domain are different and the first zinc finger domain and the second zinc finger domain are different, and such that the first and second antibiotic resistance genes confer resistance to two different antibiotics;

(2) assembling two cassettes, a first cassette including a first gene flanked by a first endogenous flanking region and a second cassette including a second gene flanked by a second endogenous flanking region by each of the two endogenous flanking regions including therein a non-repeating homodimer sites each binding one of the first chimeric recombinase according to the present invention and the second chimeric recombinase according to the present invention such that intra-plasmid excision by the two chimeric recombinases is precluded;

(3) inserting one cassette into each plasmid to generate two plasmids including cassettes therein; and (4) co-transfecting a bacterial host with the first plasmid including a cassette and the second plasmid including a cassette so that recombination occurs.

Yet another aspect of the present invention is a method for identifying cis-inactivating zinc finger binding sites comprising the steps of:

(1) generating single half-site libraries including zinc finger binding sites in two compatible plasmids using primers containing randomized nucleotides;

(2) co-transforming the single-half site libraries generated in step (1) into a suitable host to generate transformants;

(3) co-maintaining the transformants using two antibiotics for selection;

(4) purifying plasmids from the co-maintained transformants;

(5) retransforming the suitable host at low concentration;

(6) allowing the retransformed host to grow on a culture medium containing the two antibiotics; and (7) screening colonies growing on the culture medium containing the two antibiotics by PCR for unidirectional integration to identify cis-inactivating zinc finger binding sites.

Analogously, another aspect of the invention is a method for identifying cis-inactivating spacer sequences comprising the steps of:

(1) generating single half-site libraries including spacer sequences in two compatible plasmids using primers containing randomized nucleotides;

(2) co-transforming the single-half site libraries generated in step (1) into a suitable host to generate transformants;

(3) co-maintaining the transformants using two antibiotics for selection;

(4) purifying plasmids from the co-maintained transformants;

(5) retransforming the suitable host at low concentration;

(6) allowing the retransformed host to grow on a culture medium containing the two antibiotics; and (7) screening colonies growing on the culture medium containing the two antibiotics by PCR for unidirectional integration to identify cis-inactivating spacer sequences.

Again, analogously, another aspect of the invention is a method for identifying cis-inactivating DNA binding domains comprising the steps of:

(1) generating a target substrate, the target substrate including therein a recombination site including therein two different DNA binding domain recognition sequences, a selection target sequence and a transactivator sequence;

(2) incubating the target substrate with a library of chimeric recombinases according to the present invention with different DNA binding domains in the presence of a fixed chimeric recombinase according to the present invention that is perfectly complementary to the transactivator sequence to generate a single half-site library;

(3) co-transforming the single-half site library generated in step (2) into a suitable host to generate transformants;

(4) co-maintaining the transformants using two antibiotics for selection;

(5) purifying plasmids from the co-maintained transformants;

(6) retransforming the suitable host at low concentration;

(7) allowing the retransformed host to grow on a culture medium containing the two antibiotics; and (8) screening colonies growing on the culture medium containing the two antibiotics by PCR for unidirectional integration to identify cis-inactivating DNA binding domains.

Yet another aspect of the present invention is a method of using substrate-linked protein evolution to generate a new chimeric recombinase from an existing chimeric recombinase comprising the steps of:

(1) creating a library of recombinase mutants to generate mutagenized recombinase domains;

(2) fusing the mutagenized recombinase domains to a DNA binding domain that has not been mutagenized to generate a library of mutagenized fusion proteins;

(3) cloning the library of mutagenized fusion proteins into a plasmid, the plasmid including a recombinase substrate, for functional selection; and (4) selecting active mutagenized fusion proteins by selecting plasmids that are modified by the activity of recombinase.

The invention further encompasses methods for gene therapy. One embodiment of these methods is a method for gene therapy in which a deleterious gene is removed by recombinational excision comprising the steps of (1) administering to an individual having a deleterious gene in the genome a composition including therein a nucleic acid encoding a site-specific recombinase according to the present invention, the site-specific recombinase, when expressed, specifically removing the deleterious gene from the genome; and (2) causing the site-specific recombinase to be expressed to specifically remove the deleterious gene from the genome.

Another embodiment of these methods is a method for gene therapy in which a deleterious gene is removed by recombinational excision and subsequently replaced by recombinational integration comprising the steps of:

(1) administering to an individual having a deleterious gene in the genome a nucleic acid encoding a site-specific recombinase according to the present invention, the site-specific recombinase, when expressed, removing the deleterious gene from the genome;

(2) causing the site-specific recombinase to be expressed to specifically remove the deleterious gene from the genome;

(3) administering to the individual a nucleic acid including therein a functional replacement gene for the deleterious gene; and (4) inserting the functional replacement gene into the genome by recombinational integration catalyzed by the site-specific recombinase.

Another aspect of the present invention is a method for gene therapy in which therapeutic integration is performed in order to disrupt the structure or functioning of a deleterious gene and to deliver a gene with improved function into a selected genomic locus comprising administering to an individual with a deleterious gene in the genome: (1) a DNA segment including therein the gene with improved function; and (2) at least one chimeric recombinase according to the present invention that acts to integrate the DNA segment including therein the gene with improved function into the genomic locus of the deleterious gene.

Another aspect of the invention is pharmaceutical compositions. One pharmaceutical composition according to the present invention comprises:

(1) a therapeutically effective quantity of a chimeric recombinase protein according to the present invention as described above; and (2) a pharmaceutically acceptable carrier.

Another pharmaceutical composition according to the present invention comprises:

(1) a therapeutically effective quantity of a nucleotide sequence that encodes a chimeric recombinase protein according to the present invention; and (2) a pharmaceutically acceptable carrier.

Yet another aspect of the invention is a transgenic organism produced by an act of recombination catalyzed by a chimeric recombinase according to the present invention.

This technology will be widely used for the genetic modification of crop plants and animals and microorganisms and multicellular organisms such as insects. The genetic modification of crop plants and animals can be undertaken for a variety of purposes, including resistance to disease, improved growth profile, reduced nutritional requirements, or other purposes.

BRIEF DESCRIPTION OF THE DRAWINGS

The following invention will become better understood with reference to the specification, appended claims, and accompanying drawings, where:

DETAILED DESCRIPTION OF THE INVENTION

Definitions

Figure 1:
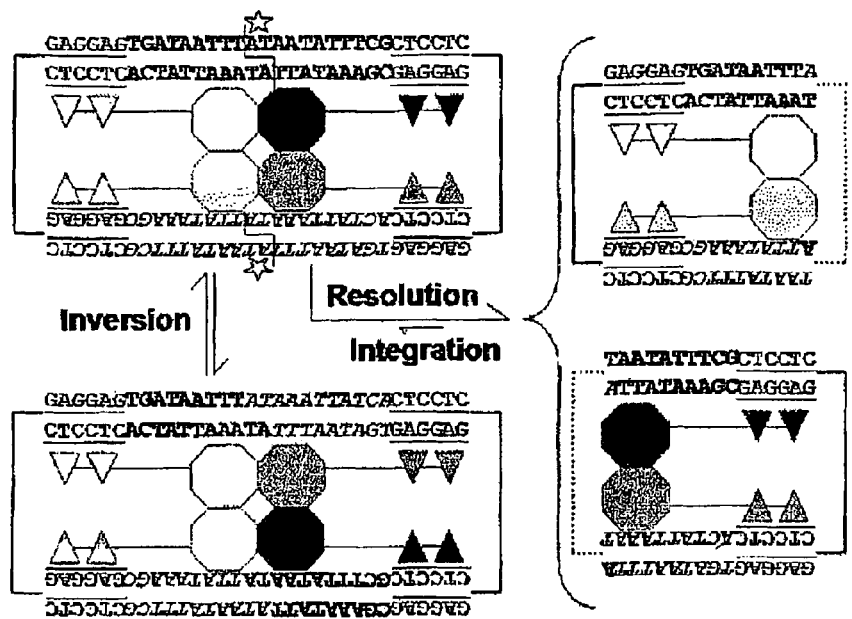
FIG. 1 is a schematic depiction of recombination events mediated by the zinc finger-recombinase fusion protein Tn3$_{GAGGAG}$ on substrate 20T-GFP-20T. (A) Four enzyme monomers are shown; triangles represent zinc finger domains, octagons, recombinase catalytic domains. Although the synapse above is a homo-tetramer, four different colors are used for clarity. The zinc finger domain binds to its cognate sequence, GAGGAG (SEQ ID NO: 1), on either strand (underlined). Flanked by inverted binding sites, the two identical 'spacer' regions are uniquely delineated by bold and italic characters. The central base pairs, AT, at the cleavage sites (denoted by stars), allow either resolution or inversion to take place; synapsis with sites in opposite orientation (shown here) enables inversion, same orientation (not shown) enables resolution. Solid lines represent intervening plasmid DNA; dotted lines, a connection between adjacent base pairs. (B) Cartoon of the corresponding plasmids; boxes represent recombination sites, with shading indicating the position of each recombinase monomer.
Figure 1:
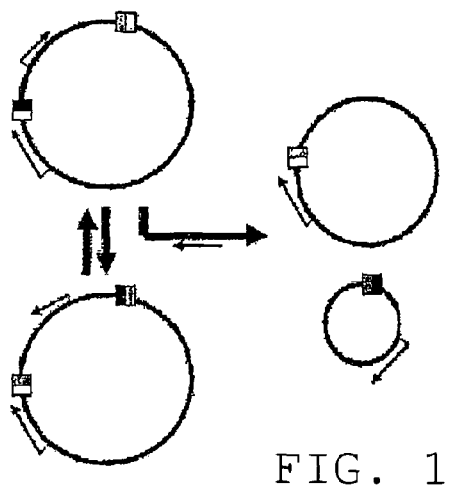

Unless defined otherwise, all technical and scientific terms used herein have the same meaning as is commonly understood by one of skill in the art to which this invention belongs.

As used herein, the term "nucleic acid," "nucleic acid sequence," "polynucleotide," or similar terms, refers to a deoxyribonucleotide or ribonucleotide oligonucleotide or polynucleotide, including single- or double-stranded forms, and coding or non-coding (e.g., "antisense") forms. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically, such as zinc finger proteins. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal; methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones; such as N-(2-aminoethyl) glycine units. Phosphorothioate linkages are described, e.g., by U.S. Pat. Nos. 6,031, 092; 6,001,982; 5,684,148; see also, WO 97/03211; WO 96/39154; Mata (1997) Toxicol. Appl. Pharmacol. 144:189-

197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The term "nucleic acid," "nucleotide sequence," and the like further encompass the complement of a defined sequence according to the Watson-Crick base pairing rules unless the complement is excluded. Bases included in nucleic acids include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, $N^6$-methyladenine, 7-methylguanine, 5-methylaminomethyluracil, 5-methoxy-amino-methyl-2-thiouracil, β-D-mannosylqueosine, 5'-methoxycarbonylmethyluracil, 5-methoxyuracil, 2-methylthio-$N^6$-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. DNA may be in the form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups.

As used herein, the term "zinc finger," "zinc finger nucleotide binding domain," or similar terminology refers both to naturally occurring and artificially produced zinc fingers. Such zinc fingers can have various framework structures, such as, but not limited to, $C_2H_2$, $C_4$, $H_4$, $H_3C$, $C_3X$, $H_3X$, $C_2X_2$, and $H_2X_2$, where X is a zinc ligating amino acid. In these framework structures, as is conventional in the recitation of zinc finger structures, "C" represents a cysteine residue and "H" represents a histidine residue. Zinc fingers of having the framework $C_2H_2$ include, but are not limited to, zinc fingers described, for example, in U.S. Pat. No. 7,101,972 to Barbas, U.S. Pat. No. 7,067,617 to Barbas et al., U.S. Pat. No. 6,790,941 to Barbas et al., U.S. Pat. No. 6,610,512 to Barbas, U.S. Pat. No. 6,242,568 to Barbas et al., U.S. Pat. No. 6,140,466 to Barbas et al., U.S. Pat. No. 6,140,081 to Barbas, United States Patent Application Publication No. 20060223757 by Barbas, United States Patent Application Publication No. 20060211846 by Barbas et al., United States Patent Application Publication No. 20060078880 by Barbas et al., United States Patent Application Publication No. 20050148075 by Barbas, United States Patent Application Publication No. 20050084885 by Barbas et al., United States Patent Application Publication No. 20040224385 by Barbas et al., United States Patent Application Publication No. 20030059767 by Barbas et al., and United States Patent Application Publication No. 20020165356 by Barbas et al., all of which are incorporated herein by this reference. Other zinc fingers are described in: U.S. Pat. No. 7,067,317 to Rebar et al.; U.S. Pat. No. 7,030,215 to Liu et al.; U.S. Pat. No. 7,026,462 to Rebar et al.; U.S. Pat. No. 7,013,219 to Case et al.; U.S. Pat. No. 6,979,539 to Cox III et al.; U.S. Pat. No. 6,933,113 to Case et al.; U.S. Pat. No. 6,824,978 to Cox III et al.; U.S. Pat. No. 6,794,136 to Eisenberg et al.; U.S. Pat. No. 6,785,613 to Eisenberg et al.; U.S. Pat. No. 6,777,185 to Case et al.; U.S. Pat. No. 6,706,470 to Choo at al.; U.S. Pat. No. 6,607,882 to Cox III et al.; U.S. Pat. No. 6,599,692 to Case et al.; U.S. Pat. No. 6,534,261 to Cox III et al.; U.S. Pat. No. 6,503,717 to Case et al.; U.S. Pat. No. 6,453,242 to Eisenberg et al.; United States Patent Application Publication No. 2006/0246588 to Rebar et al.; United States Patent Application Publication No. 2006/0246567 to Rebar et. al.; United States Patent Application Publication No. 2006/0166263 to Case et al.; United States Patent Application Publication No. 2006/0078878 to Cox III et al; United States Patent Application Publication No. 2005/0257062 to Rebar et al.; United States Patent Application Publication No. 2005/0215502 to Cox III et al.; United States Patent Application Publication No. 2005/0130304 to Cox III et al.; United States Patent Application Publication No. 2004/0203064 to Case et al.; United States Patent Application Publication No. 2003/0166141 to Case et al.; United States Patent Application Publication No. 2003/0134318 to Case et al.; United States Patent Application Publication No. 2003/0105593 to Eisenberg et al.; United States Patent Application Publication No. 2003/0087817 to Cox III et al.; United States Patent Application Publication No. 2003/0021776 to Rebar et al.; and United States Patent Application Publication No. 2002/0081614 to Case et al., all of which are incorporated herein by this reference. For example, one alternative described in these patents and patent publications involves the use of so-called "D-able sites" and zinc finger modules or zinc finger DNA binding domains that can bind to such sites. A "D-able" site is a region of a target site that allows an appropriately designed zinc finger module or zinc finger DNA binding domain to bind to four bases rather than three of the target strand. Such a zinc finger module or zinc finger DNA binding domain binds to a triplet of three bases on one strand of a double-stranded DNA target segment (target strand) and a fourth base on the other, complementary, strand. Binding of a single zinc finger to a four base target segment imposes constraints both on the sequence of the target strand and on the amino acid sequence of the zinc finger. The target site within the target strand should include the "D-able" site motif 5' NNGK 3', in which N and K are conventional IUPAC-IUB ambiguity codes. A zinc finger for binding to such a site should include an arginine residue at position −1 and an aspartic acid, (or less preferably a glutamic acid) at position +2. The arginine residues at position −1 interacts with the G residue in the D-able site. The aspartic acid (or glutamic acid) residue at position +2 of the zinc finger interacts with the opposite strand base complementary to the K base in the D-able site. It is the interaction between aspartic acid (symbol D) and the opposite strand base (fourth base) that confers the name D-able site. As is apparent from the D-able site formula, there are two subtypes of D-able sites: 5' NNGG 3' and 5' NNGT 3'. For the former site, the aspartic acid or glutamic acid at position +2 of a zinc finger interacts with a C in the opposite strand to the D-able site. In the latter site, the aspartic acid or glutamic acid at position +2 of a zinc finger interacts with an A in the opposite strand to the D-able site. In general, NNGG is preferred over NNGT. In the design of a ZFP with three fingers, a target site should be selected in which at least one finger of the protein, and optionally, two or all three fingers have the potential to bind a D-able site. Such can be achieved by selecting a target site from within a larger target gene having the formula 5'-NNx aNy bNzc-3', wherein each of the sets (x,a), (y,b) and (z,c) is either (N,N) or (G,K); at least one of (x,a), (y,b) and (z,c) is (G,K), and N and K are IUPAC-IUB ambiguity codes. In other words, at least one of the three sets (x,a), (y,b) and (z,c) is the set (G,K), meaning that the first position of the set is G and the second position is G or T. Those of the three sets (if any) which are not (G,K) are (N,N), meaning that the first position of the set can be occupied by any nucleotide and the second position of the set can be occupied by any nucleotide. As an example, the set (x,a) can be (G,K) and the sets (y,b) and (z,c) can both be (N,N). In the formula 5'-NNx aNy bNzc-3', the triplets of NNx aNy and bNzc represent the triplets of bases on the target strand bound by the three fingers in a ZFP. If only one of x, y and z is a G, and this G is followed by a K, the target site includes a single D-able subsite.

As used herein, the term "chimeric zinc finger recombinases" or "Rec$_{ZF}$s" includes without limitation recombinases having nucleotide binding domains derived from artificial or naturally-occurring zinc fingers or zinc-finger-like proteins with sequence-specific binding activity. These terms are not limited to recombinases having nucleotide binding domains derived from actual zinc fingers.

As used herein, the term "transcription regulating domain or factor" refers to the portion of the fusion polypeptide provided herein that functions to regulate gene transcription. Exemplary and preferred transcription repressor domains are ERD, KRAB, SID, Deacetylase, and derivatives, multimers and combinations thereof such as KRAB-ERD, SID-ERD, (KRAB)$_2$, (KRAB)$_3$, KRAB-A, (kRAB-A)$_2$, (SID)$_2$, (KRAB-A)-SID and SID-(KRAB-A). As used herein, the term "nucleotide binding domain or region" refers to the portion of a polypeptide or composition provided herein that provides specific nucleic acid binding capability. The nucleotide binding region functions to target a subject polypeptide to specific genes. As used herein, the term "operatively linked" means that elements of a polypeptide, for example, are linked such that each performs or functions as intended. For example, a repressor is attached to the binding domain in such a manner that, when bound to a target nucleotide via that binding domain, the repressor acts to inhibit or prevent transcription. Linkage between and among elements may be direct or indirect, such as via a linker. The elements are not necessarily adjacent. Hence a repressor domain can be linked to a nucleotide binding domain using any linking procedure well known in the art. It may be necessary to include a linker moiety between the two domains. Such a linker moiety is typically a short sequence of amino acid residues that provides spacing between the domains. So long as the linker does not interfere with any of the functions of the binding or repressor domains, any sequence can be used.

As used herein, the term "modulating" envisions the inhibition or suppression of expression from a promoter containing a zinc finger-nucleotide binding motif when it is overactivated, or augmentation or enhancement of expression from such a promoter when it is underactivated.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gin or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (F or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

As used herein, the term "expression vector" refers to a plasmid, virus, phagemid, or other vehicle known in the art that has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in a cell. The expression vector typically contains an origin of replication, a promoter, as well as specific genes that permit phenotypic selection of transformed cells.

As used herein, the term "host cells" refers to cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, genetic therapy involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced:

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease. Typically, DNA encoding a desired gene product is cloned into a plasmid vector and introduced by routine methods, such as calcium-phosphate mediated DNA uptake (see, (1981) Somat. Cell. Mol. Genet. 7:603-616) or microinjection, into producer cells, such as packaging cells. After amplification in producer cells, the vectors that contain the heterologous DNA are introduced into selected target cells.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors".

Also included are vectors that allow cloning of cDNA (complementary DNA) from mRNAs produced using reverse transcriptase.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, the term "isolated" with reference to a nucleic acid molecule or polypeptide or other biomolecule means that the nucleic acid or polypeptide has been separated from the genetic environment from which the polypeptide or nucleic acid were obtained. It may also mean that the biomolecule has been altered from the natural state. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:3140. The terms isolated and purified are sometimes used interchangeably.

Thus, by "isolated" is meant that the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

"Isolated" or "purified" as those terms are used to refer to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. Particularly for proteins, the procedures may include for example, but are not limited to, ammonium sulfate fractionation, gel filtration, ion exchange change chromatography, affinity chromatography, density gradient centrifugation, electrofocusing, chromatofocusing, and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, "modulate" refers to the suppression; enhancement or induction of a function. For example, zinc finger-nucleic acid binding domains and variants thereof may modulate a promoter sequence by binding to a motif within the promoter, thereby enhancing or suppressing transcription of a gene operatively linked to the promoter cellular nucleotide sequence. Alternatively, modulation may include inhibition of transcription of a gene where the zinc finger-nucleotide binding polypeptide variant binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

As used herein, the term "inhibit" refers to the suppression of the level of activation of transcription of a structural gene operably linked to a promoter. For example, for the methods herein the gene includes a zinc finger-nucleotide binding motif.

As used herein, the term "transcriptional regulatory region" refers to a region that drives gene expression in the target cell. Transcriptional regulatory regions suitable for use herein include but are not limited to the human cytomegalovirus (CMV) immediate-early enhancer/promoter, the SV40 early enhancer/promoter, the JC polyoma virus promoter, the albumin promoter, PGK and the α-actin promoter coupled to the CMV enhancer. Other transcriptional regulatory regions are also known in the art.

As used herein, a promoter region of a gene includes the regulatory element or elements that typically lie 5' to a structural gene; multiple regulatory elements can be present, separated by intervening nucleotide sequences. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or, for example, an onco-promoter. An onco-promoter is generally a virus-derived promoter. Viral promoters to which zinc finger binding polypeptides may be targeted include, but are not limited to, retroviral long terminal repeats (LTRs), and Lentivirus promoters, such as promoters from human T-cell lymphotrophic virus (HTLV) 1 and 2 and human immunodeficiency virus (HIV) 1 or 2.

As used herein, the term "truncated" or similar terminology refers to a zinc finger-nucleotide binding polypeptide derivative that contains less than the full number of zinc fingers found in the native zinc finger binding protein or that has been deleted of non-desired sequences. For example, truncation of the zinc finger-nucleotide binding protein TFIIIA, which naturally contains nine zinc fingers, might result in a polypeptide with only zinc fingers one through three. The term "expanded" or similar terminology refers to a zinc finger polypeptide to which additional zinc finger modules have been added. For example, TFIIIA can be expanded to 12 fingers by adding 3 zinc finger domains. In addition, a truncated zinc finger-nucleotide binding polypeptide may include zinc finger modules from more than one wild type polypeptide, thus resulting in a "hybrid" zinc finger-nucleotide binding polypeptide.

As used herein, the term "mutagenized" refers to a zinc finger derived-nucleotide binding polypeptide that has been obtained by performing any of the known methods for accomplishing random or site-directed mutagenesis of the DNA encoding the protein. For instance, in TFIIIA, mutagenesis can be performed to replace nonconserved residues in one or more of the repeats of the consensus sequence. Truncated or expanded zinc finger-nucleotide binding proteins can also be mutagenized.

As used herein, a polypeptide "variant" or "derivative" refers to a polypeptide that is a mutagenized form of a polypeptide or one produced through recombination but that still retains a desired activity, such as the ability to bind to a ligand or a nucleic acid molecule or to modulate transcription.

As used herein, a zinc finger-nucleotide binding polypeptide "variant" or "derivative" refers to a polypeptide that is a mutagenized form of a zinc finger protein or one produced through recombination. A variant may be a hybrid that contains zinc finger domain(s) from one protein linked to zinc finger domain(s) of a second protein, for example. The domains may be wild type or mutagenized. A "variant" or "derivative" can include a truncated form of a wild type zinc finger protein, which contains fewer than the original number of fingers in the wild type protein. Examples of zinc finger-nucleotide binding polypeptides from which a derivative or variant may be produced include TFIIIA and zif268. Similar terms are used to refer to "variant" or "derivative" nuclear hormone receptors and "variant" or "derivative" transcription effector domains.

As used herein a "zinc finger-nucleotide binding target or motif" refers to any two or three-dimensional feature of a nucleotide segment to which a zinc finger-nucleotide binding derivative polypeptide binds with specificity. Included within this definition are nucleotide sequences, generally of five nucleotides or less, as well as the three dimensional aspects of the DNA double helix, such as, but are not limited to, the major and minor grooves and the face of the helix. The motif is typically any sequence of suitable length to which the zinc finger polypeptide can bind. For example, a three finger polypeptide binds to a motif typically having about 9 to about 14 base pairs. Preferably, the recognition sequence is at least about 16 base pairs to ensure specificity within the genome. Therefore, zinc finger-nucleotide binding polypeptides of any specificity are provided. The zinc finger binding motif can be any sequence designed empirically or to which the zinc finger protein binds. The motif may be found in any DNA or RNA sequence, including regulatory sequences, exons, introns, or any non-coding sequence.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier. Vectors include, but are not necessarily limited to, expression vectors.

As used herein with regard to nucleic acid molecules, including DNA fragments, the phrase "operatively linked" means the sequences or segments have been covalently joined, preferably by conventional phosphodiester bonds, into one strand of DNA, whether in single or double-stranded form such that operatively linked portions function as intended. The choice of vector to which transcription unit or a cassette provided herein is operatively linked depends directly, as is well known in the art, on the functional properties desired, e.g., vector replication and protein expression, and the host cell to be transformed, these being limitations inherent in the art of constructing recombinant DNA molecules.

As used herein, administration of a therapeutic composition can be effected by any means, and includes, but is not limited to, oral, subcutaneous, intravenous, intramuscular, intrasternal, infusion techniques, intraperitoneal administration and parenteral administration.

Cognizant of the factors which circumscribe modification of the SSRs mentioned above, we sought to retarget recombination to endogenous sites using a modular library of exogenous DNA binding domains. With high affinity, high specificity binding to over $10^9$ different 18 base pair sequences, polydactyl zinc finger proteins are well suited for this application. From the unique method of DNA recognition afforded by the $Cys_2$-$His_2$ zinc finger motif, our lab has derived modular building blocks that bind tri-nucleotide sequences (23). Having discovered unnatural zinc fingers corresponding to every GNN and ANN triplet (22, 23, 55), along with most CNNs and TNNs, we can now construct polydactyl proteins that preferentially bind 6 to 18 by DNA sites. Chimeric proteins containing these novel DNA binding domains have effectively targeted transcriptional activation and repression (13, 14, 23, 27, 28, 40, 42, 56), DNA cleavage (10, 11, 12, 20, 33, 39, 49, 57, 58), and genetic integration (64). Recently Stark and coworkers fused the natural zinc finger protein Zif268 to a hyperactive Tn3 resolvase catalytic domain (6), thereby constructing the first functional zinc finger—recombinases (3).

Stark's Z-resolvases, along with zinc finger—recombinases ($Rec_{ZF}s$) concurrently assembled in our lab (data not published), drew their inspiration from the modular structure of the Tn3 resolvase. A member of the 'Resolvase/Invertase' family of serine recombinases (59), this protein is composed of spatially separated catalytic and DNA binding domains (as seen in a crystal structure of the highly homologous γδ resolvase bound to DNA (66)). Mechanistic studies (17, 19, 21, 30, 37, 44, 45, 52), structural characterization (46) and functional chimeras (3) have confirmed a 'DNA-outside' model of synapsis in which all synaptic interactions are mediated by the recombinase catalytic domain (FIG. 1). While many details regarding the highly coordinated cleavage events and large-scale complex rearrangement remain unknown, it seems clear that the DNA binding domain plays, at most, a minor role.

We anticipate that sequence-specific recombinases can be important components of a new gene therapy strategy. Our preliminary studies reveal that zinc finger-recombinase fusion proteins efficiently catalyze site-specific resolution, inversion, and integration (FIG. 1). With serine invertase activity already observed in higher eukaryotes (41), $Rec_{ZF}s$ may afford the ability to site-specifically edit the endogenous genomes mammalian cells, in vivo. The small size of these proteins (~700 bp) makes it feasible to consider the delivery of several resolvases with a single vector, thereby directing the excision of DNA between two asymmetric recombination sites. Because $Rec_{ZF}s$ affect a permanent change upon the genome, their presence need only be transient. Accordingly, this approach may avoid the hazards associated with stable integration that currently plague the field of gene therapy. In addition to such therapeutic application, $Rec_{ZF}s$ may also, facilitate the genetic manipulation of model organisms. Although the sophisticated application of homologous recombination has revolutionized modern biology, this technique is often highly inefficient and unsuitable for many species and cell types. These deficiencies suggest the scope of the $Rec_{ZF}$'s potential significance.

Construction and evaluation of a functional zinc finger-Tn3 resolvase chimera. Mutants of several invertase/resolvase serine recombinases have been found which no longer require accessory factors or orthogonal binding sites for their function (6, 29, 34). Minimal recombination sites for these hyperactive variants contain nothing more than an inversely repeated recognition sequence for the DNA binding domain. Once monomers have been anchored at each sequence, every subsequent step—including dimer formation, strand cleavage, exchange, and ligation—is mediated solely by the catalytic domain. This functional division of labor is mirrored in the structural modularity of these two domain proteins. We reasoned that if the endogenous DNA binding domain were replaced with polydactyl zinc finger domains, site-specific recombination sites could be designed for any genetic context.

Figure 2:
FIG. 2 is a depiction of the Rec$_{ZF}$ protein structure and the Rec$_{ZF}$ plasmid resolution between 20T recombinant sites. (A) Rec$_{ZF}$ structure approximated by the alignment of DNA bound γδ resolvase (66) and Zif268 (24). (B) Diagram of Rec$_{ZF}$ plasmid resolution between 20T recombination sites, ResA and ResB; the relative intensities of substrate and product PCR bands indicate the extent of this reaction. Note the change in PCR product size following successful resolution.
Figure 2:
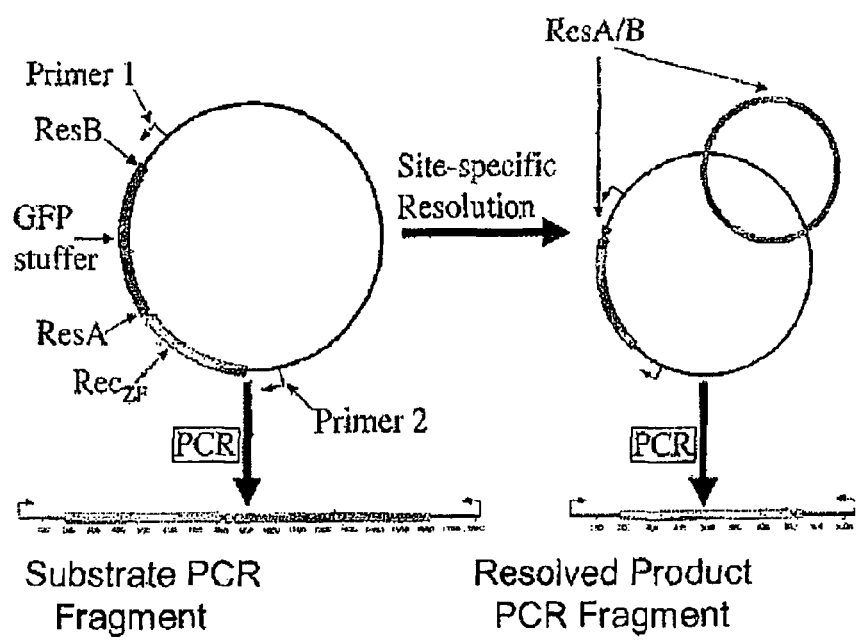

To evaluate the function of zinc finger-recombinase fusion proteins ($Rec_{ZF}s$), a hyperactive catalytic domain from the Tn3 resolvase (D102Y, E124Q) (6) was fused to a bidactyl zinc finger protein, which preferentially binds the sequence GAGGAG, to create $Tn3_{GAGGAG}$. The choice of linker site (145T), length of the linker (6 amino acids), and composition, was informed by computer modeling (FIG. 2A, INSIGHT II) and a review of relevant DNA/protein interactions.[66,51,32] Our model of a Zif268-γδ resolvase chimera ($γδ_{Zif268}$) suggested an optimal distance of 20 base pairs between inverted binding sites. Accordingly, the first $Rec_{ZF}$ recombination site contained GAGGAG in inverse repeat, separated by the central 20 bp of the Tn3 recombination site "20T" ( GAGGAGTGATAATTTATAATATTTCGCTCCTC (SEQ ID NO: 2); zinc finger binding sites are underlined). A substrate plasmid containing two such 32 bp recombination sites flanking a GFPuv (CLONTECH) reporter gene was constructed in *Escherichia coli* (*E. coli*) from pBluescript II SK-(Stratagene)(FIG. 2B). $Tn3_{GAGGAG}$ was ligated behind the lac promoter on this plasmid, and transformed cells were allowed to grow overnight at 37°.

Because its hyperactive catalytic domain functions without regard to regulatory context, we suspected that $Tn3_{GAGGAG}$ might undergo free synapsis, Once bound at a recombination site, each $Rec_{ZF}$ dimer will associate with another dimer to form either an intra- or inter-plasmid synapse. Because this tetrameric synapse is formed by random association, $Rec_{ZF}s$ have the potential to catalyze a variety of recombination events (FIG. 1). Because the central base pairs (AT) are their own reversed complement, the 20T spacer sequence permits recombination between sites in the same or opposite orientation.

Figure 3:
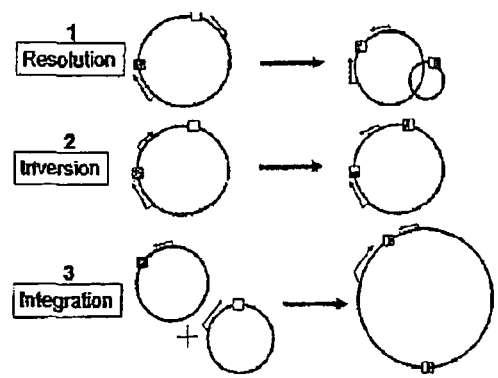
FIG. 3 shows Rec$_{ZF}$ site-specific recombination by free synapsis. (A) Cartoon depiction of three recombination assays; in the presence of product, primers, indicated by arrows, generate a unique PCR band. (B) Site specific recombination by Tn3$_{GAGGAG}$: resolution (1039 bp, 1), inversion (1263 bp, 2), and integration (370 bp, 3). With the exception of 3B, 'B' always represents a substrate free PCR control; 3B is a control for non-specific integration.
Figure 3:
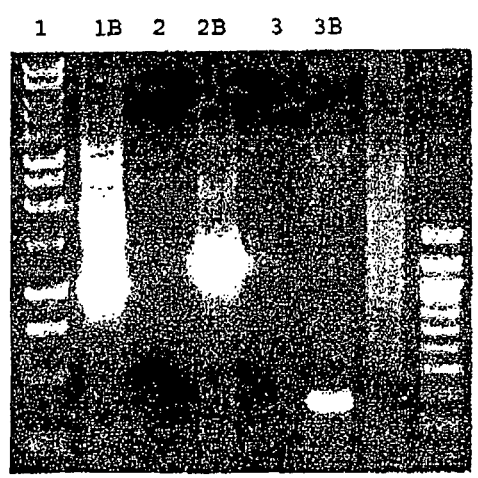

In order to detect recombination events catalyzed by $Tn3_{GAGGAG}$, we developed three PCR assays: resolution, inversion, and integration (FIG. 3A). In each case, product formation correlates with the appearance of a unique band as visualized on an agarose gel. The resolution assay amplifies substrate and product bands (1814 bp and 1039 bp, respectively; FIG. 2B) in relation to their relative abundance. Inversion and integration, however, are each evidenced by the appearance of a single band (1263 bp and 370 bp, respectively). This occurs because only products of these two reactions contain a complementary primer pair. Accordingly, these two assays are highly sensitive, but provide little information about the extent of reaction. While the resolution and inversion systems report on manipulation of the GFPuv region, detection of $Rec_{ZF}$ catalyzed integration reaction requires a second, non-homologous, plasmid. For this purpose, a single recombination site was ligated into pACYC184 (New England Biolabs). The pBluescript II SK-resolution product was cotransformed with the modified pACYC184. These two compatible plasmids were co-maintained under carbenicillin and chloramphenicol selection. Integrative products are detected when primers isolated on either plasmid are able to complement each other. The control for this reaction, shown in lane 3b of FIG. 3, is co-transformation with unmodified pACYC184 (which lacks any potential recombination sites).

Positive results in all three assays confirmed our hypothesis of free synapsis by $Tn3_{GAGGAG}$ (FIG. 3B). The expected site-specific resolution product was isolated and its identity confirmed by DNA sequencing. While integration does not give rise to a stable product, the corresponding PCR band could be purified from an agarose gel. Sequencing of that band revealed the site-specific fusion of two substrate plasmids, linked together by their shared $Rec_{ZF}$ recombination site.

Our initial experiments targeted site-specific recombination to a novel 32 base pair sequence. In principle, almost any sequence could become a $Rec_{ZF}$ substrate. Considering only the published 32 GNN and ANN zinc finger domains, a randomized 100 bp region would contain an average of nine minimal recombination sites (ex. inverted GAGGAG (SEQ ID NO: 1) flanking a 20 bp sequence). In practice, the application of these enzymes might be limited by requisite spacer-protein interactions. The γδ resolvase crystal structure contains multiple interactions between Arginine 142 and an A/T rich minor groove 4-8 bp from the center of the recombination site (66). Mutational studies have shown that both of these elements are required for the proper function of Tn3 resolvase (51) and Hin invertase (32). The significance of such NT rich regions is further evidenced by their presence in many of the sites characterized for this family of recombinases (59).

Figure 12:
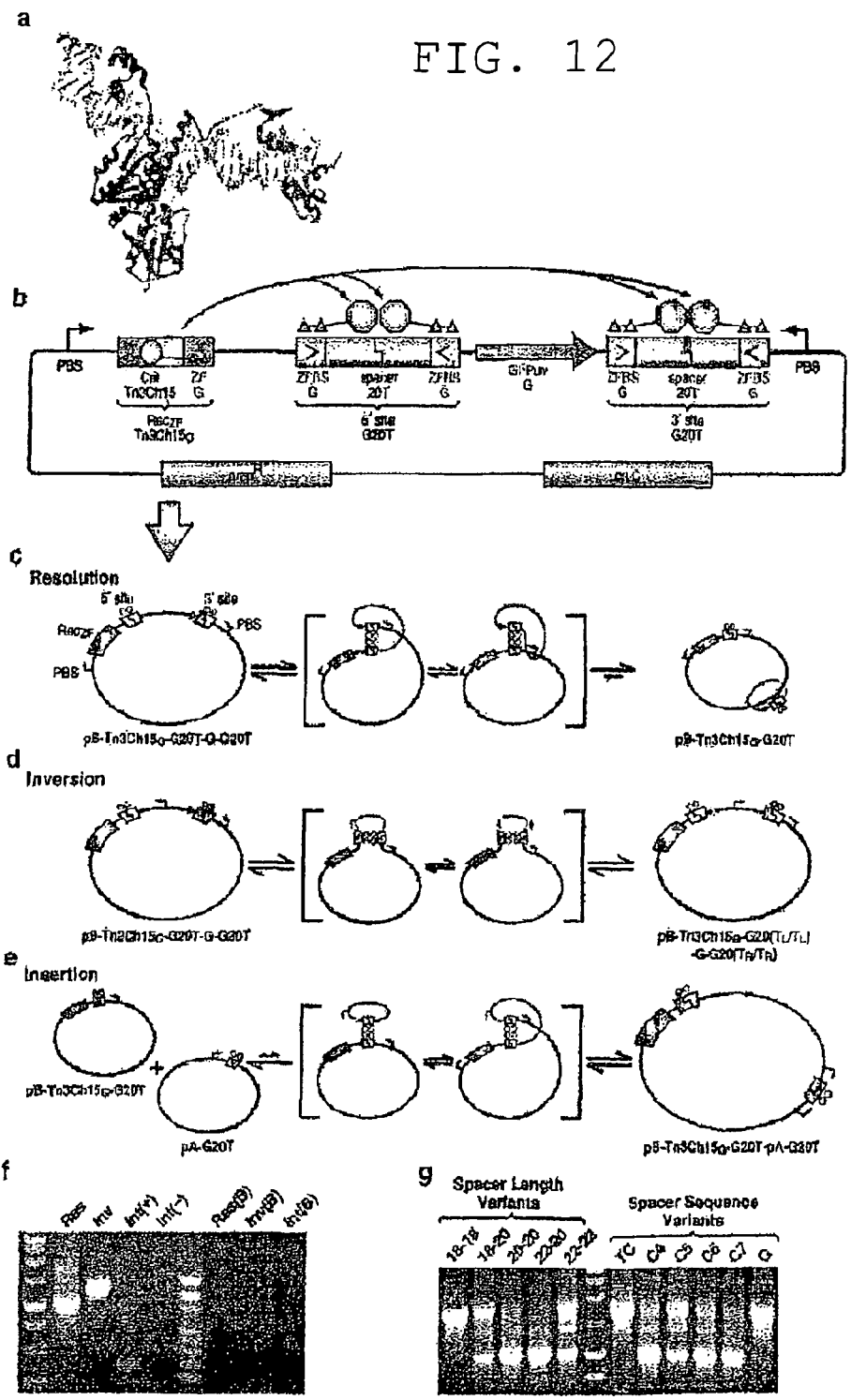
FIG. 12 depicts Rec$_{ZF}$ design and functional assay. (a) A model of a tridactyl Rec$_{ZF}$ chimera dimerized with the gamma delta resolvase. (b). The combined substrate and Rec$_{ZF}$ expression plasmid used in resolution and inversion assays, and directed evolution. (c-e) Pictorial descriptions of PCR assays of site-specific resolutions (c) inversion (d), and integration (e); between 20T recombination sites by Tn3Ch15$_G$. (f) PCR assays of recombination between 20T recombination sites by Tn2Ch15$_G$. Lane 1 contains molecular weight markers at 250, 500, 750, 1000, 4500 2000, 2500, 3000, 4000, 5000, 6000, 8000, and 10,000 bp (Promega 1 kb ladder). Results of resolution assays (Res) are shown in lanes 2 and 7 (Res(B), PCR negative control). Successful resolution increases the intensity of the product band. (1.0 kb) relative to the substrate band (1.8 kb). Results of the inversion assays (Inv) are shown in lanes 3 and 8 (Inv(B), PCR negative control.) Successful integration generates a product band (0.4 kb). Integration reactions were performed in the presence of a second plasmid, which either contained (Int(+), lane 4), or lacked (Int(–), lane 5) a G20T recombination site. Lane 6 contains molecular weight markers at 100, 200, 300, 400, 500, 600 700, 800, 900, 1000, 1200, and 1500 bp (Roche 100 bp ladder). For all assays, the plasmid was introduced by electroporation into E. coli, and culture maintained at 37° C. overnight. PCR was performed with 30 ng plasmid DNA, and analyzed on a 1% agarose gel. PCR negative control reactions were performed without template (lanes 7, 8, and 9). (g) Resolution assays, performed in the same manner, of cassettes, containing 20T spacer derivatives (Table 1): G18T-G-G18T (lane 1, 18-18), G18-T-G20T (lane 2, 18-20) G20T-G-G20-T (lane 3, 20-20), G22T-G-G20T (lane 4, 22-20, G22T-G-G22T (lane 5, 22-22) G20TC-G-G20T (lane 7, TC), G20TC4-G-G20T (lane 8, C4), G20TC5-G-G20T (lane 9, C5); G20TC6-G-G20T (lane 10, C6), G20TC7-G-G20T (lane 11, C7), G20G-G-G20T (lane 12, g). Lane 6 contains the Promega 1 kb ladder. The negative control PCR reaction performed without template is shown in f, lane 7.

To gauge the extent to which $Tn3_{GAGGAG}$ recombination is similarly constrained, we constructed a panel of substrates in which the spacer was altered in either length or sequence (FIG. 12). Resolution assays revealed a strong functional dependence on spacer length; recombination was scarcely detectable between sites with 18 bp spacer regions, most rapid with 20 bp spacer regions (and in a mismatched 22/20 arrangement in which the 5' and 3' sites differ), and intermediate on 22 bp sites. Further details are given in Example 1, below.

Our first spacer sequence variants, by contrast, revealed the $Rec_{ZF}$ to have a surprising degree of functional promiscuity. In contrast to wild type Tn3, $Tn3_{GAGGAG}$ tolerated point mutations throughout the spacer region, including the NT rich groove (FIG. 12; further details in Example 1, below). We hypothesized that the secondary DNA binding interaction may be unnecessary in the presence of a relatively tight binding zinc finger domain. This optimistic perspective was clouded by results with a chimeric substrate (20G-GFP-20T), in which one of the two spacer regions was derived from that of Gin invertase (TCCAAAACCATGGTTTACAG (SEQ ID NO: 632); FIG. 4B, lane 11). Impaired recombination in this context suggests significant spacer sequence dependence—a limitation of the number (and hence frequency) of potential $Tn3_{GAGGAG}$ recombination sites.

Construction and evolution of Hin and Gin zinc finger-recombinases. Confronted with the problem of spacer sequence dependence, we sought to generate additional $Rec_{ZF}$s whose substrate range might complement that of $Tn3_{GAGGAG}$. Rather than select for mutant Tn3 catalytic domains, we opted to draw upon the natural diversity of the resolvase/invertase family of serine recombinases. Beyond ensuring a variety of spacer sequence biases, the use of different catalytic domains enables $Rec_{ZF}$s to perform orthogonal recombination events—either in parallel (ex. simultaneous resolution of different genes) or, more interestingly, in series (ex. cassette exchange).

Hyperactive mutants, functional on a minimal recombination site in the absence of cofactors, had been previously characterized for the invertases of Hin (29) and Gin (34). The closely related Hin and Gin invertases differ significantly in primary structure from the Tn3 resolvase. The presence of many conserved elements, however, enabled sequence alignment of these three proteins and the determination of analogous linker sites for $Hin_{GAGGAG}$ (145N) and $Gin_{GAGGAG}$ (144T) construction. The chimeras produced by this simple fusion did not catalyze a detectable level of resolution. A PCR inversion assay, however, revealed that $Hin_{GAGGAG}$ and $Gin_{GAGGAG}$ both retained some of their native catalytic activity. Including $Tn3_{GAGGAG}$, all three $Rec_{ZF}$s are able to site-specifically invert a $GFP_{UV}$ reporter gene flanked by zinc-finger recombination sites. Because the hyperactive catalytic domains function without regard to regulatory context, the chimeras undergo free synapsis. Once bound at a recombination site, each $Rec_{ZF}$ dimer may associate with another dimer to form either an intra- or inter-plasmid synapse. The strand cleavage enabled by synapsis produces an intermediate complex held together entirely by protein-protein interactions. Since rotation within this intermediate is uncontrolled, $Rec_{ZF}$ enzymes may catalyze every possible recombination event—including resolution, inversion, and integration. Accordingly, our survey of $Hin_{GAGGAG}$ and $Gin_{GAGGAG}$ functionality may have revealed only inversion activity simply because the inversion PCR assay (in which only product is amplified) is significantly more sensitive than the resolution assay (in which both product and substrate are amplified, FIGS. 3A, B).

Figure 13:
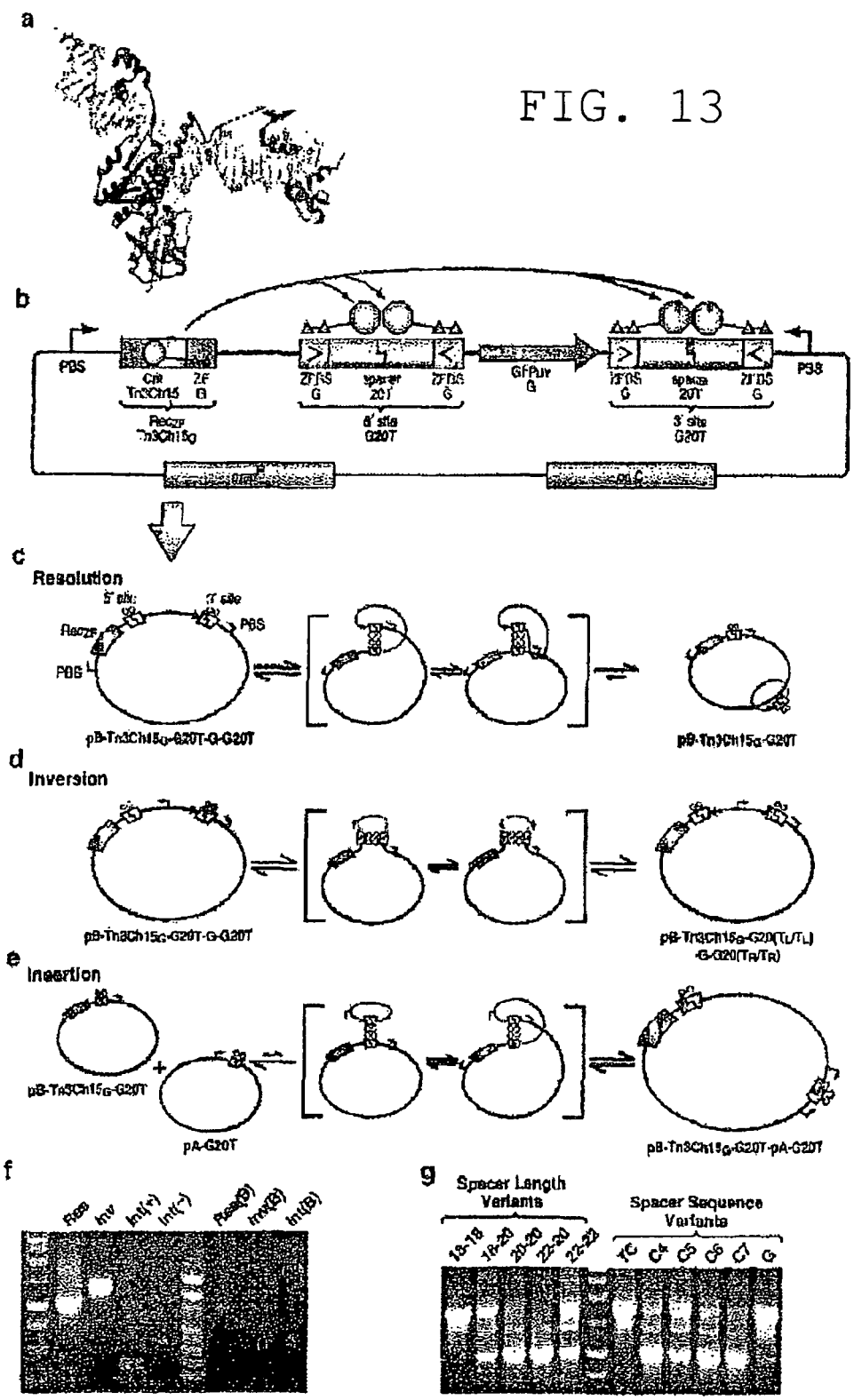
FIG. 13 depicts the directed evolution of Rec$_{ZF}$ G20G-G-G20T resolvase. (a) Substrate Linked Directed Evolution (SLiPE) with a product specific selection primer. Lane 1 contains the Promega 1 kb ladder. Results of selection assays are shown in lanes 2-4. Successful resolution generates a product band (0.8 kb). Lane 2) Product mixture isolated after incubation of pB-GinL7C7$_G$-G20G-G-G20T in E. coli, overnight at 37° C. (Rec$_{ZF}$ (+)); Lane 3) Rec$_{ZF}$ substrate plasmid pBSS-G20G-G-G20T (Rec$_{ZF}$(–)); Lane 4) PCR negative control performed without template (Rec$_{ZF}$(B)). (b) Functional improvement from the starting clones (sc; Tn3Ch15$_G$, Gin$_G$, Hin$_G$) and naïve libraries (1; Tn3L1$_G$, GinL1$_G$, HinL1$_G$), through rounds of interactive selection (2-8), to highly active clones (*; Tn3L8C18$_G$, GinL7C7$_G$, HinL6C4$_G$). Lane 1 contains the Promega 1 kb ladder. The negative control PCR reaction performed without template is shown in f, lane 7. Resolution assays were performed in the manner previously described. (c,d) Mutations selected in greater than and equal to 50% of highly active clones are depicted within a primary sequence alignment (c), and mapped onto the crystal structure of a DNA—bound gamma delta resolvase dimmer (d), Blue, novel Tn3 catalytic domain mutations; green, novel Gin catalytic domain mutations; orange, novel Hin, catalytic domain mutations; pink, hyperactivating mutations present in the original clones; red, the catalytic serine, S10.

From the initial $Hin_{GAGGAG}$ and $Gin_{GAGGAG}$ chimeras we generated highly active resolvases using a strategy of Substrate Linked Protein Evolution (SLiPE). This approach places recombination sites adjacent to each recombinase gene. Accordingly, a gene which encodes a successful recombinase is physically marked by the action of that enzyme. This distinguishing mark allows the gene to be easily retrieved from a large background of unsuccessful candidates by PCR amplification. Having observed $Tn3_{GAGGAG}$ activity on a variety of substrates, our selection relied on recombination between two different spacer sequences (20T and a Gin spacer derivative, 20G, TCCAAAACCATGGTTTACAG (SEQ ID NO: 632)). Excision of the intervening GFP stuffer leaves a single recombination site with a hybrid spacer sequence (20G/T, TCCAAAACCATAATATTTCG (SEQ ID NO: 633). An oligonucleotide complementary to, this novel sequence was used to selectively amplify $Rec_{ZF}$s which catalyzed site-specific resolution (FIG. 13; further details in Example 1, below). Compared to the original SLIPE strategy, developed by Buchholz and Stewart for the Cre recombinase (18), the approach adopted here has three principal advantages: preferential product amplification for reduced background and improved sensitivity, sequence specific selectivity, and, lastly, no possibility of homologous recombination.

Libraries of $Rec_{ZF}$ mutants were created by error-prone PCR by the method of Zaccolo and coworkers (67). Amplification of the hyperactive Hin and Gin catalytic domains in the presence of the dNTP analogues, dPTP (12.5 µM) and 8-oxo-dGTP (12.5 µM), generated templates with randomly placed nucleotide analogous. Subsequent overlap PCR fused each catalytic domain (containing an average of 3.2 amino acid changes) to an error-free zinc finger domain. These Rec$_{ZF}$ libraries were subsequently cloned into the substrate plasmid for the first round of functional selection. After three rounds of selection, the remaining mutants in each pool were recombined using the PCR shuffling method first described by Stemmer (63). Several additional rounds of PCR selection enriched for genes encoding the most active chimeras in each Rec$_{ZF}$ pool (FIG. 13B; further details in Example 1, below). Six clones from each round were assayed individually, and the fastest resolvases were sequenced. Analysis of these clones indicates a selection for a single mutation, equivalent in both Hin and Gin catalytic domains. At a second position, evolved Gin catalytic domains had a mutation that matched the equivalent residue in native Hin. While the functional significance of the mutations remains unclear, the two best clones discovered so far, HinL6C4 and GinL7C7, are potent resolvases (FIG. 13B; further details in Example 1, below). Preliminary work suggests that these two enzymes have spacer distance biases similar to that observed for Tn3$_{GAGGAG}$ (20 bp>22 bp>18 bp, in order of descending activity).

Strategies for Rec$_{ZF}$ mediated stable integration. The Cre-lox system is a powerful and versatile tool for genetic manipulation. Although the Cre recombinase preferentially catalyzes excision between loxP sites, mutant lox sites can be used to promote integrative reactions. For this purpose, two types of recombination sites have been developed: "weak" and orthogonal (4, 5, 9, 15, 25, 26, 35, 61). Analogous sites can be developed for chimeric recombinases according to the present invention without the use of loxP sites or mutants thereof.

Figure 4:
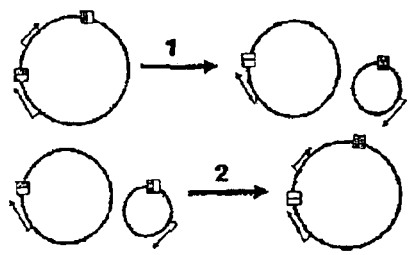
FIG. 4 depicts Tn3$_{GAGGAG}$ recombination of substrates with suboptimal zinc finger binding sites. (A) Cartoon of RE/LE strategy for unidirectional resolution (1) and integration (2). (B) Recombination sites present in each substrate; bold signifies zinc finger-substrate mismatch. (C) Resolution PCR assay of Tn3$_{GAGGAG}$ on hetero-sites (lanes 1-4), and integration assay of Tn3$_{GAGGAG}$ on weak site homodimers (lanes 5-8); resolution products of each hetero-site were co-incubated with another plasmid bearing the optimal recombination site.
Figure 4:
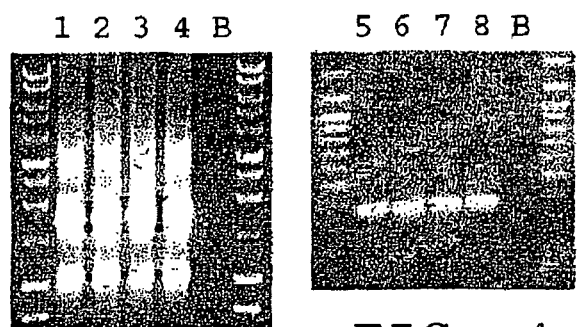

Half-sites which bind Cre at significantly lowered affinity (the LE mutant lox, lox71, and the RE mutant lox, lox66) can be complemented with native half-sites from loxP (4). A similar approach can be used with chimeric recombinases according to the present invention without using loxP sites or sites that bind Cre. While the hetero-sites are functional for recombination, the "weak" site homodimer created by integration is not (FIG. 4A). Rec$_{ZF}$ sites with suboptimal zinc finger-DNA interactions might enable the conditional recombination required for such a right element/left element (LE/RE) strategy. In addition to GAG, the repeated zinc finger in Tn3$_{GAGGAG}$ binds three other tri-nucleotide sequences with significantly lower affinities (GGG>GTG>GCG, in decreasing order of affinity). Three substrates were prepared, wherein GFPuv is flanked by GXGGAG hetero sites (FIG. 4B, 2-4). In each case, Tn3$_{GAGGAG}$ mediated resolution proceeded rapidly (FIG. 4C, lanes 1-4). This result suggests that there will be a significant number of suboptimal sites which remain functional for recombination—a fraction of which may function only in the context of a hetero-site. Unfortunately, these particular weak site homodimers (FIG. 4B, 6-8) demonstrated full functionality, integrating efficiently into a GAGGAG homodimer located on a second plasmid (FIG. 4C, lanes 5-8)).

The second strategy for stable integration involves mutant lox sites which are incompatible with loxP (9, 15, 25, 61). Because such a full site (ex. lox511, lox2272 and lox5171) (36) is functionally orthogonal to the native Cre site, the two may be used in concert for sequential recombination reactions. Again, an analogous strategy, using orthogonal sites, can be used with chimeric recombinases according to the present invention without the use of mutant lox sites or any sites that bind Cre. The orthogonal sites are rendered orthogonal by their interaction with chimeric recombinases of different and non-overlapping specificities. If integration at one site is followed by excision at the other, the result is a cassette exchange (FIG. 5A). This strategy for stable genetic integration may be readily adapted for Rec$_{ZF}$s by replacing orthogonal spacer sequences with orthogonal catalytic domains. Before this approach could be evaluated, however, it was first necessary that we confirm that Rec$_{ZF}$s could be targeted, with high specificity, by different zinc finger binding domains. Two tri-dactyl zinc finger proteins were selected for this task, H1 (whose cognate 9 bp sequence is GGAGGCGTG (SEQ ID NO: 634)) and P2 (GCAGTGGCG (SEQ ID NO: 635)). Substrates analogous to the one used for Hin and Gin evolution (20G-GFP-20T) were constructed with H1 and P2 zinc finger binding sites. PCR fusion of H1 and P2 to GinL7C7 catalytic domain created genes encoding GinL7C7$_{H1}$ and GinL7C7$_{P2}$, respectively. These new Rec$_{ZF}$s were ligated into both substrates such that four pairs arose, two matched and two mismatched. Happily, the Rec$_{ZF}$s were both highly active and highly selective—inversion (FIG. 5B) and resolution (FIG. 5C) were only observed when the zinc finger matched the recombination site. Having assembled all of the requisite actors, the stage is now set for an evaluation of Rec$_{ZF}$ mediated cassette exchange.

Figure 5:
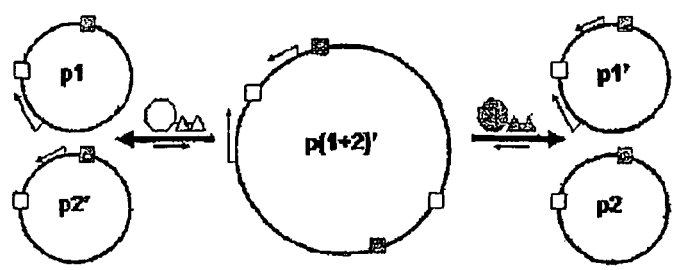
FIG. 5 depicts the cassette exchange strategy. (A). Cartoon of the cassette exchange strategy. Integration can take place at either of the two orthogonal sites, so long as it is directly followed by resolution at the other site; only one of the two possible mechanisms is shown here. Here p1 and p2 are different plasmid backbones, and 'prime' denotes the presence of the cassette of interest. (B) Selective inversion by GinL7C7$_{H1}$(1) and GinL7C7$_{P2}$(2). The top row of numbers corresponds to the substrate's DNA binding site, the bottom row to the expressed Rec$_{ZF}$. (C) Selective resolution by GinL7C7$_{H1}$(1) and GinL7C7$_{P2}$(2).
Figure 5:
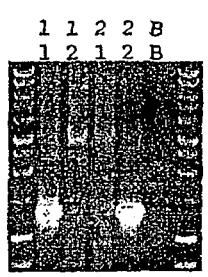
Figure 5:
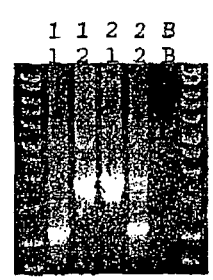

Generation of Highly Active Zinc Finger—Recombinases (Rec$_{ZF}$s) Which Are Functional in a Diversity of Sequence Contexts. The capacity of Rec$_{ZF}$s to perform therapeutic recombination is directly dependent upon the frequency of potential recombination sites within an endogenous genome. This frequency is a function of the number of high specificity DNA binding domains, and of any spacer sequence dependence. We addressed the first of these two restrictions with GinL7C7$_{H1}$ and GinL7L7$_{P2}$ (FIG. 5). The high activity of each Rec$_{ZF}$ (specific to their own substrate) demonstrates the modularity of the catalytic and DNA binding domains. Using only GNN and ANN binding domains, two suitably spaced 9 bp zinc finger binding sites would arise every 64 bp in a random sequence. Unfortunately, this frequency may be compromised by spacer sequence dependence. Preliminary data suggests each catalytic domain possesses a distinct bias. Although Tn3$_{GAGGAG}$ was largely unaffected by point mutations within a single Tn3 derived half-site, its ability to excise GFP$_{UV}$ was significantly impaired by the Gin derived spacer (FIG. 12; further details in Example 1, below). Similarly, GinL7C7 and HinL6C4 have exhibited a bias toward the substrate 20G-GFP-20T, on which they were selected.

The sequence bias we observed may arise at the level of either substrate binding or catalysis. If low affinity is rate limiting, then Rec$_{ZF}$s possessing more (and tighter binding) zinc finger domains will exhibit less spacer sequence dependence. We will move quickly to investigate this simple solution. Our group possesses many well characterized tri-dactyl and hexa-dactyl zinc finger proteins suitable for this work. Rec$_{ZF}$ substrates, prepared with each domain's cognate binding sequence, will be generated for the direct comparison of recombinase activity. If the bias cannot be overcome in this manner, spacers will have to be matched to the known substrate tolerance of a particular catalytic domain.

Figure 6:
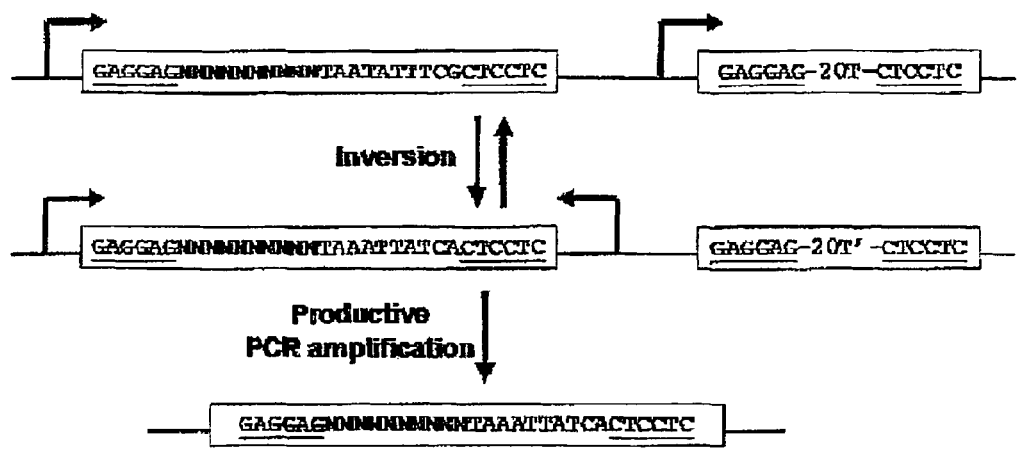
FIG. 6 depicts the PCR strategy for surveying catalytic domain spacer sequence bias. Bent black arrows signify primer binding sites. The spacer sequence 20T' is the symmetrical product of inversion, depicted in FIG. 1.

We will address the challenge of mechanistic spacer sequence dependence by first characterizing the bias inherent in all three existing Rec$_{ZF}$ catalytic domains. For this purpose, libraries of recombination sites will be generated with primers containing randomized nucleotides. Initial surveys of sequence space will assay one fully randomized half-sites in the context of three unaltered half-sites (FIG. 6). After incubation with the Rec$_{ZF}$, products of inversion will be isolated for sequencing. It is anticipated that our initial results will inform the design of subsequent libraries and test substrates. By these means we may efficiently characterize the spacer sequence bias of each catalytic domain.

Knowledge of current limitations will direct our design of new $Rec_{ZF}$ catalytic domains. Catalytic domains for novel spacer sequences will be generated in one of three ways: adaptation of additional serine recombinases, selection of new Hin, Gin, or Tn3 $Rec_{ZF}$ mutants, and rational modification of existing $Rec_{ZF}$s. With five hyperactive catalytic domains already reported, we anticipate that many, if not all, of the more than 30 serine recombinases in the resolvase/invertase family (59) may be suitable for use in $Rec_{ZF}$s. Examination of native substrates reveals a natural diversity which may be tapped to cover a broad range of spacer sequences. Adaptation of structurally homologous catalytic domains would be directly analogous to work with Hin and Gin described above.

Our experience with the two invertases also demonstrates the facility with which recombinases can be trained to function in an unnatural context. With a better understanding of spacer sequence dependence, we will construct SLIPE substrates in order to select for catalytic domains of altered specificity or, preferably, generalists with high activity on a broad range of substrates. Toward this aim, we will initiate another evolution experiment in which $Rec_{ZF}$ libraries are split among six different substrates. Once output from each substrate has been normalized, active recombinases will be pooled for the next round of selection. This evolutionary selection, should favor the selection of recombinases that are indifferent to spacer region sequence but selective for the flanking zinc finger protein sites.

Characterization of an increasing number of $Rec_{ZF}$s should shed light on the particular protein elements which confer spacer sequence dependence. This level of understanding will enable us to rationally modify catalytic domains and generate focused libraries with loci of saturation mutagenesis.

Demonstration of Genomic Resolution with Purified Enzyme and Through Transient Expression in Mammalian Cells. We will purify $Rec_{ZF}$ proteins for the characterization of their in vitro kinetics. Recombinase-zinc finger-maltose binding protein (MBP) fusion proteins will be generated for affinity purification on a maltose column (adapted from the pMal Protein Fusion and Purification System, New England Biolabs). If the large C-terminal MBP domain appears to inhibit recombinase activity (in *E. coli*), a Factor Xa protease site may be used to cleave the bulky tag away from each purified $Rec_{ZF}$. Alternatively, unmodified $Rec_{ZF}$s may be purified by DNA affinity chromatography. Once successful in isolating active $Rec_{ZF}$s, we will pursue crystallographic studies for their structural characterization together with Ian Wilson here at Scripps. Once an efficient purification strategy has been developed, that capacity will enable future studies in which $Rec_{ZF}$s are delivered directly into cells by microinjection. This strategy for genome tailoring might be employed in situations where an expression vector is either unsuitable or unavailable.

Figure 7:
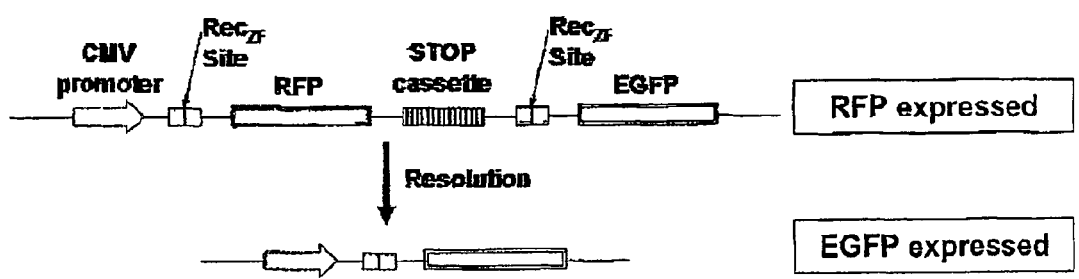
FIG. 7 depicts a system for demonstrating Rec$_{ZF}$ mediated resolution in mammalian cells.

$Rec_{ZF}$ excision from the human genome will be first examined in the context of simplified transgene excision. The reporter gene RFP (Clontech), along with an adjacent STOP cassette (a head-to-tail array of four Simian Virus 40 (SV40) polyA sequences coupled with translational stop codons in all reading frames (43, 60), will be flanked by $Rec_{ZF}$ recombination sites. Each half-site will contain the same zinc finger binding site, such that RFP-STOP can be excised by a $Rec_{ZF}$ homo-tetramer. On one side of this region will be a constitutive promoter (CMV), on the other, the reporter gene EGFP (Clontech). This arrangement should promote only RFP expression before resolution, and only EGFP expression afterwards (FIG. 7). This entire $Rec_{ZF}$-responsive region will be stably integrated into 293 T cells using the retroviral vector pMX (47). Fluorescence-activated cell sorting (FACS) will be used to isolate cells positive for RFP expression. This pool will then be transfected with a $Rec_{ZF}$ expression vector (pcDNA3.1, Invitrogen). Subsequent FACS analysis will quantify ratios of GFP to RFP expression proportional to the extent of genomic excision.

Figure 8:
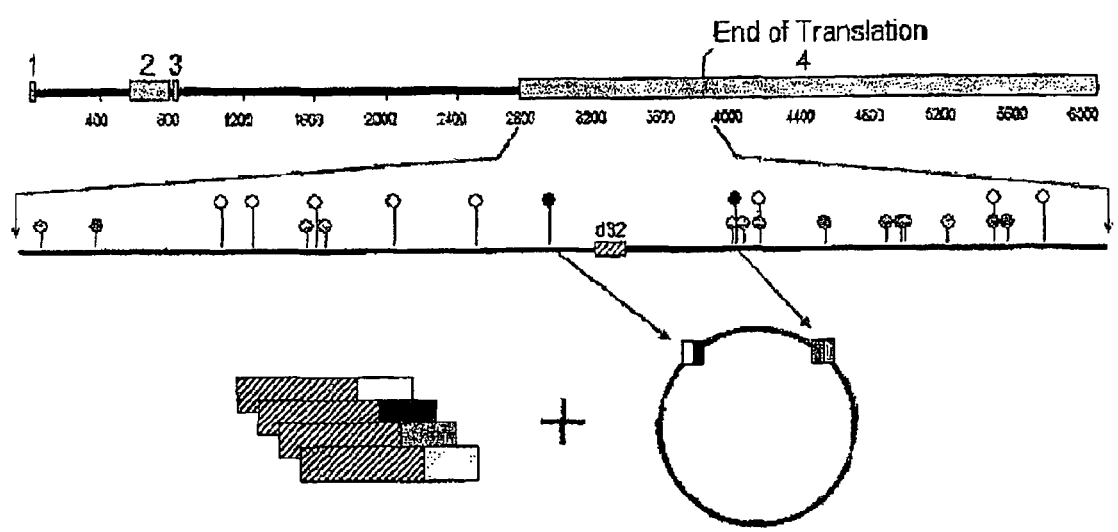
FIG. 8 depicts a strategy for evaluating Rec$_{ZF}$ mediated excision within the endogenous gene CCR5. (A) The genomic region encoding the four exons of CCR5. (B) A map of some of the potential Rec$_{ZF}$ sites present within the fourth exon's translated region. The 'd32' rectangle occupies the genomic region missing in individuals who carry the natural ΔCCR5 variant. By disabling this HIV co-receptor, the ΔCCR5 mutation confers general immunity from X5 HIV infection to homozygous carriers of this allele (38). Raised white circles are 20 bp spacer sites, while lowered grey circles are 22 bp sites. The two darkened circles represent candidates selected for characterization in E. coli. (C) Evaluation of Rec$_{ZF}$ resolution on the selected sites; each of the four selected half-sites will require the assembly, and co-expression, of a different Rec$_{ZF}$ monomer.
Figure 9:
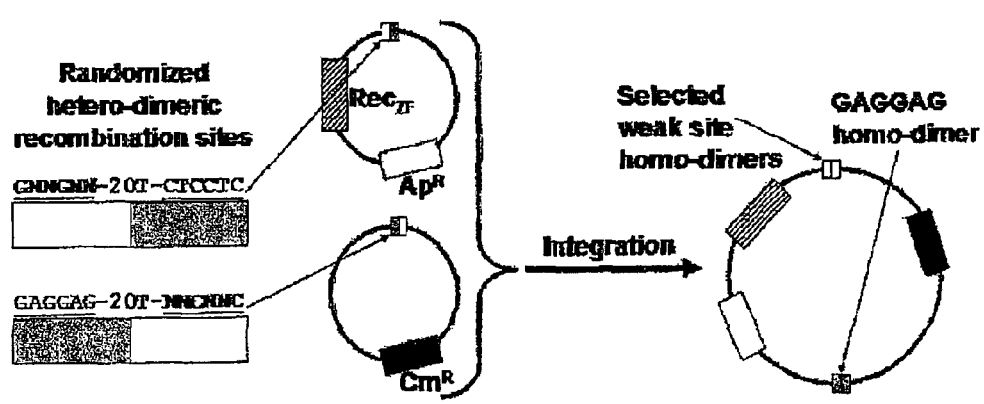
FIG. 9 depicts a strategy to discover trans-activated ("weak") recombination sites for Tn3$_{GAGGAG}$ using randomized DNA binding sites. Following substrate co-incubation in E. coli, sites which promote unidirectional integration will be selected on dual antibiotic media.

If we are able to demonstrate that $Rec_{ZF}$s can mediate genomic recombination, we will proceed to assay their function in an endogenous context. At that time, the contemporaneous limitations on spacer sequence (as discussed above) will determine which gene we select for excision. Recombination sites which meet those constraints will be found using the GCG PATTERNFINDER program (1). Current candidates for gene excision include ICAM-1 and CCR5. Our laboratory has experience in modulating the function of both of these proteins and assays are readily available to assess the success of the approach (8, 42, 62). Once a gene has been selected, a substrate vector containing the relevant genomic region will be prepared for recombination in *Escherichia coli* (FIG. 8). Two additional plasmids will be generated which each express two of the $Rec_{ZF}$ monomers required for heterotetramer synapsis. $Rec_{ZF}$ codon usage will be varied to preclude homologous recombination. All three plasmids will be transformed into *E. coli* and co-maintained under antibiotic selection. Successful resolution events will be detected by PCR assay in the manner previously described. Should this test yield a positive result, we will transiently co-transfect appropriate mammalian cells (which constitutively express the target protein) with expression vectors encoding each of the four $Rec_{ZF}$ monomers. Excision events will be detected by FACS analysis and genomic PCR. Further details on this approach, including experimental results indicating its success, are given in Example 1, below.

Figure 11:
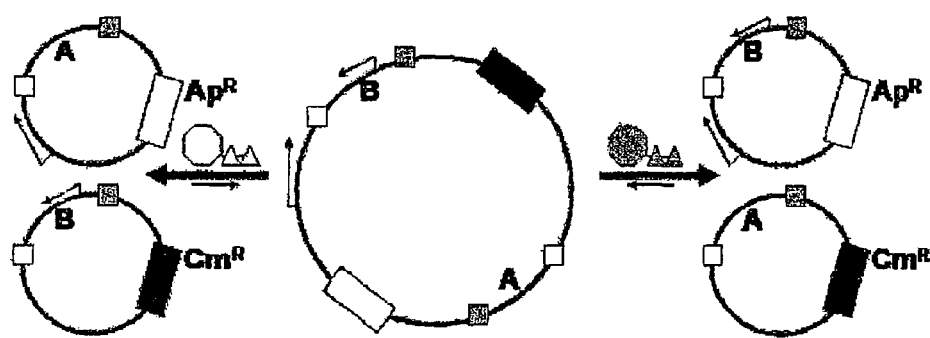
FIG. 11 depicts two mechanisms for stable integrative reactions by sequential recombination at orthogonal sites. (A) Exchange of GFPuv(A) and mCD2(B) cassettes between two compatible plasmids; products of this reaction will be isolated on selective media and identified by the unique combination of two PCR primers. (B) Unidirectional plasmid fusion; the small 2×cassette resolution product (dotted line) will be lost because it does not carry an origin of replication. Plasmids are drawn for clarity but the genes could be encoded on chromosome(s) or linear DNA.
Figure 11:
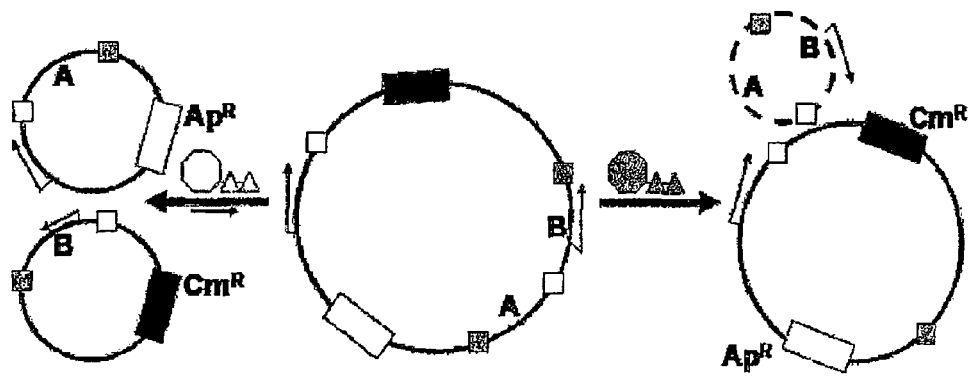

Evaluation of Strategies for Stable, Site-Specific Integration Catalyzed by $Rec_{ZF}$s. We will continue to develop the two strategies for stable integration described above, "weak" site homodimer formation (FIG. 4A) and cassette exchange by orthogonal recombination (FIG. 4A). Having demonstrated that some suboptimal zinc finger binding sites remain competent for recombination, the search for weak sites can proceed along two tracks. In addition to the systematic evaluation of GXGGXG (SEQ ID NO: 636) sequences, we propose a high throughput strategy for rapidly discovering cis activated zinc finger binding sites (FIG. 11). In two compatible plasmids, single half-site libraries ($6.6 \times 10^4$ variants for GNNGNN (SEQ ID NO: 637) site randomization, $1.7 \times 10^7$ for NNNNNN (SEQ ID NO: 638) will be generated with primers containing randomized nucleotides. These two pools will be co-transformed into *E. coli* and co-maintained under carbenicillin and chloramphenicol selection. Plasmid purified from this culture will be retransformed at low concentration and allowed to grow on plates containing both antibiotics. Colonies which grow on this selective media will be screened by PCR for unidirectional integration. If additional stringency is required, another reporter gene will be added, one which is expressed solely by the integration product.

Figure 10:
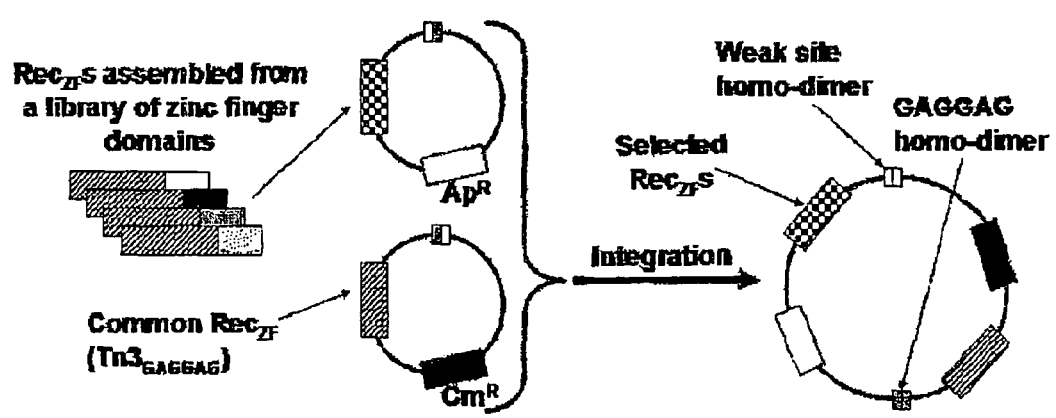
FIG. 10 depicts a strategy to discover trans-activated ("weak") Rec$_{ZF}$s for a particular 6 bp DNA binding sequence using Rec$_{ZF}$s assembled from a library of zinc finger domains.

A library of $Rec_{ZF}$ proteins (>1024 variants) can be assembled from the fusion of a zinc finger domain drawn from a collection of artificial zinc finger domains to a common catalytic domain (13, 40, 42). We may then discover suitably weak binders by challenging this $Rec_{ZF}$ library with a defined DNA binding sequence. While the characterization of GXGGXG (SEQ ID NO: 636) is well suited to establish the existence of suitable weak sites, $Rec_{ZF}$ libraries may be a superior strategy for addressing particular sites within an endogenous genome. To explore this option, we will construct a similar two plasmid selection system. In this case, one plasmid will express the library of recombinases, the other, a single Rec$_{ZF}$. The sites upon which these enzymes will function will be hetero-dimeric—one binding site corresponding to the 6 bp target, and one which is the common Rec$_{ZF}$'s cognate sequence (FIG. 10). Selection and analysis will be performed in the manner previously described.

Once a weak site has been discovered, we will determine the affinity of the zinc finger-DNA interaction. This knowledge may enable us to rapidly pair sequence and Rec$_{ZF}$ for the endogenous application of the weak site strategy.

With selective zinc finger targeting now conclusively demonstrated (GinL7C7$_{H1}$ and GinL7C7$_{P2}$, FIGS. 5, B and C), Rec$_{ZF}$ mediated cassette exchange may be evaluated. This system requires the expression of two Rec$_{ZF}$s, composed of differing catalytic and zinc finger domains. To minimize the potential for homologous recombination, vector sequences will be optimized. Each plasmid will confer a unique antibiotic resistance so as to enable their co-maintenance under carbenicillin and chloramphenicol selection. Two cassettes will be assembled by flanking GFPuv and mCD2 encoding regions with non-repeating homodimer Rec$_{ZF}$ sites; in this arrangement, there should be no possibility for intra-plasmid excision by the two orthogonal Rec$_{ZF}$s. Depending on the placement of the recombination sites, we might be able to promote either inter-plasmid cassette exchange (FIG. 11A), or plasmid fusion accompanied by loss of both cassettes (FIG. 11B). The inversion reactions which would interconvert the two plasmid intermediates, will be prevented by using a directly repeated site whose central base pair, unlike AT, is not its own reversed complement. Finally, integrative products will be identified by antibiotic selection and PCR screening.

The following references are applicable to the specification, except for Example 1, and are incorporated herein by reference; these references are referenced by the reference numbers assigned to them. Additional references are also recited in the specification and also are incorporated herein by reference. References for Example 1 are given below with their own numbers specific to that Example.

1. (1991) Program Manual for the GCG Package. In., 7 Ed., Genetics Computer Group
2. Adams, V., Lucet, I. S., Lyras, D., and Rood, J. I. (2004) *Mol Microbiol* 53(4), 1195-1207
3. Akopian, A., He, J., Boocock, M. R., and Stark, W. M. (2003) *Proc Natl Acad Sci USA* 100(15), 8688-8691
4. Araki, K., Araki, M., and Yamamura, K. (1997) *Nucleic Acids Res* 25(4), 868-872
5. Araki, K., Araki, M., and Yamamura, K. (2002) *Nucleic Acids Res* 30(19), e103
6. Arnold, P. H., Blake, D. G., Grindley, N. D., Boocock, M. R., and Stark, W. M. (1999) *Embo J* 18(5), 1407-1414
7. Baldwin, E. P., Martin, S. S., Abel, J., Gelato, K. A., Kim, H., Schultz, P. G., and Santoro, S. W. (2003) *Chem Biol* 10(11), 1085-1094
8. Beerli, R. R., Dreier, B., and Barbas, C. F., 3rd. (2000) *Proc Natl Acad Sci USA* 97(4), 1495-1500
9. Bethke, B., and Sauer, B. (1997) *Nucleic Acids Res* 25(14), 2828-2834
10. Bibikova, M., Beumer, K., Trautman, J. K., and Carroll, D. (2003) *Science* 300(5620), 764
11. Bibikova, M., Carroll, D., Segal, D. J., Trautman, J. K., Smith, J., Kim, Y. G., and Chandrasegaran, S. (2001) *Mol Cell Biol* 21(1), 289-297
12. Bibikova, M., Golic, M., Golic, K. G., and Carroll, D. (2002) *Genetics* 161(6), 1169-1175
13. Blancafort, P., Magnenat, L., and Barbas, C. F., 3rd. (2003) *Nat Biotechnol* 21(3), 269-274
14. Blancafort, P., Segal, D. J., and Barbas, C. F., 3rd. (2004) *Mol Pharmacol* 66(6), 1361-1371
15. Bouhassira, E. E., Westerman, K., and Leboulch, P. (1997) *Blood* 90(9), 3332-3344
16. Branda, C. S., and Dymecki, S. M. (2004) *Dev Cell* 6(1), 7-28
17. Brown, J. L., He, J., Sherratt, D. J., Stark, W. M., and Boocock, M. R. (2002) *J Mol Biol* 319(2), 371-383
18. Buchholz, F., and Stewart, A. F. (2001) *Nat Biotechnol* 19(11), 1047-1052
19. Burke, M. E., Arnold, P. H., He, J., Wenwieser, S. V., Rowland, S. J., Boocock, M. R., and Stark, W. M. (2004) *Mol Microbiol* 51(4), 937-948
20. Carroll, D. (2004) *Methods Mol Biol* 262, 195-207
21. Dhar, G., Sanders, E. R., and Johnson, R. C. (2004) *Cell* 119(1), 33-45
22. Dreier, B., Beerli, R. R., Segal, D. J., Flippin, J. D., and Barbas, C. F., 3rd. (2001) *J Biol Chem* 276(31), 29466-29478
23. Dreier, B., Segal, D. J., and Barbas, C. F., 3rd. (2000) *J Mol Biol* 303(4), 489-502
24. Elrod-Erickson, M., Rould, M. A., Nekludova, L., and Pabo, C. O. (1996) *Structure* 4(10), 1171-1180
25. Feng, Y. Q., Seibler, J., Alami, R., Eisen, A., Westerman, K. A., Leboulch, P., Fiering, S., and Bouhassira, E. E: (1999) *J Mol Biol* 292(4), 779-785
26. Fukushige, S., and Sauer, B. (1992) *Proc Natl Acad Sci USA* 89(17), 7905-7909
27. Graslund, T., Li, X., Magnenat, L., Popkov, M., and Barbas, C. F., 3rd. (2005) *J Biol Chem* 280(5), 3707-3714
28. Guan, X., Stege, J.; Kim, M., Dahmani, Z., Fan, N., Heifetz, P., Barbas, C. F., 3rd, and Briggs, S. P. (2002) *Proc Natl Acad Sci USA* 99(20), 13296-13301
29. Haykinson, M. J., Johnson, L. M., Soong, J., and Johnson, R. C. (1996) *Curr Biol* 6(2), 163-177
30. He, J., McIlwraith, M. J., Burke, M. E., Boocock, M. R., and Stark, W. M. (2002) *J Mol Biol* 319(2), 385-393
31. Held, P. K., Olivares, E. C., Aguilar, C. P., Finegold, M., Calos, M. P., and Grompe, M. (2005) *Mol Ther* 11(3), 399-408
32. Hughes, K. T., Gaines, P. C., Karlinsey, J. E., Vinayak, R., and Simon, M. I. (1992) *Embo J* 11(7), 2695-2705
33. Kim, Y. G., Cha, J., and Chandrasegaran, S. (1996) *Proc Natl Acad Sci USA* 93(3), 1156-1160
34. Klippel, A., Cloppenborg, K., and Kahmann, R. (1988) *Embo J* 7(12), 3983-3989
35. Kolb, A. F. (200.1) *Anal Biochem* 290(2), 260-271
36. Lee, G., and Saito, I. (1998) Gene 216(1), 55-65
37. Leschziner, A. E., and Grindley, N. D. (2003) *Mol Cell* 12(3), 775-781
38. Liu, R., Paxton, W. A., Choe, S., Ceradini, D., Martin, S. R., Horuk, R., MacDonald, M. E., Stuhlmann, H., Koup, R. A., and Landau, N. R. (1996) *Cell* 86(3), 367-377
39. Lloyd, A., Plaisier, C. L., Carroll, D., and Drews, G. N. (2005) *Proc Natl Acad Sci U S A* 102(6), 2232-2237
40. Lund, C. V., Blancafort, P., Popkov, M., and Barbas, C. F., 3rd. (2004) *J Mol Biol.* 340(3), 599-613
41. Maeser, S., and Kahmann, R. (1991) *Mol Gen Genet* 230(1-2), 170-176
42. Magnenat, L., Blancafort, P., and Barbas, C. F., 3rd. (2004) *J Mol Biol* 341(3), 635-649
43. Maxwell, I. H., Harrison, G. S., Wood, W. M., and Maxwell, F. (1989) *Biotechniques* 7(3), 276-280
44. McIlwraith, M. J., Boocock, M. R., and Stark, W. M. (19.97) *J Mol Biol* 266(1), 108-121
45. Merickel, S. K., and Johnson, R. C. (2004) *Mol Microbiol* 51(4), 1143-1154

46. Nollmann, M., He, J., Byron, O., and Stark, W. M. (2004) *Mol Cell* 16(1), 127-137
47. Onishi, M., Kinoshita, S., Morikawa, Y., Shibuya, A., Phillips, J., Lanier, L. L., Gorman, D. M., Nolan, G. P., Miyajima, A., and Kitamura, T. (1996) *Exp Hematol* 24(2), 324-329
48. Ortiz-Urda, S., Thyagarajan, B., Keene, D. R., Lin, Q., Calos, M. P., and Khavari, P. A. (2003) *Hum Gene Ther* 14(9), 923-928
49. Porteus, M. H., and Baltimore, D. (2003) *Science* 300 (5620), 763
50. Quenneville, S. P., Chapdelaine, P., Rousseau, J., Beaulieu, J., Caron, N. J., Skuk, D., Mills, P., Olivares, E. C., Calos, M. P., and Tremblay, J. P. (2004) *Mol Ther* 10(4), 679-687
51. Rimphanitchayakit, V., and Grindley, N. D. (1990) *Embo J* 9(3), 719-725
52. Sanders, E. R., and Johnson, R. C. (2004) *J Mol Biol* 340(4), 753-766
53. Santoro, S. W., and Schultz, P. G. (2002) *Proc Natl Acad Sci USA* 99(7), 4185-4190
54. Sclimenti, C. R., Thyagarajan, B., and Calos, M. P. (2001) *Nucleic Acids Res* 29(24), 5044-5051
55. Segal, D. J., Dreier, B., Beerli, R. R., and Barbas, C. F., 3rd. (1999) *Proc Natl Acad Sci USA* 96(6), 2758-2763
56. Segal, D. J., Goncalves, J., Eberhardy, S., Swan, C. H., Torbett, B. E., Li, X., and Barbas, C. F., 3rd. (2004) *J Biol Chem* 279(15), 14509-14519
57. Smith, J., Berg, J. M., and Chandrasegaran, S. (1999) *Nucleic Acids Res* 27(2), 674-681
58. Smith, J., Bibikova, M., Whitby, F. G., Reddy, A. R., Chandrasegaran, S., and Carroll, D. (2000) *Nucleic Acids Res* 28(17), 3361-3369
59. Smith, M. C., and Thorpe, H. M. (2002) *Mol Microbiol* 44(2), 299-307
60. Soriano, P. (1999) *Nat Genet* 21(1), 70-71
61. Soukharev, S., Miller, J. L., and Sauer, B. (1999) *Nucleic Acids Res* 27(18), e21
62. Steinberger, P., Andris-Widhopf, J., Buhler, B., Torbett, B. E., and Barbas, C. F., 3rd. (2000) *Proc Natl Aced Sci USA* 97(2), 805-810
63. Stemmer, W. P. (1994) *Nature* 370(6488), 389-391
64. Tan, W., Zhu, K., Segal, D. J., Barbas, C. F., 3rd, and Chow, S. A. (2004) *J Virol* 78(3), 1301-1313
65. Thyagarajan, B., Olivares, E. C., Hollis, R. P., Ginsburg, D. S., and Cabs, M. P. (2001) *Mol Cell Biol* 21(12), 3926-3934
66. Yang, W., and Steitz, T. A. (1995) *Cell* 82(2), 193-207
67. Zaccolo, M., and Gherardi, E. (1999) *J Mol Biol* 285(2), 775-783

The present invention is therefore directed to all chimeras assembled with such catalytic domains for the modification of any double-stranded DNA substrate, in any fashion, including, but not limited to resolution or excision, inversion, integration, translocation, double-strand cleavage, covalent linkage, stimulation of homologous recombination, and transposes targeting, in any context. The context can be in vitro, in any kind of cell, or in any kind of organism).

More particularly, the present invention is directed to all applications of site-specific recombination, i.e., targeted or non-targeted and conservative or non-conservative. Each reaction will be carried out by 1-4 different chimeric recombinases (also referred to herein as "RecZFs") working in concert. Of particular note is the application of endogenous recombination, where sites are "found" in the endogenous genomic sequence for which corresponding RecZFs can be constructed. (This is the opposite of the current paradigm where exogenous sites (ex. lox, FRT) are introduced into a genome to suit pre-existing recombinases (ex. Cre, Flp)). The use of chimeric recombinases therefore provides greater flexibility without the need to introduce exogenous sites for recombination into genomes. This is particularly advantageous where the introduction of such exogenous sites would be deleterious, difficult, or inconvenient.

Accordingly, one aspect of the invention is a chimeric recombinase protein comprising a serine recombinase operatively linked to a zinc finger nucleotide binding domain such that the chimeric recombinase protein catalyzes site-specific recombination at a DNA site specifically bound by the zinc finger nucleotide binding domain and such that the serine recombinase is selected or evolved to catalyze recombination efficiently in the context of the chimeric protein. Typically, the serine recombinase domain is a recombinase domain with a catalytic serine nucleophile that catalyzes a general strand exchange mechanism. Typically, the serine recombinase is selected from the group consisting of Gin, Hin, Tn3, Sin, Beta, Pin. Min, Din, and Cin and muteins of Gin, muteins of Hin, muteins of Sin, muteins of Beta, muteins of Pin, muteins of Min, muteins of Din, muteins of Cin, muteins of Tn3. However, other suitable serine recombinases are described below. Typically, the zinc finger nucleotide binding domain is a bidactyl zinc finger nucleotide binding domain that specifically binds a hexanucleotide. In other alternatives, the zinc finger nucleotide binding domain is a tridactyl zinc finger nucleotide binding domain that binds 9 base pairs, a 4-finger zinc finger nucleotide binding domain that binds 12 base pairs, a 5-finger zinc finger nucleotide binding domain that binds 15 base pairs, or a 6-finger zinc finger nucleotide binding domain that binds 18 base pairs. The greater the number of base pairs bound, the greater is the specificity of the recombinase and the fewer are the number of sites at which it will act. However, as defined above, the terms "zinc finger," "zinc finger nucleotide binding domain," and the like do not require that the amino acid sequence specified thereby originate from an actual zinc finger or necessarily have substantial homology with a naturally-occurring or constructed zinc finger protein. They are used to describe the general nature of the protein domains involved and do not necessarily require the participation of a zinc ion in the protein structure.

Zinc finger nucleotide binding domains that are included in chimeric recombinases according to the present invention comprise two subdomains.

The first of these subdomains is the DNA binding subdomain. As described below, typically this subdomain comprises from about 7 to about 10 amino acids, most commonly 7 or 8 amino acids, and possesses the specific DNA binding capacity described below. The DNA binding subdomain can alternatively be referred to as a domain and is so referred to herein.

The second of these subdomains is the framework subdomain. In one alternative, based on the structure of naturally-occurring zinc finger proteins, the framework subdomain is split into two halves, a first half that is located such that the amino-terminus of the DNA binding subdomain is located at the carboxyl terminus of the first half of the framework subdomain, and the second located such that the carboxyl-terminus of the DNA binding subdomain is located at the amino-terminus of the second half of the framework subdomain.

In this alternative, the framework subdomain can include two cysteine residues and two histidine residues, as is commonly found in wild-type zinc finger proteins. This arrangement is designated herein as $C_2H_2$. In wild-type zinc finger proteins in the $C_2H_2$ arrangement, the two cysteine residues are located to the amino-terminal side of the DNA binding subdomain, and the two histidine residues are located to the carboxyl-terminal side of the DNA binding subdomain. The cysteine and histidine residues bind the zinc ion in the zinc finger protein.

Although wild-type zinc finger proteins generally, but not exclusively have the $C_2H_2$ arrangement, it is possible to interchange the cysteine and histidine residues in the framework subdomain in order to generate framework domains with three cysteine residues and one histidine residue ($C_3H$), with four cysteine residues ($C_4$), which are known for a few naturally-occurring zinc finger proteins. Additionally, mutagenesis has been employed to generate $H_4$ and $CH_3$ arrangements of these framework subdomains. In the $CH_3$ arrangements, any of the four relevant residues can be cysteine; the other three are all histidine. These mutated zinc finger proteins are disclosed in S, Neri et al., "Creation and Characteristics of Unnatural CysHis$_3$-Type Zinc Finger Protein," *Biochem. Biophys. Res. Commun.* 325: 421-425 (2004), incorporated herein by this reference. Similar mutated zinc finger proteins are also disclosed in Y. Hori et al., "The Engineering, Structure, and DNA Binding Properties of a Novel His$_4$-Type Zinc Finger Peptide," *Nucleic Acids Symp.* 44: 295-296 (2000), incorporated herein by this reference.

Additionally, there exist zinc finger proteins with a $C_6$ (six cysteine residues) arrangement, and that arrangement can be incorporated into framework subdomains that form part of zinc finger nucleotide binding domains in chimeric recombinases according to the present invention (Y. Hori et al., "The Engineering, Structure, and DNA Binding Properties of a Novel His$_4$-Type Zinc Finger Peptide," *Nucleic Acids Symp.* 44: 295-296 (2000)).

An additional framework subdomain is that based on the protein avian pancreatic polypeptide (aPP). The small protein aPP has a solvent-exposed α-helical face and a solvent-exposed Type II polyproline helical face. In zinc finger nucleotide binding domains based on aPP, the DNA binding subdomains from zinc finger nucleotide binding domains, as described above, are grafted onto either the solvent-exposed α-helical face or the solvent-exposed Type II polyproline helical face of aPP. Residues can be mutated to provide tighter or more specific DNA binding. This approach is described in L. Yang & A. Schepartz, "Relationship Between Folding and Function in a Sequence-Specific Miniature DNA-Binding Protein," *Biochemistry* 44: 7469-7478 (2005), and in N. J. Zondlo & A. Schepartz, "Highly Specific DNA, Recognition by a Designed Miniature Protein," *J. Am. Chem. Soc.* 121: 6938-6939 (1999), both incorporated herein by this reference. Typically, the residues are grafted onto the solvent-exposed α-helical face of aPP. In this approach, the DNA binding subdomains can be interspersed with α-helical residues.

Serine recombinases suitable for construction of chimeric recombinases according to the present invention include, but are not necessarily limited to, those that function in the general strand exchange mechanism described in N. D. F. Grindley et al., "Mechanisms of Site-Specific Recombination," *Annu. Rev. Biochem.* 75: 567-605 (2006), incorporated herein by this reference.

Examples of 9-base sequences bound by zinc finger nucleotide binding domains incorporated in chimeric recombinases according to the present invention include, but are not limited to, GGAGGGGTG (SEQ ID NO: 3) and GCAGTGGCG (SEQ ID NO: 4).

Specific chimeric recombinases according to the present invention include Tn3$_{GAGGAG}$, which has domains from Tn3 fused through a linker to a bidactyl zinc finger protein that preferentially binds the 6-bp sequence GAGGAG (SEQ ID NO: 1). The chimeric recombinase Tn3$_{GAGGAG}$ is effective in catalyzing recombination at DNA sequences separated by a 20-bp spacer site (GAGGAGTGATAATTTATAATATTTCGCTCCTC) (SEQ ID NO: 2) (zinc finger binding sites are underlined).

Other chimeric recombinases according to the present invention include Hin$_{GAGGAG}$ and Gin$_{GAGGAG}$. These chimeric recombinases have the recombinase Hin and Gin, respectively, fused to a zinc finger nucleotide binding domain that binds the hexanucleotide GAGGAG (SEQ ID NO: 1).

Accordingly, within the scope of the invention are the following chimeric recombinases as described in more detail in Example 1: Tn3Ch15$_G$, GinL7C7$_{H1}$, and GinL7C7$_{P2}$, together with variants thereof in which another recombinase catalytic domain replaces the Tn3 or Gin serine recombinase.

Also, accordingly, within the scope of the invention are chimeric recombinases in which one or more of the following mutations are introduced in the serine recombinase: (1) G70S, D102Y, or E124Q in a Tn3 serine recombinase catalytic domain; (2) H107Y in a Hin serine recombinase catalytic domain; (3) M70V, T96A, or H106Y in a Gin serine recombinase catalytic domain; or (4) I12V, D13G, K65R, way, I80M, V108A, K53E, and K151M in a Tn3 serine recombinase catalytic domain, together with mutations of corresponding homologous residues in Hin and Gin (numbering is that of Tn3 (see FIG. 13). Mutations in proteins are designated herein by the standard notation in which the original residue, the residue number, and the replacement residue are used, so that "I12V" is a mutation in which isoleucine (I) at position 12 is replaced with valine (V). This notation is generally known in the art.

Similarly, within the scope of the invention are chimeric recombinases in which the serine recombinase is a Gin domain that includes the following mutations: D12G, N14S, N20D, K50E, M70V, I94V, Y109H, M114V, and K148M, wherein Y109H is a reversion to wild-type Gin and K148M is a linker mutation. Accordingly, also within the scope of the invention are chimeric recombinases in which the recombinase catalytic domain is a Gin domain that includes the following mutations: D12G, N14S, N20D, K50E, M70V, I94V, and M114V (excluding Y109H and K148M).

Still other chimeric recombinases according to the present invention include chimeric recombinases constructed to reduce spacer sequence dependence. The sequence bias that has been observed may arise at the level of either substrate binding or catalysis. If low affinity is rate limiting, then Rec$_{ZF}$s possessing more (and tighter binding) zinc finger domains will exhibit less spacer sequence dependence. Therefore, spacer sequence dependence or sequence bias can be reduced by constructing chimeric recombinases with a greater number of zinc finger domains or zinc finger domains that bind more tightly to their target nucleotide sequences. In another alternative, spacers can be matched to the known substrate tolerance of a particular catalytic domain by determining the affinity of the catalytic domain for the spacer and modifying the spacer with site-directed mutagenesis techniques to achieve greater affinity. Methods for determining the affinity of nucleic-acid-protein interactions are well known in the art.

Therefore, serine recombinases useful in constructing chimeric recombinases according to the present invention, include, but are not limited to:

(1) Tn3, also known as EcoTn3; Hin, also known as StyHin; Gin, also known as MuGin; Sin; Beta; Pin; Min; Din; Cin; EcoTn21; SfaTn917; BmeTn5083; Bme53; Cpe; SauSK1; SauSK41; SauTn552; Ran; Aac; Lla; pMER05; Mlo92; Mlo90; Rrh; Pje; Req; PpsTn5501; Pae; Xan; ISXc5; Spy; RhizY4cG; SarpNL1; SsoISC1904a; SsoISC1904b;

SsoISC1913; Aam606; MjaM0014; Pab; HpyIS607; MtulS_Y349; MtuRv2792c; MtuRv2979c; MtuRv3828c; MtuRv0921; MceRv0921; TnpX; TndX; WwK; lactococcal phage TP901-1 serine recombinase; *S. pyogenes* phage φ370.1 serine recombinase; *S. pyogenes* phage φFC1 serine recombinase; *Listeria* phage A118 serine recombinase; *S. coelicolor* chromosome SC3C8.24 serine recombinase; *S. coelicolor* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c mine recombinase; *S. coelicolor* chromosome SCC88.14 serine recombinase; *Streptomyces* phage φC31 serine recombinase; *Streptomyces* phage R4 serine recombinase; *Bacillus* phage φ105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculosis* prophage φRV1 serine recombinase; YBCK_ECOLI; Y4bA; Bja; Spn; Cac 1956; and Cac 1954; and (2) muteins of serine recombinases of (a).

For these purposes, the bias inherent in all three existing $Rec_{ZF}$ catalytic domains is characterized by a method comprising the following steps, which is another embodiment of the invention:

(1) generating a plurality of libraries of recombination sites with primers containing randomized nucleotides;

(2) assaying sites containing one fully-randomized half-site with three unaltered half-sites to determine the efficiency of recombination carried out by at least one $Rec_{ZF}$ on these sites; and (3) isolating products of inversion from step (2) for sequencing to characterize sequence bias.

Typically, the method generates a structure-activity profile for sequence bias for each of the $Rec_{ZF}$ sites.

Additionally, other chimeric recombinases according to the present invention include at least one catalytic domain that is one of the following: (1) a catalytic domain that is generated by adaptation of a serine recombinase other than Hin, Gin, or Tn3; (2) a catalytic domain that is generated by the selection of a new Hin, Gin, or Tn3 $Rec_{ZF}$ mutant; or (3) a catalytic domain that is generated by rational modification of an existing $Rec_{ZF}$. Methods for rational modification of protein structures are well known in the art and are described, for example, in J. L. Cleland & C. S. Craik, eds., "Protein Engineering: Principles and Practice" (Wiley-Liss, New York, 1996). Specifically, such methods include, but are not limited to: the identification of functionally important residues in the catalytic domains, by molecular modeling, NMR spectroscopy, X-ray crystallography, or other methods; the mutation of residues identified from structural information, by methods such as, but not limited to, random mutagenesis, deletion analysis, or linker scanning mutagenesis; the use of protein homology, such as between catalytic domains of recombinases, to identify functional residues, such as highly conserved residues or residues identified by biochemical methods such as chemical crosslinking, affinity labeling, or protection from chemical modification; or charged-to-alanine scanning mutagenesis. The rational design can also include mutations intended to maximize binding affinity and/or specificity on a residue-by-residue basis, taking into account transient covalent interactions between amino acid residues and nucleic acid substrates, as well as noncovalent interactions such as hydrogen bonds, hydrophobic interactions, salt links, and van der Waals interactions.

With five hyperactive catalytic domains already reported, it is anticipated that many, if not all, of the more than 30 serine recombinases in the resolvase/invertase family are suitable for use in $Rec_{ZF}$s. Any recombinase, invertase or integrase that operates through the use of a covalent serine intermediate is suitable for this approach. These are of varied origins, including bacterial, fungal, and from bacteriophage. These are described in M. C. M. Smith & H. M. Thorpe, "Diversity in the Serine Recombinases," *Mol. Microbiol.* 44: 299-307 (2002), incorporated by this reference. Muteins of these serine recombinases having specific serine recombinase activity can also be used in chimeric recombinases according to the present invention. Examination of native substrates reveals a natural diversity which may be tapped to cover a broad range of spacer sequences. Adaptation of structurally homologous catalytic domains would be directly analogous to work with Hin and Gin described above.

Additional chimeric recombinases that are within the scope of the invention are those that are generated by the use of substrate-linked protein evolution (SLiPE) as described below. SLiPE can be used to select for catalytic domains of altered specificity or, preferably, generalists with high activity on a broad range of substrates. These catalytic domains can then be incorporated into chimeric recombinases according to the present invention The zinc finger nucleotide binding domain can bind any selected sequence of nucleotides; as described above. In one alternative, the zinc finger nucleotide binding domain binds a hexanucleotide, such as GAGGAG (SEQ ID NO: 1); this would typically be a bidactyl zinc finger nucleotide binding domain. In another alternative, the zinc finger nucleotide binding domain binds a 9-bp sequence such as GGAGGGGTG (SEQ ID NO: 3) or GCAGTGGCG (SEQ ID NO: 4); this would typically be a tridactyl zinc finger nucleotide binding domain. In other alternatives, the zinc finger nucleotide binding domain is a 4-finger zinc finger nucleotide binding domain that binds 12 base pairs; a 5-finger zinc finger nucleotide binding domain that binds 15 base pairs; or a 6-finger zinc finger nucleotide binding domain that binds 18 base pairs.

Appropriate zinc finger nucleotide binding domains can be built up from individual domains binding trinucleotide sequences of the form ANN, CNN, GNN, or TNN. Zinc finger nucleotide binding domains binding trinucleotide sequences of the form ANN are disclosed in U.S. Patent Application Publication No. 2002/0165356 by Barbas et al., published Nov. 7, 2002, entitled "Zinc Finger Binding Domains for Nucleotide Sequence ANN," and incorporated herein by this reference. Zinc finger nucleotide binding domains binding trinucleotide sequences of the form CNN are disclosed in U.S. Patent Application Publication No. 2004/0224385 by Barbas, published Nov. 11, 2004, entitled "Zinc Finger Binding Domains for CNN, and incorporated herein by this reference. Zinc finger nucleotide binding domains binding trinucleotide sequences of the form GNN are disclosed in U.S. Pat. No. 6,610,512 to Barbas, issued Aug. 26, 2003, entitled "Zinc Finger Binding Domains for GNN," and incorporated herein by this reference. Zinc finger nucleotide binding domains binding trinucleotide sequences of the form TNN are disclosed in U.S. patent application Ser. No. 11/564,141 by Barbas et al., filed Nov. 28, 2006, entitled "Zinc Finger Binding Domains for TNN," and incorporated herein by this reference. Additionally, zinc finger nucleotide binding domains binding trinucleotide sequences of the form AGC are disclosed in U.S. patent application Ser. No. 11/613,075 by Barbas et al., filed Dec. 19, 2006, entitled "Zinc Finger Domains Specifically Binding AGC," and incorporated herein by this reference.

In general, individual zinc finger nucleotide domains binding trinucleotide sequences of the form ANN, CNN, GNN, or TNN, from which the zinc finger nucleotide binding domains that are incorporated into chimeric recombinase proteins according to the present invention are built up, are a nucleotide binding domain of from 5 to 10 amino acid residues and, preferably about 7 amino acid residues. Typically, the nucleotide binding domain is a sequence of seven amino acids, referred to herein as a "triplet-binding domain," that is predominantly α-helical in its conformation. The structure of this triplet-binding domain is described below in further detail. However, the nucleotide binding region can be flanked by up to five amino acids on each side and the term "triplet binding domain," as used herein, includes these additional amino acids.

Preferred binding domains for ANN include: STNTKLHA (SEQ ID NO: 5); SSDRTLRR (SEQ ID NO: 6); STKERLKT (SEQ ID NO: 7); SQRANLRA (SEQ ID NO: 8); SSPADLTR (SEQ ID NO: 9); SSHSDLVR (SEQ ID NO: 10); SNGGELIR (SEQ ID NO: 11); SNQLILLK (SEQ ID NO: 12); SSRMDLKR (SEQ ID NO: 13); SRSDHLTN (SEQ ID NO: 14); SQLAHLRA (SEQ ID NO: 15); SQASSLKA (SEQ ID NO: 16); SQKSSLIA (SEQ ID NO: 17); SRKDNLKN (SEQ ID NO: 18); SDSGNLRV (SEQ ID NO: 19); SDRRNLRR (SEQ ID NO: 20); SDKKDLSR (SEQ ID NO: 21); SDASHLHT (SEQ ID NO: 22); STNSGLKN (SEQ ID NO: 23); STRMSLST (SEQ ID NO: 24); SNHDALRA (SEQ ID NO: 25); SRRSACRR (SEQ ID NO: 26); SRRSSCRK (SEQ ID NO: 27); SRSDTLSN (SEQ ID NO: 28); SRMGNLIR (SEQ ID NO: 29); SRSDTLRD (SEQ ID NO:30); SRAHDLVR (SEQ ID NO: 31); SRSDHLAE (SEQ ID NO: 32); SRRDALNV (SEQ ID NO: 33); STTGNLTV (SEQ ID NO: 34); STSGNLLV (SEQ ID NO: 35); STLTILKN (SEQ ID NO: 36); SRMSTLRH (SEQ ID NO: 37); STRSDLLR (SEQ ID NO: 38); STKTDLKR (SEQ ID NO: 39); STHIDLIR (SEQ ID NO: 40); SHRSTLLN (SEQ ID NO: 41); STSHGLTT (SEQ ID NO: 42); SHKNALQN (SEQ ID NO: 43); QRANLRA (SEQ ID NO: 44); DSGNLRV (SEQ ID NO: 45); RSDTLSN (SEQ ID NO: 46); TTGNLTV (SEQ ID NO: 47); SPADLTR (SEQ ID NO: 48); DKKDLTR (SEQ ID NO: 49); RTDTLRD (SEQ ID NO: 50); THLDLIR (SEQ ID NO: 51); QLAHLRA (SEQ ID NO: 52); RSDHLAE (SEQ ID NO: 53); HRTTLLN (SEQ ID NO: 54); QKSSLIA (SEQ ID NO: 55); RRDALNV (SEQ ID NO: 56); HKNALQN (SEQ ID NO: 57); RSDNLSN (SEQ ID NO: 58); RKDNLKN (SEQ ID NO: 59); TSGNLLV (SEQ ID NO: 60); RSDHLTN (SEQ ID NO: 61); HRTTLTN (SEQ ID NO: 62); SHSDLVR (SEQ ID NO: 63); NGGELIR (SEQ ID NO: 64); STKDLKR (SEQ ID NO: 65); RRDELNV (SEQ ID NO: 66); QASSLKA (SEQ ID NO: 67); TSHGLTT (SEQ ID NO: 68); QSSHLVR (SEQ ID NO: 69); QSSNLVR (SEQ ID NO: 70); DPGALRV (SEQ ID NO: 71); RSDNLVR (SEQ ID NO: 72); QSGDLRR (SEQ ID NO: 73); and DCRDLAR (SEQ ID NO: 74).

Particularly preferred binding domains for ANN include: SEQ ID NOs: 44-53.

Preferred additional domains for AGC include: DPGALIN (SEQ ID NO: 75); ERSHLRE (SEQ ID NO: 76); DPGHLTE (SEQ ID NO: 77); EPGALIN (SEQ ID NO: 78); DRSHLRE (SEQ ID NO: 79); EPGHLTE (SEQ ID NO: 80); ERSLLRE (SEQ ID NO: 81); DRSKLRE (SEQ ID NO: 82); DPGKLTE (SEQ ID NO: 83); EPGKLTE (SEQ ID NO: 84); DPGWLIN (SEQ ID NO: 85); DPGTLIN (SEQ ID NO: 86); DPGHLIN (SEQ ID NO: 87); ERSWLIN (SEQ ID NO: 88); ERSTLIN (SEQ ID NO: 89); DPGWLTE (SEQ ID NO: 90); DPGTLTE (SEQ ID NO: 91); EPGWLIN (SEQ ID NO: 92); EPGTLIN (SEQ ID NO: 93); EPGHLIN (SEQ ID NO: 94); DRSWLRE (SEQ ID NO: 95); DRSTLRE (SEQ ID NO: 96); EPGWLTE (SEQ ID NO: 97); EPGTLTE (SEQ ID NO: 98); ERSWLRE (SEQ ID NO: 99); ERSTLRE (SEQ ID NO: 100); DPGALRE (SEQ ID NO: 101); DPGALTE (SEQ ID NO: 102); ERSHLIN (SEQ ID NO: 103); ERSHLTE (SEQ ID NO: 104; DPGHLIN (SEQ ID NO: 105); DPGHLRE (SEQ ID NO: 106); EPGALRE (SEQ ID NO: 107); EPGALTE (SEQ ID NO: 108); DRSHLIN (SEQ ID NO: 109); DRSHLTE (SEQ ID NO: 110); EPGHLRE (SEQ ID NO: 111); ERSKLIN (SEQ ID NO: 112); ERSKLTE (SEQ ID NO: 113); DRSKLIN (SEQ ID NO: 114); DRSKLTE (SEQ ID NO: 115); DPGKLIN (SEQ ID NO: 116); DPGKLRE (SEQ ID NO: 117); EPGKLIN (SEQ ID NO: 118); EPGKLRE (SEQ ID NO: 119); DPGWLRE (SEQ ID NO: 120); DPGTLRE (SEQ ID NO: 121); DPGHLRE (SEQ ID NO: 122); DPGHLTE (SEQ ID NO: 123); ERSWLTE (SEQ ID NO: 124); ERSTLTE (SEQ ID NO: 125); EPGWLRE (SEQ ID NO: 126); EPGTLRE (SEQ ID NO: 127); DRSWLIN (SEQ ID NO: 128); DRSWLTE (SEQ ID NO: 129); DRSTLIN (SEQ ID NO: 130); and DRSTLTE (SEQ ID NO: 131).

Particularly preferred binding domains for AGC include SEQ NOs: 75-84.

Preferred binding domains for CNN include: QRHNLTE (SEQ ID NO: 132); QSGNLTE (SEQ ID NO: 133); NLQHLGE (SEQ ID NO: 134); RADNLTE (SEQ ID NO: 135); RADNLAI (SEQ ID NO: 136); NTTHLEH (SEQ ID NO: 137); SKKHLAE (SEQ ID NO: 138); RNDTLTE (SEQ. ID NO: 139); RNDTLQA (SEQ ID NO: 140); QSGNLTE (SEQ ID NO: 141); QLAHLKE (SEQ ID NO: 142); QRAHLTE (SEQ ID NO: 143); HTGHLLE (SEQ ID NO: 144); RSDHLTE (SEQ ID NO: 145); RSDKLTE (SEQ ID NO: 146); RSDHLTD (SEQ ID NO: 147); RSDHLTN (SEQ ID NO: 148); SRRTCRA (SEQ ID NO: 149); QLRHLRE (SEQ ID NO: 150); QRHSLTE (SEQ ID NO: 151); QLAHLKR (SEQ ID NO: 152); NLQHLGE (SEQ ID NO: 153); RNDALTE (SEQ ID NO: 154); TKQTLTE (SEQ ID NO: 155); and QSGDLTE (SEQ ID NO: 156).

Preferred binding domains for GNN include: QSSNLVR (SEQ ID NO: 157); DPGNLVR (SEQ ID NO: 158); RSDNLVR (SEQ ID NO: 159); TSGNLVR (SEQ ID NO: 160); QSGDLRR (SEQ ID NO: 161); DCRDLAR (SEQ ID NO: 162); RSDDLVK (SEQ ID NO: 163); TSGELVR (SEQ ID NO: 164); QRAHLER (SEQ ID NO: 165); DPGHLVR (SEQ ID NO: 166); RSDKLVR (SEQ ID NO: 167); TSGHLVR (SEQ ID NO: 168); QSSSLVR (SEQ ID NO: 169); DPGALVR (SEQ ID NO: 170); RSDELVR (SEQ ID NO: 171); TSGSLVR (SEQ ID NO: 172); QRSNLVR (SEQ ID NO: 173); QSGNLVR (SEQ ID NO: 174); QPGNLVR (SEQ ID NO: 175); DPGNLKR (SEQ ID NO: 176); RSDNLRR (SEQ ID NO: 177); KSANLVR (SEQ ID NO: 178); RSDNLVK (SEQ ID NO: 179); KSAQLVR (SEQ ID NO: 180); QSSTLVR (SEQ ID NO: 181); QSGTLRR (SEQ ID NO: 182); QPGDLVR (SEQ ID NO: 183); QGPDLVR (SEQ ID NO: 184); QAGTLMR (SEQ ID NO: 185); QPGTLVR (SEQ ID NO: 186); QGPELVR (SEQ ID NO: 187); GCRELSR (SEQ ID NO: 188); DPSTLKR (SEQ ID NO: 189); DPSDLKR (SEQ ID NO: 190); DSGDLVR (SEQ ID NO: 191); DSGELVR (SEQ ID NO: 192); DSGELKR (SEQ ID NO: 193); RLDTLGR (SEQ ID NO: 194); RPGDLVR (SEQ ID NO: 195); RSDTLVR (SEQ ID NO: 196); KSADLKR (SEQ ID NO: 197); RSDDLVR (SEQ ID NO: 198); RSDTLVK (SEQ ID NO: 199); KSAELKR (SEQ ID NO: 200); KSAELVR (SEQ ID NO: 201); RGPELVR (SEQ ID NO: 202); KPGELVR (SEQ ID NO: 203); SSQTLTR (SEQ ID NO: 204); TPGELVR (SEQ ID NO: 205); TSGDLVR (SEQ ID NO: 206); SSQTLVR (SEQ ID NO: 207); TSQTLTR (SEQ ID NO: 208); TSGELKR (SEQ ID NO: 209); QSSDLVR (SEQ ID NO: 210); SSGTLVR (SEQ ID NO: 211); TPGTLVR (SEQ ID NO: 212); TSQDLKR (SEQ ID NO: 213); TSGTLVR (SEQ ID NO: 214); QSSHLVR (SEQ ID NO: 215); QSGHLVR (SEQ ID NO: 216); QPGHLVR (SEQ ID NO: 217); ERSKLAR (SEQ ID NO: 218); DPGHLAR (SEQ ID NO: 219); QRAKLER (SEQ ID NO: 220); QSSKLVR (SEQ ID NO: 221); DRSKLAR (SEQ ID NO: 222); DPGKLAR (SEQ ID NO: 223); RSKDLTR (SEQ ID NO: 224); RSDHLTR (SEQ ID NO: 225); KSAKLER (SEQ ID NO: 226); TADHLSR (SEQ ID NO: 227); TADKLSR (SEQ ID NO: 228); TPGHLVR (SEQ ID NO: 229); TSSHLVR (SEQ ID NO: 230); TSGKLVR (SEQ ID NO: 231); QPGELVR (SEQ ID NO: 232); QSGELVR (SEQ ID NO: 233); QSGELRR (SEQ ID NO: 234); DPGSLVR (SEQ ID NO: 235); RKDSLVR (SEQ ID NO: 236); RSDVLVR (SEQ ID NO: 237); RHDSLLR (SEQ ID NO: 238); RSDALVR (SEQ ID NO: 239); RSSSLVR (SEQ ID NO: 240); RSSHVR (SEQ ID NO: 241); RSDELVK (SEQ ID NO: 242); RSDALVK (SEQ ID NO: 243); RSDVLVK (SEQ ID NO: 244); RSSALVR (SEQ ID NO: 245); RKDSLVK (SEQ ID NO: 246); RSASLVR (SEQ ID NO: 247); RSDSLVR (SEQ ID NO: 248); RIHSLVR (SEQ ID NO: 249); RPGSLVR (SEQ ID NO: 250); RGPSLVR (SEQ ID NO: 251); RPGALVR (SEQ ID NO: 252); KSASKVR (SEQ ID NO: 253); KSAALVR (SEQ ID NO: 254); KSAVLVR (SEQ ID NO: 255); TSGSLTR (SEQ ID NO: 256); TSQSLVR (SEQ ID NO: 257); TSSSLVR (SEQ ID NO: 258); TPGSLVR (SEQ ID NO: 259); TSGALVR (SEQ ID NO: 260); TPGALVR (SEQ ID NO: 261); TGGSLVR (SEQ ID NO: 262); TSGELVR (SEQ ID NO: 263); TSGELTR (SEQ ID NO: 264); TSSALVK (SEQ ID NO: 265); and TSSALVR (SEQ ID NO: 266).

Particularly preferred binding domains for GNN include SEQ ID NOs: 157-172.

Preferred binding domains for TNN include: QASNLIS (SEQ ID NO: 267); SRGNLKS (SEQ ID NO: 268); RLDNLQT (SEQ ID NO: 269); ARGNLRT (SEQ ID NO: 270); RKDALRG (SEQ ID NO: 271); REDNLHT (SEQ ID NO: 272); ARGNLKS (SEQ ID NO: 273); RSDNLTT (SEQ ID NO: 274); VRGNLKS (SEQ ID NO: 275); VRGNLRT (SEQ ID NO: 276); RLRALDR (SEQ ID NO: 277); DMGALEA (SEQ ID NO: 278); EKDALRG (SEQ ID NO: 279); RSDHLTT (SEQ ID NO: 280); AQQLLMW (SEQ ID NO: 281); RSDERKR (SEQ ID NO: 282); DYQSLRQ (SEQ ID NO: 283); CFSRLVR (SEQ ID NO: 284); GDGGLWE (SEQ ID NO: 285); LQRPLRG (SEQ ID NO: 286); QGLACAA (SEQ ID NO: 287); WVGWLGS (SEQ ID NO: 288); RLRDIQF (SEQ ID NO: 289); GRSQLSC (SEQ. ID NO: 290); GWQRLLT (SEQ ID NO: 291); SGRPLAS (SEQ ID NO: 292); APRLLGP (SEQ ID NO: 293); APKALGW (SEQ ID NO: 294); SVHELQG (SEQ ID NO: 295); AQAALSW (SEQ ID NO: 296); GANALRR (SEQ ID NO: 297); QSLLLGA (SEQ ID NO: 298); HRGTLGG (SEQ ID NO: 299); QVGLLAR (SEQ ID NO: 300); GARGLRG (SEQ ID NO: 301); DKHMLDT (SEQ ID NO: 302); DLGGLRQ (SEQ ID NO: 303); QCYRLER (SEQ ID NO: 304); AEAELQR (SEQ ID NO: 305); QGGVLAA (SEQ ID NO: 306); QGRCLVT (SEQ ID NO: 307); HPEALDN (SEQ ID NO: 308); GRGALQA (SEQ ID NO: 309); LASRLQQ (SEQ ID NO: 310); REDNLIS (SEQ ID NO: 311); DASNLIS (SEQ ID NO: 312); EASNLIS (SEQ ID NO: 313); RASNLIS (SEQ ID NO: 314); TASNLIS (SEQ ID NO: 315); SASNLIS (SEQ ID NO: 316); QASTLIS (SEQ ID NO: 317); QASDLIS (SEQ ID NO: 318); QASELIS (SEQ ID NO: 319); QASHLIS (SEQ ID NO: 320); QASKLIS (SEQ ID NO: 321); QASSLIS (SEQ ID NO: 322); QASALIS (SEQ ID NO: 323); DASTLIS (SEQ ID NO: 324); DASDLIS (SEQ ID NO: 325); DASELIS (SEQ ID NO: 326); DASHLIS (SEQ ID NO: 327); DASKLIS (SEQ ID NO: 328); DASSLIS (SEQ ID NO: 329); DASALIS (SEQ ID NO: 330); EASTLIS (SEQ ID NO: 331); EASDLIS (SEQ ID NO: 332); EASELIS (SEQ ID NO: 333); EASHLIS (SEQ ID NO: 334); EASKLIS (SEQ ID NO: 335); EASSLIS (SEQ ID NO: 336); EASALIS (SEQ ID NO: 337); RASTLIS (SEQ ID NO: 338); RASDLIS (SEQ ID NO: 339); RASELIS (SEQ ID NO: 340); RASHLIS (SEQ ID NO: 341); RASKLIS (SEQ ID NO: 342); RASSLIS (SEQ ID NO: 343); RASAUS (SEQ ID NO: 344); TASTLIS (SEQ ID NO: 345); TASDLIS (SEQ ID NO: 346); TASELIS (SEQ ID NO: 347); TASHLIS (SEQ ID NO: 348); TASKLIS (SEQ ID NO: 349); (SEQ ID NO: 350); TASALIS (SEQ ID NO: 351); SASTLIS (SEQ ID NO: 352); SASDLIS (SEQ ID NO: 353); SASELIS (SEQ ID NO: 354); SASHLIS (SEQ ID NO: 355); SASKLIS (SEQ ID NO: 356); SASSLIS (SEQ ID NO: 357); SASALIS (SEQ. ID NO: 358); QLDNLQT (SEQ ID NO: 359); DLDNLQT (SEQ ID NO: 360); ELDNLQT (SEQ ID NO: 361); TLDNLQT (SEQ ID NO: 362); SLDNLQT (SEQ ID NO: 363); RLDTLQT (SEQ ID NO: 364); RLDDLQT (SEQ ID NO: 365); RLDELQT (SEQ ID NO: 366); RLDHLQT (SEQ ID NO: 367); RLDKLQT (SEQ ID NO: 368); RLDSLQT (SEQ ID NO: 369); RLDALQT (SEQ ID NO: 370); QLDTLQT (SEQ ID NO: 371); QLDDLQT (SEQ ID NO: 372); QLDELQT (SEQ ID NO: 373); QLDHLQT (SEQ ID NO: 374); QLDKLQT (SEQ ID NO: 375); QLDSLQT (SEQ ID NO: 376); QLDALQT (SEQ ID NO: 377); DLDTLQT (SEQ ID NO: 378); DLDDLQT (SEQ ID NO: 379); DLDELQT (SEQ ID NO: 380); DLDHLQT (SEQ ID NO: 381); DLDKLQT (SEQ ID NO: 382); DLDSLQT (SEQ ID NO: 383); DLDALQT (SEQ ID NO: 384); ELDTLQT (SEQ ID NO: 385); ELDDLQT (SEQ ID NO: 386); ELDELQT (SEQ ID NO: 387); ELDHLQT (SEQ ID NO: 388); ELDKLQT (SEQ ID NO: 389); ELDSLQT (SEQ ID NO: 390); ELDALQT (SEQ ID NO: 391); TLDTLQT (SEQ ID NO: 392); TLDDLQT (SEQ ID NO: 393); TLDELQT (SEQ ID NO: 394); TLDHLQT (SEQ ID NO: 395); TLDKLQT (SEQ ID NO: 396); TLDSLQT (SEQ ID NO: 397); TLDALQT (SEQ ID NO: 398); SLDTLQT (SEQ ID NO: 399); SLDDLQT (SEQ ID NO: 400); SLDELQT (SEQ ID NO: 401); SLDHLQT (SEQ ID NO: 402); SLDKLQT (SEQ ID NO: 403); SLDSLQT (SEQ ID NO: 404); SLDALQT (SEQ ID NO 405); ARGTLRT (SEQ ID NO: 406); ARGDLRT (SEQ ID NO: 407); ARGELRT (SEQ ID NO: 408); ARGHLRT (SEQ ID NO: 409); ARGKLRT (SEQ ID NO: 410); ARGSLRT (SEQ ID NO: 411); ARGALRT (SEQ ID NO: 412); SRGTLRT (SEQ ID NO: 413); SRGDLRT (SEQ ID NO: 414); SRGELRT (SEQ ID NO: 415); SRGHLRT (SEQ ID NO: 416); SRGKLRT (SEQ ID NO: 417); SRGSLRT (SEQ ID NO: 418); SRGALRT (SEQ ID NO: 419); QKDALRG (SEQ ID NO: 420); DKDALRG (SEQ ID NO: 421); EKDALRG (SEQ ID NO: 422); TKDALRG (SEQ ID NO: 423); SKDALRG (SEQ ID NO: 424); RKDNLRG (SEQ ID NO: 425); RKDTLRG (SEQ ID NO: 426); RKDDLRG (SEQ ID NO: 427); RKDELRG (SEQ ID NO: 428); RKDHLRG (SEQ ID NO: 429); RKDKLRG (SEQ ID NO: 430); RKDSLRG (SEQ ID NO: 431); QKDNLRG (SEQ ID NO: 432); QKDTLRG (SEQ ID NO: 433); QKDDLRG (SEQ ID NO: 434); QKDELRG (SEQ ID NO: 435); QKDHLRG (SEQ ID NO: 436); QKDKLRG (SEQ ID NO: 437); QKDSLRG (SEQ ID NO: 438); DKDNLRG (SEQ ID NO: 439); DKDTLRG (SEQ ID NO: 440); DKDDLRG (SEQ ID NO: 441); DKDELRG (SEQ ID NO: 442); DKDHLRG (SEQ ID NO: 443); DKDKLRG (SEQ ID NO: 444); DKDSLRG (SEQ ID NO: 445); EKDNLRG (SEQ ID NO: 446); EKDTLRG (SEQ ID NO: 447); EKDDLRG (SEQ ID NO: 448); EKDELRG (SEQ-ID NO: 449); EKDHLRG (SEQ ID NO: 450); EKDKLRG (SEQ ID NO: 451); EKDSLRG (SEQ ID NO: 452); TKDNLRG (SEQ ID NO: 453); TKDTLRG (SEQ ID NO: 454); TKDDLRG (SEQ ID NO: 455); TKDELRG (SEQ ID NO: 456); TKDHLRG (SEQ ID NO: 457); TKDKLRG (SEQ ID NO: 458); TKDSLRG (SEQ ID NO: 459); SKDNLRG (SEQ ID NO: 460); SKDTLRG (SEQ ID NO: 461); SKDDLRG (SEQ ID NO: 462); SKDELRG (SEQ ID NO: 463); SKDHLRG (SEQ ID NO: 464); SKDKLRG (SEQ ID NO: 465); SKDSLRG (SEQ ID NO: 466); VRGTLRT (SEQ ID NO: 467); VRGDLRT (SEQ ID NO: 468); VRGELRT (SEQ ID NO: 469); VRGHLRT (SEQ ID NO: 470); VRGKLRT (SEQ ID NO: 471); VRGSLRT (SEQ ID NO: 472); VRGTLRT (SEQ ID NO: 473); QLRALDR (SEQ ID NO: 474); DLRALDR (SEQ ID NO: 475); ELRALDR (SEQ ID NO: 476); TLRALDR (SEQ ID NO: 477); SLRALDR (SEQ ID NO: 478); RSDNRKR (SEQ ID NO: 479); RSDTRKR (SEQ ID NO: 480); RSDDRKR (SEQ ID NO: 481); RSDHRKR (SEQ ID NO: 482); RSDKRKR (SEQ ID NO: 483); RSDSRKR (SEQ ID NO: 484); RSDARKR (SEQ ID NO: 485); QYQSLRQ (SEQ ID NO: 486); EYQSLRQ (SEQ. ID NO: 487); RYQSLRQ (SEQ ID NO: 488); TYQSLRQ (SEQ ID NO: 489); SYQSLRQ (SEQ ID NO: 490); RLRNIQF (SEQ ID NO: 491); RLRTIQF (SEQ ID NO: 492); RLREIQF (SEQ ID NC: 493); RLRHIQF (SEQ ID NO: 494); RLRKIQF (SEQ ID NO: 495); RLRSIQF (SEQ ID NO: 496); RLRAIQF (SEQ ID NO: 497); DSLLLGA (SEQ ID NO: 498); ESLLLGA (SEQ ID NO: 499); RSLLLGA (SEQ ID NO: 500); TSLLLGA (SEQ ID NO: 501); SSLLLGA (SEQ ID NO: 502); HRGNLGG (SEQ ID NO: 503); HRGDLGG (SEQ ID NO: 504); HRGELGG (SEQ ID NO: 505); HRGHLGG (SEQ ID NO: 506); HRGKLGG (SEQ ID NO: 507); HRGSLGG (SEQ ID NO: 508); HRGALGG (SEQ ID NO: 509); QKHMLDT (SEQ ID NO: 510); EKHMLDT (SEQ ID NO: 511); RKHMLDT (SEQ ID NO: 512); TKHMLDT (SEQ ID NO: 513); SKHMLDT (SEQ ID NO: 514); QLGGLRQ (SEQ ID NO: 515); ELGGLRQ (SEQ ID NO: 516); RLGGLRQ (SEQ ID NO: 517); TLGGLRQ (SEQ ID NO: 518); SLGGLRQ (SEQ ID NO: 519); AEANLQR (SEQ ID NO: 520); AEATLQR (SEQ ID NO: 521); AEADLQR (SEQ ID NO: 522); AEAHLQR (SEQ ID NO: 523); AEAKLQR (SEQ ID NO: 524); AEASLQR (SEQ ID NO: 525); AEAALQR (SEQ ID NO: 526); DGRCLVT (SEQ ID NO: 527); EGRCLVT (SEQ ID NO: 528); RGRCLVT (SEQ ID NO: 529); TGRCLVT (SEQ ID NO: 530); SGRCLVT (SEQ ID NO: 531); QEDNLHT (SEQ ID NO: 532); DEDNLHT (SEQ ID NC: 533); EEDNLHT (SEQ ID NO: 534); SEDNLHT (SEQ ID NO: 535); REDTLHT (SEQ ID NO: 536); REDDLHT (SEQ ID NO: 537); REDELHT (SEQ ID NO: 538); REDHLHI (SEQ ID NO: 539); REDKLHT (SEQ ID NO: 540); REDSLHT (SEQ ID NO: 541); REDALHT (SEQ ID NO: 542); QEDTLHT (SEQ ID NO: 543); QEDDLHT (SEQ ID NO: 544); QEDELHT (SEQ ID NO: 545); QEDHLHT (SEQ ID NO: 546); QEDKLHT (SEQ ID NO: 547); QEDSLHT (SEQ ID NO: 548); QEDALHT (SEQ ID NO: 549); DEDTLHT (SEQ ID NO: 550); DEDDLHT (SEQ ID NO: 551); DEDELHT (SEQ ID NO: 552); DEDHLHT (SEQ ID NO: 553); DEDKLHT (SEQ ID NO: 554); DEDSLHT (SEQ ID NO: 555); DEDALHT (SEQ ID NO: 556); EEDTLHT (SEQ ID NO: 557); EEDDLHT (SEQ ID NO: 558); EEDELHT (SEQ ID NO: 559); EEDHLHT (SEQ ID NO: 560); EEDKLHT (SEQ ID NO: 561); EEDSLHT (SEQ ID NO: 562); EEDALHT (SEQ ID NO: 563); TEDTLHT (SEQ ID NO: 564); TEDDLHT (SEQ ID NO: 565); TEDELHT (SEQ ID NO: 566); TEDHLHT (SEQ ID NO: 567); TEDKLHT (SEQ ID NO: 568); TEDSLHT (SEQ ID NO: 569); TEDALHT (SEQ ID NO: 570); SEDTLHT (SEQ ID NO: 571); SEDDLHT (SEQ ID NO: 572); SEDELHT (SEQ ID NO: 573); SEDHLHT (SEQ ID NO: 574); SEDKLHT (SEQ ID NO: 575); SEDSLHT (SEQ ID NO: 576); SEDALHT (SEQ ID NO: 577); QEDNLIS (SEQ ID NO: 578); DEDNLIS (SEQ ID NO: 579); EEDNLIS (SEQ ID NO: 580); SEDNLIS (SEQ ID NO: 581); REDTLIS (SEQ ID NO: 582); REDDLIS (SEQ ID NO: 583); REDELIS (SEQ ID NO: 584); REDHLIS; (SEQ ID NO: 585); REDKLIS (SEQ ID NO: 586); REDSLIS (SEQ ID NO: 587); REDALIS (SEQ ID NO: 588); QEDTLIS (SEQ ID NO: 589); QEDDLIS (SEQ ID NO: 590); QEDELIS (SEQ ID NO: 591); QEDHLIS (SEQ ID NO: 592); QEDKLIS (SEQ ID NO: 593); QEDSLIS (SEQ ID NO: 594); QEDALIS (SEQ ID NO: 595); DEDTLIS (SEQ ID NO: 596); DEDDLIS (SEQ ID NO: 597); DEDELIS (SEQ ID NO: 598); DEDHLIS (SEQ ID NO: 599); DEDKLIS (SEQ ID NO: 600); DEDSLIS (SEQ ID NO: 601); DEDALIS (SEQ ID NO: 602); EEDTLIS (SEQ ID NO: 603); EEDDLIS (SEQ ID NO: 604); EEDELIS (SEQ ID NO: 605); EEDHLIS (SEQ ID NO: 606); EEDKLIS (SEQ ID NO: 607); EEDSLIS (SEQ ID NO: 608); EEDALIS (SEQ ID NO: 609); TEDTLIS (SEQ ID NO: 610); TEDDLIS (SEQ ID NO: 611); TEDELIS (SEQ ID NO: 612); TEDHLIS (SEQ ID NO: 613); TEDKLIS (SEQ ID NO: 614); TEDSLIS (SEQ ID NO: 615); TEDALIS (SEQ ID NO: 616); SEDTLIS (SEQ ID NO: 617); SEDDLISu (SEQ ID NO: 618); SEDELIS (SEQ ID NO: 619); SEDHLIS (SEQ ID NO: 620); SEDKLIS (SEQ ID NO: 621); SEDSLIS (SEQ ID NO: 622); SEDALIS (SEQ ID NO: 623); TGGWLQA (SEQ ID NO: 653); SGGWLQA (SEQ ID NO: 654); DGGWLQA (SEQ ID NO: 655); EGGWLQA (SEQ ID NO: 656); QGGWLQA (SEQ ID NO: 657); RGGTLQA (SEQ ID NO: 658); RGGDLQA (SEQ ID NO: 659); RGGELQA (SEQ ID NO: 660); RGGNLQA (SEQ ID NO: 661); RGGHLQA (SEQ ID NO: 662); RGGKLQA (SEQ ID NO: 663); RGGSLQA (SEQ ID NO: 664); RGGALQA (SEQ ID NO: 665); TGGTLQA (SEQ ID NO: 666); TGGDLQA (SEQ ID NO: 667); TGGELQA (SEQ ID NO: 668); TGGNLQA (SEQ ID NO: 669); TGGHLQA (SEQ ID NO: 670); TGGKLQA (SEQ ID NO: 671); TGGSLQA (SEQ ID NO: 672); TGGALQA (SEQ ID NO: 673); SGGTLQA (SEQ ID NO: 674); SGGDLQA (SEQ ID NO: 675); SGGELQA (SEQ ID NO: 676); SGGNLQA (SEQ ID NO: 677); SGGHLQA (SEQ ID NO: 678); SGGKLQA (SEQ ID NO: 679); SGGSLQA (SEQ ID NO: 680); SGGALQA (SEQ ID NO: 681); DGGTLQA (SEQ ID NO: 682); DGGDLQA (SEQ ID NO: 683); DGGELQA (SEQ ID NO: 684); DGGNLQA (SEQ ID NO: 685); DGGHLQA (SEQ ID NO: 686); DGGKLQA (SEQ ID NO: 687); DGGSLQA (SEQ ID NO: 688); DGGALQA (SEQ ID NO: 689); EGGTLQA (SEQ ID NO: 690); EGGDLQA (SEQ ID NO: 691); EGGELQA (SEQ ID NO: 692); EGGNLQA (SEQ ID NO: 693); EGGHLQA (SEQ ID NO: 694); EGGKLQA (SEQ ID NO: 695); EGGSLQA (SEQ ID NO: 696); EGGALQA (SEQ ID NO: 697); QGGTLQA (SEQ ID NO: 698); QGGDLQA (SEQ ID NO: 699); QGGELQA (SEQ ID NO: 700); QGGNLQA (SEQ ID NO: 701); QGGHLQA (SEQ ID NO: 702); QGGKLQA (SEQ ID NO: 703); QGGSLQA (SEQ ID NO: 704); and QGGALQA (SEQ ID NO: 705).

Particularly preferred binding domains for TNN include SEQ ID NOs: 267-311. More particularly preferred binding domains for TNN include SEQ ID NOs: 267-272.

Within the zinc finger nucleotide binding domain of the chimeric recombinase, the triplet binding domains are preferably linked with at least one oligopeptide linker such that the oligopeptide linker or linkers are located between triplet binding domains. Such linkers preferably resemble a linker found in naturally occurring zinc finger proteins. A preferred linker for use in the present invention is the amino acid residue sequence TGEKP (SEQ ID NO: 624). Modifications of this linker can also be used. For example, the glutamic acid (E) at position 3 of the linker can be replaced with aspartic acid (D). The threonine (T) at position 1 can be replaced with serine(S). The glycine (G) at position 2 can be replaced with alanine (A). The lysine (K) at position 4 can be replaced with arginine (R). Another preferred linker for use in the present invention is the amino acid residue sequence TGGGGSGGGGTGEKP (SEQ ID NO: 625). Modifications of this longer linker can also be used. For example, the polyglycine runs of four glycine (G) residues each can be of greater or lesser length (i.e., 3 or 5 glycine residues each). The serine residue (S) between the polyglycine runs can be replaced with threonine (T). The TGEKP (SEQ ID NO: 624) moiety that comprises part of the linker TGGGGSGGGGTGEKP (SEQ ID NO: 625) can be modified as described above for the TGEKP (SEQ ID NO: 624) linker alone. Other linkers such as glycine or serine repeats are well known in the art to link peptides (e.g., single chain antibody domains) and can be used in a composition of this invention. The use of a linker is not required for all purposes and can optionally be omitted.

Other linkers are known in the art and can alternatively be used. These include the linkers LRQKDGGGSERP (SEQ ID NO: 626), LRQKDGERP (SEQ ID NO: 627), GGRGRGR-GRQ (SEQ ID NO: 628), QNKKGGSGDGKKKQHI (SEQ ID NO: 629), TGGERP (SEQ ID NO: 630), ATGEKP (SEQ ID NO: 631), and GGGSGGGGEGP (SEQ ID NO: 706), as well as derivatives of those linkers in which amino acid substitutions are made as described above for TGEKP (SEQ ID NO: 624) and TGGGGSGGGGTGEKP (SEQ ID NO: 625). For example, in these linkers, the serine (S) residue between the diglycine or polyglycine runs in QNKKGGS-GDGKKKQHI (SEQ ID NO: 629) or GGGSGGGGEGP (SEQ ID NO: 706) can be replaced with threonine (T). In GGGSGGGGEGP (SEQ ID NO: 706), the glutamic acid (E) at position 9 can be replaced with aspartic acid (D). Polypeptide compositions including these linkers and derivatives of these linkers are included in polypeptide compositions of the present invention.

Typically, the zinc finger nucleotide binding domain of the chimeric recombinase binds a hexanucleotide and therefore includes two triplet-binding domains. However, zinc finger nucleotide binding domains of the chimeric recombinase can include a greater number of triplet-binding domains, such as 3 or 4, to obtain the appropriate specificity. Of course, the greater the number of triplet-binding domains incorporated in the zinc finger nucleotide binding domain of the chimeric recombinase, the greater the specificity for potential sites in the genome. Therefore, if the number of triplet-binding domains is increased, then recombination can occur at fewer sites in a particular genome.

A triplet-binding domain comprises a unique heptamer (contiguous sequence of 7 amino acid residues) within an α-helical domain, which heptameric sequence determines binding specificity to the target nucleotide. That heptameric sequence can be located anywhere within the α-helical domain but it is preferred that the heptamer extend from position −1 to position 6 as the residues are conventionally numbered in the art. A polypeptide of this invention can include any β-sheet and framework sequences known in the art to function as part of a zinc finger protein as needed to ensure appropriate specificity.

A chimeric recombinase of this invention is a non-naturally occurring variant. As used herein, the term "non-naturally occurring" means, for example, one or more of the following:

(a) a polypeptide comprised of a non-naturally occurring amino acid sequence; (b) a polypeptide having a non-naturally occurring secondary structure not associated with the polypeptide as it occurs in nature; (c) a polypeptide which includes one or more amino acids not normally associated with the species of organism in which that polypeptide occurs in nature; (d) a polypeptide which includes a stereoisomer of one or more of the amino acids comprising the polypeptide, which stereoisomer is not associated with the polypeptide as it occurs in nature; (e) a polypeptide which includes one or more chemical moieties other than one of the natural amino acids; or (f) an isolated portion of a naturally occurring amino acid sequence (e.g., a truncated sequence). A chimeric recombinase of this invention exists in an isolated form and purified to be substantially free of contaminating substances. The chimeric recombinase can be isolated and purified from natural sources; alternatively, the chimeric recombinase can be made de novo using techniques well known in the art such as genetic engineering or solid-phase peptide synthesis. Examples of zinc finger proteins from which a chimeric recombinase can be produced include SP1C, TFIIIA and Zif268, as well as C7 (a derivative of Zif268) and other zinc finger proteins known in the art. Any naturally occurring zinc finger domain can be recruited for use in this invention. In some applications, like transposition, zinc finger domains with limited specificity may be preferred.

Chimeric recombinases according to the present invention can additionally include domains from other proteins, as long as the additional domains do not interfere with the recombinase activity of the protein. These additional domains can be incorporated with or without spacer elements. The use of spacer elements is well known in the art. These fusion proteins can include various additional domains as are known in the art, such as purification tags, enzyme domains, ligand binding domains, cell penetrating domains, or other domains, without significantly altering the specific recombinase activity of the chimeric recombinase. Examples of enzyme domains include enzyme domains that catalyze the detectable production of light via fluorescence or bioluminescence. An example of a fluorescent protein is EGFP, which allows the performance of FAC sorting following transient transfection or other procedures that introduce the chimeric recombinase into a cell. Ligand binding domains include estrogen receptor, which affords the ability to titrate the nuclear presence of RecZFs. An example of a cell penetrating domain is the RGD motif. In one example, the polypeptides can be incorporated into two halves of a split enzyme like a β-lactamase to allow the sequences to be sensed in cells or in vivo. Binding of two halves of such a split enzyme then allows for assembly of the split enzyme (J. M. Spoils et al. "Time-Lapse Imaging of a Dynamic Phosphorylation Protein-Protein Interaction in Mammalian Cells," *Proc. Natl. Acad. Sci.* USA 99: 15142-15147 (2002)). Examples of fusion proteins that can be prepared incorporating chimeric recombinases according to the present invention are recombinase-zinc finger-maltose binding protein (MBP) fusion proteins. Typically, the MBP is located at the carboxyl- or amino-terminus of the protein. These can be used for affinity purification on a maltose column. If desired, such as to enhance the recombinase activity in situations in which the large C-terminal MBP domain appears to inhibit recombinase activity, in *E. coli*, then a Factor Xa protease site can be used to cleave the bulky tag away from the purified $Rec_{ZF}$.

As indicated above, it is well known in protein chemistry that a number of amino acid sequence changes, designated generally as "conservative amino acid substitutions," can be made in proteins without substantial disruption to the secondary structure, tertiary structure, quaternary structure, if applicable, or function of proteins. Accordingly, chimeric recombinases derived from those described above with one to five conservative amino acid substitutions are within the scope of the invention, provided that the chimeric recombinase with one to five conservative amino acid substitutions has the same DNA sequence specificity for recombination as the unmutated chimeric recombinase, has a binding affinity for the substrate of no less than about 80% of the binding affinity for the substrate of the unmutated chimeric recombinase, and has a $V_{max}$ of no less than about 80% of the $V_{max}$ of the unmutated chimeric recombinase. The one to five conservative amino acid substitutions are each selected from the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gin or Glu; Met/Leu or Tyr or Ile; Phe/Met or Leu or Tyr; Ser/Thr; Thr/Ser; Trp/Tyr; Tyr/Trp or Phe; Val/Ile or Leu. Preferably, there are no more than two conservative amino acid substitutions. More preferably, there is no more than one amino acid substitution.

Still other zinc finger nucleotide binding domains can be used in chimeric recombinases, including zinc finger nucleotide binding domains that have an amino acid sequence with the same nucleotide binding characteristics as described above, will compete for binding to a nucleotide target with one or more of the zinc finger nucleotide binding domains described above, or will displace, in a competitive manner, the binding of one or more of the zinc finger nucleotide binding domains described above. Methods for determining competitive binding affinities are known in the art.

Additionally, zinc finger nucleotide binding domains can be molecularly modeled, as is known in the art. One suitable computer program for molecular modeling is Insight II. Molecular modeling can be used to generate other zinc finger nucleotide binding domains based on variations of zinc finger nucleotide binding domains described herein and that are within the scope of the invention. When modeling establishes that such Variations have a hydrogen-bonding pattern that is substantially similar to that of a zinc finger nucleotide binding domain within the scope of the invention and that has been used as the basis for modeling, such variations are also within the scope of the invention. As used herein, the term "substantially similar" with respect to hydrogen bonding pattern means that the same number of hydrogen bonds are present, that the bond angle of each hydrogen bond varies by no more than about 10 degrees, and that the bond length of each hydrogen bond varies by no more than about 0.2 Å.

Typically, binding between the zinc finger nucleotide binding domain and the DNA of appropriate sequence occurs with a $K_D$ of from 1 μM to 10 μM. Preferably binding occurs with a $K_D$ of from 10 μM to 1 μM, from 10 pM to 100 nM, from 100 pM to 10 nM and, more preferably with a $K_D$ of from 1 nM to 10 nM. In another alternative, binding between the zinc finger nucleotide binding domain and the DNA of appropriate sequence can occur with a $K_D$ of 10 pM or less.

Still other zinc finger nucleotide binding domains that can be incorporated in polypeptides according to the present invention can be derived from the domains described above, namely SEQ ID NO: 5 through SEQ ID NO: 623, by site-derived mutagenesis and screening. Site-directed mutagenesis techniques, also known as site-specific mutagenesis techniques are well known in the art and need not be described in detail here. Such techniques are described, for example, in J. Sambrook & D. W. Russell, "Molecular Cloning: A Laboratory Manual" ($3^{rd}$ ed., Cold Spring Harbor Laboratory Press, Cold Spring Harbor, N.Y., 2001), v.2, ch. 13, pp. 13.1-13.56.

Chimeric recombinases according to the present invention can be purified by conventional protein purification techniques, including, but not limited to, techniques such as precipitation with salts such as ammonium sulfate, ion exchange chromatography, gel filtration, affinity chromatography, electrophoresis, isoelectric focusing, isotachophoresis, chromatofocusing, and other techniques are well known in the art and are described in R. K. Scopes, "Protein Purification: Principles and Practice" ($3^{rd}$ ed., Springer-Verlag, New York, 1994). One particularly useful protein purification procedure is the use of affinity chromatography on maltose columns for the purification of fusion proteins incorporating chimeric recombinases and MBP. Another useful protein purification procedure is DNA affinity chromatography, which can be used to purify unmodified $Rec_{ZF}s$.

Additionally, another aspect of the invention is a nucleotide sequence encoding a chimeric recombinase according to the present invention as described above. As defined above, nucleotide sequences encompass both DNA and RNA, but are more typically prepared and handled as DNA because of the increased stability of that form of nucleic acid. DNA sequences encoding the chimeric recombinases of the invention can be obtained by several methods. For example, the DNA can be isolated using hybridization procedures that are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See, for example, Current Protocols in Molecular Biology, Ausubel, et al., Eds., 1989).

The development of specific DNA sequences encoding chimeric recombinases of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of mammalian polypeptides due to the presence of introns. For obtaining chimeric recombinases according to the present invention, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be clones. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucleic Acid Research 11:2325, 1983).

With respect to nucleotide sequences that are within the scope of the invention, all nucleotide sequences encoding the polypeptides that are embodiments of the invention as described are included in nucleotide sequences that are within the scope of the invention. This further includes all nucleotide sequences that encode polypeptides according to the invention that incorporate conservative amino acid substitutions as defined above. This further includes nucleotide sequences that encode larger proteins incorporating the chimeric recombinases, including fusion proteins as described above. Note that, because all chimeric recombinases according to the present invention are formally fusion proteins, the term "fusion protein" as used herein refers to a protein molecule incorporating domains other than the zinc finger nucleotide binding domain and the recombinase domain.

Nucleic acid sequences of the present invention further include nucleic acid sequences that are at least 95% identical to the sequences above, with the proviso that the nucleic acid sequences retain the activity of the sequences before substitutions of bases are made, including any activity of proteins that are encoded by the nucleotide sequences and any activity of the nucleotide sequences that is expressed at the nucleic acid level, such as the binding sites for proteins affecting transcription. Preferably, the nucleic acid sequences are at least 97.5% identical. More preferably, they are at least 99% identical. For these purposes, "identity" is defined according to the Needleman-Wunsch algorithm (S. B. Needleman & C. D. Wunsch, "A General Method Applicable to the Search for Similarities in the Amino Acid Sequence of Two Proteins," *J. Mol. Biol.* 48: 443-453 (1970)).

Nucleotide sequences encompassed by the present invention can also be incorporated into a vector, including, but not limited to, an expression vector, and used to transfect or transform suitable host cells, as is well known in the art. The vectors incorporating the nucleotide sequences that are encompassed by the present invention are also within the scope of the invention. Host cells that are transformed or transfected with the vector or with polynucleotides or nucleotide sequences of the present invention are also within the scope of the invention. The host cells can be prokaryotic or eukaryotic; if eukaryotic, the host cells can be mammalian cells, insect cells, or yeast cells. If prokaryotic, the host cells are typically bacterial cells.

Transformation of a host cell with recombinant DNA may be carried out by conventional techniques as are well known to those skilled in the art. Where the host is prokaryotic, such as *Escherichia coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used.

A variety of host-expression vector systems may be utilized to express the zinc finger derived-nucleotide binding coding sequence. These include but are not limited to microorganisms such as bacteria transformed with recombinant bacteriophage DNA, plasmid DNA or cosmid DNA expression vectors containing a zinc finger derived-nucleotide binding polypeptide coding sequence; yeast transformed with recombinant yeast expression vectors containing the zinc finger-nucleotide binding coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a zinc finger derived-DNA binding coding sequence; insect cell systems infected with recombinant virus expression vectors (e.g., baculovirus) containing a zinc finger-nucleotide binding coding sequence; or animal cell systems infected with recombinant virus expression vectors (e.g., retroviruses, adenovirus, vaccinia virus) containing a zinc finger derived-nucleotide binding coding sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., Methods in Enzymology, 153:516-544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted chimeric recombinase coding sequence.

In bacterial systems a number of expression vectors may be advantageously selected depending upon the use intended for the chimeric recombinase expressed. For example, when large quantities are to be produced, vectors which direct the expression of high levels of fusion protein products that are readily purified may be desirable. Those which are engineered to contain a cleavage site to aid in recovering the protein are preferred. Such vectors include but are not limited to the *Escherichia coli* expression vector pUR278 (Ruther, et al., EMBO J., 2:1791, 1983), in which the zinc finger-nucleotide binding protein coding sequence may be ligated into the vector in frame with the lac Z coding region so that a hybrid zinc finger-lac Z protein is produced; pIN vectors (Inouye & Inouye, Nucleic Acids Res. 13:3101-3109, 1985; Van Heeke & Schuster, J. Biol. Chem. 264:5503-5509, 1989); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

In cases where plant expression vectors are used, the expression of a zinc finger-nucleotide binding polypeptide coding sequence may be driven by any of a number of promoters. For example, viral promoters such as the 35S RNA and 19S RNA promoters of CaMV (Brisson, et al., Nature, 310:511-514, 1984), or the coat protein promoter to TMV (Takamatsu, et al., EMBO J., 6:307-311, 1987) may be used; alternatively, plant promoters such as the small subunit of RUBISCO (Coruzzi, et al., EMBO J. 3:1671-1680, 1984; Broglie, et al., Science 224:838-843, 1984); or heat shock promoters, e.g., soybean hsp17.5-E or hsp17.3-B (Gurley, et al., Mol. Cell. Biol., 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421-463, 1988; and Grierson & Corey, Plant Molecular Biology, 2d Ed., Blackie, London, Ch. 7-9, 1988.

An alternative expression system that can be used, to express a chimeric recombinase of the invention is an insect system. In one such system, *Autographa californica* nuclear polyhedrosis virus (AcNPV) is used as a vector to express foreign genes. The virus grows in *Spodoptera frugiperda* cells. The zinc finger-nucleotide binding polypeptide coding sequence may be cloned into non-essential regions (in *Spodoptera frugiperda*, for example, the polyhedrin gene) of the virus and placed under control of an AcNPV promoter (for example the polyhedrin promoter). Successful insertion of the chimeric recombinase coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. (E.g., see Smith, et al., *J. Biol.* 46:584, 1983; Smith, U.S. Pat. No. 4,215,051).

Eukaryotic systems, and preferably mammalian expression systems, allow for proper post-translational modifications of expressed mammalian proteins to occur. Therefore, eukaryotic cells, such as mammalian cells that possess the cellular machinery for proper processing of the primary transcript, glycosylation, phosphorylation, and, advantageously secretion of the gene product, are the preferred host cells for the expression of a chimeric recombinase according to the present invention. Such host cell lines may include but are not limited to CHO, VERO, BHK, HeLa, COS, MDCK, 293, and WI38.

Mammalian cell systems that utilize recombinant viruses or viral elements to direct expression may be engineered. For example, when using adenovirus expression vectors, the coding sequence of a chimeric recombinase may be ligated to an adenovirus transcription/translation control complex, e.g., the late promoter and tripartite leader sequence. This ligated complex may then be inserted into the adenovirus genome by in vitro or in vivo recombination. Insertion in a non-essential region of the viral genome (e.g., region E1 or E3) will result in a recombinant virus that is viable and capable of expressing the zinc finger polypeptide in infected hosts (e.g., see Logan & Shenk, Proc. Natl. Acad. Sci. USA 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA, 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the chimeric recombinase gene in host cells (Cone & Mulligan, Proc. Natl. Acad. Sci. USA 81:6349-6353, 1984). High level expression may also be achieved using inducible promoters, including, but not limited to, the metallothionein IIA promoter and heat shock promoters.

For long-term, high-yield production of recombinant proteins, stable expression is preferred. Rather than using expression vectors which contain viral origins of replication, host cells can be transformed with the a cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in enriched media, and then are switched to a selective media. A number of selection systems may be used, including but not limited to the herpes simplex virus thymidine kinase (Wigler, et al., Cell 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes, which can be employed in $tk^-$, $hgprt^-$ or $aprt^-$ cells respectively. Also, antimetabolite resistance-conferring genes can be used as the basis of selection; for example, the genes for dhfr, which confer resistance to methotrexate (Wigler, et al., Natl. Acad. Sci. USA, 77:3567, 1980; O'Hare, et al., Proc. Natl. Acad. Sci. USA, 78:1527, 1981); gpt, which confers resistance to mycophenolic acid (Mulligan & Berg, Proc. Natl. Acad. Sci. USA, 78:2072, 1981; neo, which confers resistance to the aminoglycoside G418 (Colberre-Garapin, et al., J. Mol. Biol., 150:1, 1981); and hygro, which confers resistance to hygromycin (Santerre, et al., Gene, 30:147, 1984). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:804, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with a chimeric recombinase of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

Another aspect of the present invention is a method of using a chimeric recombinase according to the present invention to carry out a site-specific recombination event.

In recombination reactions according to the present invention, the most significant substrate is the endogenous genome of interest, such as, but not limited to, the human genome or the genome of a socially or economically important animal species such as a cow, a horse, a sheep, a pig, a goat, a cat, or a dog, as well as fish, invertebrates, plants, or prokaryotes, as described further below. In the vast majority of cases, such an endogenous RecZF site will be bound by a heterodimer—two different RecZF proteins which share a common catalytic domain but different zinc finger proteins. In addition to genomes, RecZFs could modify any genetic material composed of double stranded DNA (ex. plasmids, episomes, linearized fragments, PCR fragments, and fragments generated by other techniques such as DNA synthesis). A good example of a non-genomic substrate is a plasmid, integrated into the host genome by RecZF recombination. In this case, two recombination sites (one in the plasmid and one in the genome) are brought together and modified by the RecZF proteins.

In general, the method comprises the steps of:

(1) providing a DNA sequence having therein at least two sites specifically binding a chimeric recombinase or multiple chimeric recombinases according to the present invention, the sites being separated by a spacer; and (2) reacting the DNA sequence with a chimeric recombinase or multiple chimeric recombinases under conditions in which the chimeric recombinase catalyzes a site-specific recombination event in which both strands of the DNA sequence are cleaved between the two sites specifically binding the chimeric recombinase so that a site-specific recombination event is carried out.

In general, in this recombination reaction the two substrate recombination sites can either be located on the same DNA molecule (intra-molecular resolution or inversion) or on different DNA molecules (inter-molecular integration or translocation). This kind of recombination is carried out by 1-4 different $Rec_{ZF}$s—the difference lies in the zinc finger fusion protein, while they all share the same catalytic domain. It is likely that in some cases, different catalytic domains (such as Hin and Gin) will be functionally compatible. This simple reaction is inherently bidirectional, and kinetics favor excision over integration.

In some contexts, it can be advantageous to react $Rec_{ZF}$s bound to $Rec_{ZF}$ sites with normal serine recombinases bound to native sites. This union should facilitate recombination by retaining interactions made by endogenous co-factors, and can be particularly useful for integration where only one substrate site is dictated by the endogenous sequence.

Alternatively, another aspect of recombination reactions carried out by chimeric recombinases according to the present invention involves $Rec_{ZF}$ sites that bind $Rec_{ZF}$s at a lower affinity. Mixed sites (composed of one strong and one weak half-site; where "half-site" includes one zinc finger binding site and the proximal half of the spacer region) start the reaction on two separate strands of DNA. Integration fuses these two strands such that novel sites are generated (product recombination sites are always chimeras of substrate recombination sites). This strategy prevents the reverse reaction (excision) because one of the two product sites is composed entirely of weak half-sites (while the other contains two strong half-sites) and is disabled by its inability to bind the $Rec_{ZF}$ dimer (for any reason, including suboptimal recognition sequence and suboptimal DNA binding protein affinity for DNA (including, for example, 1-finger zinc finger domains, which are inherently weaker)). In place of suboptimal zinc finger interactions (binding affinity), suboptimal spacer sequences which cooperatively lower catalytic function can be used in a comparable half-site strategy. The use of such "weak/strong half-site" reactions is a general strategy for unidirectional recombination, and can consequently be applied to any recombination reaction. Accordingly, if two sites are present in the same DNA strand, this strategy can be used to promote unidirectional inversion. One application of this is the use of so-called "suicide substrates," whose recombination sites promote non-conservative recombination, i.e., some DNA is lost or added due to a mechanistic error on the part of the enzyme, such that product sites are not compatible substrates. This may mean that they are simply unable to react with each other, or that one or both sites are unable to react with any $Rec_{ZF}$ site.

The cassette exchange strategy described below can be applied to any molecule of double-stranded DNA, but will most likely find application in the integration of a plasmid fragment into a genome. Antibiotic resistance genes and marker genes could be used to enrich for the integrative product, but they are not essential for this strategy. In the same fashion, the exchanged cassettes could contain any genetic material. Each of the two cassette exchange substrates are composed of two orthogonal recombination sites. The sites are orthogonal because they are bound by $Rec_{ZF}$s of different catalytic domains. As a consequence, each cassette is bound by 2-4 different $Rec_{ZF}$s, and up to 8 $Rec_{ZF}$s participate in the reaction. (Orthogonal spacer sequences could also be used, in which case orthogonality would derive from the inability of $Rec_{ZF}$s to form a recombination product, rather than an inability to bring the substrate sites together for recombination. In this case, each cassette could be bound by 1-4 different $Rec_{ZF}$s.) One pair of compatible sites on the two substrates (i.e. sites bound by $Rec_{ZF}$s sharing the same catalytic domain) recombine, fusing the two substrates by integration. In the second step, the other pair of compatible sites recombine, excising a product composed of the backbone of one substrate and the cassette of the other. This approach achieves a sequence swap, where one fragment is replaced by another. It does not matter which pair of sites execute integration, so long as resolution follows between the other pair. If integration and consequent resolution occur between the same sites, the initial substrates are regenerated.

The unidirectional strategies described above, i.e., "weak-strong half-site" and the use of "suicide substrates" can be combined with the cassette exchange strategy to trap the latter's integrative products. In this case, either one pair, or both pairs of compatible recombination sites are suitable for unidirectional recombination.

Depending on the orientation of the sites and the orientation of the rejoining of the cleaved DNA strands, the site-specific recombination event can be an inversion, an integration, or a resolution. In an inversion, a segment of DNA is inverted in orientation. In an integration, a segment of DNA is inserted in between two sites. In a resolution, a segment of DNA is removed, leaving a gap that is closed. Synapsis with sites in opposite orientation enables inversion, while synapsis with sites in the same orientation enables resolution (FIG. 3).

The efficiency of recombination events, at least for resolution, depends on the spacer length. For $Tn3_{GAGGAG}$, as described above, recombination is most rapid with 20-bp spacer regions or with a mismatched 22/20 arrangement in which the 5'-sites and the 3'-sites differ, less rapid with 22-bp spacer regions, and scarcely detectable with 18-bp spacer regions.

In some contexts, there is spacer sequence dependence, although, for Tn3$_{GAGGAG}$, point mutations are tolerated throughout the spacer region, even including the A/T rich groove. In particular, the secondary DNA interaction may be unnecessary in the presence of a relatively tight binding zinc finger domain. However, with a chimeric substrate, 20G-GFP-20T, in which one of the two spacer regions was derived from that of Gln invertase (TCCAAAACCATGGTTTACAG (SEQ ID NO: 632); FIG. 4B, lane 11), recombination was impaired.

A further example of this method comprises the steps of:
(1) providing two DNA sequences, a first sequence and a second sequence, each of the first sequence and the second sequence having a site therein binding at least one chimeric recombinase according to the present invention; and
(2) reacting the first sequence and the second sequence with the at least one chimeric recombinase under conditions in which the chimeric recombinase catalyzes a site-specific recombination event in which both strands of the first sequence and the second sequence are cleaved so that a site-specific recombination event is carried out involving the first sequence and the second sequence.

In an application of this method, the recombination event that is carried out involving the first and second sequences is a nonconservative recombination event such that some DNA is lost or added and such that product sites are not compatible substrates for reaction with the at least one chimeric recombinase. The recombination event can be a cassette exchange such that either one pair or both pairs of compatible recombination sites are suitable for unidirectional recombination.

A further example of this method comprises the steps of:
(1) providing two DNA sequences, a first sequence and a second sequence, one of the first sequence and the second sequence having a site therein binding at least one chimeric recombinase according to the present invention, and the other of the first sequence and the second sequence having a site therein binding at least one naturally-occurring serine recombinase; and
(2) reacting the first sequence and the second sequence with the at least one chimeric recombinase and the naturally-occurring serine recombinase under conditions in which the chimeric recombinase and the naturally-occurring serine recombinase catalyze a site-specific recombination event in which both strands of the first sequence and the second sequence are cleaved so that a site-specific recombination event is carried out involving the first sequence and the second sequence.

Additionally, methods according to the invention can be used to achieve stable integration. One method according to the invention that can be used to achieve stable integration comprises the steps of:
(1) providing a DNA sequence having therein two sites for recombination, each site comprising:
(a) a mutated binding site for at least one chimeric recombinase according to the present invention binding the at least one chimeric recombinase at a substantially lowered affinity compared with an optimally binding site for a chimeric recombinase half-site; and
(b) a binding site for at least one chimeric recombinase half site that is optimally binding, the sites specifically binding at least one chimeric recombinase according to the present invention, the sites being separated by a spacer; and
(2) reacting the DNA sequence with at least one chimeric recombinase under conditions in which the at least one chimeric recombinase catalyzes a site-specific recombination event in which both strands of the DNA sequence are cleaved between the two sites specifically binding the chimeric recombinase so that a site-specific recombination event is carried out, the site-specific recombination event being integration, and such that a homodimer of mutated binding sites for chimeric recombinase half-sites is formed that is not functional for recombination so that the result of integration is stable.

Suitable half-sites can be constructed based on the sequences of the Rec$_{ZF}$s and the known structure-affinity relationships between DNA sequences and amino acids that bind to specific bases.

An alternative method of achieving stable integration involves use of a mutant binding site for Rec$_{ZF}$ sites that are incompatible with native binding site for Rec$_{ZF}$. In general, this method comprises:
(1) providing a first DNA sequence having therein a first site for recombination that is reactive with at least one first chimeric recombinase according to the present invention;
(2) providing a second DNA sequence having therein a second site for recombination that is reactive with at least one second chimeric recombinase of claim 1, such that the first site and the second site are functionally orthogonal;
(3) reacting the first DNA sequence with the at least one first chimeric recombinase and reacting the second DNA sequence with the at least one second chimeric recombinase to effect recombination.

In one alternative of this method, integration at either the first site for recombination or the second site for recombination is followed by excision at the one of the first and second sites not used for integration, in order to perform a cassette exchange. The recombination can result in inversion or resolution.

Another use of chimeric recombinases according to the present invention to promote recombination is a method of promoting cassette exchanges comprising the steps of:
(1) generating two plasmids:
(a) a first plasmid expressing a first chimeric recombinase according to the present invention comprising a first catalytic domain and a first zinc finger domain and expressing a first antibiotic resistance gene; and
(b) a second plasmid expressing a second chimeric recombinase according to the present invention comprising a second catalytic domain and a second zinc finger domain and expressing a second antibiotic resistance gene, such that the first catalytic domain and the second catalytic domain are different and the first zinc finger domain and the second zinc finger domain are different, and such that the first and second antibiotic resistance genes confer resistance to two different antibiotics;
(2) assembling two cassettes by flanking an encoding region of a first gene and an encoding region of a second gene with non-repeating homodimer sites each binding one of the first chimeric recombinase according to the present invention and the second chimeric recombinase according to the present invention such that intra-plasmid excision by the two chimeric recombinases is precluded;
(3) inserting one cassette into each plasmid to generate two plasmids including cassettes therein; and
(4) co-transfecting a bacterial host with the first plasmid including a cassette and the second plasmid including a cassette so that recombination occurs.

In one alternative of this method, the recombination is inter-plasmid cassette exchange. In another alternative, the recombination is between a chromosomal gene and a plasmid. In still another alternative, the recombination is between an introduced DNA and a chromosomal gene. In still another alternative, the recombination is excision promoted by cassette exchange.

Another method of promoting cassette exchanges according to the present invention comprises the steps of:

(1) generating two plasmids:
  (a) a first plasmid expressing a first chimeric recombinase according to the present invention comprising a first catalytic domain and a first zinc finger domain and expressing a first antibiotic resistance gene wherein the first chimeric recombinase is mutated or selected to bind an endogenous flanking sequence of a first gene; and
  (b) a second plasmid expressing a second chimeric recombinase according to the present invention comprising a second catalytic domain and a second zinc finger domain and expressing a second antibiotic resistance gene, wherein the second chimeric recombinase is mutated or selected to bind an endogenous flanking sequence of a second gene, such that the first catalytic domain and the second catalytic domain are different and the first zinc finger domain and the second zinc finger domain are different, and such that the first and second antibiotic resistance genes confer resistance to two different antibiotics;

(2) assembling two cassettes, a first cassette including a first gene flanked by a first endogenous flanking region and a second cassette including a second gene flanked by a second endogenous flanking region by each of the two endogenous flanking regions including therein a non-repeating homodimer sites each binding one of the first chimeric recombinase according to the present invention and the second chimeric recombinase according to the present invention such that intra-plasmid excision by the two chimeric recombinases is precluded;

(3) inserting one cassette into each plasmid to generate two plasmids including cassettes therein; and (4) co-transfecting a bacterial host with the first plasmid including a cassette and the second plasmid including a cassette so that recombination occurs.

in this method, in one alternative, the recombination is inter-plasmid cassette exchange. Similarly, as described above, the recombination can be between a chromosomal gene and a plasmid, between an introduced DNA and a chromosomal gene, or can be excision promoted by cassette exchange.

Another aspect of the present invention is a method for identifying cis-inactivating zinc finger binding sites comprising the steps of:

(1) generating single half-site libraries including zinc finger binding sites in two compatible plasmids using primers containing randomized nucleotides;

(2) co-transforming the single-half site libraries generated in step (1) into a suitable host to generate transformants;

(3) co-maintaining the transformants using two antibiotics for selection;

(4) purifying plasmids from the co-maintained transformants;

(5) retransforming the suitable host at low concentration;

(6) allowing the retransformed host to grow on a culture medium containing the two antibiotics; and (7) screening colonies growing on the culture medium containing the two antibiotics by PCR for unidirectional integration to identify cis-inactivating zinc finger binding sites.

The host can be selected from, the group consisting of a bacterial host, a yeast cell host, an insect cell host, and a mammalian cell host. A suitable bacterial host is *Escherichia coli*. Suitable antibiotics for the selection are chloramphenicol and carbenicillin, although other pairs of antibiotics can be used as long as resistance to each antibiotic fails to confer resistance to the other antibiotic of the pair.

The selection of cis-inactivating DNA binding domain recognition sites begins with the generation of substrate libraries in which those binding sites have been randomized (in part or in full, by any method of DNA synthesis). In these "single half-site" libraries only one of the two binding sites is randomized, while the other remains static (perfectly complementary to the DNA binding domain in the $Rec_{ZF}$ fusion protein). For this selection, the assay measures the ability of two such hybrid sites, on two co-maintained, plasmids, to support unidirectional integration. This method follows the strategy of "weak/strong half-site" discussed previously; members of the single half-site library bind the $Rec_{ZF}$ with reduced affinity such that while they are functional in trans (i.e. complemented by an adjacent "strong" zinc finger binding site on the other side of the same recombination site), they are inactive in cis (i.e. adjacent to another such "weak" binding site). Because all functional recombination sites will support transient integration, the final PCR screening is required to find zinc finger binding sites that do not support the opposite reaction, resolution. This selection strategy may be used to find cis-inactivating spacer sequences (where the spacer region is randomized instead of the DNA binding domain recognition sequence). This strategy can also be used for the selection of cis-inactivating DNA binding domains. In this case, the target substrates remain constant (each recombination site contains two different DNA binding domain recognition sequence, the selection target ("weak") and the trans-activator ("strong"). These substrates are incubated with a library of $Rec_{ZF}$s with different DNA binding domains, in the constant presence of a $Rec_{ZF}$ perfectly complementary to the trans-activator DNA binding site.

The method can further comprise the steps of:

(8) including another reporter gene that is expressed solely by the recombination product; and (9) screening for activity of the reporter gene.

Another aspect of the present invention is a cis-inactivating zinc finger binding site discovered by the method described above.

Another aspect of the present invention is a similar method for identifying cis-inactivating spacer sequences comprising the steps of:

(1) generating single half-site libraries including spacer sequences in two compatible plasmids using primers containing randomized nucleotides;

(2) co-transforming the single-half site libraries generated in step (1) into a suitable host to generate transformants;

(3) co-maintaining the transformants using two antibiotics for selection;

(4) purifying plasmids from the co-maintained transformants;

(5) retransforming the suitable host at low concentration;

(6) allowing the retransformed host to grow on a culture medium containing the two antibiotics; and (7) screening colonies growing on the culture medium containing the two antibiotics by PCR for unidirectional integration to identify cis-inactivating spacer sequences.

A similar method for identifying cis-inactivating DNA binding domains comprises the steps of:

(1) generating a target substrate, the target substrate including therein a recombination site including therein two different DNA binding domain recognition sequences, a selection target sequence and a transactivator sequence;

(2) incubating the target substrate with a library of chimeric recombinases according to the present invention with different DNA binding domains in the presence of a fixed chimeric recombinase according to the present invention that is perfectly complementary to the transactivator sequence to generate a single half-site library;

(3) co-transforming the single-half site library generated in step (2) into a suitable host to generate transformants;

(4) co-maintaining the transformants using two antibiotics for selection;

(5) purifying plasmids from the co-maintained transformants;

(6) retransforming the suitable host at low concentration;

(7) allowing the retransformed host to grow on a culture medium containing the two antibiotics; and (8) screening colonies growing on the culture medium containing the two antibiotics by PCR for unidirectional integration to identify cis-inactivating DNA binding domains.

Typically, in this method, one plasmid expresses a library of recombinases as described above, using randomized nucleotides for priming, and the other plasmid expresses a single $Rec_{ZF}$. The sites upon which the two enzymes will function in this alternative are heterodimeric: one binding site corresponds to a 6-bp target, and the other binding site is the common RecZF's cognate sequence.

Another aspect of the invention is a method of generating a new chimeric recombinase from an existing chimeric recombinase using substrate linked protein evolution (SLiPE). This approach places recombination sites adjacent to each recombinase gene. Accordingly, a gene that encodes a successful recombinase is physically marked by the action of that enzyme. This distinguishing mark allows the gene to be easily retrieved from a large background of unsuccessful candidates by PCR amplification.

This method is applicable to all DNA binding domains, any method of library generation, and genomic substrates. This is particularly relevant for the selection of $Rec_{ZF}$s based on their ability to modify the human genome. This selection could be performed in one of two ways: (1) introduction of two recombination sites into the genome, followed by introduction/expression of the $Rec_{ZF}$ library, leading to resolution, inversion, or translocation; or (2) introduction of one recombination site into the genome, followed by the introduction of a second site (for example, on a transfected plasmid) with coincident introduction/expression of the $Rec_{ZF}$ library, leading to integration. Accordingly, recitation of selection primers in the context of this method is defined herein as including any non-homologous spacer regions, and also including primers annealing to any desired product of recombination between such spacers. The role of the selection primer is to specifically amplify desired $Rec_{ZF}$s by binding to the desired recombination product site (immediately proximal to the active members of the $Rec_{ZF}$ library).

One method of using substrate-linked protein evolution, to generate a new chimeric recombinase from an existing chimeric recombinase comprises the steps of:

(1) creating a library of recombinase mutants to generate mutagenized recombinase domains;

(2) fusing the mutagenized recombinase domains to a DNA binding domain that has not been mutagenized to generate a library of mutagenized fusion proteins;

(3) cloning the library of mutagenized fusion proteins into a plasmid, the plasmid including a recombinase substrate, for functional selection; and (4) selecting active mutagenized fusion proteins by selecting plasmids that are modified by the activity of recombinase.

Typically, the step of creating a library of recombinase mutants is performed through a random mutagenesis process. The substrate can be genomic. The DNA binding domain is typically a zinc finger nucleotide binding domain, although other DNA binding domains can be used.

One preferred method of creating the library of recombinase mutants through a random mutagenesis process is through error-prone PCR. This can be performed by amplification of the recombinase domains in the presence of one or more dNTP analogues. Particularly preferred dNTP analogues are dPTP and 8-oxo-dGTP, depicted below. Preferably, both dPTP and 8-oxo-dGTP are used for error-prone PCR.

A preferred method of fusing the mutagenized recombinase domains to a zinc finger nucleotide binding domain that has not been mutagenized is overlap PCR.

Additionally, the zinc finger nucleotide binding domain can be mutated.

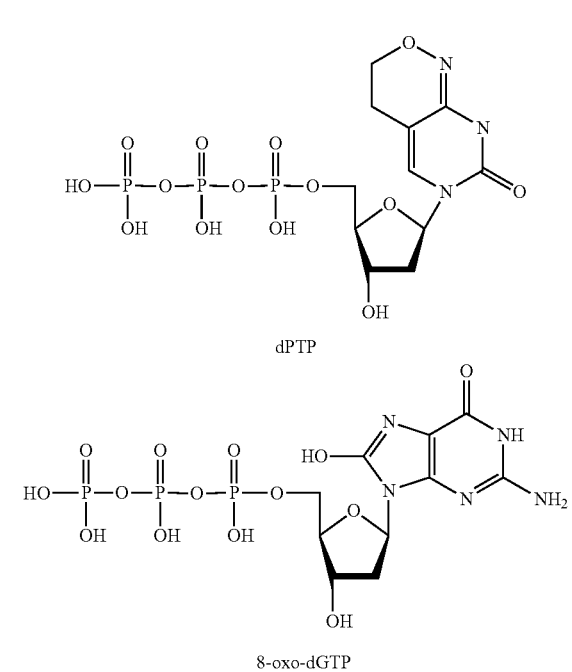

dPTP 8-oxo-dGTP

A preferred selection method is based on recombination between two difference spacer sequences, one suitable for use with Tn3 and the other suitable for use with Gin, to leave a single recombination site with a hybrid spacer sequence, followed by amplification with an oligonucleotide complementary to the hybrid spacer sequence. This selectively amplifies $Rec_{ZF}$s which catalyzed site-specific recognition. In one particularly preferred alternative, the hybrid spacer sequence is TCCAAAACCATAATATTTCG (SEQ ID NO: 633), designated 20G/T. Preferably, the selection method is designed to eliminate the possibility of homologous recombination.

The method can further comprise recombination of the active mutants after a plurality of rounds of selection using PCR shuffling. The PCR shuffling is typically employed after three rounds of selection, but can be employed after more or fewer rounds of selection.

Typically, the method further comprises recloning of active mutagenized fusion proteins. Typically, the method also further comprises sequencing of one or more fusion proteins produced by selection; the fusion proteins that are sequenced are ones that are most active in catalyzing recombination.

In at least one case, selection is for a single mutation that is equivalent in both Hin and Gin domains. In another case, selection is for a mutation in a Gin domain that matches the equivalent residue in native Hin. Typically, the selected mutagenized fusion proteins have a preference or bias for spacer sequence length that is substantially equivalent to the $Tn3_{GAGGAG}$ chimeric recombinase (20 bp>22 bp>18 bp, in order of descending activity).

Another aspect of the invention, therefore, is muteins of recombinases generated by the method described above.

In one application, chimeric recombinases according to the present invention can be used to catalyze site-specific excision from an appropriate genome. The appropriate genome can be the human genome. One context in which chimeric recombinases according to the present invention can be used to catalyze site-specific excision from the human genome is in transgene excision, as described above. Alternatively, genes such as, but not limited to, ICAM-5 and CCR5 can be excision targets. Excision events can be detected by FACS analysis and genomic PCR. Site-specific excision can also be performed by the direct use of purified chimeric recombinase proteins according to the present invention that are of appropriate specificity.

In still another approach to recombination, $Rec_{ZF}$ libraries can be used. A library of $Rec_{ZF}$ proteins (>1024 variants) can be assembled from the fusion of artificial zinc finger domains, such as are described above, to a common catalytic domain. Suitably weak binders can then be discovered by challenging this $Rec_{ZF}$ library with a defined DNA binding sequence. While the characterization of GXGGXG (SEQ ID NO: 636) is well suited to establish the existence of suitable weak sites, $Rec_{ZF}$ libraries may be a superior strategy for addressing particular sites within an endogenous genome. This is particularly useful for promoting recombination at "weak" sites as described above.

Similarly, chimeric recombinases according to the present invention can be used to promote cassette exchanges as described above. This requires the expression of two $Rec_{ZF}$s, comprising differing catalytic and zinc finger domains. Typically, vector sequences are optimized to minimize the possibility of homologous recombination.

Accordingly, methods according to the present invention can be used for site-specific excision and cassette exchange.

Additionally, unique recombinases can be constructed so that endogenous sites flanking the two genes are targeted so that genomes can be modified without placing recombination in the genes themselves that are to be recombined.

As described above, compositions according to the present invention can be used for gene therapy. In particular, compositions according to the present invention can be used for gene therapy with the object of excising harmful genes and integrating beneficial ones.

Among the harmful genes that can be excised are malignancy-associated oncogenes and the defective genes associated with junctional epidermolysis bullosa and Duchenne muscular dystrophy, as well as the defective genes associated with sickle cell anemia, thalassemia, and other hemoglobinopathies, severe combined immunodeficiency disease (SCID), Gaucher's disease, cystic fibrosis, hemophilia, familial hypercholesterolemia, and other conditions. In these examples, where the disease is due to a gene that is expressed and generates a nonfunctional or deleterious protein, such as in sickle cell anemia, and where the gene is homozygous, the gene can then be replaced by a wild-type or other functional gene by subsequent integration.

When the gene therapy involves removal of a deleterious gene by recombinational excision, in general, a method according to the present invention comprises the steps of:

(1) administering to an individual having a deleterious gene in the genome a composition including therein a nucleic acid encoding a site-specific recombinase according to the present invention, the site-specific recombinase, when expressed, specifically removing the deleterious gene from the genome; and (2) causing the site-specific recombinase to be expressed to specifically remove the deleterious gene from the genome.

These methods, alternatively, can be practiced with the use of purified chimeric recombinase proteins directly, without introduction of the gene or genes encoding them.

When the gene therapy involves removal of a deleterious gene by recombinational excision and subsequent replacement of the deleterious gene by recombinational integration, a method according to the present invention comprises the steps of:

(1) administering to an individual having a deleterious gene in the genome a nucleic acid encoding a site-specific recombinase, the site-specific recombinase, when expressed, removing the deleterious gene from the genome;

(2) causing the site-specific recombinase to be expressed to specifically remove the deleterious gene from the genome;

(3) administering to the individual a nucleic acid including therein a functional replacement gene for the deleterious gene; and (4) inserting the functional replacement gene into the genome by recombinational integration catalyzed by the site-specific recombinase.

Yet another method for gene therapy according to the present invention, and the most elegant, is a method for gene therapy in which therapeutic integration is performed in order to disrupt the structure or functioning of a deleterious gene and to deliver a gene with improved function into a selected genomic locus comprising administering to an individual with a deleterious gene in the genome: (1) a DNA segment including therein the gene with improved function; and (2) at least one chimeric recombinase according to the present invention that acts to integrate the DNA segment including therein the gene with improved function into the genomic locus of the deleterious gene. The method can further comprise administering at least one naturally-occurring serine recombinase that acts at a native recombination site.

As another application, therapeutic cassette exchange can be used for directly replacing damaged or defective alleles with functional alleles or alleles that confer a desired function.

Methods for gene therapy are well known in the art and are described, for example, in B. R. Glick & J. J. Pasternak, "Molecular Biotechnology: Principles and Applications of Recombinant DNA ($2^{nd}$ ed., 1998, ASM Press, Washington D.C.), ch. 21, pp. 555-588, incorporated herein by this reference. Briefly, viral gene delivery systems that can be used for gene therapy include, but are not limited to, retroviral vector systems, adenoviral vector systems, adeno-associated viral vector systems, and herpes simplex viral vector systems. Nonviral gene delivery systems that can be used for gene therapy include, but are not limited to, direct microinjection, such as with a gene gun, liposomal transfection, the use of DNA bound to poly-L-lysine conjugated to a specific cell receptor, the use of microchromosomes, and other techniques well known in the art.

Another aspect of the present invention is a pharmaceutical composition.

In one alternative, the present invention provides a pharmaceutical composition comprising:

(1) a therapeutically effective quantity of a chimeric recombinase according to the present invention as described above; and (2) a pharmaceutically acceptable carrier.

In another alternative, the present invention provides a pharmaceutical composition comprising:

(1) a therapeutically effective quantity of a nucleotide sequence that encodes a chimeric recombinase according to the present invention as described above; and (2) a pharmaceutically acceptable carrier.

When the pharmaceutical composition comprises a therapeutically effective quantity of a nucleotide sequence, the nucleotide sequence is preferably DNA. The nucleotide sequence can be incorporated into a delivery system for gene therapy as described above, such as a viral or nonviral system.

The preparation of a pharmaceutical composition that contains active ingredients dissolved or dispersed therein is well understood in the art. Typically such Compositions are prepared as sterile injectables either as liquid solutions or suspensions, aqueous or non-aqueous, however, solid forms suitable for solution, or suspensions, in liquid prior to use can also be prepared. The preparation can also be emulsified. The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. Other excipients are known in the art and can include, but are not necessarily limited to, calcium carbonate, calcium phosphate, various sugars or types of starch, cellulose derivatives, gelatin, vegetable oils, polyethylene glycols and physiologically compatible solvents. In addition, if desired, the composition can contain minor amounts of auxiliary substances such as wetting or emulsifying agents, as well as pH buffering agents and the like which enhance the effectiveness of the active ingredient. Still other ingredients that are conventional in the pharmaceutical art, such as chelating agents, preservatives, antibacterial agents, antioxidants, coloring agents, flavoring agents, and others, can be employed depending on the characteristics of the composition and the intended route of administration for the composition.

The pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylaminoethanol, histidine, procaine and the like. Physiologically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl deal % and water-oil emulsions.

The pharmaceutical compositions can be administered in conjunction with one or more pharmaceutically acceptable carriers. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agent, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. For administration of any of the compounds used in the present invention, preparations should meet sterility, pyrogenicity, general safety, and purity standards as required by the FDA Office of Biologics Standards or by other regulatory organizations regulating drugs.

Pharmaceutical compositions according to the present invention can be formulated for oral, sustained-release oral, buccal, sublingual, inhalation, insufflation, or parenteral administration. If the composition is administered orally, it is typically administered in a conventional unit dosage form such as a tablet, a capsule, a pill, a troche, a wafer, a powder, or a liquid such as a solution, a suspension, a tincture, or a syrup. Oral formulations typically include such normally employed excipients as, for example, pharmaceutical grades of mannitol, lactose, starch, magnesium stearate, sodium saccharin, cellulose, magnesium carbonate, and other conventional pharmaceutical excipients. In certain defined embodiments, oral pharmaceutical compositions will comprise an inert diluent and/or assimilable edible carrier, and/or they may be enclosed in hard or soft shell gelatin capsules. Alternatively, they may be compressed into tablets. As another alternative, particularly for veterinary practice, they can be incorporated directly into food. For oral therapeutic administration, they can be incorporated with excipients or used in the form of ingestible tablets, buccal tablets, dragees, pills, troches, capsules, wafers, or other conventional dosage forms.

The tablets, pills, troches, capsules, wafers, or other conventional dosage forms can also contain the following: a binder, such as gum tragacanth, acacia, cornstarch, sorbitol, mucilage of starch, polyvinylpyrrolidone, or gelatin; excipients or fillers such as dicalcium phosphate, lactose, microcrystalline cellulose, or sugar; a disintegrating agent such as potato starch, croscarmellose sodium, or sodium starch glycolate, or alginic acid; a lubricant such as magnesium stearate, stearic acid, talc, polyethylene glycol, or silica; a sweetening agent, such as sucrose, lactose, or saccharin; a wetting agent such as sodium lauryl sulfate; or a flavoring agent, such as peppermint, oil of wintergreen, orange flavoring, or cherry flavoring. When the dosage unit form is a capsule, it can contain, in addition to materials of the above types, a liquid carrier. Various other materials can be present as coatings or to otherwise modify the physical form and properties of the dosage unit. For instance, tablets, pills, or capsules can be coated with shellac, sugar, or both. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one alternative, a sustained-release formulation is used. Sustained-release formulations are well-known in the art. For example, they can include the use of polysaccharides such as xanthan gum and locust bean gum in conjunction with carriers such as dimethylsiloxane, silicic acid, a mixture of mannans and galactans, xanthans, and micronized seaweed, as recited in U.S. Pat. No. 6,039,980 to Baichwal, incorporated herein by this reference. Other sustained-release formulations incorporate a biodegradable polymer, such as the lactic acid-glycolic acid polymer recited in U.S. Pat. No. 6,740,634 to Saikawa et al., incorporated herein by this reference. Still other sustained-release formulations incorporate an expandable lattice that includes a polymer based on polyvinyl alcohol and polyethylene glycol, as recited in U.S. Pat. No. 4,428, 926 to Keith, incorporated herein by this reference. Still other sustained-release formulations are based on the Eudragit™ polymers of Rohm & Haas, that include copolymers of acrylate and methacrylates with quaternary ammonium groups as functional groups as well as ethylacrylate methylmethacrylate copolymers with a neutral ester group.

Oral liquid preparations can be in the form of, for example, aqueous or oily suspensions, solutions, emulsions, syrups, tinctures, or elixirs, or can be presented as a dry product for reconstitution with water or other suitable vehicles before use. Such liquid preparations can contain conventional additives such as suspending agents, for example, sorbitol syrup, methylcellulose, glucose/sugar syrup, gelatin, hydroxymethylcellulose, carboxymethylcellulose, aluminum stearate gel, or hydrogenated edible fats; emulsifying agents, such as lecithin, sorbitan monooleate, or acacia; non-aqueous vehicles (which may include edible oils), for example, almond oil, fractionated coconut oil, oily esters, propylene glycol, or ethyl alcohol; or preservatives, for example, methylparaben, propylparaben, or sorbic acid. The preparations can also contain buffer salts, flavoring, coloring, or sweetening agents (e.g., mannitol) as appropriate.

When compounds are formulated for parenteral administration, e.g., formulated for injection via the intravenous, intramuscular, subcutaneous, intralesional, or intraperitoneal routes, many options are possible. The preparation of an aqueous composition that contains an effective amount of the chimeric recombinase or nucleotide sequence will be known to those of skill in the art. Typically, such compositions can be prepared as injectables, either as liquid solutions and/or suspensions. Solid forms suitable for use to prepare solutions and/or suspensions upon the addition of a liquid prior to injection can also be prepared. The preparations can also be emulsified.

The pharmaceutical forms suitable for injectable use include sterile aqueous solutions and/or dispersions; formulations including sesame oil, peanut oil, synthetic fatty acid esters such as ethyl oleate, triglycerides, and/or aqueous propylene glycol; and/or sterile powders for the extemporaneous preparation of sterile injectable solutions and/or dispersions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. In all cases the form must be sterile and/or must be fluid to the extent that the solution will pass readily through a syringe and needle of suitable diameter for administration. It must be stable under the conditions of manufacture and storage and must be preserved against the contaminating action of microorganisms, such as bacteria or fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and use, these preparations contain a preservative to prevent the growth of microorganisms. Suitable non-sensitizing and non-allergenic preservatives are well known in the art.

The carrier can also be a solvent and/or dispersion medium containing, for example, water, ethanol, a polyol (for example, glycerol, propylene glycol, and/or liquid polyethylene glycol, and/or the like), suitable mixtures thereof, and/or vegetable oils. The proper fluidity can be maintained for example, by the use of a coating, such as lecithin, by the maintenance of a suitable particle size in the case of a dispersion, and/or by the use of surfactants. The prevention of the action of microorganisms can be brought about by the inclusion of various antibacterial and/or antifungal agents, for example, parabens, chlorobutanol, phenol, sorbic acid, or thimerosal. In many cases it will be preferable to include isotonic agents, for example, sugars or sodium chloride. In many cases, it is preferable to prepare the solution in physiologically compatible buffers such as Hanks's solution, Ringer's solution, or physiological saline buffer. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by sterilization. Sterilization is typically performed by filtration. Generally, dispersions are prepared by incorporating the various sterilized active ingredients into a sterile vehicle which contains the basic dispersion medium and/or the other required ingredients. In the case of sterile powders for the preparation of sterile injectable solutions, the preferred methods of preparation are vacuum-drying and/or freeze-drying techniques that yield a powder of the active ingredients plus any additional desires ingredients from a previously sterile-filtered solution thereof. The preparation of more-concentrated or highly-concentration solutions for direct injection is also contemplated, where the use of dimethyl sulfoxide (DMSO) as solvent is envisioned to result in extremely rapid penetration, delivering high concentrations of the active agents to a small area if desired.

For parenteral administration in an aqueous solution, for example, the solution should be suitably buffered if necessary and/or the liquid diluent first rendered isotonic with sufficient saline, glucose, or other tonicity agent. These particular aqueous solutions are especially suitable for intravenous, intramuscular, subcutaneous, or intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected into the proposed site of infusion (see, e.g., "Remington's Pharmaceutical Sciences" ($15^{th}$ ed.), pp. 1035-1038, 1570-1580). Some variation in dosage will necessarily occur depending on the condition of the subject being treated. The person responsible for administration will, in any event, determine the appropriate dose for the individual subject. Compounds and compositions according to the invention can also be formulated for parenteral administration by bolus injection or continuous infusion and can be presented in unit dose form, for instance as ampoules, vials, small volume infusions, or pre-filled syringes, or in multi-dose containers with an added preservative.

Another route of administration of compositions according to the present invention is nasally, using dosage forms such as nasal solutions, nasal sprays, aerosols, or inhalants. Nasal solutions are usually aqueous solutions designed to be administered to the nasal passages in drops or sprays. Nasal solutions are typically prepared so that they are similar in many respects to nasal secretions, so that normal ciliary action is maintained. Thus, the aqueous nasal solutions usually are isotonic and/or slightly buffered in order to maintain a pH of from about 5.5 to about 6.5. In addition, antimicrobial preservatives, similar to those used in ophthalmic preparations, and/or appropriate drug stabilizers, if required, can be included in the formulation. Various commercial nasal preparations are known and can include, for example, antibiotics or antihistamines. Spray compositions can be formulated, for example, as aqueous solutions or suspensions or as aerosols delivered from pressurized packs, with the use of a suitable propellant, such as dichlorodifluoromethane, trichlorofluoromethane, dichlorotetrafluoroethane, 1,1,1,2,3,3,3-heptafluoropropane, 1,1,1,2-tetrafluoroethane, carbon dioxide, or other suitable gas.

Additional formulations that are suitable for other modes of administration include vaginal suppositories and/or pessaries. A rectal pessary or suppository can also be used. Suppositories are solid dosage forms of various weights or shapes, usually medicated, for insertion into the rectum, vagina, or urethra. After insertion, suppositories soften, melt, and/or dissolve into the cavity fluids. In general, for suppositories, traditional binders or carriers can include polyalkylene glycols, cocoa butter, or triglycerides.

Other dosage forms, including but not limited to liposomal formulations, ointments, creams, lotions, powders, or creams, can alternatively be used. Ointments and creams can, for example, be formulated with an aqueous or oily base with the addition of suitable gelling agents and/or solvents. Such bases, can thus, for example, include water and/or an oil such as liquid paraffin or a vegetable oil such as arachis (peanut) oil or castor oil or a solvent such as a polyethylene glycol. Thickening agents which can be used include soft paraffin, aluminum stearate, cetostearyl alcohol, polyethylene glycols, microcrystalline wax, and beeswax. Lotions can be formulated with an aqueous or oily base and will in general also contain one or emulsifying agents, stabilizing agents, dispersing agents, suspending agents, or thickening agents.

Powders for external application can be formed with the aid of any suitable powder base, for example, talc, lactose, or starch.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps the dose frequency, will also vary according to the age, body weight, and response of the individual patient. A program comparable to that discussed above may be used in veterinary medicine.

Chimeric recombinases according to the present invention, and pharmaceutical compositions including them or nucleic acid molecules encoding them, can be used in the genetic Manipulation of all organisms with double-stranded DNA, particularly those unsuited to homologous recombination (of which there are a great number, including all plants). This could be done both in vitro and in vivo. This application of chimeric recombinases touches on almost every aspect of industrial biotechnology, including agriculture (for example, development of GMOs), pharmaceuticals (for example, therapeutics made by transgenic animals), medicine (for example, disease models), in vitro fertilization (for example, correction of diseased genes in, embryonic stem cells), and research (for example, forward and reverse genetics).

In the use of chimeric recombinases according to the present invention for forward genetics, one application is the use of $Rec_{ZF}$s with minimal DNA binding domains (for example, didactyl zinc finger proteins), such that the $Rec_{ZF}$ will have many potential recombination sites within a given genome. While each such protein may be inadequate for single site modification, it might be used to generate a unique pattern of recombination mutagenesis (for example, by integrating plasmids that either activate or inactivate nearby genes) useful for forward genetic selections. In the example of didactyl zinc finger proteins, this implies ~2000 different mutagenic patterns, each one related to the $Rec_{ZF}$ DNA specificity.

The subject to be treated can be a human patient or a socially or economically important animal, including, but not limited to, a dog, a cat, a horse, a cow, a goat, a sheep, a goat, or a pig. Methods according to the present invention are not limited to the treatment of humans.

Another aspect of the present invention is a transgenic organism produced by an act of recombination catalyzed by a chimeric recombinase according to the present invention.

In one alternative, the transgenic organism is a eukaryote. The eukaryote can be a mammal, such as a transgenic mammal that produces a product not normally produced by the species of mammal to which the transgenic mammal belongs. In another alternative, the eukaryote can be an insect, such as a transgenic insect that is modified to reduce the fertility of the insect or the ability of the insect to cause disease or economic harm. For example, this technique could be used in place of irradiation to generate sterile pests that would prevent the mating of fertile pests and the consequent spread of the pests through reproduction. An example of a pest to which this technique could be applied is the Mediterranean fruit fly or "medfly." In still another alternative; the transgenic eukaryote can be a plant. The transgenic plant can produce a product not normally produced by the species of plant to which the transgenic plant belongs. These transgenic plants could be used for the production of therapeutically significant proteins such as antibodies. Alternatively, the transgenic plant can be modified to possess improved growth characteristics, reduced nutrient requirements, or improved nutrient content. These plants could be used as the basis of improved food products.

In other alternatives, the transgenic organism can be a transgenic yeast or a transgenic bacterium. Such transgenic yeast or bacteria can be used in methods such as industrial fermentation processes.

The invention is described by the following Example. This Example is included for illustrative purposes only and is not intended to limit the invention

EXAMPLE 1

Construction, Analysis, and Activity of Chimeric Zinc Finger Recombinases

Site-specific recombinases, including Cre-lox, Flp-FRT, and φC31-att, enable researchers to manipulate chromosomal DNA with high fidelity in vitro and in vivo. Once recombination sites have been introduced into endogenous loci by homologous recombination, site-specific recombinases (SSRs) may catalyze excision, inversion, or integration. This two step methodology for endogenous genome modification has revolutionized forward and reverse genetics. When SSRs are selectively activated in vivo, the resulting conditional knockouts can reveal a gene's function with exquisite spatial and temporal specificity.

In contrast to the commonly used tyrosine recombinases (Cre and Flp) and large serine integrases (φC31), members of the resolvase/invertase family of serine recombinases are modular in both form and function. Once dimers have bound at the sites of recombination, every subsequent step—including tetramerization, strand cleavage, exchange, and ligation—is mediated solely by the catalytic domain. This modularity makes it possible to retarget recombination by replacing the endogenous DNA binding domain (1,2).

Polydactyl zinc finger proteins bind with high affinity and specificity to DNA. From $Cys_2$-$His_2$ zinc finger motifs, our laboratory has engineered modular building blocks that bind specifically to every GNN triplet, most ANNs and CNNs, and some TNNs. DNA binding domains specific for 6 to 18 by DNA sites are readily constructed using these building blocks (3-6). Chimeric proteins containing these novel DNA binding domains have effectively directed transcriptional activation and repression (3, 7-14), DNA cleavage (15-24), and genetic integration (25).

Our first $Rec_{ZF}$, similar to Z-resolvases concomitantly assembled by Stark and coworkers (1), efficiently recombined hybrid recombination sites: two inverted zinc finger binding sites flanking a 20-bp center spacer region. This simple fusion, however, produced a chimera with inherent sequence bias that confined its activity to sites closely related to the sequence recognized by the parent recombinases. In this work, we demonstrate the use of Substrate Linked Protein Evolution (SLiPE) (26) to engineer a $Rec_{ZF}$ with desired sequence specificity. We anticipate that this combination of rational design and direct evolution will permit site-specific recombination in any endogenous context.

Results

Design of RecZFs

Serine recombinases bind to their cognate crossover sites as head-to-head dimers. In nature, these dimers and adjacent, DNA-bound cofactor proteins assemble into large multimeric synapses and topological constraints ensure selective production formation. Decades of mechanistic studies (27-34), structural characterization (35-36), and analysis of functional chimeras (1,2) have revealed the elegant mechanism of recombination. A catalytic tetramer forms between two crossover sites and mediates the coordinated cleavage of all four DNA strands by serine nucleophilic attack, covalently linking each strand to a separate monomer. The ensuing intermediate contains a large, planar, hydrophobic surface that divides the tetramer, enabling the 180 degrees rotation required for strand exchange. The recombination reaction is completed when the four free DNA 3' hydroxyls attack the serine esters, generating new phosphodiester bonds.

Mutants of several invertase/resolvases serine recombinases have been found that do not require accessory factors or orthogonal binding sites for their function (37-40). Minimal recombination sites for these variants consist of just two inversely repeated DNA sequences that are recognized by the DNA binding domains. We reasoned that if the endogenous DNA binding domains of hyperactive serine recombinases were replaced with polydactyl zinc finger proteins, site-specific recombination could be targeted to any desired sequence.

Before constructing a $Rec_{ZF}$, we modeled the recombinase/zinc finger chimera using INSIGHTII by overlaying the crystal structures of the zinc finger protein ZIF268 (41) and the GammaDelta resolvase 42 (FIG. 12a). This analysis allowed us to rationally design the linker used to fuse the zinc finger protein to the Tn3, Hin, or Gin catalytic domains. We elected to truncate each recombinase near the C-terminal end of its flexible linker (residue 145 of Tn3, 143 of Hin, 142 of Gin) and add an additional three residues (SGS) before the start of the canonical zinc finger. The first zinc finger protein selected for fusion, a didactyl protein hereafter referred to as 'G,' was predicted to bind the DNA nucleotides GAGGAG (SEQ ID NO: 1). Fusion of the G zinc finger protein with hyperactive Tn3 resolvase catalytic domain (with mutations G70S, D102Y, E124Q) (38) produced the Rec ZF Tn3Ch15$_G$.

In FIG. 12, RecZF design and functional assay is shown. (a) A model of a tridactyl $Rec_{ZF}$ chimera dimerized with the gamma delta resolvase. (b). The combined substrate and $Rec_{ZF}$ expression plasmid used in resolution and inversion assays, and directed evolution. (c-e) Pictorial descriptions of PCR assays of site-specific resolutions (c) inversion (d), and integration (e), between 20T recombination sites by Tn3Ch15$_G$. (f) PCF assays of recombination between 20T recombination sites by Tn2Ch15$_G$. Lane 1 contains molecular weight markers at 250, 500, 750, 1000, 4500 2000, 2500, 3000, 4000, 5000, 6000, 8000, and 10,000 by (Promega 1 kb ladder). Results of resolution assays (Res) are shown in lanes 2 and 7 (Res(B), PCR negative control). Successful resolution increases the intensity of the product band. (1.0 kb) relative to the substrate band (1.8 kb). Results of the inversion assays (Inv) are shown in lanes 3 and 8 (Inv(B), PCR negative control.) Successful integration generates a product band (0.4 kb). Integration reactions were performed in the presence of a second plasmid, which either contained (Int(+), lane 4), or lacked (Int(−), lane 5) a G20T recombination site. Lane 6 contains molecular weight markers at 100, 200, 300, 400, 500, 600 700, 800, 900, 1000, 1200, and 1500 by (Roche 100 by ladder). For all assays, the plasmid was introduced by electroporation into *E. coli*, and culture maintained at 37° C. overnight. PCR was performed with 30 ng plasmid DNA, and analyzed on a 1% agarose gel. PCR negative control reactions were performed without template (lanes 7, 8, and 9). (g) Resolution assays, performed in the same manner, of cassettes, containing 20T spacer derivatives (Table 1): G18T-G-G18T (lane 1, 18-18), G18-T-G20T (lane 2, 1.8-20) G20T-G-G20-T (lane 3, 20-20), G221-G-G20T (lane 4, 22-20, G22T-G-G22T (lane 5, 22-22) G20TC-G-G20T (lane 7, TC), G20TC4-G-G20T (lane 8, C4), G20TC5-G-G20T (lane 9, C5), G20TC6-G-G20T (lane 10, C6), G20TC7-G-G20T (lane 11, C7), G20G-G-G20T (lane 12, g). Lane 6 contains the Promega 1 kb ladder. The negative control PCR reaction performed without template is shown in f, lane 7.

Zinc finger-recombinase fusion proteins ($Rec_{ZF}s$) bind and function, at hybrid recombination sites. These sites are composed of two zinc finger domain binding sites (in inverted repeat) flanking a central spacer region (~20 bp) (FIG. 12b). The G20T site, for example, is GAGGAGTGATAATTTATAATATTTCGCTCCTC (SEQ ID NO: 2), where each binding site for the G zinc finger protein (GAGGAG (SEQ ID NO: 1)) is underlined. The intervening spacer region, 20T, is the central 20 base pairs of site I within the res recombination site of the native Tn2 transposon (43). Substrates corresponding to zinc finger domains H1 (GGAGGCGTG) (SEQ ID NO: 634) and P2 (GCAGTG-GCG) (SEQ ID NO: 635) were also assembled. Additional spacers included point mutants of 20T and 20G, adapted from the central 20 by of the gix recombination site (Table 1). (44) Three plasmid-based PCR assays were developed to detect resolution, inversion, and integration catalyzed by RecZFs (FIG. 12c-e). When the gene encoding Tn3Ch915G was electroporated into *Escherichia coli* on plasmids bearing G20T, significant levels of all three reactions were observed (FIG. 12f). By contrast, chimeras assembled from hyperactive Hin (H107Y) (45) and Gin (H106Y) (37) catalytic domains (HinG and GinG, respectively demonstrated only weak invertase activity in the same assays with G20T (data not shown).

The optimal distance between zinc finger finding sites (ZFBSs) was determined by evaluating Tn3Ch15$_G$ activity on a panel of substrates. Each RecZF site was composed of two inverted zinc finger binding sites, separated by 18-, 20-, or 22-bp spacers (Table 1, FIG. 12b). This range of spacer distances, initially inferred from the computer model, was examined using resolution assays on a series of substrate plasmids bearing two recombination sites of varied sizes (FIG. 12g). Because the final step of the resolution assay was a PCR reaction in which substrate and product fragments were simultaneously amplified (FIG. 12c), the relative intensity of each band on an agarose gel was proportional to the rate of RecZF catalyzed resolution. Comparison of such qualitative rates suggested that whereas Tn3CH15$_G$ tolerated 18- and 22-bp spacer arrangements, 20 bp was optimal for the reaction. This result is similar to the 22-bp optimum spacer previously reported for another zinc finger-recombinase (1). The slight difference may be due to different linker lengths: five amino acids (aa) in our Tn3Ch15$_G$ resolvase and 14 aa in the best Z-resolvase. Also of note was the capacity of Tn3Ch15$_G$ to tolerate a variety of distances between zinc finger binding sites. In the final application of these enzymes, this may increase the number and/or utility of RecZF sites present with an endogenous sequence.

TABLE 1

| Spacer | Sequence 09876543211234567890 |
|---|---|
| 20T | TGATAATTTATAATATTTCG (SEQ ID NO: 639) |
| 20 (T L/T L) | TGATAATTTATAAATTATCA (a, b) (SEQ ID NO: 640) |
| 20 (T R/T R) | CGAAATATTATAATATTTCG (a, b) (SEQ ID NO: 641) |
| 18 T | GATAATTTATAATATTTC (SEQ ID NO: 642) |
| 22T | CTGATAATTTATAATATTTCGA (SEQ ID NO: 643) |
| 20TTC | TGATAATTTTCAATATTTCG (a) (SEQ ID NO: 644) |
| 20TC4 | TGATAACTTATAATATTTCG (a) (SEQ ID NO: 645) |
| 20TC5 | TGATACTTTATAATATTTCG (a) (SEQ ID NO: 646) |
| 20TC6 | TGATGATTTATAATATTTCG (a) (SEQ ID NO: 647) |
| 20TC7 | TGACAATTTATAATATTTCG (a) (SEQ ID NO: 648) |
| 20G | TCCAAAACCATGGTTTACAG (a) (SEQ ID NO: 632) |
| 20 (G L/T R) | TCCAAAACCATAATATTTCG (a, c) (SEQ ID NO: 633) |
| 20 (T L/G R) | TGATAATTTATGGTTTACAG (a, c) (SEQ ID NO: 649) |
| 20 (G L/T L) | TCCAAAACCATAAATTATCA (a, d) (SEQ ID NO: 650) |
| 20 (G R/T R) | CTGTAAACCATAATATTTCG (a, d) (SEQ ID NO: 651) |
| ZF | Binding Site |
| G | GAG GAG (SEQ ID NO: 1) |
| H1 | GGA GGC GTG (SEQ ID NO: 634) |
| P2 | GCA GTG GCG (SEQ ID NO: 635) |

Each RecZF recombination site is composed of two zinc finger binding sites in inverse repeat, flanking a spacer region (ex. G-20T-G is GAGGAG TGATAATTTATAATATTTCG CTCCTC (SEQ ID NO: 652), where binding sites are underlined)
(a) Bold signifies a mutation of the 20T spacer sequence.
(b) Product of inversion between spacers 20T and 20T
(c) Product of resolution between spacers 20G and 20T
(d) Product of inversion between spacers 20G and 20T The spacer sequence tolerance of Tn3Ch15$_G$ was also assessed using comparative resolution assays (FIG. 12g). In this case, one of the two recombination sites contained mutations within 20T, the native Tn3 recombination site sequence (Table 1). Previous studies had evaluated the tolerance of serine recombinases for mutations in this region (46-47) and had revealed that mutations 2, 3, 4, 7, 8, and 9 bp away from the center of the crossover site (positions depicted in Table 1)

are well tolerated, whereas alteration at positions 1, 5, 6, and 10 dramatically inhibits the function of the native Hin and GammaDelta recombinases. Mutation at position 1 prevents the efficient ligation of product sites (48). Cytosine and guanosine substitutions at positions 5 or 6 interrupt a critical interaction between the minor groove and a conserved arginine in the recombinase linker (142, Tn3; 140, Hin; 139, Gin). Specificity at position 10 is provided by the endogenous helix-turn-helix DNA binding domains. Tn3Ch15$_G$ tolerated substrates with point mutations at every position investigated (G20T (C4), G20T (C5), C20T (C6), and G20T (C7)), except position 1 (G20T (TC)). Simultaneous mutations at multiple positions, however, were not well tolerated. Resolution was inefficient with a substrate that contained a spacer sequence (200) derived from the native Gin site (44) that differed from 20T at 12 of 20 positions. From these experiments, we concluded that the straightforward fusion of hyperactive catalytic domain with a zinc finger protein afforded a chimera that inherited the restrictive sequence bias of its parent recombinase.

Evolution of RecZFs with Optimized Substrate Specificity

With the aim of generating tools for endogenous genome recombination, we sought to eliminate Rec$_{ZF}$ spacer sequence bias. Rec$_{ZF}$s were enriched by Substrate Linked Protein Evolution (SLiPE) (26) for proteins with the ability to efficiently recombine two non-homologous spacer sequences, 20T and 20G. The SLiPE approach united recombinase gene and substrate on the same plasmid such that each resolvase, expressed in $E.$ $coli$, is provided with the opportunity to modify its parent plasmid (FIG. 13$a$). In this way, each resolution product encoded an active recombinase and was physically distinguishable from substrate plasmids. Subsequent PCR amplification generated a unique product band, containing a pool of mutants, enriched in proportion to their fitness. Because our substrate contained non-homologous sites, we were able to design a primer, G20S3, to selectively anneal to resolution products at the hybrid recombination site G20(G$_L$/T$_R$) (Table 1). Compared to selection PCR with flanking primers (26), G20S3 conferred two advantages: dramatic enhancement of product amplification and selective enrichment for desired site-specific recombination.

Hin, Gin, and Tn3 catalytic domains were amplified by error-prone PCR and were subsequently fused to (error-free) zinc finger protein G to generate three libraries of mutant Rec$_{ZF}$s: HinL1$_G$, GinL1$_G$, and Tn3L1$_G$. After three rounds of SLiPE, Rec$_{ZF}$s within each selected pool were recombined using the DNA shuffling method first described by Stemmer (49). Five additional rounds of selection were sufficient to enrich for functional G20G-G-G20T resolvases (FIG. 13$b$). Eight highly active clones were identified from each pool by colony PCR screens and resolution assays. Mutations present in 50% or more of these clones (FIGS. 13, $c$, and $d$) are grouped into four regions: the active site loop that includes the catalytic serine residue (I12V, D13G; where all numbers correspond to Tn3 equivalent positions), the long E-helix and proximal side of the core subdomain (K65R, G70S, M72V, I80M, TI08A), the solvent exposed sub-domain surface (K53E), and the flexible linker (K151M). D13G was the most frequent mutation observed in Hin and Gin catalytic domains. This substitution likely destabilizes the adjacent A-helix, thereby increasing the flexibility of this region. The rate enhancement evolved in the mutant enzymes might arise from more optimal positioning of catalytic active site residues for strand cleavage. The same effect might be achieved with mutations that alter the relative positions of the E-helix (residues 103-137) and core subdomain (1-102). Several mutations selected in Gin (M70V, T96A) and Tn3 (I80M, V108A) domains occurred at residues that mediate this intramolecular interaction. Substitutions around the catalytic serine and helical interface may afford the flexibility required to form the tetrameric synaptic intermediate on a suboptimal spacer. One of the most active catalytic domains, GinL7C7 (D12G, N14S, N20D, K50E, M70V, I94V, Y109H, M114V, K148M; where Y109H is a reversion to wild type Gin and K148 is a linker mutation), was selected for further characterization.

In FIG. 13, directed evolution of Rec$_{ZF}$ G20G-G-G20T resolvase is shown. (a) Substrate Linked Directed Evolution (SLiPE) with a product specific selection primer. Lane 1 contains the Promega 1 kb ladder. Results of selection assays are shown in lanes 2-4. Successful resolution generates a product band (0.8 kb). Lane 2) Product mixture isolated after incubation of pB-GinL7C7$_G$-G20G-G-G20T in $E.$ $coli$, overnight at 37° C. (Rec$_{ZF}$ (+)); Lane 3) Rec$_{ZF}$ substrate plasmid pBSS-G20G-G-G20T (Rec$_{ZF}$(-)); Lane 4) PCR negative control performed without template (Rec$_{ZF}$(B)). (b) Functional improvement from the starting clones (sc; Tn3Ch15$_G$, Gin$_G$, Hin$_G$) and naïve libraries (1; Tn3L1$_G$, GinL1$_G$, HinL1$_G$), through rounds of interactive selection (2-8), to highly active clones (*; Tn3L8C18$_G$, GinL7C7$_G$; HinL6C4$_G$). Lane 1 contains the Promega 1 kb ladder. The negative control PCR reaction performed without template is shown in f, lane 7. Resolution assays were performed in the manner previously described. (c,d) Mutations selected in greater than and equal to 50% of highly active clones are depicted within a primary sequence alignment (c), and mapped onto the crystal structure of a DNA—bound gamma delta resolvase dimmer (d). Blue, novel Tn3 catalytic domains mutations; green, novel Gin catalytic domain mutations; orange, novel Hin, catalytic domain mutations; pink, hyperactivating mutations present in the original clones; red, the catalytic serine, S10.

Characterization of RetZF Specificity and Substrate Tolerance

Figure 14:
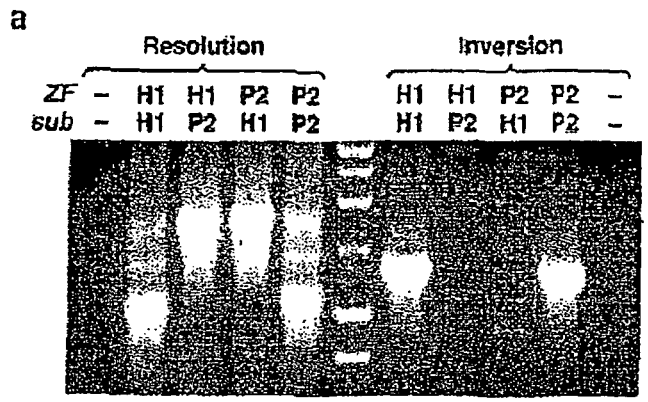
FIG. 14 depicts the characterization of the GinL7C7 catalytic domain. (a) Resolution and inversion assays, performed in the manner previously described, of GinL7C7$_{H1}$ (H1) and GinL7C7$_{P2}$ (P2), on substrates H120G-G-H120T (H1) and P220G-G-P220T (P2). Results of resolution assays are shown in lanes 1-t. Successful resolutions increase the intensity of the product band. (1.1 kb) relative to the substrate band (1.9) kb. Lane 6 contains the Promega 1 kb ladder. Results of inversion assays are shown in lanes 7-11. Successful inversion generates a product band (1.4 kb). PCR negative control reactions (–,–) were performed without template for both resolution (lane 1) and inversion (lane 11) assays. (b-c) Analysis of spacer sequence bias using Rec$_{ZF}$ substrate libraries. Inversion assays, conducted in the manner previously described, reacted GinL7C7G with four pools of substrates in which 5 bp regions has been randomized (b). Inversion related PCR products were gel purified and sequenced. The sequencing chromatogram of each aggregate of functional spacers (c, left). Full spacer regions (20T and 20G) are represented by the composite of chromatograms from two substrate libraries whose 5 bp randomized regions overlap at a single nucleotide (position 6, Table 1).
Figure 14:
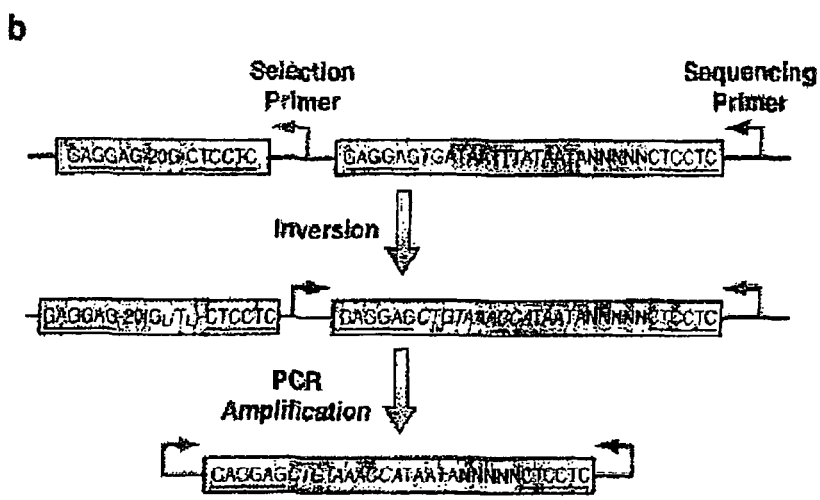
Figure 14:
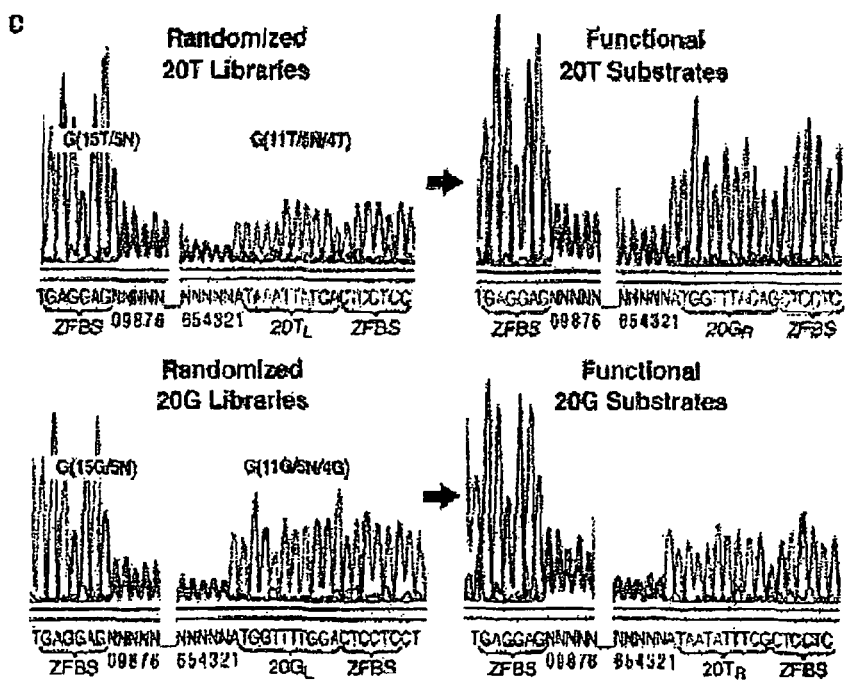

Rounds of selection on particular spacer sequences (20T and 20G) might have given rise to RecZFs with a novel substrate bias, and perhaps even fostered the ability to recombine those sequences in the absence of flanking zinc finger binding sites. To explore the latter possibility, we fused two new zinc finger proteins to catalytic domain GinL7C7. The resulting Rec$_{ZF}$s, GinL7C7$_{H1}$ and GinL7C7$_{P2}$, were expected to bind sequences 5'-GGAGGCGTG-3' (SEQ ID NO: 634) and 5'-GCAGTGGCG-3' (SEQ ID NO: 635), respectively. Substrates in which these sequences replaced 5'-GAGGAG-3' (SEQ ID NO: 1) (H120G-G-H120T, P220G-G-P220T) were prepared (Table 1). Rec$_{ZF}$s were cloned into each of the substrates and assayed for resolution and inversion (FIG. 14$a$). Recombination occurred only in samples in which the binding site and zinc finger protein were matched. This result suggests that Rec$_{ZF}$ function is restricted to loci flanked by cognate zinc finger binding sites.

In order to rapidly characterize the spacer sequence bias of the GinL7C7 catalytic domain, substrate libraries were prepared in which 5-base pair spacer regions were randomized. GinL7C7$_G$ was cloned into each library and assayed for inversion. After purifying inversion PCR products, we sequenced the aggregate population of functional recombination sites (FIG. 14$b$). The resulting chromatograms suggested an unexpectedly broad substrate tolerance, particularly within the five base pairs adjacent to the zinc finger binding site (FIG. 14$c$). This outcome shows that Rec$_{ZF}$s can be successfully targeted to sequences unrelated to a parental recombination site.

In FIG. 14, characterization of the GinL7C7 catalytic domain is shown. (a) Resolution and inversion assays, performed in the manner previously described, of GinL7C7$_{H1}$ (H1) and GinL7C7$_{P2}$ (P2), on substrates H120G-G-H120T (H1) and P220G-G-P220T (P2). Results of resolution assays are shown in lanes 1-t. Successful resolutions increase the intensity of the product band. (1.1 kb) relative to the substrate band (1.9) kb. Lane 6 contains the Promega 1 kb ladder. Results of inversion assays are shown in lanes 7-11. Successful inversion generates a product band (1.4 kb). PCR negative control reactions (−,−) were performed without template for both resolution (lane 1) and inversion (lane 11) assays. (b-c) Analysis of spacer sequence bias using Rec$_{ZF}$ substrate libraries. Inversion assays, conducted in the manner previously described, reacted GinL7C7G with four pools of substrates in which 5 bp regions has been randomized (b). Inversion related PCR products were gel purified and sequenced. The sequencing chromatogram of each aggregate of functional spacers (c, left). Full spacer regions (20T and 20G) are represented by the composite of chromatograms from two substrate libraries whose 5 bp randomized regions overlap at a single nucleotide (position 6, Table 1).

Rec$_{ZF}$ Recombination in the Human Genome

Our ultimate goal is to design Rec$_{ZF}$s that catalyze targeted and site-specific recombination at any desired site in the human genome. In order to evaluate recombination by our Rec$_{ZF}$s in human cells, we inserted a reporter cassette that encodes enhanced green fluorescent protein (EGFP) driven by a CMV promoter and flanked by recombination sites H120G and H120T into 293 embryonic kidney cells using the Invitrogen Flp-In System (FIG. 15a). Because only one copy of the cassette is present in each cell (50), site-specific resolution will generate an EGFP knockout and recombinase activity will be directly proportional to the percentage of cells with diminished fluorescence. We cloned Gin L7C7$_{N1}$ and GinL7C7$_{P2}$ into the pBabe-Puromycin expression vector (pBP) (51) The two constructs and the empty vector were introduced into the reporter cell line by retroviral transduction, and enriched by puromycin selection. When transduced cells reached confluence, nine days post-transduction, they were subjected to FACS analysis (FIGS. 15b, c) and genomic PCR (FIG. 15d). Both assays were in agreement: Rec$_{ZF}$s catalyzed genomic recombination efficiently and with zinc finger-mediated specificity. GinL7C7$_{H1}$ generated the expected product of PCR band (~200 bp) and lowered EGFP fluorescence in 17.0%±0.8% of transduced cells. By contrast, GinL7C7$_{P2}$ and the empty vector (pBP) generated neither product band nor significant numbers of non-fluorescent cells (1.7%±0.2% and 2.3%±0.4%, respectively). We verified the PCR result by sequencing the ~200 bp band, confirming that it was the expected product of site-specific resolution. In an effort to more tightly link genotype and phenotype, we isolated populations of EFGP and EGFP$^+$ cells transduced with pBP-GinL7C7$_{H1}$. Subsequent genomic PCR analysis substantiated the use of FACS as a measure of site-specific excision (FIG. 15d).

Figure 15:
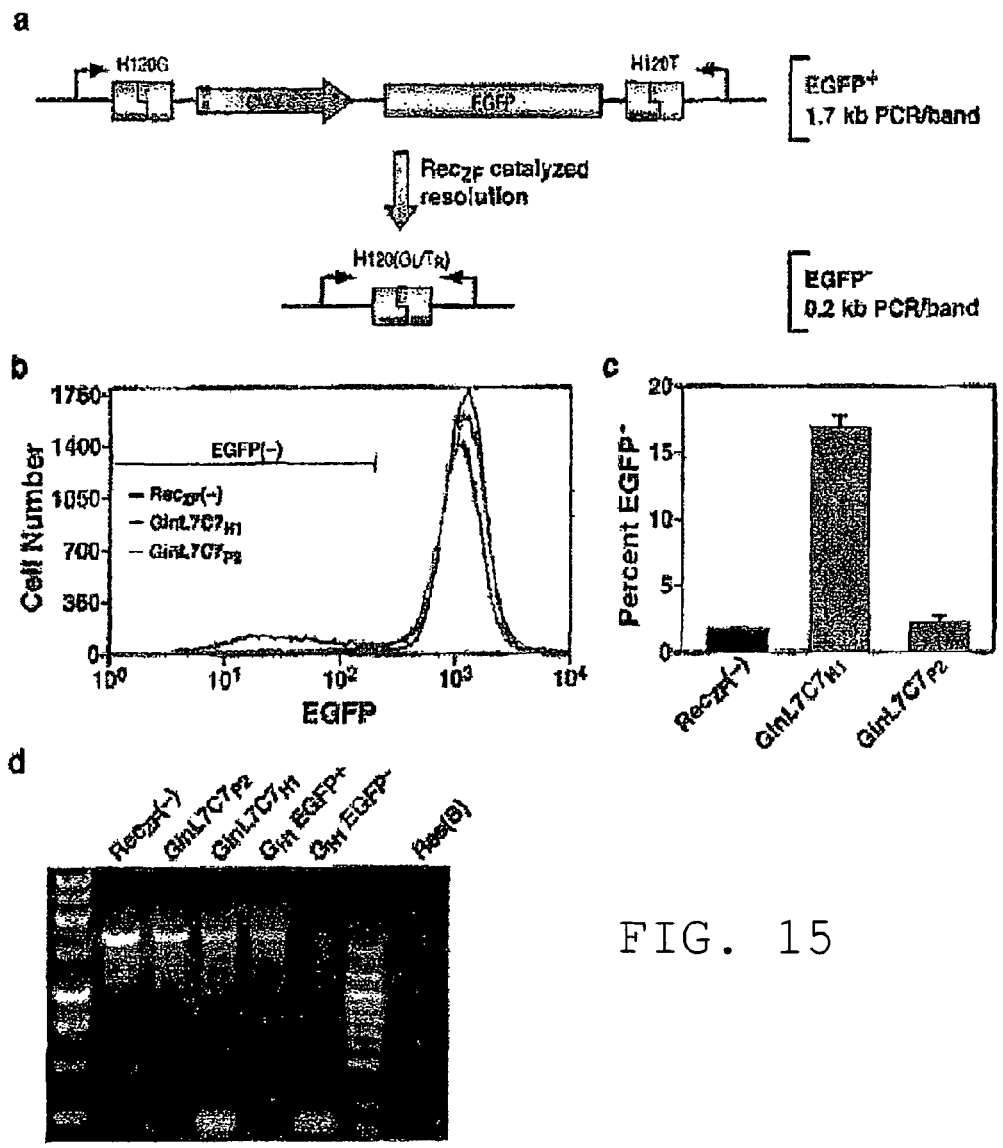
FIG. 15 shows targeted, site-specific resolution of the human genome. (a) A single copy of the reporter cassette for GinL7C7$_{H1}$ resolution was introduced into Flp-In™ 293 human embryonic kidney cells using the Flp-In system. (b, c, d) The reporter cell line was transduced with empty pBabe-Puromycin vector (RecZF (–)), GinL7C7$_{P2}$, and GinL7C7$_{H1}$, and enriched by puromycin selection (2 μg/mL). Nine days post-transduction, the fluorescence of each sample was determined by FACS (b). Percentages of cells with diminished fluorescence were averaged between three independent experiments (c). FACS samples were lysed for genomic DNA purification. Isolated DNA (100-400 ng) served as the PCR template for a genomic resolution assay (using primers depicted in (a)), and results were analyzed on a 1% agarose gel (d). Lane 1 contains the Promega 1 kb ladder. Results of resolution assays are shown in lanes 2-6 and 8 (Res(B), PCR negative control). Successful resolution increases the intensity of the product band (0.2 kb) relative to the substrate band (1.6 kb pb). Lane 6 contains the Roche 100 bp ladder.

In FIG. 15, targeted, site-specific resolution of the human genome is shown. (a) A single copy of the reporter cassette for GinL7C7$_{H1}$ resolution was introduced into Flp-In™ 293 human embryonic kidney cells using the Flp-In system. (b, c, d) The reporter cell line was transduced with empty pBabe-Puromycin vector (RecZF (−)), GinL7C7$_{P2}$, and GinL7C7$_{H1}$, and enriched by puromycin selection (2 µg/mL). Nine days post-transduction, the fluorescence of each sample was determined by FACS (b). Percentages of cells with diminished fluorescence were averaged between three independent experiments (c). FACS samples were lysed for genomic DNA purification. Isolated DNA (100-400 ng) served as the PCR template for a genomic resolution assay (using primers depicted in (a)), and results were analyzed on a 1% agarose gel (d). Lane 1 contains the Promega 1 kb ladder. Results of resolution assays are shown in lanes 2-6 and 8 (Res(B), PCR negative-control). Successful resolution increases the intensity of the product band (0.2 kb) relative to the substrate band (1.6 kb pb). Lane 6 contains the Roche 100 by ladder.

Discussion

Technologies currently used for targeted endogenous genome modification are largely based on either homologous recombination (HR) or site-specific recombination. Although HR can be readily targeted to any genetic sequence, the frequency of recombination is very low. Because HR relies on endogenous DNA repair machinery, the frequency of recombination is cell-type dependent and proportional to the degree of homology between substrates. SSRs by contrast, catalyze recombination between unrelated substrates, in any cellular environment. Applications of site-specific recombination, however, are circumscribed by the sequence specificity of known recombinases. Although much effort has been invested in improving the efficiency of HR (by the introduction of double-strand breaks (52), triplex forming oligonucleotides (53), or adeno-associated virus (54) and in altering SSR substrate preference (26, 55, 56) these limitations continue to preclude many application's of genome engineering and gene therapy.

In many ways, Rec$_{ZF}$s combine the best elements of HR and SSRs: efficient, targeted recombination of unrelated substrates in any cell type. It is now feasible to attempt resolution, inversion, or integration at, or between, genomic loci of interest. This gain in functionality, however, may appear to be offset by a coincident loss of control. HR generates stable products in the desired location and orientation, while serine integrases like C31 achieve the same end with unidirectional recombination. Simple Rec$_{ZF}$ reactions lack such precision because they are mediated by hyperactive catalytic domains insensitive to substrate orientation and topology. We envision a variety of strategies to control Rec$_{ZF}$-mediated recombination. The orientation of serine recombination is guided by the 2-bp overhang, at the center of the crossover site (48, 58) An overhang that is not its own reversed complement (unlike AT, in spacers 20G and 20T) should guide Rec$_{ZF}$ reactions in the same way; sites in direct repeat would allow resolution, whereas inverse repeats would allow inversion. Although it is possible that an unidirectional Rec$_{ZF}$ system may be created in the future, more immediate degrees of control may be gained by adapting strategies previously developed for Cre and Flp, including sub-optimal half-sites (59, 60) and recombination mediated cassette exchange (RMCE) (62) In addition to these techniques stable integration might be achieved via Rec$_{ZF}$ targeted transposition (62).

The novel functionality of Rec$_{ZF}$s should allow current SSR methodologies to be employed in any genetic context. We anticipate that the freedom to rapidly tailor endogenous genomes, in vitro and in vivo, will have broad application in research both basic and applied. The deliberate disruption of particular genes is an obvious use for Rec$_{ZF}$s and in this role they could facilitate reverse genetics in a variety of species in which HR is inefficient. Non-specific disruption, or activation, could be mediated by didactyl Rec$_{ZF}$s; in a manner comparable to transposases, each of the >200 Rec$_{ZF}$ variants would generate a unique pattern of genome mutagenesis. Rec$_{ZF}$s could also be used to manipulate the genomes of model organisms, thereby generating useful disease models in a manner analogous to HR (63) and SSRs (64-66)

Rec$_{ZF}$s may ultimately be used for therapeutic "genome surgery" to correct genetic defects and deliver life-enhancing genes. The small size of Rec$_{ZF}$ genes (~800 bp) would allow a single vector (67) to express the four different chimeras required for endogenous excision or integration. Similar gene therapies have failed because health risks outweigh the therapeutic benefits. Retroviral integrases can deliver genes with high efficiency, but non-specific integration can activate oncogenes. The specificity of HR makes it a good candidate for gene correction, but the associated DNA damage response may diminish the viability of treated cells (68). SSRs do not trigger a DNA damage response and would seem excellent vectors for therapeutic genes. Indeed, the site-specific integrase φC31 can target pseudo-sites in the mouse and human genomes (55, 69, 70), enabling successful in vivo treatment of murine disease models for junctional epidermolysis bullosa (71) Duchenne muscular dystrophy (72), and hereditary tyrosinemia type I (73) Unfortunately, φC31 shows significant levels of toxicity and inter-chromosomal recombination in human cells (70, 74).

We expect that if toxicity within the $Rec_{ZF}$s system becomes an issue with particular proteins, it can be mitigated by the careful choice of zinc finger domains. Although the tridactyl proteins in this study bind only 9 bp, hexadactyl zinc finger proteins that bind to 18 by can target a single site in the human genome. The specificity of these proteins has been demonstrated in vitro (75); hexadactyl ZFs mediate regulation of single genes in human cell and whole plants (76, 77). The ability to rapidly tune activity through DNA binding domain modification is a unique feature of these recombinases. Other issues, including intermediate disassociation (78), pseudo-site presence, and half-site activity (79) must be addressed as $Rec_{ZF}$s are evaluated for therapeutic use. However, in light of the remarkable functional plasticity evinced in this study, $Rec_{ZF}$s are promising tools that should facilitate a level of genomic modification heretofore inaccessible and may empower both the study of gene function and therapy.

Methods

Unless explicitly noted, PCR fragments and digests were purified using the PCR Purification Kit (QIAGEN, Valencia, Calif.). Vectors were treated with calf intestinal phosphatase (CIP, 1 μL for 1 hr at 37° C.; New England Biolabs, Ipswich, Mass.) to eliminate ligation background, and intermediate PCR products were gel purified (Zymoclean; Zymo Research, Orange, Calif.) prior to overlap PCR. All primer sequences are available in Supplementary Experimental Protocol 1 online.

Construction of $Rec_{ZF}$ Substrates

Each substrate plasmid contained a recombination cassette (e.g., G20T-G-G20T), composed of two $Rec_{ZF}$ recombination sites flanking a $GFP_{UV}$ gene with primers that each encoded a particular $Rec_{ZF}$ site (e.g., G20T-GFP-5' and GFP-G20T-3'). The PCR product was cloned (XbaI, HindIII) into pBSS, a variant of pBluescriptII SK(−) (pB; Stratagene, La Jolla, Calif.) in which the 1.2 kb SS stuffer (80) is inserted between the SacI and XbaI restriction enzyme sites.

Construction of $Rec_{ZF}$ Genes

The Tn3 resolvase catalytic domain was PCR amplified from the plasmid pWL625 (ATCC, Manassas, Va.) in two fragments: N-terminal (with primers Tn3Cat6-Prim1 and Tn3-resba102Y124Q) and C-terminal (with primers Tn3-resfo102Y124Q-2 and Tn3Cat6-Prim2). These fragments, along with an additional fragment encoding the zinc finger protein G (amplified from pRTBV2-HS2#11 with primers Tn3Cat8-2-Prim1 and Tn3Cat8-2-Prim2), were fused together by overlap PCR. The completed $Tn3_G$ gene was digested with SacI and XbaI and ligated into similarly digested pBSS-G20T-G-G20T. After screening colonies by resolution assay, a hyperactive single clone, $Tn3Ch15_G$, was selected for further work. In addition to hyperactivating mutations D102Y and E124Q characterized by Arnold and coworkers (38) $Tn3Ch15_G$ also contained the novel mutation S700.

The Gin invertase catalytic domain was PCR amplified from the genome of bacteriophage Mu (ATCC) in two fragments: N-terminal (with primers ResGin-Cat-Fo1-Prim1 and GinbaH106Y) and C-terminal (with primers GinfoH106Y and ResGin-Cat-Prim2). These fragments, along with an additional fragment, encoding the zinc finger protein G (amplified from pRTBV2-HS2#11 with primers Tn3Cat8-2-Prim1 and Tn3Cat8-2-Prim2), were fused together by overlap PCR. The complete $Gin_G$ gene was digested with SacI and XbaI and ligated into similarly digested pBSS-G20T-G-G20T. After screening colonies by inversion assay, a hyperactive single clone, $Gin_G$, was selected for further work. GinG contained the hyperactivating mutation H106Y characterized by Klippel and coworkers (37).

The Hin invertase catalytic domain was PCR amplified from the genome of Salmonella enterica (ATCC) in three fragments: N-terminal (with primers ResHin-Cat-Fo1-Prim1 and HinSacI-Prim2), middle (with primers HinSacI-Prim1 and HinbaH107Y), and C-terminal (with primers HinfoH107Y and ResHin-Cat-Prim2). These fragments, along with an additional fragment encoding the zinc finger protein G (amplified from pRTVV2-HS2#11 with primers Tn3Cat8-2-Prim1 and Tn3Cat8-2-Prim2), were fused together by overlap PCR. The completed $Hin_G$ gene was digested with SacI and XbaI and ligated into similarly digested pBSS-G20T-G-G20T. After screening colonies by inversion assay, a hyperactive single clone, $Hin_G$, was selected for further work. $Gin_G$ contained the hyperactivating mutation H107Y characterized by Merickel and coworkers (45).

Catalytic domains selected in each round of evolution were PCR amplified (by primers pUC18-Prim2 and ResCat-Prim2) and fused by PCR to an error-free copy of zinc finger protein G (amplified by primers RecZF-Prim 1 and pUC18-Prim 1) in the presence of pUC18-Prim1 and pUC18-Prim2. These new pools of RecZF genes were digested with SacI and XbaI and ligated into similarly digested pBSS-G20G-G-G20T for the next round of selection.

The tridactyl $Rec_{ZF}$ ($GinL7C7_{H1}$) was constructed by fusing the GinL7C7 catalytic domain and the H1 zinc finger protein. The GinL7C7 catalytic domain was PCR amplified from the resolution product (pB-G20($G_L/T_R$)-GinL7C7 with primers pUC18-Prim2 and ResCat-Prim2. The tridactyl zinc finger protein H1 was PCR amplified from pMal-HLTR3-HS1#4 with primers ResZF-Prim1 and Res3ZF-Prim2. These two fragments Were fused by PCR in the presence of pUC18-Prim2 and Res3ZF-Prim2, digested with SacI and XbaI, and ligated into a similarly digested substrate vector. Once the P2 zinc finger protein was PCR amplified from pMal-PBS-(s) HS2-J2 (with primers Res 2ZF-Prim1 and Res3ZF-Prim2), construction of GinL7C7 P2 proceeded in the same manner. When cloning $GinL7C_7H1$ and GinL7C7P2 for transduction and expression in human cells, the fusion PCR was performed with primers HBS-K0X-GinL7C7-Prim1 and Res3ZF-SEX-Prim2. The resulting fragments were digested with BG1 II and EcoRI and ligated between BamHI and ECoRI in pBabe-Puromycin (51) to create $pBP-GinL7C7_{H1}$ and $pBP-GinL7C7_{P2}$.

Recombination Assays $Rec_{ZF}$s, ligated behind the lac promoter on substrate plasmids, were electroporated into E. coli cells. On both solid and liquid media, these cells were allowed to grow overnight at 37° C. (in the absence of IPTG). Plasmid isolated the next day (from single colonies or by miniprep (QIAGEN)) was used to characterize Rec$_{ZF}$ function. In order to detect recombination events catalyzed by Rec$_{ZF}$s, we developed PCR assays for resolution, inversion, and integration (FIG. 12c-f). In each case, product information correlated with the appearance of a unique band as visualized on an agarose gel. The resolution assay (FIG. 12c; primers pUC18-Prim1 and pUC18-Prim2) amplified plasmid fragments from both substrate (1814 bp) and product (1039 bp) in proportion to the relative abundance of each. Inversion (FIG. 12d; primers pUC18-Prim2 and I-GFP-Mid-Prim2) and integration (FIG. 12e; primers pUC18-Prim1 and pACYC184-Prim3) were evidenced by the appearance of a single band (1263 by and 370 bp, respectively). In each case, only product plasmids contained complementary primer binding sites (PBS). Accordingly, the inversion and integration assays were highly sensitive, but provided little information about the extent of reaction. Whereas the resolution and inversion systems report on manipulation of the GFP$_{UV}$ region, detection of Rec$_{ZF}$ catalyzed integration reaction required a second, non-homologous, plasmid. For this purpose, pB-G20T-G-G20T and pACYC184 (New England Biolabs) were both digested with ZbaI and HindIII and the recombination cassette G20T-G-G20T was ligated into pACYC184 to generate pA-G20T-G-G20T. This construct was cotransformed with the resolution product, pB-20T-Tn3Ch15g, co-maintained under carbenicillin and chloramphenicol selection overnight at 37° C., purified by miniprep, digested with BglIII, treated with CIP, and retransformed into E. coli. Colonies that grew on chloramphenicol-selective media all contained the new resolution product, pA-20T. pB-20T-Tn3Ch15 was cotransformed with pA-20T and the two compatible plasmids were co-maintained under carbenicillin and chloramphenicol selection. Integrative products were detected when primers annealing to each plasmid (pUC18-Prim1 to pBluescript, and pACYC184-Prim3 to pACYC184) were able to complement each other. The control for this reaction, shown in lane 3b of FIG. 14, was co-transformation with unmodified pACYC184 (which lacks any potential recombination sites). All PCR assays were carried out using 30 ng of plasmid DNA and a program of 1 cycle of 5 min at 94° C.; 30 cycles of 30 s at 94° C., 30 s at 55° C., 90 s at 72° C.; and a final cycle of 7 min at 72° C.

Directed Evolution

Libraries of Rec$_{ZF}$ mutants were created by error-prone PCR by the method of Zaccolo and coworkers (81). Amplification of the hyperactive Hin, Gin, and Tn3 catalytic domains performed with primers pUC18-Prim2 and ResCat-Prim2, in the presence of the dNTP analogues, dPTP (12.5 µM) and 8-oxo-dGTP (12.5 µM), generated templates with randomly placed nucleotide analogs. Subsequent overlap PCR (with primers pUC18-Prim2 and Res2ZF-Prim2) fused each catalytic domain (containing an average of 3.2 amino acid changes) to an error-free copy of zinc finger protein G (in the manner previously described). These Rec$_{ZF}$ libraries were subsequently digested with SacI and XbaI and ligated into similarly digested pBSS-G20G-G-G20T for the first round of functional selection Plasmids were electroporated into E. coli cells (~$10^8$ transformants per ligation), allowed to grow overnight at 37° C. in liquid culture, and isolated by miniprep. This reaction aggregate was used as the template for a selection PCR (with primers G20S3 and pUC18-Prim2) carried out using 100-400 ng of plasmid DNA and a program of 1 cycle of 5 min at 94° C.; 30 cycles of 30 s at 94° C., 30 s at 55° C., 90 s at 72° C.; and a final cycle of 7 min at 72° C. After three rounds of selection, the remaining mutants in each pool were recombined using the PCR shuffling method described by Stemmer (49) After several additional rounds of selection, we sought to isolate clones of particularly high activity from each catalytic domain. In parallel, 50-200 colonies were screened for resolution activity. The 10-20 most active Rec$_{ZF}$s in each pool were PCR amplified (with primers pUC18-Prim1 and pUC18-Prim2), gel purified, and cloned into pBSS-G20G-G-G20T for a resolution assay. The sequences of the eight most active Hin, Gin, and Tn3 mutants found in this manner are represented, in aggregate, in FIGS. 2 c and d.

Substrate Tolerance Assay

Substrate libraries, G(15T/5N), G(11T/5N/4T), G(15G/5N), and G(11G/5N/4G), were generated using primers in which regions of the 3' spacer had been randomized (GFP-G(15T/5N)-3', GFP-G(11T/5N/4T)-3', GFP-G(15G/5N)-3', and GFP-G(11G/5N/4G)-3', respectively. Each library was a derivative of substrates G20G-G-G20T and G20T-G-G20G. In the case of 015T/5N, amplification with primers G20G-GFP-5' and GFP-G15T/5N-3' generated a pool of substrates in which the five base pairs on the Z terminus of 20T were randomized. Cloning, performed in the manner previously described, afforded libraries whose average number of molecules (~$10^5$) far exceeded the number of possible sequences (1024). Sequence randomization was confirmed by sequencing the aggregate population with pUC18 Prim1. GinL7G7$_G$ was ligated into each substrate library and transformed E. coli were incubated at 37° C. overnight in selective liquid media (5 µL carbenicillin), 2 mL SOC media, 3 mL SB media). Substrate and product plasmids in the aggregate culture were isolated by miniprep. Inversion PCR with the purified plasmid, performed with one primer inside the GFP$_{UV}$ gene (1-GFP-Mid-Prim1) and one outside the 3' recombination site (pUC18-Prim1), generated a product band containing only functional members of the substrate library. This mixture was subsequently sequenced and peaks in the aggregate chromatograms were presumed to be proportional to nucleotide representation in this population. The PCR strategy used for selecting inversion competent sequences precluded the use of libraries in which a more extended section of the spacer sequence was randomized. It is also noteworthy that randomization of the central base pairs compromised the site-specific precision required for use of aggregate chromatograms (data not shown).

Rec$_{ZF}$ Site-Specific Genomic Recombination

The EGFP gene (Clontech) was PCR amplified by primers containing Rec$_{ZF}$ sites (B-H120G-SII-EGFP-5' and EGFP-Z-H120T-H-3'), digested with BamHI and HindIII, and ligated between bgIII and HindIII in pcDNA5/FRT (Invitrogen, Carlsbad, Calif.). The CMV promoter of pcDNA 3.1/Hygro (Invitrogen) was amplified with primers SacII-CMV-5' and CMV-SacII-3', digested by SacII, ligated into the SacII site in the EGFP substrate plasmid and screened for orientation. Cotransfection of the CMV-EGFP substrate plasmid and Flp expression plasmid (pOG44, Invitrogen) allowed site-specific integration into the single FLP recombinase target (FRT) site present in the Flp-In™-293 cell line (Invitrogen). A single colony from this isogenic, hygromycin resistant population was isolated, characterized by FACS, and used as the substrate cell line (SubC) in all subsequent experiments. Cells were maintained in DMEM containing 10% FBS and antibiotics. Tissue culture media and reagents were Gibco/BRL (Invitrogen).

pBP-GinL7C7$_{H1}$ and pBP-GinL7C7$_{P2}$ were transfected into 293 packaging cells (12) using Lipofectamine Plus (Invitrogen) according to the manufacturers directions. The product retroviral particles were used to infect 2×$10^5$ SubC cells. At 48 h after infection, cells were exposed to 2 ng/mL puromycin. In this selective media, uninfected cells die within 48 h and the transduced population grows to confluency after nine days. The puromycin resistant population was subjected to flow cytometry analysis (using a (FACSCalibur dual laser cytometer) or sorting (for EGFP high and low populations, using a FACS Vantage DiVa). In either case, genomic DNA was subsequently isolated using the QIAamp DNA mini kit (QIAGEN) and assayed for resolution by PCR amplification with primers pcDNA-5'CMV-Prim1 and Prim-Seq2. The assays were performed in triplicate in three separate experiments. Genomic PCF of aggregate cell populations and of sorted samples were carried out using 400 ng and 100 ng of genomic DNA, respectively, and a program of 1 cycle of 5 min at 94° C.; 35 cycles of 30 s at 94° C., 30 s at 55.7° C., 30 s at 72° C., and a final cycle of 7 min at 72° C.

References

The following references are specifically applicable to Example 1 and are incorporated herein by reference; these references are referenced in Example 1 by the reference numbers assigned to them.

1. Akopiano, A., He, J., Boocock, M. R. & Stark, W. M. Chimeric recombinases with designed DNA sequence recognition. *Proc. Natl. Acad. Sci. USA* 100: 8688-869.1 (2003).
2. Schneider, F., Schwlkardi, M., Muskhelishvili, G. & Droge, P. A DNA-binding domain swap converts the invertase gin into a resolvase. *J. Mol. Biol.* 295: 767-775 (2000).
3. Dreier, B., Segal, D. J. & Barabs, C. F., 3$^{rd}$ Insights into the molecular recognition of the 5'-GNN-3' family of DNA sequences by zinc finger domains. *J. Mol. Biol.* 303: 489-502 (2000).
4. Segal, D. J. Dreier, B., Beerli, R. R. & Barbas, C. F., 3$^{rd}$ Toward controlling gene expression at will: selection and design of zinc finger domains recognizing each of the 5'-GNN-3' DNA target sequences. *Proc. Natl. Acad. Sci. USA* 96: 2758-2763 (1999).
5. Dreier, B., Beerli, R. R., Segal, D. J., Flippin, J. D. & Barbas, C. F. 3$^{rd}$ Development of zinc finger domains for recognition of the 5'-ANN-3' family of DNA sequences and their use in the construction of artificial transcription factors. *J. Biol. Chem.* 276: 29466-29478 (2001).
6. Dreier, B. et al. Development of zinc finger domains for recognition of the 5'-CNN-3' family DNA sequences and their use in the construction of artificial transcription factors. *J. Biol. Chem.* 280: 35588-35597
7. Blancafort, P., Magnenat, L. & Barbas, C. P., 3$^{rd}$ Scanning the human genome with combinatorial transcription factor libraries. *Nat. Biotechnol.* 21: 269-274 (2003).
8. Blancafort, P., Segal, D. J. & Barbas, C. F., 3$^{rd}$ Designing transcription factor architectures for drug discovery. *Mol. Pharmacol.* 66: 1361-1371 (2004).
9. Guan, X. et al Heritable endogenous gene regulation in plants with designed polydactyl zinc finger transcription factors. *Proc. Natl. Acad. Sci. USA* 99: 13296-13301 (2002).
10. Papworth, M. et al. Inhibition of herpes simplex virus 1 gene expression by designer zinc-finger transcription factors. *Proc. Natl. Acad. Sci. USA* 100: 1621-1626 (2003).
11. Xu, D., Ye, D., Fisher, M. & Juliano, R. L. Selective inhibition of P-glycoprotein expression in multidrug-resistant tumor cells by a designed transcriptional regulator. *J. Pharmacol. Exp. Ther.* 302: 963-971 (2002).
12. Beerli, R. R., Dreier, B. & Barbas, C. F., 3$^{rd}$ Positive and negative regulation of endogenous genes by designed transcription factors. *Proc. Natl. Acad. Sci. USA* 97:1495-1500 (2000).
13. Eberhardy, S. R. et al. Inhibition of human immunodeficiency virus type 1 replication with artificial transcription factors. *Proc. Natl. Acad. Sci. USA* 97: 1495-1500 (2000).
14. Xie, D. et al, An engineered vascular endothelial growth factor-activating transcription factor induces therapeutic angiogenesis in ApoE knock out mice with hindlimb ischemia. *J. Vasc. Sum.* (2006).
15. Smith, J. et al Requirements for double-strand cleavage by chimeric restriction enzymes with zinc finger DNA-recognition domains. *Nucleic Acids Res.* 28: 3361-3369 (2000).
16. Porteus, M. H & Baltimore, D. Chimeric nucleases stimulate gene targeting in human cells. *Science* 300: 763 (2003).
17. Bibikova, M. et al. Stimulation of homologous recombination through targeted cleavage by chimeric nucleases. *Mol. Cell. Biol.* 21: 289-297 (2001).
18. Smith, J., Berg, J. M. & Chandrasegaran, S. A detailed study of the substrate specificity of a chimeric restriction enzyme. *Nucleic Acids Res.* 27: 674-681 (1999).
19. Kim. Y. G., Cha, J. & Chandrasegaran, S. Hybrid restriction enzymes; zinc finger fusions to Fok I cleavage domain. *Proc. Natl. Acad. Sci. USA* 93: 1156-1160 (1996).
20. Lloyd A., Plaisier, C. L., Carroll, D. & Drews, G. N. Targeted mutagenesis using zinc-finger nucleases in *Arabidopsis. Proc. Natl. Acad. Sci. USA* 102: 2232-2237 (2005).
21. Carroll, D. Using nucleases to stimulate homologous recombination. *Methods Mol. Biol.* 262: 195-207 (2004).
22. Bibikova, M., Veumer, K., Trautman, J. K. & Carroll, D. Enhancing gene targeting with designed zinc finger nucleases. *Science* 300: 764 (2003).
23. Bibikova, M., Golic, M., Golic, K. G. & Carroll, D. Targeted chromosomal cleavage mutagenesis in *Drosophila* using zinc-finger nucleases. *Genetics* 161: 1169-1175 (2002).
24. Dural, S. et al. Zinc finger nucleases; custom-designed molecular scissors for genome engineering of plant and mammalian cells. *Nucleic Acids Res.* 33: 5978-5990 (2005).
25. Tan, W., Zhu, K., Segal, D. J., Barbas, C. F., 3$^{rd}$ & Chow, S. A. Fusion proteins consisting of human immunodeficiency virus type 1 integrase and the designed polydactyl zinc finger protein E2C direct integration of viral DNA into specific sites. *J. Virol.* 78: 1301-1313 (2004).
26. Buchholz, F. & Stewart, A. F. Alteration of Cre recombinase site specificity by substrate-linked protein evolution. *Nat. Biotechnol.* 19: 1047-1052 (2001).
27. Leschziner, A. E. & Grindley, N. D. The architecture of the gammadelta resolvase crossover site synaptic complex revealed by using constrained DNA substrates. *Mol. Cell.* 12: 775-781 (2003).
28. Dhar, G., Sanders, E. R. & Johnson, R. C. Architecture of the hin synaptic complex during recombination; the recombinase subunits translocate with the DNA strands. *Cell* 119: 33-45 (2004).
29. Burke, M. E. et al, Activating mutations of Tn3 resolvase marking interfaces important in recombination catalysis and its regulation. *Mol. Microbiol.* 51: 937-948 (2004).
30. He. J., McIlwraith, M. J, Burke, M. E, Boocock, M. R. & Stark, W. M. Synapsis of Tn 3 recombination sites;

31. Brown, J. L., He. J., Sheratt, D. J., Stark, W. M & Boocock, M. R. Interactions of protein complexes on a supercoiled DNA; the mechanism of selective synapsis by Tn3 resolvase. *J. Mol. Biol.* 319: 371-383 (2002).
32. McIlwraith, M. J., Boocock, M. R. & Stark, W. M. Tn3 resolvase catalyses multiple recombination events without intermediate rejoining of DNA ends. *J. Mol. Biol.* 266: 108-121 (1997).
33. Sanders, E. R & Johnson, R. C. Stepwise dissection of the Hin-catalyzed recombination reaction from synapsis to resolution. *J Mol Biol.* 340: 753-766 (2004).
34. Merickel, S. K. & Johnson, R. C. Topological analysis of Hin-catalysed DNA recombination in vivo and in vitro. *Mol. Microbiol.* 51: 1143-1154 (2004).
35. Nollmann, M., He., Byron, O. & Stark, W. M. Solution structure of the Tn3 resolvase crossover site synaptic complex. *Mol. Cell.* 16: 127-137 (2004).
36. Li, W. et al. Structure of a synaptic gammadelta resolvase tetramer covalently linked to two cleaved DNAs. *Science* 309: 1210-1215 (2005).
37. Klippel, A., Cloppenborg. K & Kahmann, R. Isolation and characterization of unusual gin mutants. *EMBO J.* 7: 3983-3989 (1988).
38. Arnold, P. H., Blake, D. G., Grindley, N. D., Boocock, M. R. & Stark W. M. Mutants of Tn3 resolvase which do not require accessory binding sites for recombination activity. *EMBO J.* 18: 1407-1414 (1999).
39. Haykinson, M. J., Johnson, L. M. Soong, J. & Johnson, R. C. The Hin dimer interface is critical for Fis-mediated activation of the catalytic steps of site-specific DNA inversion. *Curr. Biol.* 6: 163-177 (1996).
40. Rowland, S. J., Boocock, M. R. & Stark, W. M. Regulation of Sin recombinase by accessory proteins. *Mol. Microbiol.* 56: 371-382 (2995).
41. Elrod-Erickson, M., Rould, M. A., Nekludova, L. & Pabo, C. O. Zif268 protein-DNA complex refined at 1.6 Å: a model system for understanding zinc finger-DNA interactions. *Structure* 4: 1171-1180 (1996).
42. Yang, W. & Steitz, T. A. Crystal structure of the site-specific recombinase gamma delta resolvase complexed with a 34 by cleavage site. *Cell* 82: 193-207 (1995).
43. Bednarz, A. L., Boocock, M. R. & Sherratt, D. J Determinants of correct res site alignment in site-specific recombination by Tn3 resolvase. *Genes Dev.* 4: 2366-2375 (1990).
44. Klippel, A., Merten, G., Patschinsky, T. & Kahmann, R. The DNA invertase Gin of phage Mu: formation of a covalent complex with DNA via a phosphoserine at amino acid position 9. EMBO J. 7: 1229-1237 (1988)
45. Merickel, S. K., Haykinson, M. J. & Johnson, R. C. Communication between Hin recombinase and R is regulatory subunits during coordinate activation of Hin-catalyzed site-specific DNA inversion. *Genes Dev.* 12: 2803-2816 (1998).
46. Hughes, K. T., Gaines, P. C., Karlinsey, J. E., Vinayak, R. & Simon, M, I. Sequence-specific interaction of the *Salmonella* hin recombinase in both major and minor grooves of DNA. *EMBO J.* 11: 2695-2705 (1992).
47. Rimphanitchayakit, V. & Grindley, N. D. Saturation mutagenesis of the DNA site bound by the small carboxy-terminal domain of gamma delta resolvase. *EMBO J.* 9: 719-725 (1990).
48. Grindley, N. D., Whiteson, K. L & Rice, P. A. Mechanisms of Site-Specific Recombination. *Annu. Rev. Biochem.* 75: 567-605 (2006).
49. Stemmer, W. P. Rapid evolution of a protein in vitro by DNA shuffling. *Nature* 370: 389-391 (1994).
50. Wirth, D. & Hauser, H. Flp-mediated integration of expression cassettes into FRT-tagged chromosomal loci in mammalian cells. *Methods Mol. Biol.* 267: 467-476 (2004).
51. Morgenstern, J. P. & Land, H. Advanced mammalian gene transfer; high titre retroviral vectors with multiple drug selection markers and a complementary helper-free packaging cell line. *Nucleic Acids Res.* 18: 3587-3596 (1990).
52. Urnov, F. D. et al Highly efficient endogenous human gene correction using designed zinc-finger nucleases. *Nature* 435: 646-651 (2005).
53. Faruqui, A. F., Datta, H. J., Carroll, D., Seidman, M. M. & Glazer, P. M. Triple-helix formation induces recombination in mammalian cells via a nucleotide excision repair-dependent pathway. *Mol. Cell. Biol.* 20: 990-1000 (2000).
54. Hirata, T., Chamberlain, J., Dong. R, & Russell, D. W. Targeted transgene insertion into human chromosomes by adeno-associated virus vectors. *Nat. Biotechnol.* 20. 735-738 (2002).
55. Sclimenti, C. R., Thyagarajan, B. & Cabs, M. P. Directed evolution of a recombinase for improved genomic integration at a native human sequence. *Nucleic Acids Res.* 29: 5044-5051 (2001).
56. Santoro, S. W. & Schultz, P. G. Directed evolution of the site specificity of Cre recombinase. *Proc. Natl. Acad. Sci. USA* 99: 4185-4190 (2002).
57. Sorrell, D. A. & Kolb, A. F. Targeted modification of mammalian genomes. *Biotechnol. Adv.* 23: 431-469 (2005),
58. Smith, M. C., Till, R. & Smith, M. C. Switching the polarity of a bacteriophage integration system. *Mol. Microbiol.* 51: 1719-1728 (2004).
59. Kolb, A. F. Selection-marker-free-modification of the murine beta-casein gene using a lox2272 site. *Anal. Biochem.* 290: 260-271 (2001).
60. Le, G. & Saito, I. Role of nucleotide sequences of lozP spacer region in Cre-mediated recombination. *Gene* 216: 55-65 (1998).
61. Feng, Y. Q. et al. Site-specific chromosomal integration in mammalian cells; highly efficient CRE recombinase-mediated cassette exchange. *J. Mol. Biol.* 292: 779-785 (1999).
62. Minakhlna, S., Kholodii, G., Mindlin, S., Yurieva, O. & Nikiforov, V. Tn5053 family transposons are res site hunters sensing plasmidal res sites occupied by cognate resolvases. *Mol. Microbiol.* 33: 1059-1068 (1999).
63. Snouwaert, J. N. et al. An animal model for cystic fibrosis made by gene targeting. *Science* 257: 1083-1088 (1992).
64. Wagner, K. D et al. An inducible mouse model for PAX2-dependent glomerular disease; insights into a complex pathogenesis. *Curr. Biol.* 16: 793-800 (2006).
65. Rankin, E. B., Tomaszewski, J. E. & Haase, V. H. Renal cyst development in mice with conditional inactivation of the von Hippel-Lindau tumor suppressor. *Cancer Res.* 66: 2576-2583 (2006).
66. Langenau, D. M. et at Cre/box-regulated transgenic zebrafish model with conditional myc-induces T cell acute lymphoblastic leukemia. *Proc. Natl. Acad. Sci. USA* 102: 6068-6073 (2005).

67. Szymczak, A. L. et al., Correction of multi-gene deficiency in vivo using a single "self-cleaving" 2A peptide-based retroviral vector. *Nat. Biotechnol.* 22: 589-594 (2004).
68. Parekh-Olmedo, H., Perrara, L., Brachman, E. & Kmiec, E. B. Gene therapy progress and prospects; targeted gene repair. *Gene Ther.* 12: 639-646 (2005).
69. Thyagarajan, B., Olivares, E. C. Hollis R. P., Ginsburg, D. S. & Calos, M. P site-specific genomic integration in mammalian cells mediated by phage φC31 integrase. *Mol. Cell. Biol.* 21: 3926-3934 (2001).
70. Chalberg, T. W. et al. Integration specificity of phage φC31 intergrase in the human genome. *J. Mol. Biol.* 357: 28-48 (2006),
71. Ortiz-Urda, S. et al. φC31 integrase-mediated nonviral genetic correction of junctional epidermolysis bullosa. *Hum. Gene Ther.* 14: 923-928 (2003).
72. Quenneville, S. P. et al. Nucleofection of muscle-derived stem cells and myoblasts with φC31 integrase; stable expression of a full-length-dystrophin fusion gene by human myoblasts. *Mol. Ther.* 10, 679-687 (2004).
73. Held, P. K. et al. In vivo correction of murine hereditary tyrosinemia type I by φC31 integrase-mediated gene delivery. *Mol. Ther.* 11: 399-408 (2005).
74. Liu, J., Japanese, I., Nielsen, K & Jensen, T. G. φC31 integrase induces chromosomal aberrations in primary human fibroblasts. *Gene Ther.* (2006).
75. Segal, D. J. et al. Evaluation of a modular strategy for the construction of novel polydactyl zinc finger DNA-binding proteins. *Biochemistry* 42: 2137-2148 (2003).
76. Tan, S. et al. Zinc-finger protein-targeted gene regulation: genomewide single-gene specificity. *Proc. Natl. Acad. Sci. USA* 100: 11997-12002 (2003).
77. Zhu, T. & Wang, Z. Large-scale profiling of the *Arabidopsis* transcriptome. *Plant Physiol.* 124: 1472-1476 (2000).
78. Rice, P. A. Resolving integral questions in site-specific recombination. *Nat. Struct. Mol. Biol.* 12: 641-643 (2005).
79. Akopian, A. & Marshall Stark, W. Site-specific DNA recombinases as instruments for genomic surgery. *Adv. Genet.* 55: 1-23 (2005).
80. Carlos F. Barbas III, D. R. B. Jamie K. Scott, and Gregg J. Silverman Phage Display: A Laboratory Manual. (Cold Spring Harbor Laboratory Press, Cold Spring Harbor, N.Y.; 2001).
81. Zaccolo, M. & Gherardi, E. The effect of high-frequency random mutagenesis on in vitro protein evolution: a study on TEM-1 beta-lactamase. *J. Mol. Biol.* 285: 775-783 (1999).

Advantages of the Invention

The present invention provides compositions and methods suitable for carrying out site-specific genomic recombination. These compositions and methods can be used in gene therapy to remove deleterious genes and replace them with genes that provide normal function. These compositions and methods are versatile and highly specific in their action, and minimize undesired recombination events.

Compositions and methods according to the present invention not only provide an additional tool for the study of the genomic structure and function, but provide a means of overcoming the limited specificity of currently-available SSRs for the ~28 bp recombination sites present in their native substrates, which typically prevents the application of SSRs to endogenous genomes.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

We claim:

1. A chimeric recombinase protein comprising a serine recombinase operatively linked to a zinc finger nucleotide binding domain such that the chimeric recombinase protein catalyzes site-specific recombination at a DNA site specifically bound by the zinc finger nucleotide binding domain and,
wherein the serine recombinase is a Gin mutein having the following mutation M70V with reference to a wild-type Gin serine recombinase comprising the amino acid sequence as set forth in SEQ ID NO: 707, and one or more of the following mutations: D12G, N14S, N20D, K50E, I94V and M114V with reference to the wild-type Gin serine recombinase, and
wherein the zinc finger nucleotide binding domain is selected from the group consisting of a bidactyl zinc finger binding domain that binds a hexanucleotide, a tridactyl zinc finger nucleotide binding domain that binds 9 base pairs, a 4-finger zinc finger nucleotide binding domain that binds 12 base pairs, a 5-finger zinc finger nucleotide binding domain that binds 15 base pairs, and a 6-finger zinc finger nucleotide binding domain that binds 18 base pairs.

2. The chimeric recombinase protein of claim 1, wherein the serine recombinase is a Gin mutein having the following mutations with reference to the wild-type Gin serine recombinase: D12G, N14S, N20D, K50E, M70V, I94V and M114V.

3. The chimeric recombinase protein of claim 2, wherein the zinc finger nucleotide binding domain binds the 9-bp sequence GGAGGCGTG (SEQ ID NO: 634).

4. The chimeric recombinase protein of claim 1, wherein the zinc finger nucleotide binding domain comprises at least one oligopeptide linker located between triplet binding domains.

5. The chimeric recombinase protein of claim 1, wherein the oligopeptide linker is TGEKP (SEQ ID NO: 624).

6. A chimeric recombinase protein obtained from the chimeric recombinase protein of claim 1 by one to five conservative amino acid substitutions, wherein the conservative amino acid substitutions are each selected from the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu, and wherein the chimeric recombinase protein obtained by the conservative amino acid substitutions has the same DNA sequence specificity for recombination as the unmutated chimeric recombinase, has a binding affinity for the substrate of no less than about 80% of the binding affinity for the substrate of the unmutated chimeric recombinase, and has a Vmax of no less than about 80% of the Vmax of the unmutated chimeric recombinase.

7. The chimeric recombinase protein of claim 1, wherein the chimeric recombinase protein further includes at least one additional domain.

8. The chimeric recombinase protein of claim 7, wherein the additional domain is selected from the group consisting of a purification tag, an enzyme domain, a ligand binding domain, a cell penetrating domain, and an enzyme domain that catalyzes the detectable production of light via fluorescence or bioluminescence.

9. A composition comprising:
(a) the chimeric recombinase protein of claim 1; and
(b) a pharmaceutically acceptable carrier.

* * * * *

SEQUENCE LISTING

```
<160> NUMBER OF SEQ ID NOS: 707

<210> SEQ ID NO 1
<211> LENGTH: 6
<212> TYPE: DNA
<213> ORGANISM: Artificial Sequence
<220> FEATURE:
<223> OTHER INFORMATION: Synthetic construct

<400> SEQUENCE: 1 gaggag                                                                    6

<210> SEQ ID NO 2
<211> LENGTH: 32
<212> TYPE: DNA
<213> ORGANISM: Artificial Sequence
<220> FEATURE:
<223> OTHER INFORMATION: Synthetic construct

<400> SEQUENCE: 2
gaggagtgat aatttataat atttcgctcc tc                                       32

<210> SEQ ID NO 3
<211> LENGTH: 9
<212> TYPE: DNA
<213> ORGANISM: Artificial Sequence
<220> FEATURE:
<223> OTHER INFORMATION: Synthetic construct

<400> SEQUENCE: 3 ggaggggtg                                                                 9

<210> SEQ ID NO 4
<211> LENGTH: 9
<212> TYPE: DNA
<213> ORGANISM: Artificial Sequence
<220> FEATURE:
<223> OTHER INFORMATION: Synthetic construct

<400> SEQUENCE: 4 gcagtggcg                                                                 9

<210> SEQ ID NO 5
<211> LENGTH: 8
<212> TYPE: PRT
<213> ORGANISM: Artificial Sequence
<220> FEATURE:
<223> OTHER INFORMATION: Synthetic construct

<400> SEQUENCE: 5

Ser Thr Asn Thr Lys Leu His Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 6

Ser Ser Asp Arg Thr Leu Arg Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic construct

<400> SEQUENCE: 7

Ser Thr Lys Glu Arg Leu Lys Thr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Ser Gln Arg Ala Asn Leu Arg Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic construct

<400> SEQUENCE: 9

Ser Ser Pro Ala Asp Leu Thr Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Ser Ser His Ser Asp Leu Val Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic construct

<400> SEQUENCE: 11

Ser Asn Gly Gly Glu Leu Ile Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic construct

<400> SEQUENCE: 12
```

Ser Asn Gln Leu Ile Leu Leu Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Ser Ser Arg Met Asp Leu Lys Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

<400> SEQUENCE: 14

Ser Arg Ser Asp His Leu Thr Asn
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct

<400> SEQUENCE: 15

Ser Gln Leu Ala His Leu Arg Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic construct

<400> SEQUENCE: 16

Ser Gln Ala Ser Ser Leu Lys Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic construct

<400> SEQUENCE: 17

Ser Gln Lys Ser Ser Leu Ile Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic construct

<400> SEQUENCE: 18

Ser Arg Lys Asp Asn Leu Lys Asn

```
<210> SEQ ID NO 19
<211> LENGTH: 8
<212> TYPE: PRT
<213> ORGANISM: Artificial Sequence
<220> FEATURE:
<223> OTHER INFORMATION: Synthetic construct

<400> SEQUENCE: 19

Ser Asp Ser Gly Asn Leu Arg Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic construct

<400> SEQUENCE: 20

Ser Asp Arg Arg Asn Leu Arg Arg
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic construct

<400> SEQUENCE: 21

Ser Asp Lys Lys Asp Leu Ser Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic construct

<400> SEQUENCE: 22

Ser Asp Ala Ser His Leu His Thr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic construct

<400> SEQUENCE: 23

Ser Thr Asn Ser Gly Leu Lys Asn
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic construct

<400> SEQUENCE: 24

Ser Thr Arg Met Ser Leu Ser Thr
1               5
```

```
<210> SEQ ID NO 25
<211> LENGTH: 8
<212> TYPE: PRT
<213> ORGANISM: Artificial Sequence
<220> FEATURE:
<223> OTHER INFORMATION: Synthetic construct

<400> SEQUENCE: 25

Ser Asn His Asp Ala Leu Arg Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic construct

<400> SEQUENCE: 26

Ser Arg Arg Ser Ala Cys Arg Arg
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic construct

<400> SEQUENCE: 27

Ser Arg Arg Ser Ser Cys Arg Lys
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic construct

<400> SEQUENCE: 28

Ser Arg Ser Asp Thr Leu Ser Asn
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic construct

<400> SEQUENCE: 29

Ser Arg Met Gly Asn Leu Ile Arg
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct

<400> SEQUENCE: 30

Ser Arg Ser Asp Thr Leu Arg Asp
1               5

<210> SEQ ID NO 31
```

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 31

Ser Arg Ala His Asp Leu Val Arg
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct

<400> SEQUENCE: 32

Ser Arg Ser Asp His Leu Ala Glu
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic construct

<400> SEQUENCE: 33

Ser Arg Arg Asp Ala Leu Asn Val
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic construct

<400> SEQUENCE: 34

Ser Thr Thr Gly Asn Leu Thr Val
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic construct

<400> SEQUENCE: 35

Ser Thr Ser Gly Asn Leu Leu Val
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic construct

<400> SEQUENCE: 36

Ser Thr Leu Thr Ile Leu Lys Asn
1               5

<210> SEQ ID NO 37
<211> LENGTH: 8
<212> TYPE: PRT
```

```
<213> ORGANISM: Artificial Sequence
<220> FEATURE:
<223> OTHER INFORMATION: Synthetic construct

<400> SEQUENCE: 37

Ser Arg Met Ser Thr Leu Arg His
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic construct

<400> SEQUENCE: 38

Ser Thr Arg Ser Asp Leu Leu Arg
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic construct

<400> SEQUENCE: 39

Ser Thr Lys Thr Asp Leu Lys Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic construct

<400> SEQUENCE: 40

Ser Thr His Ile Asp Leu Ile Arg
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic construct

<400> SEQUENCE: 41

Ser His Arg Ser Thr Leu Leu Asn
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic construct

<400> SEQUENCE: 42

Ser Thr Ser His Gly Leu Thr Thr
1               5

<210> SEQ ID NO 43
<211> LENGTH: 8
<212> TYPE: PRT
<213> ORGANISM: Artificial Sequence
<220> FEATURE:
```

<223> OTHER INFORMATION: Synthetic construct

<400> SEQUENCE: 43

Ser His Lys Asn Ala Leu Gln Asn
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic construct

<400> SEQUENCE: 44

Gln Arg Ala Asn Leu Arg Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic construct

<400> SEQUENCE: 45

Asp Ser Gly Asn Leu Arg Val
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic construct

<400> SEQUENCE: 46

Arg Ser Asp Thr Leu Ser Asn
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic construct

<400> SEQUENCE: 47

Thr Thr Gly Asn Leu Thr Val
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic construct

<400> SEQUENCE: 48

Ser Pro Ala Asp Leu Thr Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 49

Asp Lys Lys Asp Leu Thr Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic construct

<400> SEQUENCE: 50

Arg Thr Asp Thr Leu Arg Asp
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic construct

<400> SEQUENCE: 51

Thr His Leu Asp Leu Ile Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic construct

<400> SEQUENCE: 52

Gln Leu Ala His Leu Arg Ala
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Arg Ser Asp His Leu Ala Glu
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic construct

<400> SEQUENCE: 54

His Arg Thr Thr Leu Leu Asn
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic construct

<400> SEQUENCE: 55
```

```
Gln Lys Ser Ser Leu Ile Ala
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic construct

<400> SEQUENCE: 56

Arg Arg Asp Ala Leu Asn Val
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic construct

<400> SEQUENCE: 57

His Lys Asn Ala Leu Gln Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic construct

<400> SEQUENCE: 58

Arg Ser Asp Asn Leu Ser Asn
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic construct

<400> SEQUENCE: 59

Arg Lys Asp Asn Leu Lys Asn
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic construct

<400> SEQUENCE: 60

Thr Ser Gly Asn Leu Leu Val
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic construct

<400> SEQUENCE: 61

Arg Ser Asp His Leu Thr Asn
1               5
```

<210> SEQ ID NO 62
<211> LENGTH: 7
<212> TYPE: PRT
<213> ORGANISM: Artificial Sequence
<220> FEATURE:
<223> OTHER INFORMATION: Synthetic construct

<400> SEQUENCE: 62

His Arg Thr Thr Leu Thr Asn
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic construct

<400> SEQUENCE: 63

Ser His Ser Asp Leu Val Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic construct

<400> SEQUENCE: 64

Asn Gly Gly Glu Leu Ile Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic construct

<400> SEQUENCE: 65

Ser Thr Lys Asp Leu Lys Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic construct

<400> SEQUENCE: 66

Arg Arg Asp Glu Leu Asn Val
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic construct

<400> SEQUENCE: 67

Gln Ala Ser Ser Leu Lys Ala
1               5

```
<210> SEQ ID NO 68
<211> LENGTH: 7
<212> TYPE: PRT
<213> ORGANISM: Artificial Sequence
<220> FEATURE:
<223> OTHER INFORMATION: Synthetic construct

<400> SEQUENCE: 68

Thr Ser His Gly Leu Thr Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic construct

<400> SEQUENCE: 69

Gln Ser Ser His Leu Val Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic construct

<400> SEQUENCE: 70

Gln Ser Ser Asn Leu Val Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic construct

<400> SEQUENCE: 71

Asp Pro Gly Ala Leu Arg Val
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic construct

<400> SEQUENCE: 72

Arg Ser Asp Asn Leu Val Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic construct

<400> SEQUENCE: 73

Gln Ser Gly Asp Leu Arg Arg
1               5

<210> SEQ ID NO 74
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 74

Asp Cys Arg Asp Leu Ala Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic construct

<400> SEQUENCE: 75

Asp Pro Gly Ala Leu Ile Asn
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic construct

<400> SEQUENCE: 76

Glu Arg Ser His Leu Arg Glu
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic construct

<400> SEQUENCE: 77

Asp Pro Gly His Leu Thr Glu
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic construct

<400> SEQUENCE: 78

Glu Pro Gly Ala Leu Ile Asn
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic construct

<400> SEQUENCE: 79

Asp Arg Ser His Leu Arg Glu
1               5

<210> SEQ ID NO 80
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 80

Glu Pro Gly His Leu Thr Glu
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic construct

<400> SEQUENCE: 81

Glu Arg Ser Leu Leu Arg Glu
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic construct

<400> SEQUENCE: 82

Asp Arg Ser Lys Leu Arg Glu
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic construct

<400> SEQUENCE: 83

Asp Pro Gly Lys Leu Thr Glu
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic construct

<400> SEQUENCE: 84

Glu Pro Gly Lys Leu Thr Glu
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic construct

<400> SEQUENCE: 85

Asp Pro Gly Trp Leu Ile Asn
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 86

Asp Pro Gly Thr Leu Ile Asn
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic construct

<400> SEQUENCE: 87

Asp Pro Gly His Leu Ile Asn
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic construct

<400> SEQUENCE: 88

Glu Arg Ser Trp Leu Ile Asn
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic construct

<400> SEQUENCE: 89

Glu Arg Ser Thr Leu Ile Asn
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic construct

<400> SEQUENCE: 90

Asp Pro Gly Trp Leu Thr Glu
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic construct

<400> SEQUENCE: 91

Asp Pro Gly Thr Leu Thr Glu
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic construct

<400> SEQUENCE: 92
```

```
<210> SEQ ID NO 93
<211> LENGTH: 7
<212> TYPE: PRT
<213> ORGANISM: Artificial Sequence
<220> FEATURE:
<223> OTHER INFORMATION: Synthetic construct

<400> SEQUENCE: 93

Glu Pro Gly Thr Leu Ile Asn
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic construct

<400> SEQUENCE: 94

Glu Pro Gly His Leu Ile Asn
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic construct

<400> SEQUENCE: 95

Asp Arg Ser Trp Leu Arg Glu
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic construct

<400> SEQUENCE: 96

Asp Arg Ser Thr Leu Arg Glu
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic construct

<400> SEQUENCE: 97

Glu Pro Gly Trp Leu Thr Glu
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic construct

<400> SEQUENCE: 98

Glu Pro Gly Thr Leu Thr Glu
```

<210> SEQ ID NO 99
<211> LENGTH: 7
<212> TYPE: PRT
<213> ORGANISM: Artificial Sequence
<220> FEATURE:
<223> OTHER INFORMATION: Synthetic construct

<400> SEQUENCE: 99

Glu Arg Ser Trp Leu Arg Glu
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic construct

<400> SEQUENCE: 100

Glu Arg Ser Thr Leu Arg Glu
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic construct

<400> SEQUENCE: 101

Asp Pro Gly Ala Leu Arg Glu
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic construct

<400> SEQUENCE: 102

Asp Pro Gly Ala Leu Thr Glu
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic construct

<400> SEQUENCE: 103

Glu Arg Ser His Leu Ile Asn
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic construct

<400> SEQUENCE: 104

Glu Arg Ser His Leu Thr Glu
1               5

```
<210> SEQ ID NO 105
<211> LENGTH: 7
<212> TYPE: PRT
<213> ORGANISM: Artificial Sequence
<220> FEATURE:
<223> OTHER INFORMATION: Synthetic construct

<400> SEQUENCE: 105

Asp Pro Gly His Leu Ile Asn
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic construct

<400> SEQUENCE: 106

Asp Pro Gly His Leu Arg Glu
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic construct

<400> SEQUENCE: 107

Glu Pro Gly Ala Leu Arg Glu
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic construct

<400> SEQUENCE: 108

Glu Pro Gly Ala Leu Thr Glu
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic construct

<400> SEQUENCE: 109

Asp Arg Ser His Leu Ile Asn
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic construct

<400> SEQUENCE: 110

Asp Arg Ser His Leu Thr Glu
1               5

<210> SEQ ID NO 111
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 111

Glu Pro Gly His Leu Arg Glu
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic construct

<400> SEQUENCE: 112

Glu Arg Ser Lys Leu Ile Asn
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic construct

<400> SEQUENCE: 113

Glu Arg Ser Lys Leu Thr Glu
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic construct

<400> SEQUENCE: 114

Asp Arg Ser Lys Leu Ile Asn
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic construct

<400> SEQUENCE: 115

Asp Arg Ser Lys Leu Thr Glu
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic construct

<400> SEQUENCE: 116

Asp Pro Gly Lys Leu Ile Asn
1               5

<210> SEQ ID NO 117
<211> LENGTH: 7
<212> TYPE: PRT
```

<213> ORGANISM: Artificial Sequence
<220> FEATURE:
<223> OTHER INFORMATION: Synthetic construct

<400> SEQUENCE: 117

Asp Pro Gly Lys Leu Arg Glu
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic construct

<400> SEQUENCE: 118

Glu Pro Gly Lys Leu Ile Asn
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic construct

<400> SEQUENCE: 119

Glu Pro Gly Lys Leu Arg Glu
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic construct

<400> SEQUENCE: 120

Asp Pro Gly Trp Leu Arg Glu
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic construct

<400> SEQUENCE: 121

Asp Pro Gly Thr Leu Arg Glu
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic construct

<400> SEQUENCE: 122

Asp Pro Gly His Leu Arg Glu
1               5

<210> SEQ ID NO 123
<211> LENGTH: 7
<212> TYPE: PRT
<213> ORGANISM: Artificial Sequence
<220> FEATURE:

<223> OTHER INFORMATION: Synthetic construct

<400> SEQUENCE: 123

Asp Pro Gly His Leu Thr Glu
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic construct

<400> SEQUENCE: 124

Glu Arg Ser Trp Leu Thr Glu
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct

<400> SEQUENCE: 125

Glu Arg Ser Thr Leu Thr Glu
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic construct

<400> SEQUENCE: 126

Glu Pro Gly Trp Leu Arg Glu
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic construct

<400> SEQUENCE: 127

Glu Pro Gly Thr Leu Arg Glu
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic construct

<400> SEQUENCE: 128

Asp Arg Ser Trp Leu Ile Asn
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 129

Asp Arg Ser Trp Leu Thr Glu
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic construct

<400> SEQUENCE: 130

Asp Arg Ser Thr Leu Ile Asn
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic construct

<400> SEQUENCE: 131

Asp Arg Ser Thr Leu Thr Glu
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic construct

<400> SEQUENCE: 132

Gln Arg His Asn Leu Thr Glu
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic construct

<400> SEQUENCE: 133

Gln Ser Gly Asn Leu Thr Glu
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic construct

<400> SEQUENCE: 134

Asn Leu Gln His Leu Gly Glu
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic construct

<400> SEQUENCE: 135
```

```
Arg Ala Asp Asn Leu Thr Glu
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic construct

<400> SEQUENCE: 136

Arg Ala Asp Asn Leu Ala Ile
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic construct

<400> SEQUENCE: 137

Asn Thr Thr His Leu Glu His
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic construct

<400> SEQUENCE: 138

Ser Lys Lys His Leu Ala Glu
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic construct

<400> SEQUENCE: 139

Arg Asn Asp Thr Leu Thr Glu
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic construct

<400> SEQUENCE: 140

Arg Asn Asp Thr Leu Gln Ala
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic construct

<400> SEQUENCE: 141

Gln Ser Gly His Leu Thr Glu
1               5
```

<210> SEQ ID NO 142
<211> LENGTH: 7
<212> TYPE: PRT
<213> ORGANISM: Artificial Sequence
<220> FEATURE:
<223> OTHER INFORMATION: Synthetic construct

<400> SEQUENCE: 142

Gln Leu Ala His Leu Lys Glu
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic construct

<400> SEQUENCE: 143

Gln Arg Ala His Leu Thr Glu
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic construct

<400> SEQUENCE: 144

His Thr Gly His Leu Leu Glu
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic construct

<400> SEQUENCE: 145

Arg Ser Asp His Leu Thr Glu
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic construct

<400> SEQUENCE: 146

Arg Ser Asp Lys Leu Thr Glu
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic construct

<400> SEQUENCE: 147

Arg Ser Asp His Leu Thr Asp
1               5

```
<210> SEQ ID NO 148
<211> LENGTH: 7
<212> TYPE: PRT
<213> ORGANISM: Artificial Sequence
<220> FEATURE:
<223> OTHER INFORMATION: Synthetic construct

<400> SEQUENCE: 148

Arg Ser Asp His Leu Thr Asn
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic construct

<400> SEQUENCE: 149

Ser Arg Arg Thr Cys Arg Ala
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic construct

<400> SEQUENCE: 150

Gln Leu Arg His Leu Arg Glu
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic construct

<400> SEQUENCE: 151

Gln Arg His Ser Leu Thr Glu
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic construct

<400> SEQUENCE: 152

Gln Leu Ala His Leu Lys Arg
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic construct

<400> SEQUENCE: 153

Asn Leu Gln His Leu Gly Glu
1               5

<210> SEQ ID NO 154
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 154

Arg Asn Asp Ala Leu Thr Glu
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic construct

<400> SEQUENCE: 155

Thr Lys Gln Thr Leu Thr Glu
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic construct

<400> SEQUENCE: 156

Gln Ser Gly Asp Leu Thr Glu
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic construct

<400> SEQUENCE: 157

Gln Ser Ser Asn Leu Val Arg
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic construct

<400> SEQUENCE: 158

Asp Pro Gly Asn Leu Val Arg
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic construct

<400> SEQUENCE: 159

Arg Ser Asp Asn Leu Val Arg
1               5

<210> SEQ ID NO 160
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 160

Thr Ser Gly Asn Leu Val Arg
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic construct

<400> SEQUENCE: 161

Gln Ser Gly Asp Leu Arg Arg
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic construct

<400> SEQUENCE: 162

Asp Cys Arg Asp Leu Ala Arg
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic construct

<400> SEQUENCE: 163

Arg Ser Asp Asp Leu Val Lys
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic construct

<400> SEQUENCE: 164

Thr Ser Gly Glu Leu Val Arg
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic construct

<400> SEQUENCE: 165

Gln Arg Ala His Leu Glu Arg
1               5

<210> SEQ ID NO 166
<211> LENGTH: 7
<212> TYPE: PRT
<213> ORGANISM: Artificial Sequence
<220> FEATURE:
<223> OTHER INFORMATION: Synthetic construct
```

<400> SEQUENCE: 166

Asp Pro Gly His Leu Val Arg
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic construct

<400> SEQUENCE: 167

Arg Ser Asp Lys Leu Val Arg
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic construct

<400> SEQUENCE: 168

Thr Ser Gly His Leu Val Arg
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic construct

<400> SEQUENCE: 169

Gln Ser Ser Ser Leu Val Arg
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic construct

<400> SEQUENCE: 170

Asp Pro Gly Ala Leu Val Arg
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic construct

<400> SEQUENCE: 171

Arg Ser Asp Glu Leu Val Arg
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic construct

<400> SEQUENCE: 172

Thr Ser Gly Ser Leu Val Arg
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic construct

<400> SEQUENCE: 173

Gln Arg Ser Asn Leu Val Arg
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic construct

<400> SEQUENCE: 174

Gln Ser Gly Asn Leu Val Arg
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic construct

<400> SEQUENCE: 175

Gln Pro Gly Asn Leu Val Arg
1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic construct

<400> SEQUENCE: 176

Asp Pro Gly Asn Leu Lys Arg
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic construct

<400> SEQUENCE: 177

Arg Ser Asp Asn Leu Arg Arg
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic construct

<400> SEQUENCE: 178

Lys Ser Ala Asn Leu Val Arg

```
<210> SEQ ID NO 179
<211> LENGTH: 7
<212> TYPE: PRT
<213> ORGANISM: Artificial Sequence
<220> FEATURE:
<223> OTHER INFORMATION: Synthetic construct

<400> SEQUENCE: 179

Arg Ser Asp Asn Leu Val Lys
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic construct

<400> SEQUENCE: 180

Lys Ser Ala Gln Leu Val Arg
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic construct

<400> SEQUENCE: 181

Gln Ser Ser Thr Leu Val Arg
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic construct

<400> SEQUENCE: 182

Gln Ser Gly Thr Leu Arg Arg
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic construct

<400> SEQUENCE: 183

Gln Pro Gly Asp Leu Val Arg
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic construct

<400> SEQUENCE: 184

Gln Gly Pro Asp Leu Val Arg
1               5
```

```
<210> SEQ ID NO 185
<211> LENGTH: 7
<212> TYPE: PRT
<213> ORGANISM: Artificial Sequence
<220> FEATURE:
<223> OTHER INFORMATION: Synthetic construct

<400> SEQUENCE: 185

Gln Ala Gly Thr Leu Met Arg
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic construct

<400> SEQUENCE: 186

Gln Pro Gly Thr Leu Val Arg
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic construct

<400> SEQUENCE: 187

Gln Gly Pro Glu Leu Val Arg
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic construct

<400> SEQUENCE: 188

Gly Cys Arg Glu Leu Ser Arg
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic construct

<400> SEQUENCE: 189

Asp Pro Ser Thr Leu Lys Arg
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic construct

<400> SEQUENCE: 190

Asp Pro Ser Asp Leu Lys Arg
1               5

<210> SEQ ID NO 191
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 191

Asp Ser Gly Asp Leu Val Arg
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic construct

<400> SEQUENCE: 192

Asp Ser Gly Glu Leu Val Arg
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic construct

<400> SEQUENCE: 193

Asp Ser Gly Glu Leu Lys Arg
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic construct

<400> SEQUENCE: 194

Arg Leu Asp Thr Leu Gly Arg
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic construct

<400> SEQUENCE: 195

Arg Pro Gly Asp Leu Val Arg
1               5

<210> SEQ ID NO 196
<211> LENGTH: 7
<212> TYPE: PRT
<213> ORGANISM: Artificial Sequence
<220> FEATURE:
<223> OTHER INFORMATION: Synthetic construct

<400> SEQUENCE: 196

Arg Ser Asp Thr Leu Val Arg
1               5

<210> SEQ ID NO 197
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 197

Lys Ser Ala Asp Leu Lys Arg
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic construct

<400> SEQUENCE: 198

Arg Ser Asp Asp Leu Val Arg
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic construct

<400> SEQUENCE: 199

Arg Ser Asp Thr Leu Val Lys
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic construct

<400> SEQUENCE: 200

Lys Ser Ala Glu Leu Lys Arg
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic construct

<400> SEQUENCE: 201

Lys Ser Ala Glu Leu Val Arg
1               5

<210> SEQ ID NO 202
<211> LENGTH: 7
<212> TYPE: PRT
<213> ORGANISM: Artificial Sequence
<220> FEATURE:
<223> OTHER INFORMATION: Synthetic construct

<400> SEQUENCE: 202

Arg Gly Pro Glu Leu Val Arg
1               5

<210> SEQ ID NO 203
<211> LENGTH: 7
<212> TYPE: PRT
<213> ORGANISM: Artificial Sequence
<220> FEATURE:
```

<223> OTHER INFORMATION: Synthetic construct

<400> SEQUENCE: 203

Lys Pro Gly Glu Leu Val Arg
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic construct

<400> SEQUENCE: 204

Ser Ser Gln Thr Leu Thr Arg
1               5

<210> SEQ ID NO 205
<211> LENGTH: 7
<212> TYPE: PRT
<213> ORGANISM: Artificial Sequence
<220> FEATURE:
<223> OTHER INFORMATION: Synthetic construct

<400> SEQUENCE: 205

Thr Pro Gly Glu Leu Val Arg
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic construct

<400> SEQUENCE: 206

Thr Ser Gly Asp Leu Val Arg
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic construct

<400> SEQUENCE: 207

Ser Ser Gln Thr Leu Val Arg
1               5

<210> SEQ ID NO 208
<211> LENGTH: 7
<212> TYPE: PRT
<213> ORGANISM: Artificial Sequence
<220> FEATURE:
<223> OTHER INFORMATION: Synthetic construct

<400> SEQUENCE: 208

Thr Ser Gln Thr Leu Thr Arg
1               5

<210> SEQ ID NO 209
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 209

Thr Ser Gly Glu Leu Lys Arg
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic construct

<400> SEQUENCE: 210

Gln Ser Ser Asp Leu Val Arg
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic construct

<400> SEQUENCE: 211

Ser Ser Gly Thr Leu Val Arg
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic construct

<400> SEQUENCE: 212

Thr Pro Gly Thr Leu Val Arg
1               5

<210> SEQ ID NO 213
<211> LENGTH: 7
<212> TYPE: PRT
<213> ORGANISM: Artificial Sequence
<220> FEATURE:
<223> OTHER INFORMATION: Synthetic construct

<400> SEQUENCE: 213

Thr Ser Gln Asp Leu Lys Arg
1               5

<210> SEQ ID NO 214
<211> LENGTH: 7
<212> TYPE: PRT
<213> ORGANISM: Artificial Sequence
<220> FEATURE:
<223> OTHER INFORMATION: Synthetic construct

<400> SEQUENCE: 214

Thr Ser Gly Thr Leu Val Arg
1               5

<210> SEQ ID NO 215
<211> LENGTH: 7
<212> TYPE: PRT
<213> ORGANISM: Artificial Sequence
<220> FEATURE:
<223> OTHER INFORMATION: Synthetic construct

<400> SEQUENCE: 215
```

```
Gln Ser Ser His Leu Val Arg
1               5

<210> SEQ ID NO 216
<211> LENGTH: 7
<212> TYPE: PRT
<213> ORGANISM: Artificial Sequence
<220> FEATURE:
<223> OTHER INFORMATION: Synthetic construct

<400> SEQUENCE: 216

Gln Ser Gly His Leu Val Arg
1               5

<210> SEQ ID NO 217
<211> LENGTH: 7
<212> TYPE: PRT
<213> ORGANISM: Artificial Sequence
<220> FEATURE:
<223> OTHER INFORMATION: Synthetic construct

<400> SEQUENCE: 217

Gln Pro Gly His Leu Val Arg
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic construct

<400> SEQUENCE: 218

Glu Arg Ser Lys Leu Ala Arg
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic construct

<400> SEQUENCE: 219

Asp Pro Gly His Leu Ala Arg
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic construct

<400> SEQUENCE: 220

Gln Arg Ala Lys Leu Glu Arg
1               5

<210> SEQ ID NO 221
<211> LENGTH: 7
<212> TYPE: PRT
<213> ORGANISM: Artificial Sequence
<220> FEATURE:
<223> OTHER INFORMATION: Synthetic construct

<400> SEQUENCE: 221

Gln Ser Ser Lys Leu Val Arg
1               5
```

```
<210> SEQ ID NO 222
<211> LENGTH: 7
<212> TYPE: PRT
<213> ORGANISM: Artificial Sequence
<220> FEATURE:
<223> OTHER INFORMATION: Synthetic construct

<400> SEQUENCE: 222

Asp Arg Ser Lys Leu Ala Arg
1               5

<210> SEQ ID NO 223
<211> LENGTH: 7
<212> TYPE: PRT
<213> ORGANISM: Artificial Sequence
<220> FEATURE:
<223> OTHER INFORMATION: Synthetic construct

<400> SEQUENCE: 223

Asp Pro Gly Lys Leu Ala Arg
1               5

<210> SEQ ID NO 224
<211> LENGTH: 7
<212> TYPE: PRT
<213> ORGANISM: Artificial Sequence
<220> FEATURE:
<223> OTHER INFORMATION: Synthetic construct

<400> SEQUENCE: 224

Arg Ser Lys Asp Leu Thr Arg
1               5

<210> SEQ ID NO 225
<211> LENGTH: 7
<212> TYPE: PRT
<213> ORGANISM: Artificial Sequence
<220> FEATURE:
<223> OTHER INFORMATION: Synthetic construct

<400> SEQUENCE: 225

Arg Ser Asp His Leu Thr Arg
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic construct

<400> SEQUENCE: 226

Lys Ser Ala Lys Leu Glu Arg
1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic construct

<400> SEQUENCE: 227

Thr Ala Asp His Leu Ser Arg
1               5
```

```
<210> SEQ ID NO 228
<211> LENGTH: 6
<212> TYPE: PRT
<213> ORGANISM: Artificial Sequence
<220> FEATURE:
<223> OTHER INFORMATION: Synthetic construct

<400> SEQUENCE: 228

Thr Ala Asp Lys Leu Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic construct

<400> SEQUENCE: 229

Thr Pro Gly His Leu Val Arg
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic construct

<400> SEQUENCE: 230

Thr Ser Ser His Leu Val Arg
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic construct

<400> SEQUENCE: 231

Thr Ser Gly Lys Leu Val Arg
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic construct

<400> SEQUENCE: 232

Gln Pro Gly Glu Leu Val Arg
1               5

<210> SEQ ID NO 233
<211> LENGTH: 7
<212> TYPE: PRT
<213> ORGANISM: Artificial Sequence
<220> FEATURE:
<223> OTHER INFORMATION: Synthetic construct

<400> SEQUENCE: 233

Gln Ser Gly Glu Leu Val Arg
1               5

<210> SEQ ID NO 234
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 234

Gln Ser Gly Glu Leu Arg Arg
1               5

<210> SEQ ID NO 235
<211> LENGTH: 7
<212> TYPE: PRT
<213> ORGANISM: Artificial Sequence
<220> FEATURE:
<223> OTHER INFORMATION: Synthetic construct

<400> SEQUENCE: 235

Asp Pro Gly Ser Leu Val Arg
1               5

<210> SEQ ID NO 236
<211> LENGTH: 7
<212> TYPE: PRT
<213> ORGANISM: Artificial Sequence
<220> FEATURE:
<223> OTHER INFORMATION: Synthetic construct

<400> SEQUENCE: 236

Arg Lys Asp Ser Leu Val Arg
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic construct

<400> SEQUENCE: 237

Arg Ser Asp Val Leu Val Arg
1               5

<210> SEQ ID NO 238
<211> LENGTH: 7
<212> TYPE: PRT
<213> ORGANISM: Artificial Sequence
<220> FEATURE:
<223> OTHER INFORMATION: Synthetic construct

<400> SEQUENCE: 238

Arg His Asp Ser Leu Leu Arg
1               5

<210> SEQ ID NO 239
<211> LENGTH: 7
<212> TYPE: PRT
<213> ORGANISM: Artificial Sequence
<220> FEATURE:
<223> OTHER INFORMATION: Synthetic construct

<400> SEQUENCE: 239

Arg Ser Asp Ala Leu Val Arg
1               5

<210> SEQ ID NO 240
<211> LENGTH: 7
<212> TYPE: PRT
<213> ORGANISM: Artificial Sequence
```

-continued

```
<220> FEATURE:
<223> OTHER INFORMATION: Synthetic construct

<400> SEQUENCE: 240

Arg Ser Ser Ser Leu Val Arg
1               5

<210> SEQ ID NO 241
<211> LENGTH: 7
<212> TYPE: PRT
<213> ORGANISM: Artificial Sequence
<220> FEATURE:
<223> OTHER INFORMATION: Synthetic construct

<400> SEQUENCE: 241

Arg Ser Ser Ser His Val Arg
1               5

<210> SEQ ID NO 242
<211> LENGTH: 7
<212> TYPE: PRT
<213> ORGANISM: Artificial Sequence
<220> FEATURE:
<223> OTHER INFORMATION: Synthetic construct

<400> SEQUENCE: 242

Arg Ser Asp Glu Leu Val Lys
1               5

<210> SEQ ID NO 243
<211> LENGTH: 7
<212> TYPE: PRT
<213> ORGANISM: Artificial Sequence
<220> FEATURE:
<223> OTHER INFORMATION: Synthetic construct

<400> SEQUENCE: 243

Arg Ser Asp Ala Leu Val Lys
1               5

<210> SEQ ID NO 244
<211> LENGTH: 7
<212> TYPE: PRT
<213> ORGANISM: Artificial Sequence
<220> FEATURE:
<223> OTHER INFORMATION: Synthetic construct

<400> SEQUENCE: 244

Arg Ser Asp Val Leu Val Lys
1               5

<210> SEQ ID NO 245
<211> LENGTH: 7
<212> TYPE: PRT
<213> ORGANISM: Artificial Sequence
<220> FEATURE:
<223> OTHER INFORMATION: Synthetic construct

<400> SEQUENCE: 245

Arg Ser Ser Ala Leu Val Arg
1               5

<210> SEQ ID NO 246
<211> LENGTH: 7
<212> TYPE: PRT
<213> ORGANISM: Artificial Sequence
<220> FEATURE:
<223> OTHER INFORMATION: Synthetic construct
```

<400> SEQUENCE: 246

Arg Lys Asp Ser Leu Val Lys
1               5

<210> SEQ ID NO 247
<211> LENGTH: 7
<212> TYPE: PRT
<213> ORGANISM: Artificial Sequence
<220> FEATURE:
<223> OTHER INFORMATION: Synthetic construct

<400> SEQUENCE: 247

Arg Ser Ala Ser Leu Val Arg
1               5

<210> SEQ ID NO 248
<211> LENGTH: 7
<212> TYPE: PRT
<213> ORGANISM: Artificial Sequence
<220> FEATURE:
<223> OTHER INFORMATION: Synthetic construct

<400> SEQUENCE: 248

Arg Ser Asp Ser Leu Val Arg
1               5

<210> SEQ ID NO 249
<211> LENGTH: 7
<212> TYPE: PRT
<213> ORGANISM: Artificial Sequence
<220> FEATURE:
<223> OTHER INFORMATION: Synthetic construct

<400> SEQUENCE: 249

Arg Ile His Ser Leu Val Arg
1               5

<210> SEQ ID NO 250
<211> LENGTH: 7
<212> TYPE: PRT
<213> ORGANISM: Artificial Sequence
<220> FEATURE:
<223> OTHER INFORMATION: Synthetic construct

<400> SEQUENCE: 250

Arg Pro Gly Ser Leu Val Arg
1               5

<210> SEQ ID NO 251
<211> LENGTH: 7
<212> TYPE: PRT
<213> ORGANISM: Artificial Sequence
<220> FEATURE:
<223> OTHER INFORMATION: Synthetic construct

<400> SEQUENCE: 251

Arg Gly Pro Ser Leu Val Arg
1               5

<210> SEQ ID NO 252
<211> LENGTH: 7
<212> TYPE: PRT
<213> ORGANISM: Artificial Sequence
<220> FEATURE:
<223> OTHER INFORMATION: Synthetic construct

<400> SEQUENCE: 252

Arg Pro Gly Ala Leu Val Arg
1               5

<210> SEQ ID NO 253
<211> LENGTH: 7
<212> TYPE: PRT
<213> ORGANISM: Artificial Sequence
<220> FEATURE:
<223> OTHER INFORMATION: Synthetic construct

<400> SEQUENCE: 253

Lys Ser Ala Ser Lys Val Arg
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic construct

<400> SEQUENCE: 254

Lys Ser Ala Ala Leu Val Arg
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic construct

<400> SEQUENCE: 255

Lys Ser Ala Val Leu Val Arg
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic construct

<400> SEQUENCE: 256

Thr Ser Gly Ser Leu Thr Arg
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic construct

<400> SEQUENCE: 257

Thr Ser Gln Ser Leu Val Arg
1               5

<210> SEQ ID NO 258
<211> LENGTH: 7
<212> TYPE: PRT
<213> ORGANISM: Artificial Sequence
<220> FEATURE:
<223> OTHER INFORMATION: Synthetic construct

<400> SEQUENCE: 258

Thr Ser Ser Ser Leu Val Arg

```
<210> SEQ ID NO 259
<211> LENGTH: 7
<212> TYPE: PRT
<213> ORGANISM: Artificial Sequence
<220> FEATURE:
<223> OTHER INFORMATION: Synthetic construct

<400> SEQUENCE: 259

Thr Pro Gly Ser Leu Val Arg
1               5

<210> SEQ ID NO 260
<211> LENGTH: 7
<212> TYPE: PRT
<213> ORGANISM: Artificial Sequence
<220> FEATURE:
<223> OTHER INFORMATION: Synthetic construct

<400> SEQUENCE: 260

Thr Ser Gly Ala Leu Val Arg
1               5

<210> SEQ ID NO 261
<211> LENGTH: 7
<212> TYPE: PRT
<213> ORGANISM: Artificial Sequence
<220> FEATURE:
<223> OTHER INFORMATION: Synthetic construct

<400> SEQUENCE: 261

Thr Pro Gly Ala Leu Val Arg
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic construct

<400> SEQUENCE: 262

Thr Gly Gly Ser Leu Val Arg
1               5

<210> SEQ ID NO 263
<211> LENGTH: 7
<212> TYPE: PRT
<213> ORGANISM: Artificial Sequence
<220> FEATURE:
<223> OTHER INFORMATION: Synthetic construct

<400> SEQUENCE: 263

Thr Ser Gly Glu Leu Val Arg
1               5

<210> SEQ ID NO 264
<211> LENGTH: 7
<212> TYPE: PRT
<213> ORGANISM: Artificial Sequence
<220> FEATURE:
<223> OTHER INFORMATION: Synthetic construct

<400> SEQUENCE: 264

Thr Ser Gly Glu Leu Thr Arg
1               5
```

```
<210> SEQ ID NO 265
<211> LENGTH: 7
<212> TYPE: PRT
<213> ORGANISM: Artificial Sequence
<220> FEATURE:
<223> OTHER INFORMATION: Synthetic construct

<400> SEQUENCE: 265

Thr Ser Ser Ala Leu Val Lys
1               5

<210> SEQ ID NO 266
<211> LENGTH: 7
<212> TYPE: PRT
<213> ORGANISM: Artificial Sequence
<220> FEATURE:
<223> OTHER INFORMATION: Synthetic construct

<400> SEQUENCE: 266

Thr Ser Ser Ala Leu Val Arg
1               5

<210> SEQ ID NO 267
<211> LENGTH: 7
<212> TYPE: PRT
<213> ORGANISM: Artificial Sequence
<220> FEATURE:
<223> OTHER INFORMATION: Synthetic construct

<400> SEQUENCE: 267

Gln Ala Ser Asn Leu Ile Ser
1               5

<210> SEQ ID NO 268
<211> LENGTH: 7
<212> TYPE: PRT
<213> ORGANISM: Artificial Sequence
<220> FEATURE:
<223> OTHER INFORMATION: Synthetic construct

<400> SEQUENCE: 268

Ser Arg Gly Asn Leu Lys Ser
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic construct

<400> SEQUENCE: 269

Arg Leu Asp Asn Leu Gln Thr
1               5

<210> SEQ ID NO 270
<211> LENGTH: 7
<212> TYPE: PRT
<213> ORGANISM: Artificial Sequence
<220> FEATURE:
<223> OTHER INFORMATION: Synthetic construct

<400> SEQUENCE: 270

Ala Arg Gly Asn Leu Arg Thr
1               5

<210> SEQ ID NO 271
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 271

Arg Lys Asp Ala Leu Arg Gly
1               5

<210> SEQ ID NO 272
<211> LENGTH: 7
<212> TYPE: PRT
<213> ORGANISM: Artificial Sequence
<220> FEATURE:
<223> OTHER INFORMATION: Synthetic construct

<400> SEQUENCE: 272

Arg Glu Asp Asn Leu His Thr
1               5

<210> SEQ ID NO 273
<211> LENGTH: 7
<212> TYPE: PRT
<213> ORGANISM: Artificial Sequence
<220> FEATURE:
<223> OTHER INFORMATION: Synthetic construct

<400> SEQUENCE: 273

Ala Arg Gly Asn Leu Lys Ser
1               5

<210> SEQ ID NO 274
<211> LENGTH: 7
<212> TYPE: PRT
<213> ORGANISM: Artificial Sequence
<220> FEATURE:
<223> OTHER INFORMATION: Synthetic construct

<400> SEQUENCE: 274

Arg Ser Asp Asn Leu Thr Thr
1               5

<210> SEQ ID NO 275
<211> LENGTH: 7
<212> TYPE: PRT
<213> ORGANISM: Artificial Sequence
<220> FEATURE:
<223> OTHER INFORMATION: Synthetic construct

<400> SEQUENCE: 275

Val Arg Gly Asn Leu Lys Ser
1               5

<210> SEQ ID NO 276
<211> LENGTH: 7
<212> TYPE: PRT
<213> ORGANISM: Artificial Sequence
<220> FEATURE:
<223> OTHER INFORMATION: Synthetic construct

<400> SEQUENCE: 276

Val Arg Gly Asn Leu Arg Thr
1               5

<210> SEQ ID NO 277
<211> LENGTH: 7
<212> TYPE: PRT
```

<213> ORGANISM: Artificial Sequence
<220> FEATURE:
<223> OTHER INFORMATION: Synthetic construct

<400> SEQUENCE: 277

Arg Leu Arg Ala Leu Asp Arg
1               5

<210> SEQ ID NO 278
<211> LENGTH: 7
<212> TYPE: PRT
<213> ORGANISM: Artificial Sequence
<220> FEATURE:
<223> OTHER INFORMATION: Synthetic construct

<400> SEQUENCE: 278

Asp Met Gly Ala Leu Glu Ala
1               5

<210> SEQ ID NO 279
<211> LENGTH: 7
<212> TYPE: PRT
<213> ORGANISM: Artificial Sequence
<220> FEATURE:
<223> OTHER INFORMATION: Synthetic construct

<400> SEQUENCE: 279

Glu Lys Asp Ala Leu Arg Gly
1               5

<210> SEQ ID NO 280
<211> LENGTH: 7
<212> TYPE: PRT
<213> ORGANISM: Artificial Sequence
<220> FEATURE:
<223> OTHER INFORMATION: Synthetic construct

<400> SEQUENCE: 280

Arg Ser Asp His Leu Thr Thr
1               5

<210> SEQ ID NO 281
<211> LENGTH: 7
<212> TYPE: PRT
<213> ORGANISM: Artificial Sequence
<220> FEATURE:
<223> OTHER INFORMATION: Synthetic construct

<400> SEQUENCE: 281

Ala Gln Gln Leu Leu Met Trp
1               5

<210> SEQ ID NO 282
<211> LENGTH: 7
<212> TYPE: PRT
<213> ORGANISM: Artificial Sequence
<220> FEATURE:
<223> OTHER INFORMATION: Synthetic construct

<400> SEQUENCE: 282

Arg Ser Asp Glu Arg Lys Arg
1               5

<210> SEQ ID NO 283
<211> LENGTH: 7
<212> TYPE: PRT
<213> ORGANISM: Artificial Sequence
<220> FEATURE:

-continued

<223> OTHER INFORMATION: Synthetic construct

<400> SEQUENCE: 283

Asp Tyr Gln Ser Leu Arg Gln
1               5

<210> SEQ ID NO 284
<211> LENGTH: 7
<212> TYPE: PRT
<213> ORGANISM: Artificial Sequence
<220> FEATURE:
<223> OTHER INFORMATION: Synthetic construct

<400> SEQUENCE: 284

Cys Phe Ser Arg Leu Val Arg
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic construct

<400> SEQUENCE: 285

Gly Asp Gly Gly Leu Trp Glu
1               5

<210> SEQ ID NO 286
<211> LENGTH: 7
<212> TYPE: PRT
<213> ORGANISM: Artificial Sequence
<220> FEATURE:
<223> OTHER INFORMATION: Synthetic construct

<400> SEQUENCE: 286

Leu Gln Arg Pro Leu Arg Gly
1               5

<210> SEQ ID NO 287
<211> LENGTH: 7
<212> TYPE: PRT
<213> ORGANISM: Artificial Sequence
<220> FEATURE:
<223> OTHER INFORMATION: Synthetic construct

<400> SEQUENCE: 287

Gln Gly Leu Ala Cys Ala Ala
1               5

<210> SEQ ID NO 288
<211> LENGTH: 7
<212> TYPE: PRT
<213> ORGANISM: Artificial Sequence
<220> FEATURE:
<223> OTHER INFORMATION: Synthetic construct

<400> SEQUENCE: 288

Trp Val Gly Trp Leu Gly Ser
1               5

<210> SEQ ID NO 289
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 289

Arg Leu Arg Asp Ile Gln Phe
1               5

<210> SEQ ID NO 290
<211> LENGTH: 7
<212> TYPE: PRT
<213> ORGANISM: Artificial Sequence
<220> FEATURE:
<223> OTHER INFORMATION: Synthetic construct

<400> SEQUENCE: 290

Gly Arg Ser Gln Leu Ser Cys
1               5

<210> SEQ ID NO 291
<211> LENGTH: 7
<212> TYPE: PRT
<213> ORGANISM: Artificial Sequence
<220> FEATURE:
<223> OTHER INFORMATION: Synthetic construct

<400> SEQUENCE: 291

Gly Trp Gln Arg Leu Leu Thr
1               5

<210> SEQ ID NO 292
<211> LENGTH: 7
<212> TYPE: PRT
<213> ORGANISM: Artificial Sequence
<220> FEATURE:
<223> OTHER INFORMATION: Synthetic construct

<400> SEQUENCE: 292

Ser Gly Arg Pro Leu Ala Ser
1               5

<210> SEQ ID NO 293
<211> LENGTH: 7
<212> TYPE: PRT
<213> ORGANISM: Artificial Sequence
<220> FEATURE:
<223> OTHER INFORMATION: Synthetic construct

<400> SEQUENCE: 293

Ala Pro Arg Leu Leu Gly Pro
1               5

<210> SEQ ID NO 294
<211> LENGTH: 7
<212> TYPE: PRT
<213> ORGANISM: Artificial Sequence
<220> FEATURE:
<223> OTHER INFORMATION: Synthetic construct

<400> SEQUENCE: 294

Ala Pro Lys Ala Leu Gly Trp
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic construct

<400> SEQUENCE: 295
```

```
Ser Val His Glu Leu Gln Gly
1               5

<210> SEQ ID NO 296
<211> LENGTH: 7
<212> TYPE: PRT
<213> ORGANISM: Artificial Sequence
<220> FEATURE:
<223> OTHER INFORMATION: Synthetic construct

<400> SEQUENCE: 296

Ala Gln Ala Ala Leu Ser Trp
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic construct

<400> SEQUENCE: 297

Gly Ala Asn Ala Leu Arg Arg
1               5

<210> SEQ ID NO 298
<211> LENGTH: 7
<212> TYPE: PRT
<213> ORGANISM: Artificial Sequence
<220> FEATURE:
<223> OTHER INFORMATION: Synthetic construct

<400> SEQUENCE: 298

Gln Ser Leu Leu Leu Gly Ala
1               5

<210> SEQ ID NO 299
<211> LENGTH: 7
<212> TYPE: PRT
<213> ORGANISM: Artificial Sequence
<220> FEATURE:
<223> OTHER INFORMATION: Synthetic construct

<400> SEQUENCE: 299

His Arg Gly Thr Leu Gly Gly
1               5

<210> SEQ ID NO 300
<211> LENGTH: 7
<212> TYPE: PRT
<213> ORGANISM: Artificial Sequence
<220> FEATURE:
<223> OTHER INFORMATION: Synthetic construct

<400> SEQUENCE: 300

Gln Val Gly Leu Leu Ala Arg
1               5

<210> SEQ ID NO 301
<211> LENGTH: 7
<212> TYPE: PRT
<213> ORGANISM: Artificial Sequence
<220> FEATURE:
<223> OTHER INFORMATION: Synthetic construct

<400> SEQUENCE: 301

Gly Ala Arg Gly Leu Arg Gly
1               5
```

<210> SEQ ID NO 302
<211> LENGTH: 7
<212> TYPE: PRT
<213> ORGANISM: Artificial Sequence
<220> FEATURE:
<223> OTHER INFORMATION: Synthetic construct

<400> SEQUENCE: 302

Asp Lys His Met Leu Asp Thr
1               5

<210> SEQ ID NO 303
<211> LENGTH: 7
<212> TYPE: PRT
<213> ORGANISM: Artificial Sequence
<220> FEATURE:
<223> OTHER INFORMATION: Synthetic construct

<400> SEQUENCE: 303

Asp Leu Gly Gly Leu Arg Gln
1               5

<210> SEQ ID NO 304
<211> LENGTH: 7
<212> TYPE: PRT
<213> ORGANISM: Artificial Sequence
<220> FEATURE:
<223> OTHER INFORMATION: Synthetic construct

<400> SEQUENCE: 304

Gln Cys Tyr Arg Leu Glu Arg
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic construct

<400> SEQUENCE: 305

Ala Glu Ala Glu Leu Gln Arg
1               5

<210> SEQ ID NO 306
<211> LENGTH: 7
<212> TYPE: PRT
<213> ORGANISM: Artificial Sequence
<220> FEATURE:
<223> OTHER INFORMATION: Synthetic construct

<400> SEQUENCE: 306

Gln Gly Gly Val Leu Ala Ala
1               5

<210> SEQ ID NO 307
<211> LENGTH: 7
<212> TYPE: PRT
<213> ORGANISM: Artificial Sequence
<220> FEATURE:
<223> OTHER INFORMATION: Synthetic construct

<400> SEQUENCE: 307

Gln Gly Arg Cys Leu Val Thr
1               5

```
<210> SEQ ID NO 308
<211> LENGTH: 7
<212> TYPE: PRT
<213> ORGANISM: Artificial Sequence
<220> FEATURE:
<223> OTHER INFORMATION: Synthetic construct

<400> SEQUENCE: 308

His Pro Glu Ala Leu Asp Asn
1               5

<210> SEQ ID NO 309
<211> LENGTH: 7
<212> TYPE: PRT
<213> ORGANISM: Artificial Sequence
<220> FEATURE:
<223> OTHER INFORMATION: Synthetic construct

<400> SEQUENCE: 309

Gly Arg Gly Ala Leu Gln Ala
1               5

<210> SEQ ID NO 310
<211> LENGTH: 7
<212> TYPE: PRT
<213> ORGANISM: Artificial Sequence
<220> FEATURE:
<223> OTHER INFORMATION: Synthetic construct

<400> SEQUENCE: 310

Leu Ala Ser Arg Leu Gln Gln
1               5

<210> SEQ ID NO 311
<211> LENGTH: 7
<212> TYPE: PRT
<213> ORGANISM: Artificial Sequence
<220> FEATURE:
<223> OTHER INFORMATION: Synthetic construct

<400> SEQUENCE: 311

Arg Glu Asp Asn Leu Ile Ser
1               5

<210> SEQ ID NO 312
<211> LENGTH: 7
<212> TYPE: PRT
<213> ORGANISM: Artificial Sequence
<220> FEATURE:
<223> OTHER INFORMATION: Synthetic construct

<400> SEQUENCE: 312

Asp Ala Ser Asn Leu Ile Ser
1               5

<210> SEQ ID NO 313
<211> LENGTH: 7
<212> TYPE: PRT
<213> ORGANISM: Artificial Sequence
<220> FEATURE:
<223> OTHER INFORMATION: Synthetic construct

<400> SEQUENCE: 313

Glu Ala Ser Asn Leu Ile Ser
1               5

<210> SEQ ID NO 314
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 314

Arg Ala Ser Asn Leu Ile Ser
1               5

<210> SEQ ID NO 315
<211> LENGTH: 7
<212> TYPE: PRT
<213> ORGANISM: Artificial Sequence
<220> FEATURE:
<223> OTHER INFORMATION: Synthetic construct

<400> SEQUENCE: 315

Thr Ala Ser Asn Leu Ile Ser
1               5

<210> SEQ ID NO 316
<211> LENGTH: 7
<212> TYPE: PRT
<213> ORGANISM: Artificial Sequence
<220> FEATURE:
<223> OTHER INFORMATION: Synthetic construct

<400> SEQUENCE: 316

Ser Ala Ser Asn Leu Ile Ser
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic construct

<400> SEQUENCE: 317

Gln Ala Ser Thr Leu Ile Ser
1               5

<210> SEQ ID NO 318
<211> LENGTH: 7
<212> TYPE: PRT
<213> ORGANISM: Artificial Sequence
<220> FEATURE:
<223> OTHER INFORMATION: Synthetic construct

<400> SEQUENCE: 318

Gln Ala Ser Asp Leu Ile Ser
1               5

<210> SEQ ID NO 319
<211> LENGTH: 7
<212> TYPE: PRT
<213> ORGANISM: Artificial Sequence
<220> FEATURE:
<223> OTHER INFORMATION: Synthetic construct

<400> SEQUENCE: 319

Gln Ala Ser Glu Leu Ile Ser
1               5

<210> SEQ ID NO 320
<211> LENGTH: 7
<212> TYPE: PRT
<213> ORGANISM: Artificial Sequence
```

<220> FEATURE:
<223> OTHER INFORMATION: Synthetic construct

<400> SEQUENCE: 320

Gln Ala Ser His Leu Ile Ser
1               5

<210> SEQ ID NO 321
<211> LENGTH: 7
<212> TYPE: PRT
<213> ORGANISM: Artificial Sequence
<220> FEATURE:
<223> OTHER INFORMATION: Synthetic construct

<400> SEQUENCE: 321

Gln Ala Ser Lys Leu Ile Ser
1               5

<210> SEQ ID NO 322
<211> LENGTH: 7
<212> TYPE: PRT
<213> ORGANISM: Artificial Sequence
<220> FEATURE:
<223> OTHER INFORMATION: Synthetic construct

<400> SEQUENCE: 322

Gln Ala Ser Ser Leu Ile Ser
1               5

<210> SEQ ID NO 323
<211> LENGTH: 7
<212> TYPE: PRT
<213> ORGANISM: Artificial Sequence
<220> FEATURE:
<223> OTHER INFORMATION: Synthetic construct

<400> SEQUENCE: 323

Gln Ala Ser Ala Leu Ile Ser
1               5

<210> SEQ ID NO 324
<211> LENGTH: 7
<212> TYPE: PRT
<213> ORGANISM: Artificial Sequence
<220> FEATURE:
<223> OTHER INFORMATION: Synthetic construct

<400> SEQUENCE: 324

Asp Ala Ser Thr Leu Ile Ser
1               5

<210> SEQ ID NO 325
<211> LENGTH: 7
<212> TYPE: PRT
<213> ORGANISM: Artificial Sequence
<220> FEATURE:
<223> OTHER INFORMATION: Synthetic construct

<400> SEQUENCE: 325

Asp Ala Ser Asp Leu Ile Ser
1               5

<210> SEQ ID NO 326
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 326

Asp Ala Ser Glu Leu Ile Ser
1               5

<210> SEQ ID NO 327
<211> LENGTH: 7
<212> TYPE: PRT
<213> ORGANISM: Artificial Sequence
<220> FEATURE:
<223> OTHER INFORMATION: Synthetic construct

<400> SEQUENCE: 327

Asp Ala Ser His Leu Ile Ser
1               5

<210> SEQ ID NO 328
<211> LENGTH: 7
<212> TYPE: PRT
<213> ORGANISM: Artificial Sequence
<220> FEATURE:
<223> OTHER INFORMATION: Synthetic construct

<400> SEQUENCE: 328

Asp Ala Ser Lys Leu Ile Ser
1               5

<210> SEQ ID NO 329
<211> LENGTH: 7
<212> TYPE: PRT
<213> ORGANISM: Artificial Sequence
<220> FEATURE:
<223> OTHER INFORMATION: Synthetic construct

<400> SEQUENCE: 329

Asp Ala Ser Ser Leu Ile Ser
1               5

<210> SEQ ID NO 330
<211> LENGTH: 7
<212> TYPE: PRT
<213> ORGANISM: Artificial Sequence
<220> FEATURE:
<223> OTHER INFORMATION: Synthetic construct

<400> SEQUENCE: 330

Asp Ala Ser Ala Leu Ile Ser
1               5

<210> SEQ ID NO 331
<211> LENGTH: 7
<212> TYPE: PRT
<213> ORGANISM: Artificial Sequence
<220> FEATURE:
<223> OTHER INFORMATION: Synthetic construct

<400> SEQUENCE: 331

Glu Ala Ser Thr Leu Ile Ser
1               5

<210> SEQ ID NO 332
<211> LENGTH: 7
<212> TYPE: PRT
<213> ORGANISM: Artificial Sequence
<220> FEATURE:
<223> OTHER INFORMATION: Synthetic construct

<400> SEQUENCE: 332
```

Glu Ala Ser Asp Leu Ile Ser
1               5

<210> SEQ ID NO 333
<211> LENGTH: 7
<212> TYPE: PRT
<213> ORGANISM: Artificial Sequence
<220> FEATURE:
<223> OTHER INFORMATION: Synthetic construct

<400> SEQUENCE: 333

Glu Ala Ser Glu Leu Ile Ser
1               5

<210> SEQ ID NO 334
<211> LENGTH: 7
<212> TYPE: PRT
<213> ORGANISM: Artificial Sequence
<220> FEATURE:
<223> OTHER INFORMATION: Synthetic construct

<400> SEQUENCE: 334

Glu Ala Ser His Leu Ile Ser
1               5

<210> SEQ ID NO 335
<211> LENGTH: 7
<212> TYPE: PRT
<213> ORGANISM: Artificial Sequence
<220> FEATURE:
<223> OTHER INFORMATION: Synthetic construct

<400> SEQUENCE: 335

Glu Ala Ser Lys Leu Ile Ser
1               5

<210> SEQ ID NO 336
<211> LENGTH: 7
<212> TYPE: PRT
<213> ORGANISM: Artificial Sequence
<220> FEATURE:
<223> OTHER INFORMATION: Synthetic construct

<400> SEQUENCE: 336

Glu Ala Ser Ser Leu Ile Ser
1               5

<210> SEQ ID NO 337
<211> LENGTH: 7
<212> TYPE: PRT
<213> ORGANISM: Artificial Sequence
<220> FEATURE:
<223> OTHER INFORMATION: Synthetic construct

<400> SEQUENCE: 337

Glu Ala Ser Ala Leu Ile Ser
1               5

<210> SEQ ID NO 338
<211> LENGTH: 7
<212> TYPE: PRT
<213> ORGANISM: Artificial Sequence
<220> FEATURE:
<223> OTHER INFORMATION: Synthetic construct

<400> SEQUENCE: 338

Arg Ala Ser Thr Leu Ile Ser

```
<210> SEQ ID NO 339
<211> LENGTH: 7
<212> TYPE: PRT
<213> ORGANISM: Artificial Sequence
<220> FEATURE:
<223> OTHER INFORMATION: Synthetic construct

<400> SEQUENCE: 339

Arg Ala Ser Asp Leu Ile Ser
1               5

<210> SEQ ID NO 340
<211> LENGTH: 7
<212> TYPE: PRT
<213> ORGANISM: Artificial Sequence
<220> FEATURE:
<223> OTHER INFORMATION: Synthetic construct

<400> SEQUENCE: 340

Arg Ala Ser Glu Leu Ile Ser
1               5

<210> SEQ ID NO 341
<211> LENGTH: 7
<212> TYPE: PRT
<213> ORGANISM: Artificial Sequence
<220> FEATURE:
<223> OTHER INFORMATION: Synthetic construct

<400> SEQUENCE: 341

Arg Ala Ser His Leu Ile Ser
1               5

<210> SEQ ID NO 342
<211> LENGTH: 7
<212> TYPE: PRT
<213> ORGANISM: Artificial Sequence
<220> FEATURE:
<223> OTHER INFORMATION: Synthetic construct

<400> SEQUENCE: 342

Arg Ala Ser Lys Leu Ile Ser
1               5

<210> SEQ ID NO 343
<211> LENGTH: 7
<212> TYPE: PRT
<213> ORGANISM: Artificial Sequence
<220> FEATURE:
<223> OTHER INFORMATION: Synthetic construct

<400> SEQUENCE: 343

Arg Ala Ser Ser Leu Ile Ser
1               5

<210> SEQ ID NO 344
<211> LENGTH: 7
<212> TYPE: PRT
<213> ORGANISM: Artificial Sequence
<220> FEATURE:
<223> OTHER INFORMATION: Synthetic construct

<400> SEQUENCE: 344

Arg Ala Ser Ala Leu Ile Ser
1               5
```

```
<210> SEQ ID NO 345
<211> LENGTH: 7
<212> TYPE: PRT
<213> ORGANISM: Artificial Sequence
<220> FEATURE:
<223> OTHER INFORMATION: Synthetic construct

<400> SEQUENCE: 345

Thr Ala Ser Thr Leu Ile Ser
1               5

<210> SEQ ID NO 346
<211> LENGTH: 7
<212> TYPE: PRT
<213> ORGANISM: Artificial Sequence
<220> FEATURE:
<223> OTHER INFORMATION: Synthetic construct

<400> SEQUENCE: 346

Thr Ala Ser Asp Leu Ile Ser
1               5

<210> SEQ ID NO 347
<211> LENGTH: 7
<212> TYPE: PRT
<213> ORGANISM: Artificial Sequence
<220> FEATURE:
<223> OTHER INFORMATION: Synthetic construct

<400> SEQUENCE: 347

Thr Ala Ser Glu Leu Ile Ser
1               5

<210> SEQ ID NO 348
<211> LENGTH: 7
<212> TYPE: PRT
<213> ORGANISM: Artificial Sequence
<220> FEATURE:
<223> OTHER INFORMATION: Synthetic construct

<400> SEQUENCE: 348

Thr Ala Ser His Leu Ile Ser
1               5

<210> SEQ ID NO 349
<211> LENGTH: 7
<212> TYPE: PRT
<213> ORGANISM: Artificial Sequence
<220> FEATURE:
<223> OTHER INFORMATION: Synthetic construct

<400> SEQUENCE: 349

Thr Ala Ser Lys Leu Ile Ser
1               5

<210> SEQ ID NO 350
<211> LENGTH: 7
<212> TYPE: PRT
<213> ORGANISM: Artificial Sequence
<220> FEATURE:
<223> OTHER INFORMATION: Synthetic construct

<400> SEQUENCE: 350

Thr Ala Ser Ser Leu Ile Ser
1               5

<210> SEQ ID NO 351
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 351

Thr Ala Ser Ala Leu Ile Ser
1               5

<210> SEQ ID NO 352
<211> LENGTH: 7
<212> TYPE: PRT
<213> ORGANISM: Artificial Sequence
<220> FEATURE:
<223> OTHER INFORMATION: Synthetic construct

<400> SEQUENCE: 352

Ser Ala Ser Thr Leu Ile Ser
1               5

<210> SEQ ID NO 353
<211> LENGTH: 7
<212> TYPE: PRT
<213> ORGANISM: Artificial Sequence
<220> FEATURE:
<223> OTHER INFORMATION: Synthetic construct

<400> SEQUENCE: 353

Ser Ala Ser Asp Leu Ile Ser
1               5

<210> SEQ ID NO 354
<211> LENGTH: 7
<212> TYPE: PRT
<213> ORGANISM: Artificial Sequence
<220> FEATURE:
<223> OTHER INFORMATION: Synthetic construct

<400> SEQUENCE: 354

Ser Ala Ser Glu Leu Ile Ser
1               5

<210> SEQ ID NO 355
<211> LENGTH: 7
<212> TYPE: PRT
<213> ORGANISM: Artificial Sequence
<220> FEATURE:
<223> OTHER INFORMATION: Synthetic construct

<400> SEQUENCE: 355

Ser Ala Ser His Leu Ile Ser
1               5

<210> SEQ ID NO 356
<211> LENGTH: 7
<212> TYPE: PRT
<213> ORGANISM: Artificial Sequence
<220> FEATURE:
<223> OTHER INFORMATION: Synthetic construct

<400> SEQUENCE: 356

Ser Ala Ser Lys Leu Ile Ser
1               5

<210> SEQ ID NO 357
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 357

Ser Ala Ser Ser Leu Ile Ser
1               5

<210> SEQ ID NO 358
<211> LENGTH: 7
<212> TYPE: PRT
<213> ORGANISM: Artificial Sequence
<220> FEATURE:
<223> OTHER INFORMATION: Synthetic construct

<400> SEQUENCE: 358

Ser Ala Ser Ala Leu Ile Ser
1               5

<210> SEQ ID NO 359
<211> LENGTH: 7
<212> TYPE: PRT
<213> ORGANISM: Artificial Sequence
<220> FEATURE:
<223> OTHER INFORMATION: Synthetic construct

<400> SEQUENCE: 359

Gln Leu Asp Asn Leu Gln Thr
1               5

<210> SEQ ID NO 360
<211> LENGTH: 7
<212> TYPE: PRT
<213> ORGANISM: Artificial Sequence
<220> FEATURE:
<223> OTHER INFORMATION: Synthetic construct

<400> SEQUENCE: 360

Asp Leu Asp Asn Leu Gln Thr
1               5

<210> SEQ ID NO 361
<211> LENGTH: 7
<212> TYPE: PRT
<213> ORGANISM: Artificial Sequence
<220> FEATURE:
<223> OTHER INFORMATION: Synthetic construct

<400> SEQUENCE: 361

Glu Leu Asp Asn Leu Gln Thr
1               5

<210> SEQ ID NO 362
<211> LENGTH: 7
<212> TYPE: PRT
<213> ORGANISM: Artificial Sequence
<220> FEATURE:
<223> OTHER INFORMATION: Synthetic construct

<400> SEQUENCE: 362

Thr Leu Asp Asn Leu Gln Thr
1               5

<210> SEQ ID NO 363
<211> LENGTH: 7
<212> TYPE: PRT
<213> ORGANISM: Artificial Sequence
<220> FEATURE:
```

<223> OTHER INFORMATION: Synthetic construct

<400> SEQUENCE: 363

Ser Leu Asp Asn Leu Gln Thr
1               5

<210> SEQ ID NO 364
<211> LENGTH: 7
<212> TYPE: PRT
<213> ORGANISM: Artificial Sequence
<220> FEATURE:
<223> OTHER INFORMATION: Synthetic construct

<400> SEQUENCE: 364

Arg Leu Asp Thr Leu Gln Thr
1               5

<210> SEQ ID NO 365
<211> LENGTH: 7
<212> TYPE: PRT
<213> ORGANISM: Artificial Sequence
<220> FEATURE:
<223> OTHER INFORMATION: Synthetic construct

<400> SEQUENCE: 365

Arg Leu Asp Asp Leu Gln Thr
1               5

<210> SEQ ID NO 366
<211> LENGTH: 7
<212> TYPE: PRT
<213> ORGANISM: Artificial Sequence
<220> FEATURE:
<223> OTHER INFORMATION: Synthetic construct

<400> SEQUENCE: 366

Arg Leu Asp Glu Leu Gln Thr
1               5

<210> SEQ ID NO 367
<211> LENGTH: 7
<212> TYPE: PRT
<213> ORGANISM: Artificial Sequence
<220> FEATURE:
<223> OTHER INFORMATION: Synthetic construct

<400> SEQUENCE: 367

Arg Leu Asp His Leu Gln Thr
1               5

<210> SEQ ID NO 368
<211> LENGTH: 7
<212> TYPE: PRT
<213> ORGANISM: Artificial Sequence
<220> FEATURE:
<223> OTHER INFORMATION: Synthetic construct

<400> SEQUENCE: 368

Arg Leu Asp Lys Leu Gln Thr
1               5

<210> SEQ ID NO 369
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 369

Arg Leu Asp Ser Leu Gln Thr
1               5

<210> SEQ ID NO 370
<211> LENGTH: 7
<212> TYPE: PRT
<213> ORGANISM: Artificial Sequence
<220> FEATURE:
<223> OTHER INFORMATION: Synthetic construct

<400> SEQUENCE: 370

Arg Leu Asp Ala Leu Gln Thr
1               5

<210> SEQ ID NO 371
<211> LENGTH: 7
<212> TYPE: PRT
<213> ORGANISM: Artificial Sequence
<220> FEATURE:
<223> OTHER INFORMATION: Synthetic construct

<400> SEQUENCE: 371

Gln Leu Asp Thr Leu Gln Thr
1               5

<210> SEQ ID NO 372
<211> LENGTH: 7
<212> TYPE: PRT
<213> ORGANISM: Artificial Sequence
<220> FEATURE:
<223> OTHER INFORMATION: Synthetic construct

<400> SEQUENCE: 372

Gln Leu Asp Asp Leu Gln Thr
1               5

<210> SEQ ID NO 373
<211> LENGTH: 7
<212> TYPE: PRT
<213> ORGANISM: Artificial Sequence
<220> FEATURE:
<223> OTHER INFORMATION: Synthetic construct

<400> SEQUENCE: 373

Gln Leu Asp Glu Leu Gln Thr
1               5

<210> SEQ ID NO 374
<211> LENGTH: 7
<212> TYPE: PRT
<213> ORGANISM: Artificial Sequence
<220> FEATURE:
<223> OTHER INFORMATION: Synthetic construct

<400> SEQUENCE: 374

Gln Leu Asp His Leu Gln Thr
1               5

<210> SEQ ID NO 375
<211> LENGTH: 7
<212> TYPE: PRT
<213> ORGANISM: Artificial Sequence
<220> FEATURE:
<223> OTHER INFORMATION: Synthetic construct

<400> SEQUENCE: 375
```

```
Gln Leu Asp Lys Leu Gln Thr
1               5
```

<210> SEQ ID NO 376
<211> LENGTH: 7
<212> TYPE: PRT
<213> ORGANISM: Artificial Sequence
<220> FEATURE:
<223> OTHER INFORMATION: Synthetic construct

<400> SEQUENCE: 376

```
Gln Leu Asp Ser Leu Gln Thr
1               5
```

<210> SEQ ID NO 377
<211> LENGTH: 7
<212> TYPE: PRT
<213> ORGANISM: Artificial Sequence
<220> FEATURE:
<223> OTHER INFORMATION: Synthetic construct

<400> SEQUENCE: 377

```
Gln Leu Asp Ala Leu Gln Thr
1               5
```

<210> SEQ ID NO 378
<211> LENGTH: 7
<212> TYPE: PRT
<213> ORGANISM: Artificial Sequence
<220> FEATURE:
<223> OTHER INFORMATION: Synthetic construct

<400> SEQUENCE: 378

```
Asp Leu Asp Thr Leu Gln Thr
1               5
```

<210> SEQ ID NO 379
<211> LENGTH: 7
<212> TYPE: PRT
<213> ORGANISM: Artificial Sequence
<220> FEATURE:
<223> OTHER INFORMATION: Synthetic construct

<400> SEQUENCE: 379

```
Asp Leu Asp Asp Leu Gln Thr
1               5
```

<210> SEQ ID NO 380
<211> LENGTH: 7
<212> TYPE: PRT
<213> ORGANISM: Artificial Sequence
<220> FEATURE:
<223> OTHER INFORMATION: Synthetic construct

<400> SEQUENCE: 380

```
Asp Leu Asp Glu Leu Gln Thr
1               5
```

<210> SEQ ID NO 381
<211> LENGTH: 7
<212> TYPE: PRT
<213> ORGANISM: Artificial Sequence
<220> FEATURE:
<223> OTHER INFORMATION: Synthetic construct

<400> SEQUENCE: 381

```
Asp Leu Asp His Leu Gln Thr
1               5
```

```
<210> SEQ ID NO 382
<211> LENGTH: 7
<212> TYPE: PRT
<213> ORGANISM: Artificial Sequence
<220> FEATURE:
<223> OTHER INFORMATION: Synthetic construct

<400> SEQUENCE: 382

Asp Leu Asp Lys Leu Gln Thr
1               5

<210> SEQ ID NO 383
<211> LENGTH: 7
<212> TYPE: PRT
<213> ORGANISM: Artificial Sequence
<220> FEATURE:
<223> OTHER INFORMATION: Synthetic construct

<400> SEQUENCE: 383

Asp Leu Asp Ser Leu Gln Thr
1               5

<210> SEQ ID NO 384
<211> LENGTH: 7
<212> TYPE: PRT
<213> ORGANISM: Artificial Sequence
<220> FEATURE:
<223> OTHER INFORMATION: Synthetic construct

<400> SEQUENCE: 384

Asp Leu Asp Ala Leu Gln Thr
1               5

<210> SEQ ID NO 385
<211> LENGTH: 7
<212> TYPE: PRT
<213> ORGANISM: Artificial Sequence
<220> FEATURE:
<223> OTHER INFORMATION: Synthetic construct

<400> SEQUENCE: 385

Glu Leu Asp Thr Leu Gln Thr
1               5

<210> SEQ ID NO 386
<211> LENGTH: 7
<212> TYPE: PRT
<213> ORGANISM: Artificial Sequence
<220> FEATURE:
<223> OTHER INFORMATION: Synthetic construct

<400> SEQUENCE: 386

Glu Leu Asp Asp Leu Gln Thr
1               5

<210> SEQ ID NO 387
<211> LENGTH: 7
<212> TYPE: PRT
<213> ORGANISM: Artificial Sequence
<220> FEATURE:
<223> OTHER INFORMATION: Synthetic construct

<400> SEQUENCE: 387

Glu Leu Asp Glu Leu Gln Thr
1               5
```

```
<210> SEQ ID NO 388
<211> LENGTH: 7
<212> TYPE: PRT
<213> ORGANISM: Artificial Sequence
<220> FEATURE:
<223> OTHER INFORMATION: Synthetic construct

<400> SEQUENCE: 388

Glu Leu Asp His Leu Gln Thr
1               5

<210> SEQ ID NO 389
<211> LENGTH: 7
<212> TYPE: PRT
<213> ORGANISM: Artificial Sequence
<220> FEATURE:
<223> OTHER INFORMATION: Synthetic construct

<400> SEQUENCE: 389

Glu Leu Asp Lys Leu Gln Thr
1               5

<210> SEQ ID NO 390
<211> LENGTH: 7
<212> TYPE: PRT
<213> ORGANISM: Artificial Sequence
<220> FEATURE:
<223> OTHER INFORMATION: Synthetic construct

<400> SEQUENCE: 390

Glu Leu Asp Ser Leu Gln Thr
1               5

<210> SEQ ID NO 391
<211> LENGTH: 7
<212> TYPE: PRT
<213> ORGANISM: Artificial Sequence
<220> FEATURE:
<223> OTHER INFORMATION: Synthetic construct

<400> SEQUENCE: 391

Glu Leu Asp Ala Leu Gln Thr
1               5

<210> SEQ ID NO 392
<211> LENGTH: 7
<212> TYPE: PRT
<213> ORGANISM: Artificial Sequence
<220> FEATURE:
<223> OTHER INFORMATION: Synthetic construct

<400> SEQUENCE: 392

Thr Leu Asp Thr Leu Gln Thr
1               5

<210> SEQ ID NO 393
<211> LENGTH: 7
<212> TYPE: PRT
<213> ORGANISM: Artificial Sequence
<220> FEATURE:
<223> OTHER INFORMATION: Synthetic construct

<400> SEQUENCE: 393

Thr Leu Asp Asp Leu Gln Thr
1               5

<210> SEQ ID NO 394
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 394

Thr Leu Asp Glu Leu Gln Thr
1               5

<210> SEQ ID NO 395
<211> LENGTH: 7
<212> TYPE: PRT
<213> ORGANISM: Artificial Sequence
<220> FEATURE:
<223> OTHER INFORMATION: Synthetic construct

<400> SEQUENCE: 395

Thr Leu Asp His Leu Gln Thr
1               5

<210> SEQ ID NO 396
<211> LENGTH: 7
<212> TYPE: PRT
<213> ORGANISM: Artificial Sequence
<220> FEATURE:
<223> OTHER INFORMATION: Synthetic construct

<400> SEQUENCE: 396

Thr Leu Asp Lys Leu Gln Thr
1               5

<210> SEQ ID NO 397
<211> LENGTH: 7
<212> TYPE: PRT
<213> ORGANISM: Artificial Sequence
<220> FEATURE:
<223> OTHER INFORMATION: Synthetic construct

<400> SEQUENCE: 397

Thr Leu Asp Ser Leu Gln Thr
1               5

<210> SEQ ID NO 398
<211> LENGTH: 7
<212> TYPE: PRT
<213> ORGANISM: Artificial Sequence
<220> FEATURE:
<223> OTHER INFORMATION: Synthetic construct

<400> SEQUENCE: 398

Thr Leu Asp Ala Leu Gln Thr
1               5

<210> SEQ ID NO 399
<211> LENGTH: 7
<212> TYPE: PRT
<213> ORGANISM: Artificial Sequence
<220> FEATURE:
<223> OTHER INFORMATION: Synthetic construct

<400> SEQUENCE: 399

Ser Leu Asp Thr Leu Gln Thr
1               5

<210> SEQ ID NO 400
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 400

Ser Leu Asp Asp Leu Gln Thr
1               5

<210> SEQ ID NO 401
<211> LENGTH: 7
<212> TYPE: PRT
<213> ORGANISM: Artificial Sequence
<220> FEATURE:
<223> OTHER INFORMATION: Synthetic construct

<400> SEQUENCE: 401

Ser Leu Asp Glu Leu Gln Thr
1               5

<210> SEQ ID NO 402
<211> LENGTH: 7
<212> TYPE: PRT
<213> ORGANISM: Artificial Sequence
<220> FEATURE:
<223> OTHER INFORMATION: Synthetic construct

<400> SEQUENCE: 402

Ser Leu Asp His Leu Gln Thr
1               5

<210> SEQ ID NO 403
<211> LENGTH: 7
<212> TYPE: PRT
<213> ORGANISM: Artificial Sequence
<220> FEATURE:
<223> OTHER INFORMATION: Synthetic construct

<400> SEQUENCE: 403

Ser Leu Asp Lys Leu Gln Thr
1               5

<210> SEQ ID NO 404
<211> LENGTH: 7
<212> TYPE: PRT
<213> ORGANISM: Artificial Sequence
<220> FEATURE:
<223> OTHER INFORMATION: Synthetic construct

<400> SEQUENCE: 404

Ser Leu Asp Ser Leu Gln Thr
1               5

<210> SEQ ID NO 405
<211> LENGTH: 7
<212> TYPE: PRT
<213> ORGANISM: Artificial Sequence
<220> FEATURE:
<223> OTHER INFORMATION: Synthetic construct

<400> SEQUENCE: 405

Ser Leu Asp Ala Leu Gln Thr
1               5

<210> SEQ ID NO 406
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 406

Ala Arg Gly Thr Leu Arg Thr
1               5

<210> SEQ ID NO 407
<211> LENGTH: 7
<212> TYPE: PRT
<213> ORGANISM: Artificial Sequence
<220> FEATURE:
<223> OTHER INFORMATION: Synthetic construct

<400> SEQUENCE: 407

Ala Arg Gly Asp Leu Arg Thr
1               5

<210> SEQ ID NO 408
<211> LENGTH: 7
<212> TYPE: PRT
<213> ORGANISM: Artificial Sequence
<220> FEATURE:
<223> OTHER INFORMATION: Synthetic construct

<400> SEQUENCE: 408

Ala Arg Gly Glu Leu Arg Thr
1               5

<210> SEQ ID NO 409
<211> LENGTH: 7
<212> TYPE: PRT
<213> ORGANISM: Artificial Sequence
<220> FEATURE:
<223> OTHER INFORMATION: Synthetic construct

<400> SEQUENCE: 409

Ala Arg Gly His Leu Arg Thr
1               5

<210> SEQ ID NO 410
<211> LENGTH: 7
<212> TYPE: PRT
<213> ORGANISM: Artificial Sequence
<220> FEATURE:
<223> OTHER INFORMATION: Synthetic construct

<400> SEQUENCE: 410

Ala Arg Gly Lys Leu Arg Thr
1               5

<210> SEQ ID NO 411
<211> LENGTH: 7
<212> TYPE: PRT
<213> ORGANISM: Artificial Sequence
<220> FEATURE:
<223> OTHER INFORMATION: Synthetic construct

<400> SEQUENCE: 411

Ala Arg Gly Ser Leu Arg Thr
1               5

<210> SEQ ID NO 412
<211> LENGTH: 7
<212> TYPE: PRT
<213> ORGANISM: Artificial Sequence
<220> FEATURE:
<223> OTHER INFORMATION: Synthetic construct

<400> SEQUENCE: 412
```

```
Ala Arg Gly Ala Leu Arg Thr
1               5

<210> SEQ ID NO 413
<211> LENGTH: 7
<212> TYPE: PRT
<213> ORGANISM: Artificial Sequence
<220> FEATURE:
<223> OTHER INFORMATION: Synthetic construct

<400> SEQUENCE: 413

Ser Arg Gly Thr Leu Arg Thr
1               5

<210> SEQ ID NO 414
<211> LENGTH: 7
<212> TYPE: PRT
<213> ORGANISM: Artificial Sequence
<220> FEATURE:
<223> OTHER INFORMATION: Synthetic construct

<400> SEQUENCE: 414

Ser Arg Gly Asp Leu Arg Thr
1               5

<210> SEQ ID NO 415
<211> LENGTH: 7
<212> TYPE: PRT
<213> ORGANISM: Artificial Sequence
<220> FEATURE:
<223> OTHER INFORMATION: Synthetic construct

<400> SEQUENCE: 415

Ser Arg Gly Glu Leu Arg Thr
1               5

<210> SEQ ID NO 416
<211> LENGTH: 7
<212> TYPE: PRT
<213> ORGANISM: Artificial Sequence
<220> FEATURE:
<223> OTHER INFORMATION: Synthetic construct

<400> SEQUENCE: 416

Ser Arg Gly His Leu Arg Thr
1               5

<210> SEQ ID NO 417
<211> LENGTH: 7
<212> TYPE: PRT
<213> ORGANISM: Artificial Sequence
<220> FEATURE:
<223> OTHER INFORMATION: Synthetic construct

<400> SEQUENCE: 417

Ser Arg Gly Lys Leu Arg Thr
1               5

<210> SEQ ID NO 418
<211> LENGTH: 7
<212> TYPE: PRT
<213> ORGANISM: Artificial Sequence
<220> FEATURE:
<223> OTHER INFORMATION: Synthetic construct

<400> SEQUENCE: 418

Ser Arg Gly Ser Leu Arg Thr
```

```
<210> SEQ ID NO 419
<211> LENGTH: 7
<212> TYPE: PRT
<213> ORGANISM: Artificial Sequence
<220> FEATURE:
<223> OTHER INFORMATION: Synthetic construct

<400> SEQUENCE: 419

Ser Arg Gly Ala Leu Arg Thr
1               5

<210> SEQ ID NO 420
<211> LENGTH: 7
<212> TYPE: PRT
<213> ORGANISM: Artificial Sequence
<220> FEATURE:
<223> OTHER INFORMATION: Synthetic construct

<400> SEQUENCE: 420

Gln Lys Asp Ala Leu Arg Gly
1               5

<210> SEQ ID NO 421
<211> LENGTH: 7
<212> TYPE: PRT
<213> ORGANISM: Artificial Sequence
<220> FEATURE:
<223> OTHER INFORMATION: Synthetic construct

<400> SEQUENCE: 421

Asp Lys Asp Ala Leu Arg Gly
1               5

<210> SEQ ID NO 422
<211> LENGTH: 7
<212> TYPE: PRT
<213> ORGANISM: Artificial Sequence
<220> FEATURE:
<223> OTHER INFORMATION: Synthetic construct

<400> SEQUENCE: 422

Glu Lys Asp Ala Leu Arg Gly
1               5

<210> SEQ ID NO 423
<211> LENGTH: 7
<212> TYPE: PRT
<213> ORGANISM: Artificial Sequence
<220> FEATURE:
<223> OTHER INFORMATION: Synthetic construct

<400> SEQUENCE: 423

Thr Lys Asp Ala Leu Arg Gly
1               5

<210> SEQ ID NO 424
<211> LENGTH: 7
<212> TYPE: PRT
<213> ORGANISM: Artificial Sequence
<220> FEATURE:
<223> OTHER INFORMATION: Synthetic construct

<400> SEQUENCE: 424

Ser Lys Asp Ala Leu Arg Gly
1               5
```

```
<210> SEQ ID NO 425
<211> LENGTH: 7
<212> TYPE: PRT
<213> ORGANISM: Artificial Sequence
<220> FEATURE:
<223> OTHER INFORMATION: Synthetic construct

<400> SEQUENCE: 425

Arg Lys Asp Asn Leu Arg Gly
1               5

<210> SEQ ID NO 426
<211> LENGTH: 7
<212> TYPE: PRT
<213> ORGANISM: Artificial Sequence
<220> FEATURE:
<223> OTHER INFORMATION: Synthetic construct

<400> SEQUENCE: 426

Arg Lys Asp Thr Leu Arg Gly
1               5

<210> SEQ ID NO 427
<211> LENGTH: 7
<212> TYPE: PRT
<213> ORGANISM: Artificial Sequence
<220> FEATURE:
<223> OTHER INFORMATION: Synthetic construct

<400> SEQUENCE: 427

Arg Lys Asp Asp Leu Arg Gly
1               5

<210> SEQ ID NO 428
<211> LENGTH: 7
<212> TYPE: PRT
<213> ORGANISM: Artificial Sequence
<220> FEATURE:
<223> OTHER INFORMATION: Synthetic construct

<400> SEQUENCE: 428

Arg Lys Asp Glu Leu Arg Gly
1               5

<210> SEQ ID NO 429
<211> LENGTH: 7
<212> TYPE: PRT
<213> ORGANISM: Artificial Sequence
<220> FEATURE:
<223> OTHER INFORMATION: Synthetic construct

<400> SEQUENCE: 429

Arg Lys Asp His Leu Arg Gly
1               5

<210> SEQ ID NO 430
<211> LENGTH: 7
<212> TYPE: PRT
<213> ORGANISM: Artificial Sequence
<220> FEATURE:
<223> OTHER INFORMATION: Synthetic construct

<400> SEQUENCE: 430

Arg Lys Asp Lys Leu Arg Gly
1               5

<210> SEQ ID NO 431
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 431

Arg Lys Asp Ser Leu Arg Gly
1               5

<210> SEQ ID NO 432
<211> LENGTH: 7
<212> TYPE: PRT
<213> ORGANISM: Artificial Sequence
<220> FEATURE:
<223> OTHER INFORMATION: Synthetic construct

<400> SEQUENCE: 432

Gln Lys Asp Asn Leu Arg Gly
1               5

<210> SEQ ID NO 433
<211> LENGTH: 7
<212> TYPE: PRT
<213> ORGANISM: Artificial Sequence
<220> FEATURE:
<223> OTHER INFORMATION: Synthetic construct

<400> SEQUENCE: 433

Gln Lys Asp Thr Leu Arg Gly
1               5

<210> SEQ ID NO 434
<211> LENGTH: 7
<212> TYPE: PRT
<213> ORGANISM: Artificial Sequence
<220> FEATURE:
<223> OTHER INFORMATION: Synthetic construct

<400> SEQUENCE: 434

Gln Lys Asp Asp Leu Arg Gly
1               5

<210> SEQ ID NO 435
<211> LENGTH: 7
<212> TYPE: PRT
<213> ORGANISM: Artificial Sequence
<220> FEATURE:
<223> OTHER INFORMATION: Synthetic construct

<400> SEQUENCE: 435

Gln Lys Asp Glu Leu Arg Gly
1               5

<210> SEQ ID NO 436
<211> LENGTH: 7
<212> TYPE: PRT
<213> ORGANISM: Artificial Sequence
<220> FEATURE:
<223> OTHER INFORMATION: Synthetic construct

<400> SEQUENCE: 436

Gln Lys Asp His Leu Arg Gly
1               5

<210> SEQ ID NO 437
<211> LENGTH: 7
<212> TYPE: PRT
```

<213> ORGANISM: Artificial Sequence
<220> FEATURE:
<223> OTHER INFORMATION: Synthetic construct

<400> SEQUENCE: 437

Gln Lys Asp Lys Leu Arg Gly
1               5

<210> SEQ ID NO 438
<211> LENGTH: 7
<212> TYPE: PRT
<213> ORGANISM: Artificial Sequence
<220> FEATURE:
<223> OTHER INFORMATION: Synthetic construct

<400> SEQUENCE: 438

Gln Lys Asp Ser Leu Arg Gly
1               5

<210> SEQ ID NO 439
<211> LENGTH: 7
<212> TYPE: PRT
<213> ORGANISM: Artificial Sequence
<220> FEATURE:
<223> OTHER INFORMATION: Synthetic construct

<400> SEQUENCE: 439

Asp Lys Asp Asn Leu Arg Gly
1               5

<210> SEQ ID NO 440
<211> LENGTH: 7
<212> TYPE: PRT
<213> ORGANISM: Artificial Sequence
<220> FEATURE:
<223> OTHER INFORMATION: Synthetic construct

<400> SEQUENCE: 440

Asp Lys Asp Thr Leu Arg Gly
1               5

<210> SEQ ID NO 441
<211> LENGTH: 7
<212> TYPE: PRT
<213> ORGANISM: Artificial Sequence
<220> FEATURE:
<223> OTHER INFORMATION: Synthetic construct

<400> SEQUENCE: 441

Asp Lys Asp Asp Leu Arg Gly
1               5

<210> SEQ ID NO 442
<211> LENGTH: 7
<212> TYPE: PRT
<213> ORGANISM: Artificial Sequence
<220> FEATURE:
<223> OTHER INFORMATION: Synthetic construct

<400> SEQUENCE: 442

Asp Lys Asp Glu Leu Arg Gly
1               5

<210> SEQ ID NO 443
<211> LENGTH: 7
<212> TYPE: PRT
<213> ORGANISM: Artificial Sequence
<220> FEATURE:

<223> OTHER INFORMATION: Synthetic construct

<400> SEQUENCE: 443

Asp Lys Asp His Leu Arg Gly
1               5

<210> SEQ ID NO 444
<211> LENGTH: 7
<212> TYPE: PRT
<213> ORGANISM: Artificial Sequence
<220> FEATURE:
<223> OTHER INFORMATION: Synthetic construct

<400> SEQUENCE: 444

Asp Lys Asp Lys Leu Arg Gly
1               5

<210> SEQ ID NO 445
<211> LENGTH: 7
<212> TYPE: PRT
<213> ORGANISM: Artificial Sequence
<220> FEATURE:
<223> OTHER INFORMATION: Synthetic construct

<400> SEQUENCE: 445

Asp Lys Asp Ser Leu Arg Gly
1               5

<210> SEQ ID NO 446
<211> LENGTH: 7
<212> TYPE: PRT
<213> ORGANISM: Artificial Sequence
<220> FEATURE:
<223> OTHER INFORMATION: Synthetic construct

<400> SEQUENCE: 446

Glu Lys Asp Asn Leu Arg Gly
1               5

<210> SEQ ID NO 447
<211> LENGTH: 7
<212> TYPE: PRT
<213> ORGANISM: Artificial Sequence
<220> FEATURE:
<223> OTHER INFORMATION: Synthetic construct

<400> SEQUENCE: 447

Glu Lys Asp Thr Leu Arg Gly
1               5

<210> SEQ ID NO 448
<211> LENGTH: 7
<212> TYPE: PRT
<213> ORGANISM: Artificial Sequence
<220> FEATURE:
<223> OTHER INFORMATION: Synthetic construct

<400> SEQUENCE: 448

Glu Lys Asp Asp Leu Arg Gly
1               5

<210> SEQ ID NO 449
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 449

Glu Lys Asp Glu Leu Arg Gly
1               5

<210> SEQ ID NO 450
<211> LENGTH: 7
<212> TYPE: PRT
<213> ORGANISM: Artificial Sequence
<220> FEATURE:
<223> OTHER INFORMATION: Synthetic construct

<400> SEQUENCE: 450

Glu Lys Asp His Leu Arg Gly
1               5

<210> SEQ ID NO 451
<211> LENGTH: 7
<212> TYPE: PRT
<213> ORGANISM: Artificial Sequence
<220> FEATURE:
<223> OTHER INFORMATION: Synthetic construct

<400> SEQUENCE: 451

Glu Lys Asp Lys Leu Arg Gly
1               5

<210> SEQ ID NO 452
<211> LENGTH: 7
<212> TYPE: PRT
<213> ORGANISM: Artificial Sequence
<220> FEATURE:
<223> OTHER INFORMATION: Synthetic construct

<400> SEQUENCE: 452

Glu Lys Asp Ser Leu Arg Gly
1               5

<210> SEQ ID NO 453
<211> LENGTH: 7
<212> TYPE: PRT
<213> ORGANISM: Artificial Sequence
<220> FEATURE:
<223> OTHER INFORMATION: Synthetic construct

<400> SEQUENCE: 453

Thr Lys Asp Asn Leu Arg Gly
1               5

<210> SEQ ID NO 454
<211> LENGTH: 7
<212> TYPE: PRT
<213> ORGANISM: Artificial Sequence
<220> FEATURE:
<223> OTHER INFORMATION: Synthetic construct

<400> SEQUENCE: 454

Thr Lys Asp Thr Leu Arg Gly
1               5

<210> SEQ ID NO 455
<211> LENGTH: 7
<212> TYPE: PRT
<213> ORGANISM: Artificial Sequence
<220> FEATURE:
<223> OTHER INFORMATION: Synthetic construct

<400> SEQUENCE: 455
```

Thr Lys Asp Leu Arg Gly
1               5

<210> SEQ ID NO 456
<211> LENGTH: 7
<212> TYPE: PRT
<213> ORGANISM: Artificial Sequence
<220> FEATURE:
<223> OTHER INFORMATION: Synthetic construct

<400> SEQUENCE: 456

Thr Lys Asp Glu Leu Arg Gly
1               5

<210> SEQ ID NO 457
<211> LENGTH: 7
<212> TYPE: PRT
<213> ORGANISM: Artificial Sequence
<220> FEATURE:
<223> OTHER INFORMATION: Synthetic construct

<400> SEQUENCE: 457

Thr Lys Asp His Leu Arg Gly
1               5

<210> SEQ ID NO 458
<211> LENGTH: 7
<212> TYPE: PRT
<213> ORGANISM: Artificial Sequence
<220> FEATURE:
<223> OTHER INFORMATION: Synthetic construct

<400> SEQUENCE: 458

Thr Lys Asp Lys Leu Arg Gly
1               5

<210> SEQ ID NO 459
<211> LENGTH: 7
<212> TYPE: PRT
<213> ORGANISM: Artificial Sequence
<220> FEATURE:
<223> OTHER INFORMATION: Synthetic construct

<400> SEQUENCE: 459

Thr Lys Asp Ser Leu Arg Gly
1               5

<210> SEQ ID NO 460
<211> LENGTH: 7
<212> TYPE: PRT
<213> ORGANISM: Artificial Sequence
<220> FEATURE:
<223> OTHER INFORMATION: Synthetic construct

<400> SEQUENCE: 460

Ser Lys Asp Asn Leu Arg Gly
1               5

<210> SEQ ID NO 461
<211> LENGTH: 7
<212> TYPE: PRT
<213> ORGANISM: Artificial Sequence
<220> FEATURE:
<223> OTHER INFORMATION: Synthetic construct

<400> SEQUENCE: 461

Ser Lys Asp Thr Leu Arg Gly
1               5

<210> SEQ ID NO 462
<211> LENGTH: 7
<212> TYPE: PRT
<213> ORGANISM: Artificial Sequence
<220> FEATURE:
<223> OTHER INFORMATION: Synthetic construct

<400> SEQUENCE: 462

Ser Lys Asp Asp Leu Arg Gly
1               5

<210> SEQ ID NO 463
<211> LENGTH: 7
<212> TYPE: PRT
<213> ORGANISM: Artificial Sequence
<220> FEATURE:
<223> OTHER INFORMATION: Synthetic construct

<400> SEQUENCE: 463

Ser Lys Asp Glu Leu Arg Gly
1               5

<210> SEQ ID NO 464
<211> LENGTH: 7
<212> TYPE: PRT
<213> ORGANISM: Artificial Sequence
<220> FEATURE:
<223> OTHER INFORMATION: Synthetic construct

<400> SEQUENCE: 464

Ser Lys Asp His Leu Arg Gly
1               5

<210> SEQ ID NO 465
<211> LENGTH: 7
<212> TYPE: PRT
<213> ORGANISM: Artificial Sequence
<220> FEATURE:
<223> OTHER INFORMATION: Synthetic construct

<400> SEQUENCE: 465

Ser Lys Asp Lys Leu Arg Gly
1               5

<210> SEQ ID NO 466
<211> LENGTH: 7
<212> TYPE: PRT
<213> ORGANISM: Artificial Sequence
<220> FEATURE:
<223> OTHER INFORMATION: Synthetic construct

<400> SEQUENCE: 466

Ser Lys Asp Ser Leu Arg Gly
1               5

<210> SEQ ID NO 467
<211> LENGTH: 7
<212> TYPE: PRT
<213> ORGANISM: Artificial Sequence
<220> FEATURE:
<223> OTHER INFORMATION: Synthetic construct

<400> SEQUENCE: 467

Val Arg Gly Thr Leu Arg Thr
1               5

```
<210> SEQ ID NO 468
<211> LENGTH: 7
<212> TYPE: PRT
<213> ORGANISM: Artificial Sequence
<220> FEATURE:
<223> OTHER INFORMATION: Synthetic construct

<400> SEQUENCE: 468

Val Arg Gly Asp Leu Arg Thr
1               5

<210> SEQ ID NO 469
<211> LENGTH: 7
<212> TYPE: PRT
<213> ORGANISM: Artificial Sequence
<220> FEATURE:
<223> OTHER INFORMATION: Synthetic construct

<400> SEQUENCE: 469

Val Arg Gly Glu Leu Arg Thr
1               5

<210> SEQ ID NO 470
<211> LENGTH: 7
<212> TYPE: PRT
<213> ORGANISM: Artificial Sequence
<220> FEATURE:
<223> OTHER INFORMATION: Synthetic construct

<400> SEQUENCE: 470

Val Arg Gly His Leu Arg Thr
1               5

<210> SEQ ID NO 471
<211> LENGTH: 7
<212> TYPE: PRT
<213> ORGANISM: Artificial Sequence
<220> FEATURE:
<223> OTHER INFORMATION: Synthetic construct

<400> SEQUENCE: 471

Val Arg Gly Lys Leu Arg Thr
1               5

<210> SEQ ID NO 472
<211> LENGTH: 7
<212> TYPE: PRT
<213> ORGANISM: Artificial Sequence
<220> FEATURE:
<223> OTHER INFORMATION: Synthetic construct

<400> SEQUENCE: 472

Val Arg Gly Ser Leu Arg Thr
1               5

<210> SEQ ID NO 473
<211> LENGTH: 7
<212> TYPE: PRT
<213> ORGANISM: Artificial Sequence
<220> FEATURE:
<223> OTHER INFORMATION: Synthetic construct

<400> SEQUENCE: 473

Val Arg Gly Thr Leu Arg Thr
1               5

<210> SEQ ID NO 474
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 474

Gln Leu Arg Ala Leu Asp Arg
1               5

<210> SEQ ID NO 475
<211> LENGTH: 7
<212> TYPE: PRT
<213> ORGANISM: Artificial Sequence
<220> FEATURE:
<223> OTHER INFORMATION: Synthetic construct

<400> SEQUENCE: 475

Asp Leu Arg Ala Leu Asp Arg
1               5

<210> SEQ ID NO 476
<211> LENGTH: 7
<212> TYPE: PRT
<213> ORGANISM: Artificial Sequence
<220> FEATURE:
<223> OTHER INFORMATION: Synthetic construct

<400> SEQUENCE: 476

Glu Leu Arg Ala Leu Asp Arg
1               5

<210> SEQ ID NO 477
<211> LENGTH: 7
<212> TYPE: PRT
<213> ORGANISM: Artificial Sequence
<220> FEATURE:
<223> OTHER INFORMATION: Synthetic construct

<400> SEQUENCE: 477

Thr Leu Arg Ala Leu Asp Arg
1               5

<210> SEQ ID NO 478
<211> LENGTH: 7
<212> TYPE: PRT
<213> ORGANISM: Artificial Sequence
<220> FEATURE:
<223> OTHER INFORMATION: Synthetic construct

<400> SEQUENCE: 478

Ser Leu Arg Ala Leu Asp Arg
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic construct

<400> SEQUENCE: 479

Arg Ser Asp Asn Arg Lys Arg
1               5

<210> SEQ ID NO 480
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 480

Arg Ser Asp Thr Arg Lys Arg
1               5

<210> SEQ ID NO 481
<211> LENGTH: 7
<212> TYPE: PRT
<213> ORGANISM: Artificial Sequence
<220> FEATURE:
<223> OTHER INFORMATION: Synthetic construct

<400> SEQUENCE: 481

Arg Ser Asp Asp Arg Lys Arg
1               5

<210> SEQ ID NO 482
<211> LENGTH: 7
<212> TYPE: PRT
<213> ORGANISM: Artificial Sequence
<220> FEATURE:
<223> OTHER INFORMATION: Synthetic construct

<400> SEQUENCE: 482

Arg Ser Asp His Arg Lys Arg
1               5

<210> SEQ ID NO 483
<211> LENGTH: 7
<212> TYPE: PRT
<213> ORGANISM: Artificial Sequence
<220> FEATURE:
<223> OTHER INFORMATION: Synthetic construct

<400> SEQUENCE: 483

Arg Ser Asp Lys Arg Lys Arg
1               5

<210> SEQ ID NO 484
<211> LENGTH: 7
<212> TYPE: PRT
<213> ORGANISM: Artificial Sequence
<220> FEATURE:
<223> OTHER INFORMATION: Synthetic construct

<400> SEQUENCE: 484

Arg Ser Asp Ser Arg Lys Arg
1               5

<210> SEQ ID NO 485
<211> LENGTH: 7
<212> TYPE: PRT
<213> ORGANISM: Artificial Sequence
<220> FEATURE:
<223> OTHER INFORMATION: Synthetic construct

<400> SEQUENCE: 485

Arg Ser Asp Ala Arg Lys Arg
1               5

<210> SEQ ID NO 486
<211> LENGTH: 7
<212> TYPE: PRT
<213> ORGANISM: Artificial Sequence
<220> FEATURE:
<223> OTHER INFORMATION: Synthetic construct
```

<400> SEQUENCE: 486

Gln Tyr Gln Ser Leu Arg Gln
1               5

<210> SEQ ID NO 487
<211> LENGTH: 7
<212> TYPE: PRT
<213> ORGANISM: Artificial Sequence
<220> FEATURE:
<223> OTHER INFORMATION: Synthetic construct

<400> SEQUENCE: 487

Glu Tyr Gln Ser Leu Arg Gln
1               5

<210> SEQ ID NO 488
<211> LENGTH: 7
<212> TYPE: PRT
<213> ORGANISM: Artificial Sequence
<220> FEATURE:
<223> OTHER INFORMATION: Synthetic construct

<400> SEQUENCE: 488

Arg Tyr Gln Ser Leu Arg Gln
1               5

<210> SEQ ID NO 489
<211> LENGTH: 7
<212> TYPE: PRT
<213> ORGANISM: Artificial Sequence
<220> FEATURE:
<223> OTHER INFORMATION: Synthetic construct

<400> SEQUENCE: 489

Thr Tyr Gln Ser Leu Arg Gln
1               5

<210> SEQ ID NO 490
<211> LENGTH: 7
<212> TYPE: PRT
<213> ORGANISM: Artificial Sequence
<220> FEATURE:
<223> OTHER INFORMATION: Synthetic construct

<400> SEQUENCE: 490

Ser Tyr Gln Ser Leu Arg Gln
1               5

<210> SEQ ID NO 491
<211> LENGTH: 7
<212> TYPE: PRT
<213> ORGANISM: Artificial Sequence
<220> FEATURE:
<223> OTHER INFORMATION: Synthetic construct

<400> SEQUENCE: 491

Arg Leu Arg Asn Ile Gln Phe
1               5

<210> SEQ ID NO 492
<211> LENGTH: 7
<212> TYPE: PRT
<213> ORGANISM: Artificial Sequence
<220> FEATURE:
<223> OTHER INFORMATION: Synthetic construct

<400> SEQUENCE: 492

```
Arg Leu Arg Thr Ile Gln Phe
1               5

<210> SEQ ID NO 493
<211> LENGTH: 7
<212> TYPE: PRT
<213> ORGANISM: Artificial Sequence
<220> FEATURE:
<223> OTHER INFORMATION: Synthetic construct

<400> SEQUENCE: 493

Arg Leu Arg Glu Ile Gln Phe
1               5

<210> SEQ ID NO 494
<211> LENGTH: 7
<212> TYPE: PRT
<213> ORGANISM: Artificial Sequence
<220> FEATURE:
<223> OTHER INFORMATION: Synthetic construct

<400> SEQUENCE: 494

Arg Leu Arg His Ile Gln Phe
1               5

<210> SEQ ID NO 495
<211> LENGTH: 7
<212> TYPE: PRT
<213> ORGANISM: Artificial Sequence
<220> FEATURE:
<223> OTHER INFORMATION: Synthetic construct

<400> SEQUENCE: 495

Arg Leu Arg Lys Ile Gln Phe
1               5

<210> SEQ ID NO 496
<211> LENGTH: 7
<212> TYPE: PRT
<213> ORGANISM: Artificial Sequence
<220> FEATURE:
<223> OTHER INFORMATION: Synthetic construct

<400> SEQUENCE: 496

Arg Leu Arg Ser Ile Gln Phe
1               5

<210> SEQ ID NO 497
<211> LENGTH: 7
<212> TYPE: PRT
<213> ORGANISM: Artificial Sequence
<220> FEATURE:
<223> OTHER INFORMATION: Synthetic construct

<400> SEQUENCE: 497

Arg Leu Arg Ala Ile Gln Phe
1               5

<210> SEQ ID NO 498
<211> LENGTH: 7
<212> TYPE: PRT
<213> ORGANISM: Artificial Sequence
<220> FEATURE:
<223> OTHER INFORMATION: Synthetic construct

<400> SEQUENCE: 498

Asp Ser Leu Leu Leu Gly Ala
```

```
1               5

<210> SEQ ID NO 499
<211> LENGTH: 7
<212> TYPE: PRT
<213> ORGANISM: Artificial Sequence
<220> FEATURE:
<223> OTHER INFORMATION: Synthetic construct

<400> SEQUENCE: 499

Glu Ser Leu Leu Leu Gly Ala
1               5

<210> SEQ ID NO 500
<211> LENGTH: 7
<212> TYPE: PRT
<213> ORGANISM: Artificial Sequence
<220> FEATURE:
<223> OTHER INFORMATION: Synthetic construct

<400> SEQUENCE: 500

Arg Ser Leu Leu Leu Gly Ala
1               5

<210> SEQ ID NO 501
<211> LENGTH: 7
<212> TYPE: PRT
<213> ORGANISM: Artificial Sequence
<220> FEATURE:
<223> OTHER INFORMATION: Synthetic construct

<400> SEQUENCE: 501

Thr Ser Leu Leu Leu Gly Ala
1               5

<210> SEQ ID NO 502
<211> LENGTH: 7
<212> TYPE: PRT
<213> ORGANISM: Artificial Sequence
<220> FEATURE:
<223> OTHER INFORMATION: Synthetic construct

<400> SEQUENCE: 502

Ser Ser Leu Leu Leu Gly Ala
1               5

<210> SEQ ID NO 503
<211> LENGTH: 7
<212> TYPE: PRT
<213> ORGANISM: Artificial Sequence
<220> FEATURE:
<223> OTHER INFORMATION: Synthetic construct

<400> SEQUENCE: 503

His Arg Gly Asn Leu Gly Gly
1               5

<210> SEQ ID NO 504
<211> LENGTH: 7
<212> TYPE: PRT
<213> ORGANISM: Artificial Sequence
<220> FEATURE:
<223> OTHER INFORMATION: Synthetic construct

<400> SEQUENCE: 504

His Arg Gly Asp Leu Gly Gly
1               5
```

```
<210> SEQ ID NO 505
<211> LENGTH: 7
<212> TYPE: PRT
<213> ORGANISM: Artificial Sequence
<220> FEATURE:
<223> OTHER INFORMATION: Synthetic construct

<400> SEQUENCE: 505

His Arg Gly Glu Leu Gly Gly
1               5

<210> SEQ ID NO 506
<211> LENGTH: 7
<212> TYPE: PRT
<213> ORGANISM: Artificial Sequence
<220> FEATURE:
<223> OTHER INFORMATION: Synthetic construct

<400> SEQUENCE: 506

His Arg Gly His Leu Gly Gly
1               5

<210> SEQ ID NO 507
<211> LENGTH: 7
<212> TYPE: PRT
<213> ORGANISM: Artificial Sequence
<220> FEATURE:
<223> OTHER INFORMATION: Synthetic construct

<400> SEQUENCE: 507

His Arg Gly Lys Leu Gly Gly
1               5

<210> SEQ ID NO 508
<211> LENGTH: 7
<212> TYPE: PRT
<213> ORGANISM: Artificial Sequence
<220> FEATURE:
<223> OTHER INFORMATION: Synthetic construct

<400> SEQUENCE: 508

His Arg Gly Ser Leu Gly Gly
1               5

<210> SEQ ID NO 509
<211> LENGTH: 7
<212> TYPE: PRT
<213> ORGANISM: Artificial Sequence
<220> FEATURE:
<223> OTHER INFORMATION: Synthetic construct

<400> SEQUENCE: 509

His Arg Gly Ala Leu Gly Gly
1               5

<210> SEQ ID NO 510
<211> LENGTH: 7
<212> TYPE: PRT
<213> ORGANISM: Artificial Sequence
<220> FEATURE:
<223> OTHER INFORMATION: Synthetic construct

<400> SEQUENCE: 510

Gln Lys His Met Leu Asp Thr
1               5

<210> SEQ ID NO 511
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 511

Glu Lys His Met Leu Asp Thr
1               5

<210> SEQ ID NO 512
<211> LENGTH: 7
<212> TYPE: PRT
<213> ORGANISM: Artificial Sequence
<220> FEATURE:
<223> OTHER INFORMATION: Synthetic construct

<400> SEQUENCE: 512

Arg Lys His Met Leu Asp Thr
1               5

<210> SEQ ID NO 513
<211> LENGTH: 7
<212> TYPE: PRT
<213> ORGANISM: Artificial Sequence
<220> FEATURE:
<223> OTHER INFORMATION: Synthetic construct

<400> SEQUENCE: 513

Thr Lys His Met Leu Asp Thr
1               5

<210> SEQ ID NO 514
<211> LENGTH: 7
<212> TYPE: PRT
<213> ORGANISM: Artificial Sequence
<220> FEATURE:
<223> OTHER INFORMATION: Synthetic construct

<400> SEQUENCE: 514

Ser Lys His Met Leu Asp Thr
1               5

<210> SEQ ID NO 515
<211> LENGTH: 7
<212> TYPE: PRT
<213> ORGANISM: Artificial Sequence
<220> FEATURE:
<223> OTHER INFORMATION: Synthetic construct

<400> SEQUENCE: 515

Gln Leu Gly Gly Leu Arg Gln
1               5

<210> SEQ ID NO 516
<211> LENGTH: 7
<212> TYPE: PRT
<213> ORGANISM: Artificial Sequence
<220> FEATURE:
<223> OTHER INFORMATION: Synthetic construct

<400> SEQUENCE: 516

Glu Leu Gly Gly Leu Arg Gln
1               5

<210> SEQ ID NO 517
<211> LENGTH: 7
<212> TYPE: PRT
```

<213> ORGANISM: Artificial Sequence
<220> FEATURE:
<223> OTHER INFORMATION: Synthetic construct

<400> SEQUENCE: 517

Arg Leu Gly Gly Leu Arg Gln
1               5

<210> SEQ ID NO 518
<211> LENGTH: 7
<212> TYPE: PRT
<213> ORGANISM: Artificial Sequence
<220> FEATURE:
<223> OTHER INFORMATION: Synthetic construct

<400> SEQUENCE: 518

Thr Leu Gly Gly Leu Arg Gln
1               5

<210> SEQ ID NO 519
<211> LENGTH: 7
<212> TYPE: PRT
<213> ORGANISM: Artificial Sequence
<220> FEATURE:
<223> OTHER INFORMATION: Synthetic construct

<400> SEQUENCE: 519

Ser Leu Gly Gly Leu Arg Gln
1               5

<210> SEQ ID NO 520
<211> LENGTH: 7
<212> TYPE: PRT
<213> ORGANISM: Artificial Sequence
<220> FEATURE:
<223> OTHER INFORMATION: Synthetic construct

<400> SEQUENCE: 520

Ala Glu Ala Asn Leu Gln Arg
1               5

<210> SEQ ID NO 521
<211> LENGTH: 7
<212> TYPE: PRT
<213> ORGANISM: Artificial Sequence
<220> FEATURE:
<223> OTHER INFORMATION: Synthetic construct

<400> SEQUENCE: 521

Ala Glu Ala Thr Leu Gln Arg
1               5

<210> SEQ ID NO 522
<211> LENGTH: 7
<212> TYPE: PRT
<213> ORGANISM: Artificial Sequence
<220> FEATURE:
<223> OTHER INFORMATION: Synthetic construct

<400> SEQUENCE: 522

Ala Glu Ala Asp Leu Gln Arg
1               5

<210> SEQ ID NO 523
<211> LENGTH: 7
<212> TYPE: PRT
<213> ORGANISM: Artificial Sequence
<220> FEATURE:

<223> OTHER INFORMATION: Synthetic construct

<400> SEQUENCE: 523

Ala Glu Ala His Leu Gln Arg
1               5

<210> SEQ ID NO 524
<211> LENGTH: 7
<212> TYPE: PRT
<213> ORGANISM: Artificial Sequence
<220> FEATURE:
<223> OTHER INFORMATION: Synthetic construct

<400> SEQUENCE: 524

Ala Glu Ala Lys Leu Gln Arg
1               5

<210> SEQ ID NO 525
<211> LENGTH: 7
<212> TYPE: PRT
<213> ORGANISM: Artificial Sequence
<220> FEATURE:
<223> OTHER INFORMATION: Synthetic construct

<400> SEQUENCE: 525

Ala Glu Ala Ser Leu Gln Arg
1               5

<210> SEQ ID NO 526
<211> LENGTH: 7
<212> TYPE: PRT
<213> ORGANISM: Artificial Sequence
<220> FEATURE:
<223> OTHER INFORMATION: Synthetic construct

<400> SEQUENCE: 526

Ala Glu Ala Ala Leu Gln Arg
1               5

<210> SEQ ID NO 527
<211> LENGTH: 7
<212> TYPE: PRT
<213> ORGANISM: Artificial Sequence
<220> FEATURE:
<223> OTHER INFORMATION: Synthetic construct

<400> SEQUENCE: 527

Asp Gly Arg Cys Leu Val Thr
1               5

<210> SEQ ID NO 528
<211> LENGTH: 7
<212> TYPE: PRT
<213> ORGANISM: Artificial Sequence
<220> FEATURE:
<223> OTHER INFORMATION: Synthetic construct

<400> SEQUENCE: 528

Glu Gly Arg Cys Leu Val Thr
1               5

<210> SEQ ID NO 529
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 529

Arg Gly Arg Cys Leu Val Thr
1               5

<210> SEQ ID NO 530
<211> LENGTH: 7
<212> TYPE: PRT
<213> ORGANISM: Artificial Sequence
<220> FEATURE:
<223> OTHER INFORMATION: Synthetic construct

<400> SEQUENCE: 530

Thr Gly Arg Cys Leu Val Thr
1               5

<210> SEQ ID NO 531
<211> LENGTH: 7
<212> TYPE: PRT
<213> ORGANISM: Artificial Sequence
<220> FEATURE:
<223> OTHER INFORMATION: Synthetic construct

<400> SEQUENCE: 531

Ser Gly Arg Cys Leu Val Thr
1               5

<210> SEQ ID NO 532
<211> LENGTH: 7
<212> TYPE: PRT
<213> ORGANISM: Artificial Sequence
<220> FEATURE:
<223> OTHER INFORMATION: Synthetic construct

<400> SEQUENCE: 532

Gln Glu Asp Asn Leu His Thr
1               5

<210> SEQ ID NO 533
<211> LENGTH: 7
<212> TYPE: PRT
<213> ORGANISM: Artificial Sequence
<220> FEATURE:
<223> OTHER INFORMATION: Synthetic construct

<400> SEQUENCE: 533

Asp Glu Asp Asn Leu His Thr
1               5

<210> SEQ ID NO 534
<211> LENGTH: 7
<212> TYPE: PRT
<213> ORGANISM: Artificial Sequence
<220> FEATURE:
<223> OTHER INFORMATION: Synthetic construct

<400> SEQUENCE: 534

Glu Glu Asp Asn Leu His Thr
1               5

<210> SEQ ID NO 535
<211> LENGTH: 7
<212> TYPE: PRT
<213> ORGANISM: Artificial Sequence
<220> FEATURE:
<223> OTHER INFORMATION: Synthetic construct

<400> SEQUENCE: 535
```

Ser Glu Asp Asn Leu His Thr
1               5

<210> SEQ ID NO 536
<211> LENGTH: 7
<212> TYPE: PRT
<213> ORGANISM: Artificial Sequence
<220> FEATURE:
<223> OTHER INFORMATION: Synthetic construct

<400> SEQUENCE: 536

Arg Glu Asp Thr Leu His Thr
1               5

<210> SEQ ID NO 537
<211> LENGTH: 7
<212> TYPE: PRT
<213> ORGANISM: Artificial Sequence
<220> FEATURE:
<223> OTHER INFORMATION: Synthetic construct

<400> SEQUENCE: 537

Arg Glu Asp Asp Leu His Thr
1               5

<210> SEQ ID NO 538
<211> LENGTH: 7
<212> TYPE: PRT
<213> ORGANISM: Artificial Sequence
<220> FEATURE:
<223> OTHER INFORMATION: Synthetic construct

<400> SEQUENCE: 538

Arg Glu Asp Glu Leu His Thr
1               5

<210> SEQ ID NO 539
<211> LENGTH: 7
<212> TYPE: PRT
<213> ORGANISM: Artificial Sequence
<220> FEATURE:
<223> OTHER INFORMATION: Synthetic construct

<400> SEQUENCE: 539

Arg Glu Asp His Leu His Thr
1               5

<210> SEQ ID NO 540
<211> LENGTH: 7
<212> TYPE: PRT
<213> ORGANISM: Artificial Sequence
<220> FEATURE:
<223> OTHER INFORMATION: Synthetic construct

<400> SEQUENCE: 540

Arg Glu Asp Lys Leu His Thr
1               5

<210> SEQ ID NO 541
<211> LENGTH: 7
<212> TYPE: PRT
<213> ORGANISM: Artificial Sequence
<220> FEATURE:
<223> OTHER INFORMATION: Synthetic construct

<400> SEQUENCE: 541

Arg Glu Asp Ser Leu His Thr
1               5

```
<210> SEQ ID NO 542
<211> LENGTH: 7
<212> TYPE: PRT
<213> ORGANISM: Artificial Sequence
<220> FEATURE:
<223> OTHER INFORMATION: Synthetic construct

<400> SEQUENCE: 542

Arg Glu Asp Ala Leu His Thr
1               5

<210> SEQ ID NO 543
<211> LENGTH: 7
<212> TYPE: PRT
<213> ORGANISM: Artificial Sequence
<220> FEATURE:
<223> OTHER INFORMATION: Synthetic construct

<400> SEQUENCE: 543

Gln Glu Asp Thr Leu His Thr
1               5

<210> SEQ ID NO 544
<211> LENGTH: 7
<212> TYPE: PRT
<213> ORGANISM: Artificial Sequence
<220> FEATURE:
<223> OTHER INFORMATION: Synthetic construct

<400> SEQUENCE: 544

Gln Glu Asp Asp Leu His Thr
1               5

<210> SEQ ID NO 545
<211> LENGTH: 7
<212> TYPE: PRT
<213> ORGANISM: Artificial Sequence
<220> FEATURE:
<223> OTHER INFORMATION: Synthetic construct

<400> SEQUENCE: 545

Gln Glu Asp Glu Leu His Thr
1               5

<210> SEQ ID NO 546
<211> LENGTH: 7
<212> TYPE: PRT
<213> ORGANISM: Artificial Sequence
<220> FEATURE:
<223> OTHER INFORMATION: Synthetic construct

<400> SEQUENCE: 546

Gln Glu Asp His Leu His Thr
1               5

<210> SEQ ID NO 547
<211> LENGTH: 8
<212> TYPE: PRT
<213> ORGANISM: Artificial Sequence
<220> FEATURE:
<223> OTHER INFORMATION: Synthetic construct

<400> SEQUENCE: 547

Gln Glu Asp Lys Leu His Thr Ser
1               5
```

```
<210> SEQ ID NO 548
<211> LENGTH: 7
<212> TYPE: PRT
<213> ORGANISM: Artificial Sequence
<220> FEATURE:
<223> OTHER INFORMATION: Synthetic construct

<400> SEQUENCE: 548

Gln Glu Asp Ser Leu His Thr
1               5

<210> SEQ ID NO 549
<211> LENGTH: 7
<212> TYPE: PRT
<213> ORGANISM: Artificial Sequence
<220> FEATURE:
<223> OTHER INFORMATION: Synthetic construct

<400> SEQUENCE: 549

Gln Glu Asp Ala Leu His Thr
1               5

<210> SEQ ID NO 550
<211> LENGTH: 7
<212> TYPE: PRT
<213> ORGANISM: Artificial Sequence
<220> FEATURE:
<223> OTHER INFORMATION: Synthetic construct

<400> SEQUENCE: 550

Asp Glu Asp Thr Leu His Thr
1               5

<210> SEQ ID NO 551
<211> LENGTH: 7
<212> TYPE: PRT
<213> ORGANISM: Artificial Sequence
<220> FEATURE:
<223> OTHER INFORMATION: Synthetic construct

<400> SEQUENCE: 551

Asp Glu Asp Asp Leu His Thr
1               5

<210> SEQ ID NO 552
<211> LENGTH: 7
<212> TYPE: PRT
<213> ORGANISM: Artificial Sequence
<220> FEATURE:
<223> OTHER INFORMATION: Synthetic construct

<400> SEQUENCE: 552

Asp Glu Asp Glu Leu His Thr
1               5

<210> SEQ ID NO 553
<211> LENGTH: 7
<212> TYPE: PRT
<213> ORGANISM: Artificial Sequence
<220> FEATURE:
<223> OTHER INFORMATION: Synthetic construct

<400> SEQUENCE: 553

Asp Glu Asp His Leu His Thr
1               5

<210> SEQ ID NO 554
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 554

Asp Glu Asp Lys Leu His Thr
1               5

<210> SEQ ID NO 555
<211> LENGTH: 7
<212> TYPE: PRT
<213> ORGANISM: Artificial Sequence
<220> FEATURE:
<223> OTHER INFORMATION: Synthetic construct

<400> SEQUENCE: 555

Asp Glu Asp Ser Leu His Thr
1               5

<210> SEQ ID NO 556
<211> LENGTH: 7
<212> TYPE: PRT
<213> ORGANISM: Artificial Sequence
<220> FEATURE:
<223> OTHER INFORMATION: Synthetic construct

<400> SEQUENCE: 556

Asp Glu Asp Ala Leu His Thr
1               5

<210> SEQ ID NO 557
<211> LENGTH: 7
<212> TYPE: PRT
<213> ORGANISM: Artificial Sequence
<220> FEATURE:
<223> OTHER INFORMATION: Synthetic construct

<400> SEQUENCE: 557

Glu Glu Asp Thr Leu His Thr
1               5

<210> SEQ ID NO 558
<211> LENGTH: 7
<212> TYPE: PRT
<213> ORGANISM: Artificial Sequence
<220> FEATURE:
<223> OTHER INFORMATION: Synthetic construct

<400> SEQUENCE: 558

Glu Glu Asp Asp Leu His Thr
1               5

<210> SEQ ID NO 559
<211> LENGTH: 7
<212> TYPE: PRT
<213> ORGANISM: Artificial Sequence
<220> FEATURE:
<223> OTHER INFORMATION: Synthetic construct

<400> SEQUENCE: 559

Glu Glu Asp Glu Leu His Thr
1               5

<210> SEQ ID NO 560
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 560

Glu Glu Asp His Leu His Thr
1               5

<210> SEQ ID NO 561
<211> LENGTH: 7
<212> TYPE: PRT
<213> ORGANISM: Artificial Sequence
<220> FEATURE:
<223> OTHER INFORMATION: Synthetic construct

<400> SEQUENCE: 561

Glu Glu Asp Lys Leu His Thr
1               5

<210> SEQ ID NO 562
<211> LENGTH: 7
<212> TYPE: PRT
<213> ORGANISM: Artificial Sequence
<220> FEATURE:
<223> OTHER INFORMATION: Synthetic construct

<400> SEQUENCE: 562

Glu Glu Asp Ser Leu His Thr
1               5

<210> SEQ ID NO 563
<211> LENGTH: 7
<212> TYPE: PRT
<213> ORGANISM: Artificial Sequence
<220> FEATURE:
<223> OTHER INFORMATION: Synthetic construct

<400> SEQUENCE: 563

Glu Glu Asp Ala Leu His Thr
1               5

<210> SEQ ID NO 564
<211> LENGTH: 7
<212> TYPE: PRT
<213> ORGANISM: Artificial Sequence
<220> FEATURE:
<223> OTHER INFORMATION: Synthetic construct

<400> SEQUENCE: 564

Thr Glu Asp Thr Leu His Thr
1               5

<210> SEQ ID NO 565
<211> LENGTH: 7
<212> TYPE: PRT
<213> ORGANISM: Artificial Sequence
<220> FEATURE:
<223> OTHER INFORMATION: Synthetic construct

<400> SEQUENCE: 565

Thr Glu Asp Asp Leu His Thr
1               5

<210> SEQ ID NO 566
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 566

Thr Glu Asp Glu Leu His Thr
1               5

<210> SEQ ID NO 567
<211> LENGTH: 7
<212> TYPE: PRT
<213> ORGANISM: Artificial Sequence
<220> FEATURE:
<223> OTHER INFORMATION: Synthetic construct

<400> SEQUENCE: 567

Thr Glu Asp His Leu His Thr
1               5

<210> SEQ ID NO 568
<211> LENGTH: 7
<212> TYPE: PRT
<213> ORGANISM: Artificial Sequence
<220> FEATURE:
<223> OTHER INFORMATION: Synthetic construct

<400> SEQUENCE: 568

Thr Glu Asp Lys Leu His Thr
1               5

<210> SEQ ID NO 569
<211> LENGTH: 7
<212> TYPE: PRT
<213> ORGANISM: Artificial Sequence
<220> FEATURE:
<223> OTHER INFORMATION: Synthetic construct

<400> SEQUENCE: 569

Thr Glu Asp Ser Leu His Thr
1               5

<210> SEQ ID NO 570
<211> LENGTH: 7
<212> TYPE: PRT
<213> ORGANISM: Artificial Sequence
<220> FEATURE:
<223> OTHER INFORMATION: Synthetic construct

<400> SEQUENCE: 570

Thr Glu Asp Ala Leu His Thr
1               5

<210> SEQ ID NO 571
<211> LENGTH: 7
<212> TYPE: PRT
<213> ORGANISM: Artificial Sequence
<220> FEATURE:
<223> OTHER INFORMATION: Synthetic construct

<400> SEQUENCE: 571

Ser Glu Asp Thr Leu His Thr
1               5

<210> SEQ ID NO 572
<211> LENGTH: 7
<212> TYPE: PRT
<213> ORGANISM: Artificial Sequence
<220> FEATURE:
<223> OTHER INFORMATION: Synthetic construct

<400> SEQUENCE: 572
```

Ser Glu Asp Leu His Thr
1               5

<210> SEQ ID NO 573
<211> LENGTH: 7
<212> TYPE: PRT
<213> ORGANISM: Artificial Sequence
<220> FEATURE:
<223> OTHER INFORMATION: Synthetic construct

<400> SEQUENCE: 573

Ser Glu Asp Glu Leu His Thr
1               5

<210> SEQ ID NO 574
<211> LENGTH: 7
<212> TYPE: PRT
<213> ORGANISM: Artificial Sequence
<220> FEATURE:
<223> OTHER INFORMATION: Synthetic construct

<400> SEQUENCE: 574

Ser Glu Asp His Leu His Thr
1               5

<210> SEQ ID NO 575
<211> LENGTH: 7
<212> TYPE: PRT
<213> ORGANISM: Artificial Sequence
<220> FEATURE:
<223> OTHER INFORMATION: Synthetic construct

<400> SEQUENCE: 575

Ser Glu Asp Lys Leu His Thr
1               5

<210> SEQ ID NO 576
<211> LENGTH: 7
<212> TYPE: PRT
<213> ORGANISM: Artificial Sequence
<220> FEATURE:
<223> OTHER INFORMATION: Synthetic construct

<400> SEQUENCE: 576

Ser Glu Asp Ser Leu His Thr
1               5

<210> SEQ ID NO 577
<211> LENGTH: 7
<212> TYPE: PRT
<213> ORGANISM: Artificial Sequence
<220> FEATURE:
<223> OTHER INFORMATION: Synthetic construct

<400> SEQUENCE: 577

Ser Glu Asp Ala Leu His Thr
1               5

<210> SEQ ID NO 578
<211> LENGTH: 7
<212> TYPE: PRT
<213> ORGANISM: Artificial Sequence
<220> FEATURE:
<223> OTHER INFORMATION: Synthetic construct

<400> SEQUENCE: 578

Gln Glu Asp Asn Leu Ile Ser

-continued

<210> SEQ ID NO 579
<211> LENGTH: 7
<212> TYPE: PRT
<213> ORGANISM: Artificial Sequence
<220> FEATURE:
<223> OTHER INFORMATION: Synthetic construct

<400> SEQUENCE: 579

Asp Glu Asp Asn Leu Ile Ser
1               5

<210> SEQ ID NO 580
<211> LENGTH: 7
<212> TYPE: PRT
<213> ORGANISM: Artificial Sequence
<220> FEATURE:
<223> OTHER INFORMATION: Synthetic construct

<400> SEQUENCE: 580

Glu Glu Asp Asn Leu Ile Ser
1               5

<210> SEQ ID NO 581
<211> LENGTH: 7
<212> TYPE: PRT
<213> ORGANISM: Artificial Sequence
<220> FEATURE:
<223> OTHER INFORMATION: Synthetic construct

<400> SEQUENCE: 581

Ser Glu Asp Asn Leu Ile Ser
1               5

<210> SEQ ID NO 582
<211> LENGTH: 7
<212> TYPE: PRT
<213> ORGANISM: Artificial Sequence
<220> FEATURE:
<223> OTHER INFORMATION: Synthetic construct

<400> SEQUENCE: 582

Arg Glu Asp Thr Leu Ile Ser
1               5

<210> SEQ ID NO 583
<211> LENGTH: 7
<212> TYPE: PRT
<213> ORGANISM: Artificial Sequence
<220> FEATURE:
<223> OTHER INFORMATION: Synthetic construct

<400> SEQUENCE: 583

Arg Glu Asp Asp Leu Ile Ser
1               5

<210> SEQ ID NO 584
<211> LENGTH: 7
<212> TYPE: PRT
<213> ORGANISM: Artificial Sequence
<220> FEATURE:
<223> OTHER INFORMATION: Synthetic construct

<400> SEQUENCE: 584

Arg Glu Asp Glu Leu Ile Ser
1               5

<210> SEQ ID NO 585
<211> LENGTH: 7
<212> TYPE: PRT
<213> ORGANISM: Artificial Sequence
<220> FEATURE:
<223> OTHER INFORMATION: Synthetic construct

<400> SEQUENCE: 585

Arg Glu Asp His Leu Ile Ser
1               5

<210> SEQ ID NO 586
<211> LENGTH: 7
<212> TYPE: PRT
<213> ORGANISM: Artificial Sequence
<220> FEATURE:
<223> OTHER INFORMATION: Synthetic construct

<400> SEQUENCE: 586

Arg Glu Asp Lys Leu Ile Ser
1               5

<210> SEQ ID NO 587
<211> LENGTH: 7
<212> TYPE: PRT
<213> ORGANISM: Artificial Sequence
<220> FEATURE:
<223> OTHER INFORMATION: Synthetic construct

<400> SEQUENCE: 587

Arg Glu Asp Ser Leu Ile Ser
1               5

<210> SEQ ID NO 588
<211> LENGTH: 7
<212> TYPE: PRT
<213> ORGANISM: Artificial Sequence
<220> FEATURE:
<223> OTHER INFORMATION: Synthetic construct

<400> SEQUENCE: 588

Arg Glu Asp Ala Leu Ile Ser
1               5

<210> SEQ ID NO 589
<211> LENGTH: 7
<212> TYPE: PRT
<213> ORGANISM: Artificial Sequence
<220> FEATURE:
<223> OTHER INFORMATION: Synthetic construct

<400> SEQUENCE: 589

Gln Glu Asp Thr Leu Ile Ser
1               5

<210> SEQ ID NO 590
<211> LENGTH: 7
<212> TYPE: PRT
<213> ORGANISM: Artificial Sequence
<220> FEATURE:
<223> OTHER INFORMATION: Synthetic construct

<400> SEQUENCE: 590

Gln Glu Asp Asp Leu Ile Ser
1               5

<210> SEQ ID NO 591

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 591

Gln Glu Asp Glu Leu Ile Ser
1               5

<210> SEQ ID NO 592
<211> LENGTH: 7
<212> TYPE: PRT
<213> ORGANISM: Artificial Sequence
<220> FEATURE:
<223> OTHER INFORMATION: Synthetic construct

<400> SEQUENCE: 592

Gln Glu Asp His Leu Ile Ser
1               5

<210> SEQ ID NO 593
<211> LENGTH: 7
<212> TYPE: PRT
<213> ORGANISM: Artificial Sequence
<220> FEATURE:
<223> OTHER INFORMATION: Synthetic construct

<400> SEQUENCE: 593

Gln Glu Asp Lys Leu Ile Ser
1               5

<210> SEQ ID NO 594
<211> LENGTH: 7
<212> TYPE: PRT
<213> ORGANISM: Artificial Sequence
<220> FEATURE:
<223> OTHER INFORMATION: Synthetic construct

<400> SEQUENCE: 594

Gln Glu Asp Ser Leu Ile Ser
1               5

<210> SEQ ID NO 595
<211> LENGTH: 7
<212> TYPE: PRT
<213> ORGANISM: Artificial Sequence
<220> FEATURE:
<223> OTHER INFORMATION: Synthetic construct

<400> SEQUENCE: 595

Gln Glu Asp Ala Leu Ile Ser
1               5

<210> SEQ ID NO 596
<211> LENGTH: 7
<212> TYPE: PRT
<213> ORGANISM: Artificial Sequence
<220> FEATURE:
<223> OTHER INFORMATION: Synthetic construct

<400> SEQUENCE: 596

Asp Glu Asp Thr Leu Ile Ser
1               5

<210> SEQ ID NO 597
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 597

Asp Glu Asp Asp Leu Ile Ser
1               5

<210> SEQ ID NO 598
<211> LENGTH: 7
<212> TYPE: PRT
<213> ORGANISM: Artificial Sequence
<220> FEATURE:
<223> OTHER INFORMATION: Synthetic construct

<400> SEQUENCE: 598

Asp Glu Asp Glu Leu Ile Ser
1               5

<210> SEQ ID NO 599
<211> LENGTH: 7
<212> TYPE: PRT
<213> ORGANISM: Artificial Sequence
<220> FEATURE:
<223> OTHER INFORMATION: Synthetic construct

<400> SEQUENCE: 599

Asp Glu Asp His Leu Ile Ser
1               5

<210> SEQ ID NO 600
<211> LENGTH: 7
<212> TYPE: PRT
<213> ORGANISM: Artificial Sequence
<220> FEATURE:
<223> OTHER INFORMATION: Synthetic construct

<400> SEQUENCE: 600

Asp Glu Asp Lys Leu Ile Ser
1               5

<210> SEQ ID NO 601
<211> LENGTH: 7
<212> TYPE: PRT
<213> ORGANISM: Artificial Sequence
<220> FEATURE:
<223> OTHER INFORMATION: Synthetic construct

<400> SEQUENCE: 601

Asp Glu Asp Ser Leu Ile Ser
1               5

<210> SEQ ID NO 602
<211> LENGTH: 7
<212> TYPE: PRT
<213> ORGANISM: Artificial Sequence
<220> FEATURE:
<223> OTHER INFORMATION: Synthetic construct

<400> SEQUENCE: 602

Asp Glu Asp Ser Leu Ile Ser
1               5

<210> SEQ ID NO 603
<211> LENGTH: 7
<212> TYPE: PRT
<213> ORGANISM: Artificial Sequence
<220> FEATURE:
```

<223> OTHER INFORMATION: Synthetic construct

<400> SEQUENCE: 603

Glu Glu Asp Thr Leu Ile Ser
1               5

<210> SEQ ID NO 604
<211> LENGTH: 7
<212> TYPE: PRT
<213> ORGANISM: Artificial Sequence
<220> FEATURE:
<223> OTHER INFORMATION: Synthetic construct

<400> SEQUENCE: 604

Glu Glu Asp Asp Leu Ile Ser
1               5

<210> SEQ ID NO 605
<211> LENGTH: 7
<212> TYPE: PRT
<213> ORGANISM: Artificial Sequence
<220> FEATURE:
<223> OTHER INFORMATION: Synthetic construct

<400> SEQUENCE: 605

Glu Glu Asp Glu Leu Ile Ser
1               5

<210> SEQ ID NO 606
<211> LENGTH: 7
<212> TYPE: PRT
<213> ORGANISM: Artificial Sequence
<220> FEATURE:
<223> OTHER INFORMATION: Synthetic construct

<400> SEQUENCE: 606

Glu Glu Asp His Leu Ile Ser
1               5

<210> SEQ ID NO 607
<211> LENGTH: 7
<212> TYPE: PRT
<213> ORGANISM: Artificial Sequence
<220> FEATURE:
<223> OTHER INFORMATION: Synthetic construct

<400> SEQUENCE: 607

Glu Glu Asp Lys Leu Ile Ser
1               5

<210> SEQ ID NO 608
<211> LENGTH: 7
<212> TYPE: PRT
<213> ORGANISM: Artificial Sequence
<220> FEATURE:
<223> OTHER INFORMATION: Synthetic construct

<400> SEQUENCE: 608

Glu Glu Asp Ser Leu Ile Ser
1               5

<210> SEQ ID NO 609
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 609

Glu Glu Asp Ala Leu Ile Ser
1               5

<210> SEQ ID NO 610
<211> LENGTH: 7
<212> TYPE: PRT
<213> ORGANISM: Artificial Sequence
<220> FEATURE:
<223> OTHER INFORMATION: Synthetic construct

<400> SEQUENCE: 610

Thr Glu Asp Thr Leu Ile Ser
1               5

<210> SEQ ID NO 611
<211> LENGTH: 7
<212> TYPE: PRT
<213> ORGANISM: Artificial Sequence
<220> FEATURE:
<223> OTHER INFORMATION: Synthetic construct

<400> SEQUENCE: 611

Thr Glu Asp Asp Leu Ile Ser
1               5

<210> SEQ ID NO 612
<211> LENGTH: 7
<212> TYPE: PRT
<213> ORGANISM: Artificial Sequence
<220> FEATURE:
<223> OTHER INFORMATION: Synthetic construct

<400> SEQUENCE: 612

Thr Glu Asp Glu Leu Ile Ser
1               5

<210> SEQ ID NO 613
<211> LENGTH: 7
<212> TYPE: PRT
<213> ORGANISM: Artificial Sequence
<220> FEATURE:
<223> OTHER INFORMATION: Synthetic construct

<400> SEQUENCE: 613

Thr Glu Asp His Leu Ile Ser
1               5

<210> SEQ ID NO 614
<211> LENGTH: 7
<212> TYPE: PRT
<213> ORGANISM: Artificial Sequence
<220> FEATURE:
<223> OTHER INFORMATION: Synthetic construct

<400> SEQUENCE: 614

Thr Glu Asp Lys Leu Ile Ser
1               5

<210> SEQ ID NO 615
<211> LENGTH: 7
<212> TYPE: PRT
<213> ORGANISM: Artificial Sequence
<220> FEATURE:
<223> OTHER INFORMATION: Synthetic construct

<400> SEQUENCE: 615
```

Thr Glu Asp Ser Leu Ile Ser
1               5

<210> SEQ ID NO 616
<211> LENGTH: 7
<212> TYPE: PRT
<213> ORGANISM: Artificial Sequence
<220> FEATURE:
<223> OTHER INFORMATION: Synthetic construct

<400> SEQUENCE: 616

Thr Glu Asp Ala Leu Ile Ser
1               5

<210> SEQ ID NO 617
<211> LENGTH: 7
<212> TYPE: PRT
<213> ORGANISM: Artificial Sequence
<220> FEATURE:
<223> OTHER INFORMATION: Synthetic construct

<400> SEQUENCE: 617

Ser Glu Asp Thr Leu Ile Ser
1               5

<210> SEQ ID NO 618
<211> LENGTH: 7
<212> TYPE: PRT
<213> ORGANISM: Artificial Sequence
<220> FEATURE:
<223> OTHER INFORMATION: Synthetic construct

<400> SEQUENCE: 618

Ser Glu Asp Asp Leu Ile Ser
1               5

<210> SEQ ID NO 619
<211> LENGTH: 7
<212> TYPE: PRT
<213> ORGANISM: Artificial Sequence
<220> FEATURE:
<223> OTHER INFORMATION: Synthetic construct

<400> SEQUENCE: 619

Ser Glu Asp Glu Leu Ile Ser
1               5

<210> SEQ ID NO 620
<211> LENGTH: 7
<212> TYPE: PRT
<213> ORGANISM: Artificial Sequence
<220> FEATURE:
<223> OTHER INFORMATION: Synthetic construct

<400> SEQUENCE: 620

Ser Glu Asp His Leu Ile Ser
1               5

<210> SEQ ID NO 621
<211> LENGTH: 7
<212> TYPE: PRT
<213> ORGANISM: Artificial Sequence
<220> FEATURE:
<223> OTHER INFORMATION: Synthetic construct

<400> SEQUENCE: 621

Ser Glu Asp Lys Leu Ile Ser
1               5

```
<210> SEQ ID NO 622
<211> LENGTH: 7
<212> TYPE: PRT
<213> ORGANISM: Artificial Sequence
<220> FEATURE:
<223> OTHER INFORMATION: Synthetic construct

<400> SEQUENCE: 622

Ser Glu Asp Ser Leu Ile Ser
1               5

<210> SEQ ID NO 623
<211> LENGTH: 7
<212> TYPE: PRT
<213> ORGANISM: Artificial Sequence
<220> FEATURE:
<223> OTHER INFORMATION: Synthetic construct

<400> SEQUENCE: 623

Ser Glu Asp Ala Leu Ile Ser
1               5

<210> SEQ ID NO 624
<211> LENGTH: 5
<212> TYPE: PRT
<213> ORGANISM: Artificial Sequence
<220> FEATURE:
<223> OTHER INFORMATION: Synthetic construct

<400> SEQUENCE: 624

Thr Gly Glu Lys Pro
1               5

<210> SEQ ID NO 625
<211> LENGTH: 15
<212> TYPE: PRT
<213> ORGANISM: Artificial Sequence
<220> FEATURE:
<223> OTHER INFORMATION: Synthetic construct

<400> SEQUENCE: 625

Thr Gly Gly Gly Gly Ser Gly Gly Gly Gly Thr Gly Glu Lys Pro
1               5                   10                  15

<210> SEQ ID NO 626
<211> LENGTH: 12
<212> TYPE: PRT
<213> ORGANISM: Artificial Sequence
<220> FEATURE:
<223> OTHER INFORMATION: Synthetic construct

<400> SEQUENCE: 626

Leu Arg Gln Lys Asp Gly Gly Gly Ser Glu Arg Pro
1               5                   10

<210> SEQ ID NO 627
<211> LENGTH: 9
<212> TYPE: PRT
<213> ORGANISM: Artificial Sequence
<220> FEATURE:
<223> OTHER INFORMATION: Synthetic construct

<400> SEQUENCE: 627

Leu Arg Gln Lys Asp Gly Glu Arg Pro
1               5
```

```
<210> SEQ ID NO 628
<211> LENGTH: 10
<212> TYPE: PRT
<213> ORGANISM: Artificial Sequence
<220> FEATURE:
<223> OTHER INFORMATION: Synthetic construct

<400> SEQUENCE: 628

Gly Gly Arg Gly Arg Gly Arg Gly Arg Gln
1               5                   10

<210> SEQ ID NO 629
<211> LENGTH: 16
<212> TYPE: PRT
<213> ORGANISM: Artificial Sequence
<220> FEATURE:
<223> OTHER INFORMATION: Synthetic construct

<400> SEQUENCE: 629

Gln Asn Lys Lys Gly Gly Ser Gly Asp Gly Lys Lys Lys Gln His Ile
1               5                   10                  15

<210> SEQ ID NO 630
<211> LENGTH: 6
<212> TYPE: PRT
<213> ORGANISM: Artificial Sequence
<220> FEATURE:
<223> OTHER INFORMATION: Synthetic construct

<400> SEQUENCE: 630

Thr Gly Gly Glu Arg Pro
1               5

<210> SEQ ID NO 631
<211> LENGTH: 6
<212> TYPE: PRT
<213> ORGANISM: Artificial Sequence
<220> FEATURE:
<223> OTHER INFORMATION: Synthetic construct

<400> SEQUENCE: 631

Ala Thr Gly Glu Lys Pro
1               5

<210> SEQ ID NO 632
<211> LENGTH: 20
<212> TYPE: DNA
<213> ORGANISM: Artificial Sequence
<220> FEATURE:
<223> OTHER INFORMATION: Synthetic construct

<400> SEQUENCE: 632
tccaaaacca tggtttacag                                              20

<210> SEQ ID NO 633
<211> LENGTH: 20
<212> TYPE: DNA
<213> ORGANISM: Artificial Sequence
<220> FEATURE:
<223> OTHER INFORMATION: Synthetic construct

<400> SEQUENCE: 633
tccaaaacca taatatttcg                                              20

<210> SEQ ID NO 634
<211> LENGTH: 9
<212> TYPE: DNA
<213> ORGANISM: Artificial Sequence
```

```
<220> FEATURE:
<223> OTHER INFORMATION: Synthetic construct

<400> SEQUENCE: 634 ggaggcgtg                                                                                              9

<210> SEQ ID NO 635
<211> LENGTH: 9
<212> TYPE: DNA
<213> ORGANISM: Artificial Sequence
<220> FEATURE:
<223> OTHER INFORMATION: Synthetic construct

<400> SEQUENCE: 635 gcagtggcg                                                                                              9

<210> SEQ ID NO 636
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 636

Gly Xaa Gly Gly Xaa Gly
1               5

<210> SEQ ID NO 637
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t

<400> SEQUENCE: 637 gnngnn                                                                                                 6

<210> SEQ ID NO 638
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: n is a, c, g, or t

<400> SEQUENCE: 638 nnnnnn                                                                                                 6

<210> SEQ ID NO 639
<211> LENGTH: 20
<212> TYPE: DNA
```

```
<213> ORGANISM: Artificial Sequence
<220> FEATURE:
<223> OTHER INFORMATION: Synthetic construct

<400> SEQUENCE: 639
tgataattta taatatttcg                                                  20

<210> SEQ ID NO 640
<211> LENGTH: 20
<212> TYPE: DNA
<213> ORGANISM: Artificial Sequence
<220> FEATURE:
<223> OTHER INFORMATION: Synthetic construct

<400> SEQUENCE: 640
tgataattta taaattatca                                                  20

<210> SEQ ID NO 641
<211> LENGTH: 20
<212> TYPE: PRT
<213> ORGANISM: Artificial Sequence
<220> FEATURE:
<223> OTHER INFORMATION: Synthetic construct

<400> SEQUENCE: 641

Cys Gly Ala Ala Ala Thr Ala Thr Thr Ala Thr Ala Ala Thr Ala Thr
1               5                   10                  15

Thr Thr Cys Gly
            20

<210> SEQ ID NO 642
<211> LENGTH: 18
<212> TYPE: DNA
<213> ORGANISM: Artificial Sequence
<220> FEATURE:
<223> OTHER INFORMATION: Synthetic construct

<400> SEQUENCE: 642
gataatttat aatatttc                                                    18

<210> SEQ ID NO 643
<211> LENGTH: 22
<212> TYPE: DNA
<213> ORGANISM: Artificial Sequence
<220> FEATURE:
<223> OTHER INFORMATION: Synthetic construct

<400> SEQUENCE: 643
ctgataattt ataatatttc ga                                               22

<210> SEQ ID NO 644
<211> LENGTH: 20
<212> TYPE: DNA
<213> ORGANISM: Artificial Sequence
<220> FEATURE:
<223> OTHER INFORMATION: Synthetic construct

<400> SEQUENCE: 644
tgataatttt caatatttcg                                                  20

<210> SEQ ID NO 645
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 645
tgataactta taatatttcg                                              20

<210> SEQ ID NO 646
<211> LENGTH: 20
<212> TYPE: DNA
<213> ORGANISM: Artificial Sequence
<220> FEATURE:
<223> OTHER INFORMATION: Synthetic construct

<400> SEQUENCE: 646
tgatacttta taatatttcg                                              20

<210> SEQ ID NO 647
<211> LENGTH: 20
<212> TYPE: DNA
<213> ORGANISM: Artificial Sequence
<220> FEATURE:
<223> OTHER INFORMATION: Synthetic construct

<400> SEQUENCE: 647
tgatcattta taatatttcg                                              20

<210> SEQ ID NO 648
<211> LENGTH: 20
<212> TYPE: DNA
<213> ORGANISM: Artificial Sequence
<220> FEATURE:
<223> OTHER INFORMATION: Synthetic construct

<400> SEQUENCE: 648
tgacaattta taatatttcg                                              20

<210> SEQ ID NO 649
<211> LENGTH: 20
<212> TYPE: DNA
<213> ORGANISM: Artificial Sequence
<220> FEATURE:
<223> OTHER INFORMATION: Synthetic construct

<400> SEQUENCE: 649
tgataattta tggtttacag                                              20

<210> SEQ ID NO 650
<211> LENGTH: 20
<212> TYPE: DNA
<213> ORGANISM: Artificial Sequence
<220> FEATURE:
<223> OTHER INFORMATION: Synthetic construct

<400> SEQUENCE: 650
tccaaaacca taaattatca                                              20

<210> SEQ ID NO 651
<211> LENGTH: 20
<212> TYPE: DNA
<213> ORGANISM: Artificial Sequence
<220> FEATURE:
<223> OTHER INFORMATION: Synthetic construct

<400> SEQUENCE: 651
ctgtaaacca taatatttcg                                              20

<210> SEQ ID NO 652
<211> LENGTH: 26
<212> TYPE: DNA
```

<213> ORGANISM: Artificial Sequence
<220> FEATURE:
<223> OTHER INFORMATION: Synthetic construct

<400> SEQUENCE: 652
gaggagtgat aatttataat atttcg                                26

<210> SEQ ID NO 653
<211> LENGTH: 7
<212> TYPE: PRT
<213> ORGANISM: Artificial Sequence
<220> FEATURE:
<223> OTHER INFORMATION: Synthetic construct

<400> SEQUENCE: 653

Thr Gly Gly Trp Leu Gln Ala
1               5

<210> SEQ ID NO 654
<211> LENGTH: 7
<212> TYPE: PRT
<213> ORGANISM: Artificial Sequence
<220> FEATURE:
<223> OTHER INFORMATION: Synthetic construct

<400> SEQUENCE: 654

Ser Gly Gly Trp Leu Gln Ala
1               5

<210> SEQ ID NO 655
<211> LENGTH: 7
<212> TYPE: PRT
<213> ORGANISM: Artificial Sequence
<220> FEATURE:
<223> OTHER INFORMATION: Synthetic construct

<400> SEQUENCE: 655

Asp Gly Gly Trp Leu Gln Ala
1               5

<210> SEQ ID NO 656
<211> LENGTH: 7
<212> TYPE: PRT
<213> ORGANISM: Artificial Sequence
<220> FEATURE:
<223> OTHER INFORMATION: Synthetic construct

<400> SEQUENCE: 656

Glu Gly Gly Trp Leu Gln Ala
1               5

<210> SEQ ID NO 657
<211> LENGTH: 7
<212> TYPE: PRT
<213> ORGANISM: Artificial Sequence
<220> FEATURE:
<223> OTHER INFORMATION: Synthetic construct

<400> SEQUENCE: 657

Gln Gly Gly Trp Leu Gln Ala
1               5

<210> SEQ ID NO 658
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 658

Arg Gly Gly Thr Leu Gln Ala
1               5

<210> SEQ ID NO 659
<211> LENGTH: 7
<212> TYPE: PRT
<213> ORGANISM: Artificial Sequence
<220> FEATURE:
<223> OTHER INFORMATION: Synthetic construct

<400> SEQUENCE: 659

Arg Gly Gly Asp Leu Gln Ala
1               5

<210> SEQ ID NO 660
<211> LENGTH: 7
<212> TYPE: PRT
<213> ORGANISM: Artificial Sequence
<220> FEATURE:
<223> OTHER INFORMATION: Synthetic construct

<400> SEQUENCE: 660

Arg Gly Gly Glu Leu Gln Ala
1               5

<210> SEQ ID NO 661
<211> LENGTH: 7
<212> TYPE: PRT
<213> ORGANISM: Artificial Sequence
<220> FEATURE:
<223> OTHER INFORMATION: Synthetic construct

<400> SEQUENCE: 661

Arg Gly Gly Asn Leu Gln Ala
1               5

<210> SEQ ID NO 662
<211> LENGTH: 7
<212> TYPE: PRT
<213> ORGANISM: Artificial Sequence
<220> FEATURE:
<223> OTHER INFORMATION: Synthetic construct

<400> SEQUENCE: 662

Arg Gly Gly His Leu Gln Ala
1               5

<210> SEQ ID NO 663
<211> LENGTH: 7
<212> TYPE: PRT
<213> ORGANISM: Artificial Sequence
<220> FEATURE:
<223> OTHER INFORMATION: Synthetic construct

<400> SEQUENCE: 663

Arg Gly Gly Lys Leu Gln Ala
1               5

<210> SEQ ID NO 664
<211> LENGTH: 7
<212> TYPE: PRT
<213> ORGANISM: Artificial Sequence
<220> FEATURE:
<223> OTHER INFORMATION: Synthetic construct

<400> SEQUENCE: 664
```

Arg Gly Gly Ser Leu Gln Ala
1               5

<210> SEQ ID NO 665
<211> LENGTH: 7
<212> TYPE: PRT
<213> ORGANISM: Artificial Sequence
<220> FEATURE:
<223> OTHER INFORMATION: Synthetic construct

<400> SEQUENCE: 665

Arg Gly Gly Ala Leu Gln Ala
1               5

<210> SEQ ID NO 666
<211> LENGTH: 7
<212> TYPE: PRT
<213> ORGANISM: Artificial Sequence
<220> FEATURE:
<223> OTHER INFORMATION: Synthetic construct

<400> SEQUENCE: 666

Thr Gly Gly Thr Leu Gln Ala
1               5

<210> SEQ ID NO 667
<211> LENGTH: 7
<212> TYPE: PRT
<213> ORGANISM: Artificial Sequence
<220> FEATURE:
<223> OTHER INFORMATION: Synthetic construct

<400> SEQUENCE: 667

Thr Gly Gly Asp Leu Gln Ala
1               5

<210> SEQ ID NO 668
<211> LENGTH: 7
<212> TYPE: PRT
<213> ORGANISM: Artificial Sequence
<220> FEATURE:
<223> OTHER INFORMATION: Synthetic construct

<400> SEQUENCE: 668

Thr Gly Gly Glu Leu Gln Ala
1               5

<210> SEQ ID NO 669
<211> LENGTH: 7
<212> TYPE: PRT
<213> ORGANISM: Artificial Sequence
<220> FEATURE:
<223> OTHER INFORMATION: Synthetic construct

<400> SEQUENCE: 669

Thr Gly Gly Asn Leu Gln Ala
1               5

<210> SEQ ID NO 670
<211> LENGTH: 7
<212> TYPE: PRT
<213> ORGANISM: Artificial Sequence
<220> FEATURE:
<223> OTHER INFORMATION: Synthetic construct

<400> SEQUENCE: 670

Thr Gly Gly His Leu Gln Ala

-continued

```
1               5

<210> SEQ ID NO 671
<211> LENGTH: 7
<212> TYPE: PRT
<213> ORGANISM: Artificial Sequence
<220> FEATURE:
<223> OTHER INFORMATION: Synthetic construct

<400> SEQUENCE: 671

Thr Gly Gly Lys Leu Gln Ala
1               5

<210> SEQ ID NO 672
<211> LENGTH: 7
<212> TYPE: PRT
<213> ORGANISM: Artificial Sequence
<220> FEATURE:
<223> OTHER INFORMATION: Synthetic construct

<400> SEQUENCE: 672

Thr Gly Gly Ser Leu Gln Ala
1               5

<210> SEQ ID NO 673
<211> LENGTH: 7
<212> TYPE: PRT
<213> ORGANISM: Artificial Sequence
<220> FEATURE:
<223> OTHER INFORMATION: Synthetic construct

<400> SEQUENCE: 673

Thr Gly Gly Ala Leu Gln Ala
1               5

<210> SEQ ID NO 674
<211> LENGTH: 7
<212> TYPE: PRT
<213> ORGANISM: Artificial Sequence
<220> FEATURE:
<223> OTHER INFORMATION: Synthetic construct

<400> SEQUENCE: 674

Ser Gly Gly Thr Leu Gln Ala
1               5

<210> SEQ ID NO 675
<211> LENGTH: 7
<212> TYPE: PRT
<213> ORGANISM: Artificial Sequence
<220> FEATURE:
<223> OTHER INFORMATION: Synthetic construct

<400> SEQUENCE: 675

Ser Gly Gly Asp Leu Gln Ala
1               5

<210> SEQ ID NO 676
<211> LENGTH: 7
<212> TYPE: PRT
<213> ORGANISM: Artificial Sequence
<220> FEATURE:
<223> OTHER INFORMATION: Synthetic construct

<400> SEQUENCE: 676

Ser Gly Gly Glu Leu Gln Ala
1               5
```

<210> SEQ ID NO 677
<211> LENGTH: 7
<212> TYPE: PRT
<213> ORGANISM: Artificial Sequence
<220> FEATURE:
<223> OTHER INFORMATION: Synthetic construct

<400> SEQUENCE: 677

Ser Gly Gly Asn Leu Gln Ala
1               5

<210> SEQ ID NO 678
<211> LENGTH: 7
<212> TYPE: PRT
<213> ORGANISM: Artificial Sequence
<220> FEATURE:
<223> OTHER INFORMATION: Synthetic construct

<400> SEQUENCE: 678

Ser Gly Gly His Leu Gln Ala
1               5

<210> SEQ ID NO 679
<211> LENGTH: 7
<212> TYPE: PRT
<213> ORGANISM: Artificial Sequence
<220> FEATURE:
<223> OTHER INFORMATION: Synthetic construct

<400> SEQUENCE: 679

Ser Gly Gly Lys Leu Gln Ala
1               5

<210> SEQ ID NO 680
<211> LENGTH: 7
<212> TYPE: PRT
<213> ORGANISM: Artificial Sequence
<220> FEATURE:
<223> OTHER INFORMATION: Synthetic construct

<400> SEQUENCE: 680

Ser Gly Gly Ser Leu Gln Ala
1               5

<210> SEQ ID NO 681
<211> LENGTH: 7
<212> TYPE: PRT
<213> ORGANISM: Artificial Sequence
<220> FEATURE:
<223> OTHER INFORMATION: Synthetic construct

<400> SEQUENCE: 681

Ser Gly Gly Ala Leu Gln Ala
1               5

<210> SEQ ID NO 682
<211> LENGTH: 7
<212> TYPE: PRT
<213> ORGANISM: Artificial Sequence
<220> FEATURE:
<223> OTHER INFORMATION: Synthetic construct

<400> SEQUENCE: 682

Asp Gly Gly Thr Leu Gln Ala
1               5

<210> SEQ ID NO 683

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 683

Asp Gly Gly Asp Leu Gln Ala
1               5

<210> SEQ ID NO 684
<211> LENGTH: 7
<212> TYPE: PRT
<213> ORGANISM: Artificial Sequence
<220> FEATURE:
<223> OTHER INFORMATION: Synthetic construct

<400> SEQUENCE: 684

Asp Gly Gly Glu Leu Gln Ala
1               5

<210> SEQ ID NO 685
<211> LENGTH: 7
<212> TYPE: PRT
<213> ORGANISM: Artificial Sequence
<220> FEATURE:
<223> OTHER INFORMATION: Synthetic construct

<400> SEQUENCE: 685

Asp Gly Gly Asn Leu Gln Ala
1               5

<210> SEQ ID NO 686
<211> LENGTH: 7
<212> TYPE: PRT
<213> ORGANISM: Artificial Sequence
<220> FEATURE:
<223> OTHER INFORMATION: Synthetic construct

<400> SEQUENCE: 686

Asp Gly Gly His Leu Gln Ala
1               5

<210> SEQ ID NO 687
<211> LENGTH: 7
<212> TYPE: PRT
<213> ORGANISM: Artificial Sequence
<220> FEATURE:
<223> OTHER INFORMATION: Synthetic construct

<400> SEQUENCE: 687

Asp Gly Gly Lys Leu Gln Ala
1               5

<210> SEQ ID NO 688
<211> LENGTH: 7
<212> TYPE: PRT
<213> ORGANISM: Artificial Sequence
<220> FEATURE:
<223> OTHER INFORMATION: Synthetic construct

<400> SEQUENCE: 688

Asp Gly Gly Ser Leu Gln Ala
1               5

<210> SEQ ID NO 689
<211> LENGTH: 7
<212> TYPE: PRT
```

<213> ORGANISM: Artificial Sequence
<220> FEATURE:
<223> OTHER INFORMATION: Synthetic construct

<400> SEQUENCE: 689

Asp Gly Gly Ala Leu Gln Ala
1               5

<210> SEQ ID NO 690
<211> LENGTH: 7
<212> TYPE: PRT
<213> ORGANISM: Artificial Sequence
<220> FEATURE:
<223> OTHER INFORMATION: Synthetic construct

<400> SEQUENCE: 690

Glu Gly Gly Thr Leu Gln Ala
1               5

<210> SEQ ID NO 691
<211> LENGTH: 7
<212> TYPE: PRT
<213> ORGANISM: Artificial Sequence
<220> FEATURE:
<223> OTHER INFORMATION: Synthetic construct

<400> SEQUENCE: 691

Glu Gly Gly Asp Leu Gln Ala
1               5

<210> SEQ ID NO 692
<211> LENGTH: 7
<212> TYPE: PRT
<213> ORGANISM: Artificial Sequence
<220> FEATURE:
<223> OTHER INFORMATION: Synthetic construct

<400> SEQUENCE: 692

Glu Gly Gly Glu Leu Gln Ala
1               5

<210> SEQ ID NO 693
<211> LENGTH: 7
<212> TYPE: PRT
<213> ORGANISM: Artificial Sequence
<220> FEATURE:
<223> OTHER INFORMATION: Synthetic construct

<400> SEQUENCE: 693

Glu Gly Gly Asn Leu Gln Ala
1               5

<210> SEQ ID NO 694
<211> LENGTH: 7
<212> TYPE: PRT
<213> ORGANISM: Artificial Sequence
<220> FEATURE:
<223> OTHER INFORMATION: Synthetic construct

<400> SEQUENCE: 694

Glu Gly Gly His Leu Gln Ala
1               5

<210> SEQ ID NO 695
<211> LENGTH: 7
<212> TYPE: PRT
<213> ORGANISM: Artificial Sequence
<220> FEATURE:

<223> OTHER INFORMATION: Synthetic construct

<400> SEQUENCE: 695

Glu Gly Gly Lys Leu Gln Ala
1               5

<210> SEQ ID NO 696
<211> LENGTH: 7
<212> TYPE: PRT
<213> ORGANISM: Artificial Sequence
<220> FEATURE:
<223> OTHER INFORMATION: Synthetic construct

<400> SEQUENCE: 696

Glu Gly Gly Ser Leu Gln Ala
1               5

<210> SEQ ID NO 697
<211> LENGTH: 7
<212> TYPE: PRT
<213> ORGANISM: Artificial Sequence
<220> FEATURE:
<223> OTHER INFORMATION: Synthetic construct

<400> SEQUENCE: 697

Glu Gly Gly Ala Leu Gln Ala
1               5

<210> SEQ ID NO 698
<211> LENGTH: 7
<212> TYPE: PRT
<213> ORGANISM: Artificial Sequence
<220> FEATURE:
<223> OTHER INFORMATION: Synthetic construct

<400> SEQUENCE: 698

Gln Gly Gly Thr Leu Gln Ala
1               5

<210> SEQ ID NO 699
<211> LENGTH: 7
<212> TYPE: PRT
<213> ORGANISM: Artificial Sequence
<220> FEATURE:
<223> OTHER INFORMATION: Synthetic construct

<400> SEQUENCE: 699

Gln Gly Gly Asp Leu Gln Ala
1               5

<210> SEQ ID NO 700
<211> LENGTH: 7
<212> TYPE: PRT
<213> ORGANISM: Artificial Sequence
<220> FEATURE:
<223> OTHER INFORMATION: Synthetic construct

<400> SEQUENCE: 700

Gln Gly Gly Glu Leu Gln Ala
1               5

<210> SEQ ID NO 701
<211> LENGTH: 7
<212> TYPE: PRT
<213> ORGANISM: Artificial Sequence
<220> FEATURE:
<223> OTHER INFORMATION: Synthetic construct -continued

```
<400> SEQUENCE: 701

Gln Gly Gly Asn Leu Gln Ala
1               5

<210> SEQ ID NO 702
<211> LENGTH: 7
<212> TYPE: PRT
<213> ORGANISM: Artificial Sequence
<220> FEATURE:
<223> OTHER INFORMATION: Synthetic construct

<400> SEQUENCE: 702

Gln Gly Gly His Leu Gln Ala
1               5

<210> SEQ ID NO 703
<211> LENGTH: 7
<212> TYPE: PRT
<213> ORGANISM: Artificial Sequence
<220> FEATURE:
<223> OTHER INFORMATION: Synthetic construct

<400> SEQUENCE: 703

Gln Gly Gly Lys Leu Gln Ala
1               5

<210> SEQ ID NO 704
<211> LENGTH: 7
<212> TYPE: PRT
<213> ORGANISM: Artificial Sequence
<220> FEATURE:
<223> OTHER INFORMATION: Synthetic construct

<400> SEQUENCE: 704

Gln Gly Gly Ser Leu Gln Ala
1               5

<210> SEQ ID NO 705
<211> LENGTH: 7
<212> TYPE: PRT
<213> ORGANISM: Artificial Sequence
<220> FEATURE:
<223> OTHER INFORMATION: Synthetic construct

<400> SEQUENCE: 705

Gln Gly Gly Ala Leu Gln Ala
1               5

<210> SEQ ID NO 706
<211> LENGTH: 11
<212> TYPE: PRT
<213> ORGANISM: Artificial Sequence
<220> FEATURE:
<223> OTHER INFORMATION: Synthetic construct

<400> SEQUENCE: 706

Gly Gly Gly Ser Gly Gly Gly Gly Glu Gly Pro
1               5                   10

<210> SEQ ID NO 707
<211> LENGTH: 142
<212> TYPE: PRT
<213> ORGANISM: Phage Mu

<400> SEQUENCE: 707

Met Leu Ile Gly Tyr Val Arg Val Ser Thr Asn Asp Gln Asn Thr Asp
1               5                   10                  15
```

```
Leu Gln Arg Asn Ala Leu Val Cys Ala Gly Cys Glu Gln Ile Phe Glu
            20              25                  30

Asp Lys Leu Ser Gly Thr Arg Thr Asp Arg Pro Gly Leu Lys Arg Ala
            35              40                  45

Leu Lys Arg Leu Gln Lys Gly Asp Thr Leu Val Val Trp Lys Leu Asp
     50              55                  60

Arg Leu Gly Arg Ser Met Lys His Leu Ile Ser Leu Val Gly Glu Leu
 65              70                  75                  80

Arg Glu Arg Gly Ile Asn Phe Arg Ser Leu Thr Asp Ser Ile Asp Thr
                 85                  90                  95

Ser Ser Ala Met Gly Arg Phe Phe Phe His Val Met Gly Ala Leu Ala
            100             105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys
        130                 135                 140
```